(12) United States Patent
Harrah et al.

(10) Patent No.: US 11,872,049 B2
(45) Date of Patent: *Jan. 16, 2024

(54) SYSTEM AND METHOD FOR DETECTING PRESENCE OF ILLNESS SYMPTOMS

(71) Applicants: Shane Harrah, Pleasanton, CA (US); Christina J. Harrah, Pleasanton, CA (US)

(72) Inventors: Shane Harrah, Pleasanton, CA (US); Christina J. Harrah, Pleasanton, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/867,527

(22) Filed: Jul. 18, 2022

(65) Prior Publication Data

US 2023/0119965 A1    Apr. 20, 2023

Related U.S. Application Data

(63) Continuation-in-part of application No. 17/167,451, filed on Feb. 4, 2021, now Pat. No. 11,393,594.

(60) Provisional application No. 63/065,243, filed on Aug. 13, 2020, provisional application No. 63/054,731, filed on Jul. 21, 2020, provisional application No. 63/045,798, filed on Jun. 29, 2020, provisional application No. 63/102,344, filed on Jun. 10, 2020.

(51) Int. Cl.
| | | |
|---|---|---|
| A61B 5/00 | (2006.01) | |
| A61B 5/16 | (2006.01) | |
| A61B 5/01 | (2006.01) | |
| A61B 5/08 | (2006.01) | |

(52) U.S. Cl.
CPC .......... *A61B 5/4011* (2013.01); *A61B 5/4088* (2013.01); *A61B 5/41* (2013.01)

(58) Field of Classification Search
CPC ....... A61B 5/0823; A61B 5/01; A61B 5/4011; A61B 5/7275; G16H 50/30; G16H 50/80; G06T 7/0012; G06T 7/0014
See application file for complete search history.

(56) References Cited

U.S. PATENT DOCUMENTS 11,393,594 B2 * 7/2022 Harrah .................. G16H 50/20

\* cited by examiner

*Primary Examiner* — Jon Eric C Morales

(57) ABSTRACT

A system and method for collecting symptomatic data to screen for a targeted disease. Testing hardware incorporates a plurality of testing units with corresponding indicators that can be altered to indicate whether a symptom is present or not. The resulting data from the testing use can then be analyzed to determine the likelihood of presence of a disease.

172 Claims, 149 Drawing Sheets

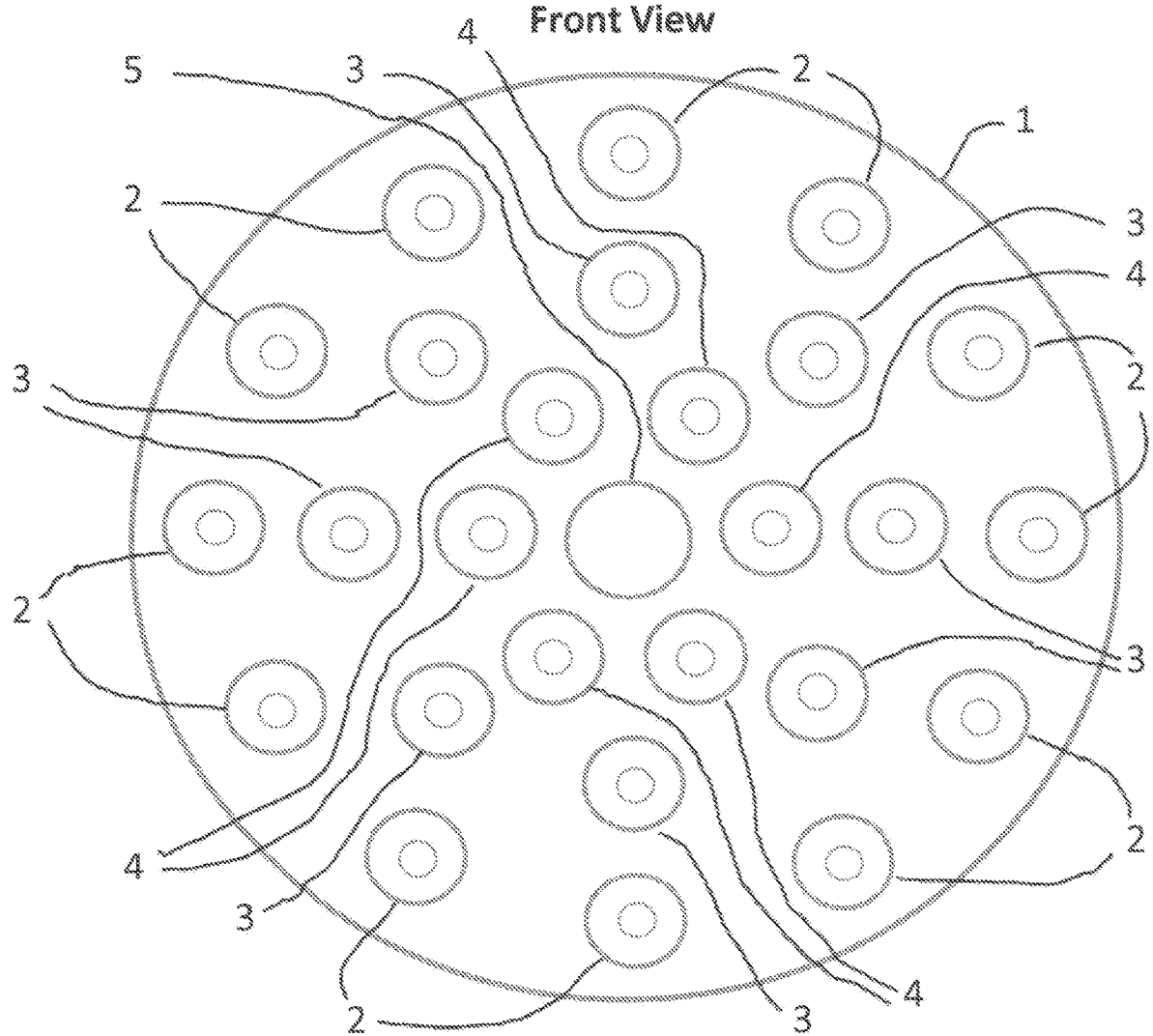

Coronavirus Symptom Test Kit

Coronavirus Symptom Test Kit

Coronavirus Symptom Test Kit

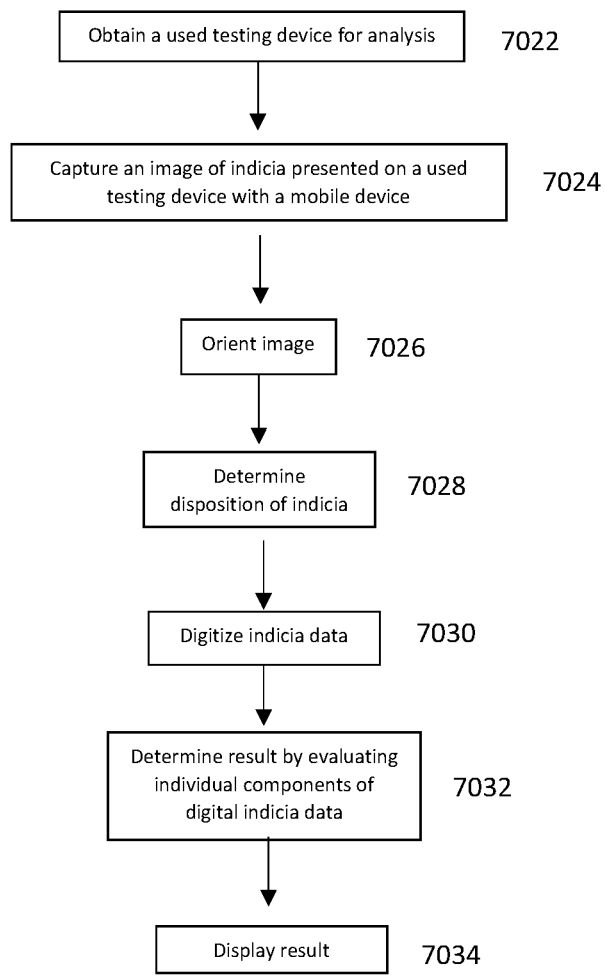

7102 Mobile Device
7104 Camera
7106 Server
7108 Database

Target Disease Symptoms Lookup Table

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 1 | 4 | | | | | | | | |
| 2 | 4 | | | | | | | | |
| 2 | 3 | | | | | | | | |
| 3 | 4 | | | | | | | | |
| 3 | 3 | | | | | | | | |
| 3 | 2 | | | | | | | | |
| 4 | 4 | | | | | | | | |
| 4 | 3 | | | | | | | | |
| 4 | 2 | | | | | | | | |
| 4 | 1 | | | | | | | | |
| 0 | 4 | 0 | 0 | 0 | 0 | 0 | 0 | 0 | 0 |
| 1 | 3 | 0 | 0 | 0 | 0 | 0 | 0 | 0 | 0 |
| 2 | 2 | 0 | 0 | 0 | 0 | 0 | 0 | 0 | 0 |
| 3 | 1 | 0 | 0 | 0 | 0 | 0 | 0 | 0 | 0 |
| 4 | 0 | 0 | 0 | 0 | 0 | 0 | 0 | 0 | 0 |
| 0 | 4 | 1 | 0 | 0 | 0 | 0 | 0 | 0 | 0 |
| 1 | 3 | 1 | 0 | 0 | 0 | 0 | 0 | 0 | 0 |
| 2 | 2 | 1 | 0 | 0 | 0 | 0 | 0 | 0 | 0 |
| 3 | 1 | 1 | 0 | 0 | 0 | 0 | 0 | 0 | 0 |
| 4 | 0 | 1 | 0 | 0 | 0 | 0 | 0 | 0 | 0 |
| 0 | 4 | 0 | 1 | 0 | 0 | 0 | 0 | 0 | 0 |

Fig. 72A(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 1 | 3 | 0 | 1 | 0 | 0 | 0 | 0 | 0 | 0 |
| 2 | 2 | 0 | 1 | 0 | 0 | 0 | 0 | 0 | 0 |
| 3 | 1 | 0 | 1 | 0 | 0 | 0 | 0 | 0 | 0 |
| 4 | 0 | 0 | 1 | 0 | 0 | 0 | 0 | 0 | 0 |
| 0 | 4 | 0 | 0 | 1 | 0 | 0 | 0 | 0 | 0 |
| 1 | 3 | 0 | 0 | 1 | 0 | 0 | 0 | 0 | 0 |
| 2 | 2 | 0 | 0 | 1 | 0 | 0 | 0 | 0 | 0 |
| 3 | 1 | 0 | 0 | 1 | 0 | 0 | 0 | 0 | 0 |
| 4 | 0 | 0 | 0 | 1 | 0 | 0 | 0 | 0 | 0 |
| 0 | 4 | 0 | 0 | 0 | 1 | 0 | 0 | 0 | 0 |
| 1 | 3 | 0 | 0 | 0 | 1 | 0 | 0 | 0 | 0 |
| 2 | 2 | 0 | 0 | 0 | 1 | 0 | 0 | 0 | 0 |
| 3 | 1 | 0 | 0 | 0 | 1 | 0 | 0 | 0 | 0 |
| 4 | 0 | 0 | 0 | 0 | 1 | 0 | 0 | 0 | 0 |
| 0 | 4 | 1 | 0 | 0 | 1 | 0 | 0 | 0 | 0 |

Fig. 72B(i)

Target Disease Symptoms Lookup Table

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 1 | 3 | 1 | 0 | 0 | 1 | 0 | 0 | 0 | 0 |
| 2 | 2 | 1 | 0 | 0 | 1 | 0 | 0 | 0 | 0 |
| 3 | 1 | 1 | 0 | 0 | 1 | 0 | 0 | 0 | 0 |
| 4 | 0 | 1 | 0 | 0 | 1 | 0 | 0 | 0 | 0 |
| 0 | 4 | 0 | 1 | 0 | 1 | 0 | 0 | 0 | 0 |
| 1 | 3 | 0 | 1 | 0 | 1 | 0 | 0 | 0 | 0 |
| 2 | 2 | 0 | 1 | 0 | 1 | 0 | 0 | 0 | 0 |
| 3 | 1 | 0 | 1 | 0 | 1 | 0 | 0 | 0 | 0 |
| 4 | 0 | 0 | 1 | 0 | 1 | 0 | 0 | 0 | 0 |
| 0 | 4 | 0 | 0 | 1 | 1 | 0 | 0 | 0 | 0 |
| 1 | 3 | 0 | 0 | 1 | 1 | 0 | 0 | 0 | 0 |
| 2 | 2 | 0 | 0 | 1 | 1 | 0 | 0 | 0 | 0 |
| 3 | 1 | 0 | 0 | 1 | 1 | 0 | 0 | 0 | 0 |
| 4 | 0 | 0 | 0 | 1 | 1 | 0 | 0 | 0 | 0 |
| 0 | 4 | 0 | 0 | 0 | 0 | 1 | 0 | 0 | 0 |

Fig. 72C(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 1 | 3 | 0 | 0 | 0 | 0 | 1 | 0 | 0 | 0 |
| 2 | 2 | 0 | 0 | 0 | 0 | 1 | 0 | 0 | 0 |
| 3 | 1 | 0 | 0 | 0 | 0 | 1 | 0 | 0 | 0 |
| 4 | 0 | 0 | 0 | 0 | 0 | 1 | 0 | 0 | 0 |
| 0 | 4 | 1 | 0 | 0 | 0 | 1 | 0 | 0 | 0 |
| 1 | 3 | 1 | 0 | 0 | 0 | 1 | 0 | 0 | 0 |
| 2 | 2 | 1 | 0 | 0 | 0 | 1 | 0 | 0 | 0 |
| 3 | 1 | 1 | 0 | 0 | 0 | 1 | 0 | 0 | 0 |
| 4 | 0 | 1 | 0 | 0 | 0 | 1 | 0 | 0 | 0 |
| 0 | 4 | 0 | 1 | 0 | 0 | 1 | 0 | 0 | 0 |
| 1 | 3 | 0 | 1 | 0 | 0 | 1 | 0 | 0 | 0 |
| 2 | 2 | 0 | 1 | 0 | 0 | 1 | 0 | 0 | 0 |
| 3 | 1 | 0 | 1 | 0 | 0 | 1 | 0 | 0 | 0 |
| 4 | 0 | 0 | 1 | 0 | 0 | 1 | 0 | 0 | 0 |

Fig. 72D(i)

Target Disease Symptoms Lookup Table

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 0 | 4 | 0 | 0 | 1 | 0 | 1 | 0 | 0 | 0 |
| 1 | 3 | 0 | 0 | 1 | 0 | 1 | 0 | 0 | 0 |
| 2 | 2 | 0 | 0 | 1 | 0 | 1 | 0 | 0 | 0 |
| 3 | 1 | 0 | 0 | 1 | 0 | 1 | 0 | 0 | 0 |
| 4 | 0 | 0 | 0 | 1 | 0 | 1 | 0 | 0 | 0 |
| 0 | 4 | 0 | 0 | 0 | 0 | 0 | 1 | 0 | 0 |
| 1 | 3 | 0 | 0 | 0 | 0 | 0 | 1 | 0 | 0 |
| 2 | 2 | 0 | 0 | 0 | 0 | 0 | 1 | 0 | 0 |
| 3 | 1 | 0 | 0 | 0 | 0 | 0 | 1 | 0 | 0 |
| 4 | 0 | 0 | 0 | 0 | 0 | 0 | 1 | 0 | 0 |
| 0 | 4 | 1 | 0 | 0 | 0 | 0 | 1 | 0 | 0 |
| 1 | 3 | 1 | 0 | 0 | 0 | 0 | 1 | 0 | 0 |
| 2 | 2 | 1 | 0 | 0 | 0 | 0 | 1 | 0 | 0 |
| 3 | 1 | 1 | 0 | 0 | 0 | 0 | 1 | 0 | 0 |

Fig. 72E(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 4 | 0 | 1 | 0 | 0 | 0 | 0 | 1 | 0 | 0 |
| 0 | 4 | 0 | 1 | 0 | 0 | 0 | 1 | 0 | 0 |
| 1 | 3 | 0 | 1 | 0 | 0 | 0 | 1 | 0 | 0 |
| 2 | 2 | 0 | 1 | 0 | 0 | 0 | 1 | 0 | 0 |
| 3 | 1 | 0 | 1 | 0 | 0 | 0 | 1 | 0 | 0 |
| 4 | 0 | 0 | 1 | 0 | 0 | 0 | 1 | 0 | 0 |
| 0 | 4 | 0 | 0 | 1 | 0 | 0 | 1 | 0 | 0 |
| 1 | 3 | 0 | 0 | 1 | 0 | 0 | 1 | 0 | 0 |
| 2 | 2 | 0 | 0 | 1 | 0 | 0 | 1 | 0 | 0 |
| 3 | 1 | 0 | 0 | 1 | 0 | 0 | 1 | 0 | 0 |
| 4 | 0 | 0 | 0 | 1 | 0 | 0 | 1 | 0 | 0 |
| 0 | 4 | 0 | 0 | 0 | 0 | 0 | 0 | 1 | 0 |
| 1 | 3 | 0 | 0 | 0 | 0 | 0 | 0 | 1 | 0 |
| 2 | 2 | 0 | 0 | 0 | 0 | 0 | 0 | 1 | 0 |

Fig. 72F(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| | Target Disease Symptoms Lookup Table |
| 3 | 1 | 0 | 0 | 0 | 0 | 0 | 0 | 1 | 0 |
| 4 | 0 | 0 | 0 | 0 | 0 | 0 | 0 | 1 | 0 |
| 0 | 4 | 1 | 0 | 0 | 0 | 0 | 0 | 1 | 0 |
| 1 | 3 | 1 | 0 | 0 | 0 | 0 | 0 | 1 | 0 |
| 2 | 2 | 1 | 0 | 0 | 0 | 0 | 0 | 1 | 0 |
| 3 | 1 | 1 | 0 | 0 | 0 | 0 | 0 | 1 | 0 |
| 4 | 0 | 1 | 0 | 0 | 0 | 0 | 0 | 1 | 0 |
| 0 | 4 | 0 | 1 | 0 | 0 | 0 | 0 | 1 | 0 |
| 1 | 3 | 0 | 1 | 0 | 0 | 0 | 0 | 1 | 0 |
| 2 | 2 | 0 | 1 | 0 | 0 | 0 | 0 | 1 | 0 |
| 3 | 1 | 0 | 1 | 0 | 0 | 0 | 0 | 1 | 0 |
| 4 | 0 | 0 | 1 | 0 | 0 | 0 | 0 | 1 | 0 |
| 0 | 4 | 0 | 0 | 1 | 0 | 0 | 0 | 1 | 0 |
| 1 | 3 | 0 | 0 | 1 | 0 | 0 | 0 | 1 | 0 |

Fig. 72G(i)

Target Disease Symptoms Lookup Table

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 2 | 2 | 0 | 0 | 1 | 0 | 0 | 0 | 1 | 0 |
| 3 | 1 | 0 | 0 | 1 | 0 | 0 | 0 | 1 | 0 |
| 4 | 0 | 0 | 0 | 1 | 0 | 0 | 0 | 1 | 0 |
| 0 | 4 | 0 | 0 | 0 | 0 | 0 | 0 | 0 | 1 |
| 1 | 3 | 0 | 0 | 0 | 0 | 0 | 0 | 0 | 1 |
| 2 | 2 | 0 | 0 | 0 | 0 | 0 | 0 | 0 | 1 |
| 3 | 1 | 0 | 0 | 0 | 0 | 0 | 0 | 0 | 1 |
| 4 | 0 | 0 | 0 | 0 | 0 | 0 | 0 | 0 | 1 |
| 0 | 4 | 1 | 0 | 0 | 0 | 0 | 0 | 0 | 1 |
| 1 | 3 | 1 | 0 | 0 | 0 | 0 | 0 | 0 | 1 |
| 2 | 2 | 1 | 0 | 0 | 0 | 0 | 0 | 0 | 1 |
| 3 | 1 | 1 | 0 | 0 | 0 | 0 | 0 | 0 | 1 |
| 4 | 0 | 1 | 0 | 0 | 0 | 0 | 0 | 0 | 1 |
| 0 | 4 | 0 | 1 | 0 | 0 | 0 | 0 | 0 | 1 |

Fig. 72H(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 1 | 3 | 0 | 1 | 0 | 0 | 0 | 0 | 0 | 1 |
| 2 | 2 | 0 | 1 | 0 | 0 | 0 | 0 | 0 | 1 |
| 3 | 1 | 0 | 1 | 0 | 0 | 0 | 0 | 0 | 1 |
| 4 | 0 | 0 | 1 | 0 | 0 | 0 | 0 | 0 | 1 |
| 0 | 4 | 0 | 0 | 1 | 0 | 0 | 0 | 0 | 1 |
| 1 | 3 | 0 | 0 | 1 | 0 | 0 | 0 | 0 | 1 |
| 2 | 2 | 0 | 0 | 1 | 0 | 0 | 0 | 0 | 1 |
| 3 | 1 | 0 | 0 | 1 | 0 | 0 | 0 | 0 | 1 |
| 4 | 0 | 0 | 0 | 1 | 0 | 0 | 0 | 0 | 1 |
| 0 | 4 | 0 | 0 | 0 | 1 | 0 | 0 | 0 | 1 |
| 1 | 3 | 0 | 0 | 0 | 1 | 0 | 0 | 0 | 1 |
| 2 | 2 | 0 | 0 | 0 | 1 | 0 | 0 | 0 | 1 |
| 3 | 1 | 0 | 0 | 0 | 1 | 0 | 0 | 0 | 1 |
| 4 | 0 | 0 | 0 | 0 | 1 | 0 | 0 | 0 | 1 |

Fig. 72I(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 0 | 4 | 1 | 0 | 0 | 1 | 0 | 0 | 0 | 1 |
| 1 | 3 | 1 | 0 | 0 | 1 | 0 | 0 | 0 | 1 |
| 2 | 2 | 1 | 0 | 0 | 1 | 0 | 0 | 0 | 1 |
| 3 | 1 | 1 | 0 | 0 | 1 | 0 | 0 | 0 | 1 |
| 4 | 0 | 1 | 0 | 0 | 1 | 0 | 0 | 0 | 1 |
| 0 | 4 | 0 | 1 | 0 | 1 | 0 | 0 | 0 | 1 |
| 1 | 3 | 0 | 1 | 0 | 1 | 0 | 0 | 0 | 1 |
| 2 | 2 | 0 | 1 | 0 | 1 | 0 | 0 | 0 | 1 |
| 3 | 1 | 0 | 1 | 0 | 1 | 0 | 0 | 0 | 1 |
| 4 | 0 | 0 | 1 | 0 | 1 | 0 | 0 | 0 | 1 |
| 0 | 4 | 0 | 0 | 1 | 1 | 0 | 0 | 0 | 1 |
| 1 | 3 | 0 | 0 | 1 | 1 | 0 | 0 | 0 | 1 |
| 2 | 2 | 0 | 0 | 1 | 1 | 0 | 0 | 0 | 1 |
| 3 | 1 | 0 | 0 | 1 | 1 | 0 | 0 | 0 | 1 |

Fig. 72J(i)

Target Disease Symptoms Lookup Table

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 4 | 0 | 0 | 0 | 1 | 1 | 0 | 0 | 0 | 1 |
| 0 | 4 | 0 | 0 | 0 | 0 | 1 | 0 | 0 | 1 |
| 1 | 3 | 0 | 0 | 0 | 0 | 1 | 0 | 0 | 1 |
| 2 | 2 | 0 | 0 | 0 | 0 | 1 | 0 | 0 | 1 |
| 3 | 1 | 0 | 0 | 0 | 0 | 1 | 0 | 0 | 1 |
| 4 | 0 | 0 | 0 | 0 | 0 | 1 | 0 | 0 | 1 |
| 0 | 4 | 1 | 0 | 0 | 0 | 1 | 0 | 0 | 1 |
| 1 | 3 | 1 | 0 | 0 | 0 | 1 | 0 | 0 | 1 |
| 2 | 2 | 1 | 0 | 0 | 0 | 1 | 0 | 0 | 1 |
| 3 | 1 | 1 | 0 | 0 | 0 | 1 | 0 | 0 | 1 |
| 4 | 0 | 1 | 0 | 0 | 0 | 1 | 0 | 0 | 1 |
| 0 | 4 | 0 | 1 | 0 | 0 | 1 | 0 | 0 | 1 |
| 1 | 3 | 0 | 1 | 0 | 0 | 1 | 0 | 0 | 1 |
| 2 | 2 | 0 | 1 | 0 | 0 | 1 | 0 | 0 | 1 |

Fig. 72K(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 3 | 1 | 0 | 1 | 0 | 0 | 1 | 0 | 0 | 1 |
| 4 | 0 | 0 | 1 | 0 | 0 | 1 | 0 | 0 | 1 |
| 0 | 4 | 0 | 0 | 1 | 0 | 1 | 0 | 0 | 1 |
| 1 | 3 | 0 | 0 | 1 | 0 | 1 | 0 | 0 | 1 |
| 2 | 2 | 0 | 0 | 1 | 0 | 1 | 0 | 0 | 1 |
| 3 | 1 | 0 | 0 | 1 | 0 | 1 | 0 | 0 | 1 |
| 4 | 0 | 0 | 0 | 1 | 0 | 1 | 0 | 0 | 1 |
| 0 | 4 | 0 | 0 | 0 | 0 | 0 | 1 | 0 | 1 |
| 1 | 3 | 0 | 0 | 0 | 0 | 0 | 1 | 0 | 1 |
| 2 | 2 | 0 | 0 | 0 | 0 | 0 | 1 | 0 | 1 |
| 3 | 1 | 0 | 0 | 0 | 0 | 0 | 1 | 0 | 1 |
| 4 | 0 | 0 | 0 | 0 | 0 | 0 | 1 | 0 | 1 |
| 0 | 4 | 1 | 0 | 0 | 0 | 0 | 1 | 0 | 1 |
| 1 | 3 | 1 | 0 | 0 | 0 | 0 | 1 | 0 | 1 |

Fig. 72L(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 2 | 2 | 1 | 0 | 0 | 0 | 0 | 1 | 0 | 1 |
| 3 | 1 | 1 | 0 | 0 | 0 | 0 | 1 | 0 | 1 |
| 4 | 0 | 1 | 0 | 0 | 0 | 0 | 1 | 0 | 1 |
| 0 | 4 | 0 | 1 | 0 | 0 | 0 | 1 | 0 | 1 |
| 1 | 3 | 0 | 1 | 0 | 0 | 0 | 1 | 0 | 1 |
| 2 | 2 | 0 | 1 | 0 | 0 | 0 | 1 | 0 | 1 |
| 3 | 1 | 0 | 1 | 0 | 0 | 0 | 1 | 0 | 1 |
| 4 | 0 | 0 | 1 | 0 | 0 | 0 | 1 | 0 | 1 |
| 0 | 4 | 0 | 0 | 1 | 0 | 0 | 1 | 0 | 1 |
| 1 | 3 | 0 | 0 | 1 | 0 | 0 | 1 | 0 | 1 |
| 2 | 2 | 0 | 0 | 1 | 0 | 0 | 1 | 0 | 1 |
| 3 | 1 | 0 | 0 | 1 | 0 | 0 | 1 | 0 | 1 |
| 4 | 0 | 0 | 0 | 1 | 0 | 0 | 1 | 0 | 1 |
| 0 | 4 | 0 | 0 | 0 | 0 | 0 | 0 | 1 | 1 |

Fig. 72M(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 1 | 3 | 0 | 0 | 0 | 0 | 0 | 0 | 1 | 1 |
| 2 | 2 | 0 | 0 | 0 | 0 | 0 | 0 | 1 | 1 |
| 3 | 1 | 0 | 0 | 0 | 0 | 0 | 0 | 1 | 1 |
| 4 | 0 | 0 | 0 | 0 | 0 | 0 | 0 | 1 | 1 |
| 0 | 4 | 1 | 0 | 0 | 0 | 0 | 0 | 1 | 1 |
| 1 | 3 | 1 | 0 | 0 | 0 | 0 | 0 | 1 | 1 |
| 2 | 2 | 1 | 0 | 0 | 0 | 0 | 0 | 1 | 1 |
| 3 | 1 | 1 | 0 | 0 | 0 | 0 | 0 | 1 | 1 |
| 4 | 0 | 1 | 0 | 0 | 0 | 0 | 0 | 1 | 1 |
| 0 | 4 | 0 | 1 | 0 | 0 | 0 | 0 | 1 | 1 |
| 1 | 3 | 0 | 1 | 0 | 0 | 0 | 0 | 1 | 1 |
| 2 | 2 | 0 | 1 | 0 | 0 | 0 | 0 | 1 | 1 |
| 3 | 1 | 0 | 1 | 0 | 0 | 0 | 0 | 1 | 1 |
| 4 | 0 | 0 | 1 | 0 | 0 | 0 | 0 | 1 | 1 |

Fig. 72N(i)

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| \multicolumn{10}{c}{Target Disease Symptoms Lookup Table} |
| 0 | 4 | 0 | 0 | 1 | 0 | 0 | 0 | 1 | 1 |
| 1 | 3 | 0 | 0 | 1 | 0 | 0 | 0 | 1 | 1 |
| 2 | 2 | 0 | 0 | 1 | 0 | 0 | 0 | 1 | 1 |
| 3 | 1 | 0 | 0 | 1 | 0 | 0 | 0 | 1 | 1 |
| 4 | 0 | 0 | 0 | 1 | 0 | 0 | 0 | 1 | 1 |
| 0 | 4 | 1 | 0 | 1 | 0 | 0 | 0 | 0 | 0 |
| 1 | 3 | 1 | 0 | 1 | 0 | 0 | 0 | 0 | 0 |
| 2 | 2 | 1 | 0 | 1 | 0 | 0 | 0 | 0 | 0 |
| 3 | 1 | 1 | 0 | 1 | 0 | 0 | 0 | 0 | 0 |
| 4 | 0 | 1 | 0 | 1 | 0 | 0 | 0 | 0 | 0 |
| 0 | 4 | 1 | 1 | 1 | 0 | 0 | 0 | 0 | 0 |
| 1 | 3 | 1 | 1 | 1 | 0 | 0 | 0 | 0 | 0 |
| 2 | 2 | 1 | 1 | 1 | 0 | 0 | 0 | 0 | 0 |
| 3 | 1 | 1 | 1 | 1 | 0 | 0 | 0 | 0 | 0 |

Fig. 72O(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 4 | 0 | 1 | 1 | 1 | 0 | 0 | 0 | 0 | 0 |
| 0 | 4 | 0 | 1 | 1 | 0 | 0 | 0 | 0 | 0 |
| 1 | 3 | 0 | 1 | 1 | 0 | 0 | 0 | 0 | 0 |
| 2 | 2 | 0 | 1 | 1 | 0 | 0 | 0 | 0 | 0 |
| 3 | 1 | 0 | 1 | 1 | 0 | 0 | 0 | 0 | 0 |
| 4 | 0 | 0 | 1 | 1 | 0 | 0 | 0 | 0 | 0 |
| 0 | 4 | 1 | 1 | 0 | 0 | 0 | 0 | 0 | 0 |
| 1 | 3 | 1 | 1 | 0 | 0 | 0 | 0 | 0 | 0 |
| 2 | 2 | 1 | 1 | 0 | 0 | 0 | 0 | 0 | 0 |
| 3 | 1 | 1 | 1 | 0 | 0 | 0 | 0 | 0 | 0 |
| 4 | 0 | 1 | 1 | 0 | 0 | 0 | 0 | 0 | 0 |
| 0 | 4 | 1 | 0 | 1 | 1 | 0 | 0 | 0 | 0 |
| 1 | 3 | 1 | 0 | 1 | 1 | 0 | 0 | 0 | 0 |
| 2 | 2 | 1 | 0 | 1 | 1 | 0 | 0 | 0 | 0 |

Fig. 72P(i)

Target Disease Symptoms Lookup Table

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 3 | 1 | 1 | 0 | 1 | 1 | 0 | 0 | 0 | 0 |
| 4 | 0 | 1 | 0 | 1 | 1 | 0 | 0 | 0 | 0 |
| 0 | 4 | 1 | 1 | 1 | 1 | 0 | 0 | 0 | 0 |
| 1 | 3 | 1 | 1 | 1 | 1 | 0 | 0 | 0 | 0 |
| 2 | 2 | 1 | 1 | 1 | 1 | 0 | 0 | 0 | 0 |
| 3 | 1 | 1 | 1 | 1 | 1 | 0 | 0 | 0 | 0 |
| 4 | 0 | 1 | 1 | 1 | 1 | 0 | 0 | 0 | 0 |
| 0 | 4 | 0 | 1 | 1 | 1 | 0 | 0 | 0 | 0 |
| 1 | 3 | 0 | 1 | 1 | 1 | 0 | 0 | 0 | 0 |
| 2 | 2 | 0 | 1 | 1 | 1 | 0 | 0 | 0 | 0 |
| 3 | 1 | 0 | 1 | 1 | 1 | 0 | 0 | 0 | 0 |
| 4 | 0 | 0 | 1 | 1 | 1 | 0 | 0 | 0 | 0 |
| 0 | 4 | 1 | 1 | 0 | 1 | 0 | 0 | 0 | 0 |
| 1 | 3 | 1 | 1 | 0 | 1 | 0 | 0 | 0 | 0 |

Fig. 72Q(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 2 | 2 | 1 | 1 | 0 | 1 | 0 | 0 | 0 | 0 |
| 3 | 1 | 1 | 1 | 0 | 1 | 0 | 0 | 0 | 0 |
| 4 | 0 | 1 | 1 | 0 | 1 | 0 | 0 | 0 | 0 |
| 0 | 4 | 1 | 0 | 1 | 0 | 1 | 0 | 0 | 0 |
| 1 | 3 | 1 | 0 | 1 | 0 | 1 | 0 | 0 | 0 |
| 2 | 2 | 1 | 0 | 1 | 0 | 1 | 0 | 0 | 0 |
| 3 | 1 | 1 | 0 | 1 | 0 | 1 | 0 | 0 | 0 |
| 4 | 0 | 1 | 0 | 1 | 0 | 1 | 0 | 0 | 0 |
| 0 | 4 | 1 | 1 | 1 | 0 | 1 | 0 | 0 | 0 |
| 1 | 3 | 1 | 1 | 1 | 0 | 1 | 0 | 0 | 0 |
| 2 | 2 | 1 | 1 | 1 | 0 | 1 | 0 | 0 | 0 |
| 3 | 1 | 1 | 1 | 1 | 0 | 1 | 0 | 0 | 0 |
| 4 | 0 | 1 | 1 | 1 | 0 | 1 | 0 | 0 | 0 |
| 0 | 4 | 0 | 1 | 1 | 0 | 1 | 0 | 0 | 0 |

Fig. 72R(i)

Target Disease Symptoms Lookup Table

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 1 | 3 | 0 | 1 | 1 | 0 | 1 | 0 | 0 | 0 |
| 2 | 2 | 0 | 1 | 1 | 0 | 1 | 0 | 0 | 0 |
| 3 | 1 | 0 | 1 | 1 | 0 | 1 | 0 | 0 | 0 |
| 4 | 0 | 0 | 1 | 1 | 0 | 1 | 0 | 0 | 0 |
| 0 | 4 | 1 | 1 | 0 | 0 | 1 | 0 | 0 | 0 |
| 1 | 3 | 1 | 1 | 0 | 0 | 1 | 0 | 0 | 0 |
| 2 | 2 | 1 | 1 | 0 | 0 | 1 | 0 | 0 | 0 |
| 3 | 1 | 1 | 1 | 0 | 0 | 1 | 0 | 0 | 0 |
| 4 | 0 | 1 | 1 | 0 | 0 | 1 | 0 | 0 | 0 |
| 0 | 4 | 1 | 0 | 1 | 0 | 0 | 1 | 0 | 0 |
| 1 | 3 | 1 | 0 | 1 | 0 | 0 | 1 | 0 | 0 |
| 2 | 2 | 1 | 0 | 1 | 0 | 0 | 1 | 0 | 0 |
| 3 | 1 | 1 | 0 | 1 | 0 | 0 | 1 | 0 | 0 |
| 4 | 0 | 1 | 0 | 1 | 0 | 0 | 1 | 0 | 0 |

Fig. 72S(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 0 | 4 | 1 | 1 | 1 | 0 | 0 | 1 | 0 | 0 |
| 1 | 3 | 1 | 1 | 1 | 0 | 0 | 1 | 0 | 0 |
| 2 | 2 | 1 | 1 | 1 | 0 | 0 | 1 | 0 | 0 |
| 3 | 1 | 1 | 1 | 1 | 0 | 0 | 1 | 0 | 0 |
| 4 | 0 | 1 | 1 | 1 | 0 | 0 | 1 | 0 | 0 |
| 0 | 4 | 0 | 1 | 1 | 0 | 0 | 1 | 0 | 0 |
| 1 | 3 | 0 | 1 | 1 | 0 | 0 | 1 | 0 | 0 |
| 2 | 2 | 0 | 1 | 1 | 0 | 0 | 1 | 0 | 0 |
| 3 | 1 | 0 | 1 | 1 | 0 | 0 | 1 | 0 | 0 |
| 4 | 0 | 0 | 1 | 1 | 0 | 0 | 1 | 0 | 0 |
| 0 | 4 | 1 | 1 | 0 | 0 | 0 | 1 | 0 | 0 |
| 1 | 3 | 1 | 1 | 0 | 0 | 0 | 1 | 0 | 0 |
| 2 | 2 | 1 | 1 | 0 | 0 | 0 | 1 | 0 | 0 |
| 3 | 1 | 1 | 1 | 0 | 0 | 0 | 1 | 0 | 0 |

Fig. 72T(i)

Target Disease Symptoms Lookup Table

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 4 | 0 | 1 | 1 | 0 | 0 | 0 | 1 | 0 | 0 |
| 0 | 4 | 1 | 0 | 1 | 0 | 0 | 0 | 1 | 0 |
| 1 | 3 | 1 | 0 | 1 | 0 | 0 | 0 | 1 | 0 |
| 2 | 2 | 1 | 0 | 1 | 0 | 0 | 0 | 1 | 0 |
| 3 | 1 | 1 | 0 | 1 | 0 | 0 | 0 | 1 | 0 |
| 4 | 0 | 1 | 0 | 1 | 0 | 0 | 0 | 1 | 0 |
| 0 | 4 | 1 | 1 | 1 | 0 | 0 | 0 | 1 | 0 |
| 1 | 3 | 1 | 1 | 1 | 0 | 0 | 0 | 1 | 0 |
| 2 | 2 | 1 | 1 | 1 | 0 | 0 | 0 | 1 | 0 |
| 3 | 1 | 1 | 1 | 1 | 0 | 0 | 0 | 1 | 0 |
| 4 | 0 | 1 | 1 | 1 | 0 | 0 | 0 | 1 | 0 |
| 0 | 4 | 0 | 1 | 1 | 0 | 0 | 0 | 1 | 0 |
| 1 | 3 | 0 | 1 | 1 | 0 | 0 | 0 | 1 | 0 |
| 2 | 2 | 0 | 1 | 1 | 0 | 0 | 0 | 1 | 0 |

Fig. 72U(i)

Target Disease Symptoms Lookup Table

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 3 | 1 | 0 | 1 | 1 | 0 | 0 | 0 | 1 | 0 |
| 4 | 0 | 0 | 1 | 1 | 0 | 0 | 0 | 1 | 0 |
| 0 | 4 | 1 | 1 | 0 | 0 | 0 | 0 | 1 | 0 |
| 1 | 3 | 1 | 1 | 0 | 0 | 0 | 0 | 1 | 0 |
| 2 | 2 | 1 | 1 | 0 | 0 | 0 | 0 | 1 | 0 |
| 3 | 1 | 1 | 1 | 0 | 0 | 0 | 0 | 1 | 0 |
| 4 | 0 | 1 | 1 | 0 | 0 | 0 | 0 | 1 | 0 |
| 0 | 4 | 1 | 0 | 1 | 0 | 0 | 0 | 0 | 1 |
| 1 | 3 | 1 | 0 | 1 | 0 | 0 | 0 | 0 | 1 |
| 2 | 2 | 1 | 0 | 1 | 0 | 0 | 0 | 0 | 1 |
| 3 | 1 | 1 | 0 | 1 | 0 | 0 | 0 | 0 | 1 |
| 4 | 0 | 1 | 0 | 1 | 0 | 0 | 0 | 0 | 1 |
| 0 | 4 | 1 | 1 | 1 | 0 | 0 | 0 | 0 | 1 |
| 1 | 3 | 1 | 1 | 1 | 0 | 0 | 0 | 0 | 1 |

Fig. 72V(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 2 | 2 | 1 | 1 | 1 | 0 | 0 | 0 | 0 | 1 |
| 3 | 1 | 1 | 1 | 1 | 0 | 0 | 0 | 0 | 1 |
| 4 | 0 | 1 | 1 | 1 | 0 | 0 | 0 | 0 | 1 |
| 0 | 4 | 0 | 1 | 1 | 0 | 0 | 0 | 0 | 1 |
| 1 | 3 | 0 | 1 | 1 | 0 | 0 | 0 | 0 | 1 |
| 2 | 2 | 0 | 1 | 1 | 0 | 0 | 0 | 0 | 1 |
| 3 | 1 | 0 | 1 | 1 | 0 | 0 | 0 | 0 | 1 |
| 4 | 0 | 0 | 1 | 1 | 0 | 0 | 0 | 0 | 1 |
| 0 | 4 | 1 | 1 | 0 | 0 | 0 | 0 | 0 | 1 |
| 1 | 3 | 1 | 1 | 0 | 0 | 0 | 0 | 0 | 1 |
| 2 | 2 | 1 | 1 | 0 | 0 | 0 | 0 | 0 | 1 |
| 3 | 1 | 1 | 1 | 0 | 0 | 0 | 0 | 0 | 1 |
| 4 | 0 | 1 | 1 | 0 | 0 | 0 | 0 | 0 | 1 |
| 0 | 4 | 1 | 0 | 1 | 1 | 0 | 0 | 0 | 1 |

Fig. 72W(i)

Target Disease Symptoms Lookup Table

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 1 | 3 | 1 | 0 | 1 | 1 | 0 | 0 | 0 | 1 |
| 2 | 2 | 1 | 0 | 1 | 1 | 0 | 0 | 0 | 1 |
| 3 | 1 | 1 | 0 | 1 | 1 | 0 | 0 | 0 | 1 |
| 4 | 0 | 1 | 0 | 1 | 1 | 0 | 0 | 0 | 1 |
| 0 | 4 | 1 | 1 | 1 | 1 | 0 | 0 | 0 | 1 |
| 1 | 3 | 1 | 1 | 1 | 1 | 0 | 0 | 0 | 1 |
| 2 | 2 | 1 | 1 | 1 | 1 | 0 | 0 | 0 | 1 |
| 3 | 1 | 1 | 1 | 1 | 1 | 0 | 0 | 0 | 1 |
| 4 | 0 | 1 | 1 | 1 | 1 | 0 | 0 | 0 | 1 |
| 0 | 4 | 0 | 1 | 1 | 1 | 0 | 0 | 0 | 1 |
| 1 | 3 | 0 | 1 | 1 | 1 | 0 | 0 | 0 | 1 |
| 2 | 2 | 0 | 1 | 1 | 1 | 0 | 0 | 0 | 1 |
| 3 | 1 | 0 | 1 | 1 | 1 | 0 | 0 | 0 | 1 |
| 4 | 0 | 0 | 1 | 1 | 1 | 0 | 0 | 0 | 1 |

Fig. 72X(i)

Target Disease Symptoms Lookup Table

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 0 | 4 | 1 | 1 | 0 | 1 | 0 | 0 | 0 | 1 |
| 1 | 3 | 1 | 1 | 0 | 1 | 0 | 0 | 0 | 1 |
| 2 | 2 | 1 | 1 | 0 | 1 | 0 | 0 | 0 | 1 |
| 3 | 1 | 1 | 1 | 0 | 1 | 0 | 0 | 0 | 1 |
| 4 | 0 | 1 | 1 | 0 | 1 | 0 | 0 | 0 | 1 |
| 0 | 4 | 1 | 0 | 1 | 0 | 1 | 0 | 0 | 1 |
| 1 | 3 | 1 | 0 | 1 | 0 | 1 | 0 | 0 | 1 |
| 2 | 2 | 1 | 0 | 1 | 0 | 1 | 0 | 0 | 1 |
| 3 | 1 | 1 | 0 | 1 | 0 | 1 | 0 | 0 | 1 |
| 4 | 0 | 1 | 0 | 1 | 0 | 1 | 0 | 0 | 1 |
| 0 | 4 | 1 | 1 | 1 | 0 | 1 | 0 | 0 | 1 |
| 1 | 3 | 1 | 1 | 1 | 0 | 1 | 0 | 0 | 1 |
| 2 | 2 | 1 | 1 | 1 | 0 | 1 | 0 | 0 | 1 |
| 3 | 1 | 1 | 1 | 1 | 0 | 1 | 0 | 0 | 1 |

Fig. 72Y(i)

Target Disease Symptoms Lookup Table

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 4 | 0 | 1 | 1 | 1 | 0 | 1 | 0 | 0 | 1 |
| 0 | 4 | 0 | 1 | 1 | 0 | 1 | 0 | 0 | 1 |
| 1 | 3 | 0 | 1 | 1 | 0 | 1 | 0 | 0 | 1 |
| 2 | 2 | 0 | 1 | 1 | 0 | 1 | 0 | 0 | 1 |
| 3 | 1 | 0 | 1 | 1 | 0 | 1 | 0 | 0 | 1 |
| 4 | 0 | 0 | 1 | 1 | 0 | 1 | 0 | 0 | 1 |
| 0 | 4 | 1 | 1 | 0 | 0 | 1 | 0 | 0 | 1 |
| 1 | 3 | 1 | 1 | 0 | 0 | 1 | 0 | 0 | 1 |
| 2 | 2 | 1 | 1 | 0 | 0 | 1 | 0 | 0 | 1 |
| 3 | 1 | 1 | 1 | 0 | 0 | 1 | 0 | 0 | 1 |
| 4 | 0 | 1 | 1 | 0 | 0 | 1 | 0 | 0 | 1 |
| 0 | 4 | 1 | 0 | 1 | 0 | 0 | 1 | 0 | 1 |
| 1 | 3 | 1 | 0 | 1 | 0 | 0 | 1 | 0 | 1 |
| 2 | 2 | 1 | 0 | 1 | 0 | 0 | 1 | 0 | 1 |

Fig. 72Z(i)

Target Disease Symptoms Lookup Table

| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
|---|---|---|---|---|---|---|---|---|---|
| 3 | 1 | 1 | 0 | 1 | 0 | 0 | 1 | 0 | 1 |
| 4 | 0 | 1 | 0 | 1 | 0 | 0 | 1 | 0 | 1 |
| 0 | 4 | 1 | 1 | 1 | 0 | 0 | 1 | 0 | 1 |
| 1 | 3 | 1 | 1 | 1 | 0 | 0 | 1 | 0 | 1 |
| 2 | 2 | 1 | 1 | 1 | 0 | 0 | 1 | 0 | 1 |
| 3 | 1 | 1 | 1 | 1 | 0 | 0 | 1 | 0 | 1 |
| 4 | 0 | 1 | 1 | 1 | 0 | 0 | 1 | 0 | 1 |
| 0 | 4 | 0 | 1 | 1 | 0 | 0 | 1 | 0 | 1 |
| 1 | 3 | 0 | 1 | 1 | 0 | 0 | 1 | 0 | 1 |
| 2 | 2 | 0 | 1 | 1 | 0 | 0 | 1 | 0 | 1 |
| 3 | 1 | 0 | 1 | 1 | 0 | 0 | 1 | 0 | 1 |
| 4 | 0 | 0 | 1 | 1 | 0 | 0 | 1 | 0 | 1 |
| 0 | 4 | 1 | 1 | 0 | 0 | 0 | 1 | 0 | 1 |
| 1 | 3 | 1 | 1 | 0 | 0 | 0 | 1 | 0 | 1 |

Fig. 72AA(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 2 | 2 | 1 | 1 | 0 | 0 | 0 | 1 | 0 | 1 |
| 3 | 1 | 1 | 1 | 0 | 0 | 0 | 1 | 0 | 1 |
| 4 | 0 | 1 | 1 | 0 | 0 | 0 | 1 | 0 | 1 |
| 0 | 4 | 1 | 0 | 1 | 0 | 0 | 0 | 1 | 1 |
| 1 | 3 | 1 | 0 | 1 | 0 | 0 | 0 | 1 | 1 |
| 2 | 2 | 1 | 0 | 1 | 0 | 0 | 0 | 1 | 1 |
| 3 | 1 | 1 | 0 | 1 | 0 | 0 | 0 | 1 | 1 |
| 4 | 0 | 1 | 0 | 1 | 0 | 0 | 0 | 1 | 1 |
| 0 | 4 | 1 | 1 | 1 | 0 | 0 | 0 | 1 | 1 |
| 1 | 3 | 1 | 1 | 1 | 0 | 0 | 0 | 1 | 1 |
| 2 | 2 | 1 | 1 | 1 | 0 | 0 | 0 | 1 | 1 |
| 3 | 1 | 1 | 1 | 1 | 0 | 0 | 0 | 1 | 1 |
| 4 | 0 | 1 | 1 | 1 | 0 | 0 | 0 | 1 | 1 |
| 0 | 4 | 0 | 1 | 1 | 0 | 0 | 0 | 1 | 1 |

Fig. 72AB(i)

| Target Disease Symptoms Lookup Table | | | | | | | | | |
|---|---|---|---|---|---|---|---|---|---|
| Red Circles Quantity (Anosmia Symptoms) | Green Circles Quantity | Circle Quantity (Cough Symptom) | Circle Quantity (Fatigue Symptom) | Circle Quantity (Appetite Loss Symptom) | Circle Quantity (Age Range 20 - 39) | Circle Quantity (Age Range 40 - 59) | Circle Quantity (Age Range 60 - 79) | Circle Quantity (Age Range 80+) | Male Gender (Circle Quantity) |
| 1 | 3 | 0 | 1 | 1 | 0 | 0 | 0 | 1 | 1 |
| 2 | 2 | 0 | 1 | 1 | 0 | 0 | 0 | 1 | 1 |
| 3 | 1 | 0 | 1 | 1 | 0 | 0 | 0 | 1 | 1 |
| 4 | 0 | 0 | 1 | 1 | 0 | 0 | 0 | 1 | 1 |
| 0 | 4 | 1 | 1 | 0 | 0 | 0 | 0 | 1 | 1 |
| 1 | 3 | 1 | 1 | 0 | 0 | 0 | 0 | 1 | 1 |
| 2 | 2 | 1 | 1 | 0 | 0 | 0 | 0 | 1 | 1 |
| 3 | 1 | 1 | 1 | 0 | 0 | 0 | 0 | 1 | 1 |
| 4 | 0 | 1 | 1 | 0 | 0 | 0 | 0 | 1 | 1 |

Fig. 72AC(i)

| Target Disease Symptoms Lookup Table |||||
|---|---|---|---|---|
| Output Message |||||
| Retake smell test due to error. | none | | | |
| Retake smell test due to error. | none | | | |
| Retake smell test due to error. | none | | | |
| Retake smell test due to error. | none | | | |
| Retake smell test due to error. | none | | | |
| Retake smell test due to error. | none | | | |
| Retake smell test due to error. | none | | | |
| Retake smell test due to error. | none | | | |
| Retake smell test due to error. | none | | | |
| Retake smell test due to error. | none | | | "Recommendations: Maintain social distancing of 6 feet & wear mask when others are present, wash hands frequently.","Recommendations: As soon as possible, self-isolate, contact physician for advice, and take molecular or antigen test, if available. Refer to www.cdc.org for more information."),"") |
| 0 signs of anosmia, which is very common symptom in COVID-19. Other target symptoms: | none | | | Recommendations: Maintain social distancing of 6 feet & wear mask when others are present, wash hands frequently. |
| 1 sign of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | fatigue | | | Recommendations: As soon as possible, self-isolate, contact physician for advice, and take molecular or antigen test, if available. Refer to www.cdc.org for more information. |

Fig. 72A(ii)

| Target Disease Symptoms Lookup Table ||||||
|---|---|---|---|---|---|
| Output Message ||||||
| 1 sign of anosmia, which is very common | | fatigue | | | Recommendations: As soon as possible, self- |
| 2 signs of anosmia, which is very common symptom in COVID-19. Other target symptoms: | | fatigue | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | | appetite loss | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | appetite loss | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | | appetite loss | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | appetite loss | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | | appetite loss | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | | | Recommendations: Maintain social distancing of 6 feet & wear mask when others are present, wash hands frequently. |
| 1 sign of anosmia, which is very common symptom in COVID-19. Other target symptoms: | none | | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | | | Recommendations: As soon as possible, self-isolate, contact physician for advice, and take molecular or antigen test, if available. Refer to www.cdc.org for more information. |

Fig. 72B(ii)

| Target Disease Symptoms Lookup Table |||||
|---|---|---|---|---|
| Output Message |||||
| 1 sign of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | | appetite loss | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | appetite loss | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | | appetite loss | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | appetite loss | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | | appetite loss | table |
| 0 signs of anosmia, which is very common symptom in COVID-19. Other target symptoms: | none | | | Recommendations: Maintain social distancing of 6 feet & wear mask when others are present, wash hands frequently. |

Fig. 72C(ii)

| Target Disease Symptoms Lookup Table |||||
|---|---|---|---|---|
| Output Message |||||
| 1 sign of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | Recommendations: As soon as possible, self-isolate, contact physician for advice, and take molecular or antigen test, if available. Refer to www.cdc.org for more information. |

Fig. 72D(ii)

| Target Disease Symptoms Lookup Table | | | | |
|---|---|---|---|---|
| Output Message | | | | |
| 0 signs of anosmia, which is very common symptom in COVID-19. Other target symptoms: | | appetite loss | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | appetite loss | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | appetite loss | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | appetite loss | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | appetite loss | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | Based on your age &. gender, if you have COVID-19 your risk for serious symptoms that may require hospitalization is above average. | Recommendations: Maintain social distancing of 6 feet & wear mask when others are present, wash hands frequently. |
| 1 sign of anosmia, which is very common symptom in COVID-19. Other target symptoms: | none | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72E(ii)

| Target Disease Symptoms Lookup Table ||||||
|---|---|---|---|---|---|
| Output Message ||||||
| 4 signs of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | | Based on your age &. gender, if you have COVID-19 your risk for serious symptoms that may require hospitalization is above average. | Recommendations: Maintain social distancing of 6 feet & wear mask when others are present, wash hands frequently. |
| 1 sign of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72F(ii)

| Target Disease Symptoms Lookup Table ||||||
|---|---|---|---|---|---|
| Output Message ||||||
| 3 signs of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | cough | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | | fatigue | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | fatigue | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | | fatigue | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | fatigue | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | | fatigue | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72G(ii)

| Target Disease Symptoms Lookup Table ||||||
|---|---|---|---|---|---|
| Output Message ||||||
| 2 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | | Based on your age &. gender, if you have COVID-19 your risk for serious symptoms that may require hospitalization is above average. | Recommendations: Maintain social distancing of 6 feet & wear mask when others are present, wash hands frequently. |
| 1 sign of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72H(ii)

| Target Disease Symptoms Lookup Table ||||||
|---|---|---|---|---|---|
| Output Message ||||||
| 1 sign of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | | Based on your age &. gender, if you have COVID-19 your risk for serious symptoms that may require hospitalization is above average. | Recommendations: Maintain social distancing of 6 feet & wear mask when others are present, wash hands frequently. |
| 1 sign of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72I(ii)

| Target Disease Symptoms Lookup Table | | | | | |
|---|---|---|---|---|---|
| Output Message | | | | | |
| 0 signs of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72J(ii)

| Target Disease Symptoms Lookup Table | | | | | |
|---|---|---|---|---|---|
| Output Message | | | | | |
| 4 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | | Based on your age &. gender, if you have COVID-19 your risk for serious symptoms that may require hospitalization is above average. | Recommendations: Maintain social distancing of 6 feet & wear mask when others are present, wash hands frequently. |
| 1 sign of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72K(ii)

| Target Disease Symptoms Lookup Table ||||||
|---|---|---|---|---|---|
| Output Message ||||||
| 3 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | | Based on your age &. gender, if you have COVID-19 your risk for serious symptoms that may require hospitalization is significantly above average. | Recommendations: Maintain social distancing of 6 feet & wear mask when others are present, wash hands frequently. |
| 1 sign of anosmia, which is very common symptom in COVID-19. Other target symptoms: | none | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |

Fig. 72L(ii)

| Target Disease Symptoms Lookup Table ||||||
|---|---|---|---|---|---|
| Output Message ||||||
| 2 signs of anosmia, which is very common symptom in COVID-19. Other target symptoms: | cough | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | none | | | Based on your age &. gender, if you have COVID-19 your risk for serious symptoms that may require hospitalization is significantly above average. | Recommendations: Maintain social distancing of 6 feet & wear mask when others are present, wash hands frequently. |

Fig. 72M(ii)

| Target Disease Symptoms Lookup Table ||||||
|---|---|---|---|---|---|
| Output Message ||||||
| 1 sign of anosmia, which is very common symptom in COVID-19. Other target symptoms: | none | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | none | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | none | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | none | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |

Fig. 72N(ii)

| Target Disease Symptoms Lookup Table | | | | | |
|---|---|---|---|---|---|
| Output Message | | | | | |
| 0 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | | Recommendations: As soon as possible, self-isolate, contact physician for advice, and take molecular or antigen test, if available. Refer to www.cdc.org for more information. |

Fig. 72O(ii)

| Target Disease Symptoms Lookup Table | | | | | |
|---|---|---|---|---|---|
| Output Message | | | | | |
| 4 signs of anosmia, which is very common symptom in COVID-19. Other target symptoms: | cough | fatigue | appetite loss | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |

Fig. 72P(ii)

| Target Disease Symptoms Lookup Table |||||
|---|---|---|---|---|
| Output Message |||||
| 3 signs of anosmia, which is very common symptom in COVID-19. Other target symptoms: | cough | | appetite loss | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | appetite loss | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | appetite loss | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | Recommendations: As soon as possible, self-isolate, contact physician for advice, and take molecular or antigen test, if available. Refer to www.cdc.org for more information. |

Fig. 72Q(ii)

| Target Disease Symptoms Lookup Table ||||||
|---|---|---|---|---|---|
| Output Message ||||||
| 2 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |

Fig. 72R(ii)

| Target Disease Symptoms Lookup Table ||||||
|---|---|---|---|---|---|
| Output Message ||||||
| 1 sign of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72S(ii)

| Target Disease Symptoms Lookup Table |||||
|---|---|---|---|---|
| Output Message |||||
| 0 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: |  | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: |  | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: |  | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: |  | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: |  | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue |  | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue |  | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue |  | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue |  | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72T(ii)

| Target Disease Symptoms Lookup Table ||||||
|---|---|---|---|---|---|
| Output Message ||||||
| 4 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72U(ii)

| Target Disease Symptoms Lookup Table ||||||
|---|---|---|---|---|---|
| Output Message ||||||
| 3 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72V(ii)

| Target Disease Symptoms Lookup Table ||||||
|---|---|---|---|---|---|
| Output Message ||||||
| 2 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72W(ii)

| Target Disease Symptoms Lookup Table |||||
|---|---|---|---|---|
| Output Message |||||
| 1 sign of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72X(ii)

| Target Disease Symptoms Lookup Table ||||||
|---|---|---|---|---|---|
| Output Message ||||||
| 0 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |

Fig. 72Y(ii)

| Target Disease Symptoms Lookup Table ||||||
|---|---|---|---|---|---|
| Output Message ||||||
| 4 signs of anosmia, which is very common symptom in COVID-19. Other target symptoms: | cough | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | Based on your age &. gender, if you have COVID-19 your risk for serious symptoms that may require hospitalization is above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |

Fig. 72Z(ii)

| Target Disease Symptoms Lookup Table |||||
|---|---|---|---|---|
| Output Message |||||
| 3 signs of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |

Fig. 72AA(ii)

| Target Disease Symptoms Lookup Table ||||||
|---|---|---|---|---|---|
| Output Message ||||||
| 2 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |

Fig. 72AB(ii)

| Target Disease Symptoms Lookup Table | | | | | |
|---|---|---|---|---|---|
| Output Message | | | | | |
| 1 sign of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | | fatigue | appetite loss | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 0 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 1 sign of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 2 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 3 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |
| 4 signs of anosmia, which is very common symptom in COVID-19. Other target symptoms: | cough | fatigue | | Based on your age &. gender, if you have COVID-19 your risk for serious symptoms that may require hospitalization is significantly above average. | Recommendations: As soon as possible, self-isolate, contact physician for advice, and take molecular or antigen test, if available. Refer to www.cdc.org for more information. |

Fig. 72AC(ii)

R = Red, G = Green, B = Black, Y = Yellow, O = Orange

FIG. 76

SYSTEM AND METHOD FOR DETECTING PRESENCE OF ILLNESS SYMPTOMS

CROSS-REFERENCE TO RELATED APPLICATION(S)

Claim of Priority

This application is a continuation-in-part of U.S. patent application Ser. No. 17/167,451, filed 2 Feb. 2021, now U.S. Pat. No. 11,393,594, which claims the benefit of priority to U.S. Provisional Application Nos. 63/102,344, filed 10 Jun. 2020, 63/045,798, filed 29 Jun. 2020, 63/054,731, filed 21 Jul. 2020 and 63/065,243, filed 13 Aug. 2020, the complete contents of each of which is hereby incorporated herein by reference.

BACKGROUND

Technical Field

The present device pertains to the field of medical diagnostic testing devices and more specifically to testing devices and methods for the COVID-19 disease, dementia, and other diseases with similar symptoms.

Background

Certain illnesses, such as COVID-19, manifest with a variety of different symptoms which include loss of sense of smell as well as fever. Researchers at Kings College London found that approximately 60% of patients with COVID-19 disease lost sense of smell (anosmia). In a separate study published April 2020 in journal International Forum of Allergy & Rhinology, researchers at University of California, San Diego Health noted that 68% of COVID-19 patients experienced smell loss. According to Claire Hopkins, the president of the British Rhinological Society, anosmia can be the strongest symptom to predict COVID-19 infection and approximately 50% of patients with COVID-19 disease experience anosmia as their first or second symptom. In a study published in April 2020, Andrew Badley, leader of a virus lab at Mayo Clinic, and his colleagues found that people with COVID-19 were 27 times more likely to have lost their sense of smell when compared with non-COVID-19 patients.

In the April 2020 edition of journal Investigative Otolaryngology, Dr. Sedaghat concluded "The occurrence of sudden onset anosmia without nasal obstruction is highly predictive of COVID-19 and should trigger the individual to immediately self-quarantine . . . ," based on meta-analysis of 19 previously conducted studies. Based on an early report in the March 2020 journal Eurosurveillance that 18% of patients who tested positive for COVID-19 were asymptomatic, approximately 50% of all people with COVID-19 disease can develop anosmia. In addition, the 2/28/2020 New England Journal of Medicine article "Clinical Characteristics of Coronavirus Disease 2019 in China" reported that 89% of COVID-19 patients eventually developed fever. These symptoms provide significant indications that a person can have acquired such an illness.

Additionally, analysis of records by the US Centers for Disease Control and Prevention found that most hospitalized patients seemed to share at least one of three symptoms. The analysis, published Jul. 16, 2020 in the CDC's Morbidity and Mortality Weekly Report, covered 164 people with lab confirmed cases of Covid-19. The patients all had symptoms. Among these patients, nearly all—96%—had had either a fever, cough, or shortness of breath and about 45% experienced all three. Researchers also found that a higher percentage of people who did not have to go to the hospital lost their sense of smell or taste.

Researchers from King's College London leading The COVID Symptom Study reported online Jul. 16, 2020 that skin rash is also a key symptom of COVID-19. 17% of respondents in this study who tested positive for COVID-19 reported a rash as their first symptom of the disease. The rashes associated with COVID-19 fall into three categories: hive-type rash (urticaria), prickly heat or chickenpox-type rash (erythemato-papular or erythemato-vesicular rash) and red or purple bumps on fingers or toes (chilblains)

In addition to patients with COVID-19, patients with dementia sometimes experience anosmia as well. Researchers have discovered numerous early warning signs of dementia: Anosmia can be an early warning sign of Alzheimer's disease. According to a 2018 study in Biosensors, having trouble with a sense of smell is one of the earliest preclinical symptoms of Alzheimer's. Other research in the Journal of Alzheimer's Disease has found that the brains of people with olfactory dysfunction often have the same harmful changes as those seen in Alzheimer's patients.

Breaking the law, particularly in people who suddenly begin stealing, trespassing, or driving recklessly, can be an early sign of dementia, such as FTD (frontotemporal dementia). A 2015 study in JAMA Neurology found that in 14% of people with FTD, breaking laws was the first sign of dementia. Eating unusual things can be an early warning sign of dementia, according to a 2015 Japanese study in Plos One. Some people with dementia will eat food that is rancid or spoiled or may eat non-food objects. Falling more frequently can be an early warning sign of Alzheimer's disease. A 2013 brain imaging study in the journal Neurology that involved older adults found that those who fell most frequently were more likely to have the early onset of Alzheimer's disease. According to the study, falls as well as changes in gait may precede any cognitive symptoms of Alzheimer's.

Gum disease can be another early warning sign of Alzheimer's disease. A growing body of research, including a study in the Journal of Periodontology, has shown that periodontal (gum) disease is a risk factor for dementia. Gum disease is associated with inflammation, which has been linked with increased risk of Alzheimer's. Inability to recognize sarcasm can be caused by dementia, according to 2009 brain imaging research from the University of California, San Francisco. This study shows that the ability to discern sarcasm and other ironic speech in face-to-face encounters is diminished in people with Alzheimer's or FTD. Compulsive behaviors are another sign of early dementia in some people. Research from UCLA that looked at patients with FTD or Alzheimer's disease found that 38% of those with FTD and 10% of those with Alzheimer's exhibited compulsive behaviors. More recent findings in The Journal of Neuropsychiatry suggest that in people with early FTD, these behaviors are more likely impulse-driven due to harmful changes in the frontotemporal lobes. Depression doubles the risk of cognitive impairment in women and quadruples it in men. Research in the Archives of General Psychiatry evaluated 5,781 elderly women with tests of mood and memory. Women with 3-5 depressive symptoms were at 60% greater odds for cognitive deterioration, and women with 6 or more depressive symptoms were 230% more likely to have problems. The researchers concluded that depression in older women is associated with both poor cognitive function and subsequent cognitive decline.

Research in the International Journal of Geriatric Psychiatry shows that late-life depression can be a precursor to Alzheimer's disease.

Other untreated mental disorders significantly increase the risk of memory problems. Research shows increased dementia risk with bipolar disorder (JAMDA, 2015), schizophrenia (Neuropsychiatric Disease and Treatment, 2018), posttraumatic stress disorder (Current Psychiatry Reports, 2017), chronic stress (BMJ Open, 2013), and ADD/ADHD (Journal of Attention Disorders, 2019). The study in the Journal of Attention Disorders showed that adults with ADHD are over 3 times more likely to develop dementia compared with adults who do not have ADHD.

What is needed is a simple and efficient system and method of using test hardware for detecting several key symptoms of COVID-19, dementia, and other illnesses that can detect applicable symptoms and provide fast results.

BRIEF DESCRIPTION OF DRAWINGS

FIG. 1 depicts a top planar view of one embodiment of the present device.

FIG. 2 depicts a side cross-sectional view of a lid component of an embodiment of the device shown in FIG. 1.

FIGS. 70*a*-70*b* depict flow charts of embodiments of methods using the present system.

FIGS. 72Ai-72ACii depict an embodiment of a symptom lookup table in the present system.

FIG. 76 depicts a symptoms chart in an embodiment of the present device.

DETAILED DESCRIPTION

Figure 3:
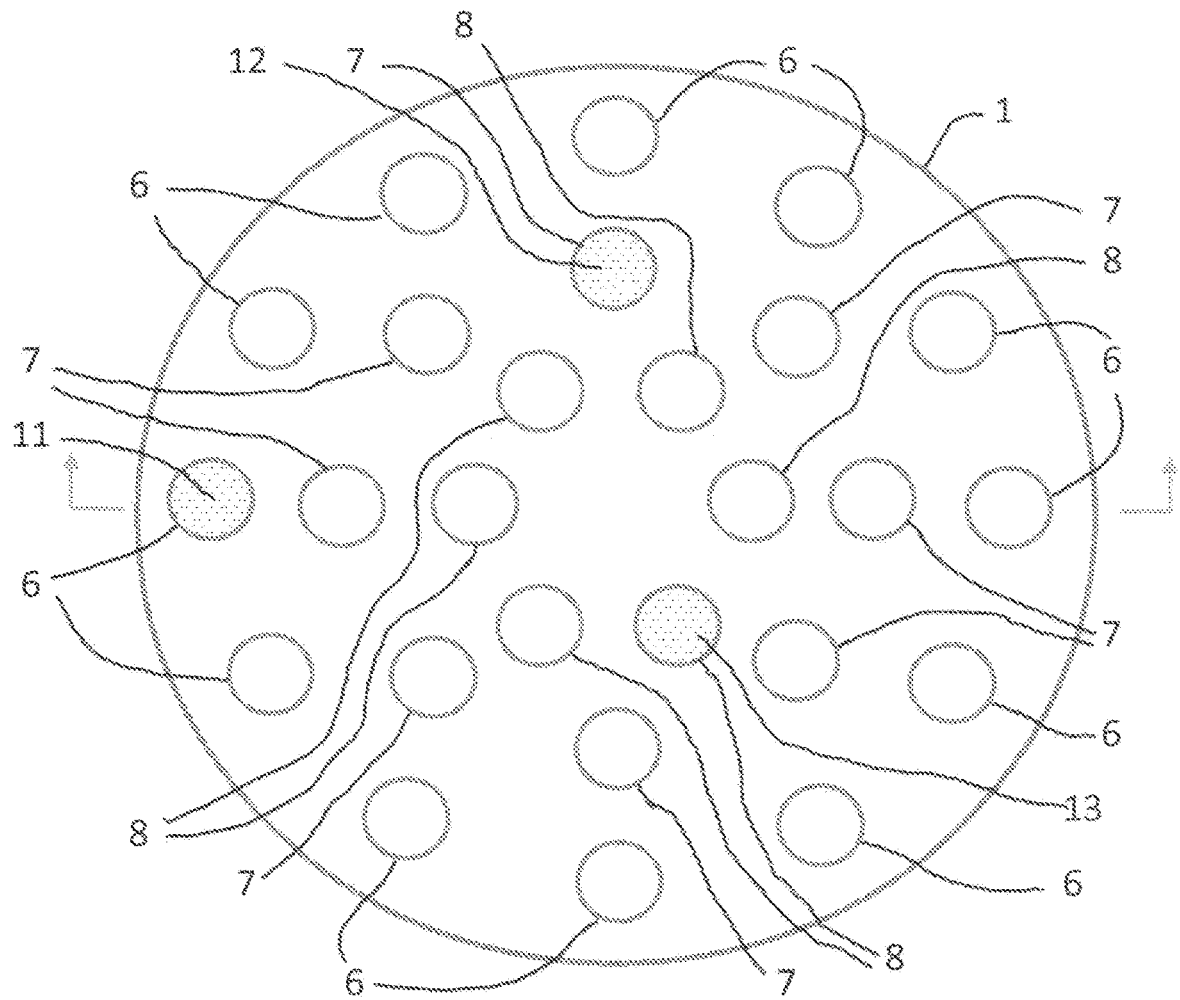
FIG. 3 depicts a top planar view of an embodiment of a base component of the present device.

FIG. 1 depicts a top view of the embodiment shown in FIG. 1, in which each of cavities 6, 7, 8 disposed in base 5 can have a lid 2, 3, 4. In some embodiments, lids 2, 3, 4 covering cavities 6, 7, 8, as shown in FIG. 1 top view can be substantially circular, but in other embodiments can have any other known and/or convenient geometry. Each such lid 2, 3, 4 can further comprise an opening 2*a* running substantially along the central longitudinal axis of a lid 2, 3, 4. As shown, an opening 2*a* can be substantially circular in some embodiments, but in others can have any other known and/or convenient geometry.

FIG. 2 depicts a side view of a lid 6, 7, 8 showing an opening 2*a* and an adhesive layer 2*b*. In such embodiments, an adhesive layer 2*b* can have a ring configuration and can be positioned on the outer edge of a bottom surface of a lid 2, 3, 4 substantially coaxial with a hole 2*a*, but in other embodiments can have any other known and/or convenient geometry. An opening 2*a* in each lid can allow odor from an odorous substance 11, 12, 13 contained in each cavity 6, 7, 8, to escape from that cavity at a rate that can be controlled by the diameter of an opening 2*a*. Each lid 2, 3, 4 can be substantially centered over a corresponding cavity 6, 7, 8 and an adhesive layer 2*b* can form a structural bond between a lid 2, 3, 4 and base 5. In addition, an adhesive layer 2*b* can form a gas seal between a cavity 6, 7, 8 and a corresponding lid 2, 3, 4.

FIG. 3 depicts a top view of an embodiment of the present device. In such embodiments, a base 5 can comprise multiple cavities 6, 7, 8 disposed in substantially concentric rings on the top or anterior surface, but in other embodiments can be arranged in any known and/or convenient configuration. As shown in FIG. 3, a base 5 can be substantially circular, but in other embodiments can be any other known and/or convenient geometry. In some embodiments, cavities 6, 7, 8 can have a substantially circular cross section, but in other embodiments can be any other known and/or convenient geometry. In other embodiments cavities 6, 7, 8 can be regions configured to accept test patches. In some embodiments a base 5 can be comprised of an injection molded or thermoformed plastic part, but in other embodiments can be produced by any other known and/or convenient method.

Figure 4:
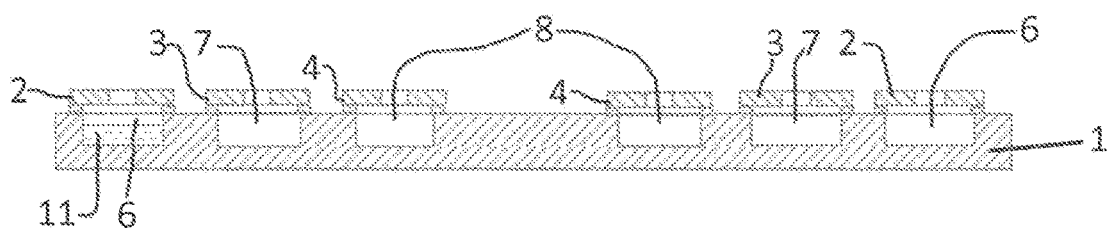
FIG. 4 depicts a side cross-sectional view of an embodiment of the present device shown in FIG. 1.

FIG. 4 depicts a side cross-sectional view of another embodiment of a base 5 of the present device. In some embodiments, substantially cylindrical cavities 6, 7, 8 can be covered by substantially circular lids 2, 3, 4. In such embodiments, lids 2, 3, 4 can have an outer diameter slightly greater than that of cavities 6, 7, 8 to rest on the top surface of a base 5 such that lids 2, 3, 4 and cavities 6, 7, 8 are substantially concentric.

Figure 5:
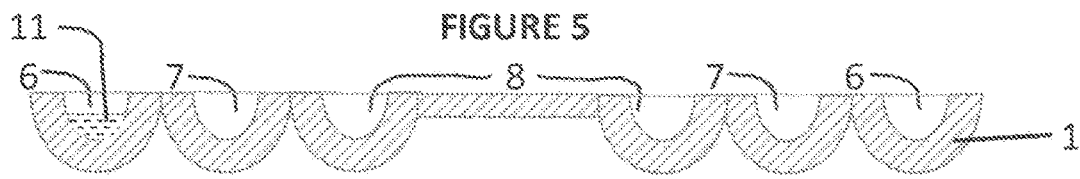
FIG. 5 depicts a side cross-sectional view of an embodiment of a base component of the present device shown in FIG. 1.
Figure 10:
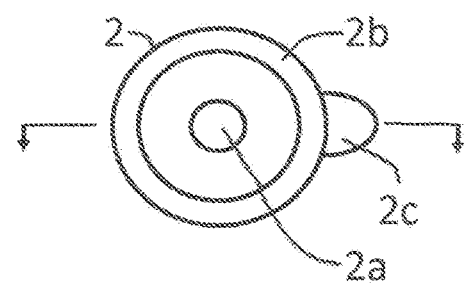
FIG. 10 depicts a bottom planar view of a lid component of the present device.

FIG. 5 depicts a side cross-sectional view of an alternative embodiment of a base 5 in the present device. As shown in FIG. 10, cavities 6, 7, 8 can have a rounded, or in some embodiments substantially hemispherical, bottom. However, in other embodiments the bottom of a cavity 6, 7, 8 can have any other known and/or convenient geometry.

It should be noted that although the embodiments shown in the various figures comprise a substantially circular base 5 with smell test substance cavities 6, 7, 8 or smell test substance patches radially disposed around center of a circular base 5, the base alternatively can be square, rectangular, or any other known and/or convenient shape instead. In addition, these smell test substance cavities 6, 7, 8 or smell test substance patches can be oriented in one or more straight rows and/or columns, or any other known and/or convenient configuration instead. Although these alternative embodiments can be different in form, they comprise similar features and the same functionality as the embodiments shown in the various figures of this patent.

A plurality, such as, but not limited to, three of cavities 6, 7, 8 can contain odorous substances 11, 12, 13, while the other cavities in base 5 do not contain any odorous substances 11, 12, 13. Each such odorous substance 11, 12, 13 can be in a liquid form, a solid form, a gas form, a sol form, an aerosol form, a gel form, or any other known and/or convenient form. When an odorous substance 11, 12, 13 is in liquid form, this substance can be disposed inside an absorbent material, such as, but not limited to, a cotton ball or sponge within the cavity, which can prevent a substance from spilling out of the cavity.

In order to test whether a person has lost the sense of smell, he or she can sniff near an opening 2a in a lid 2, 3, 4 and then peel off any lid 2, 3, 4 from a base 5 when he or she smells an odor emanating through a lid's 2, 3, 4 opening 2a. To pass this sense-of-smell test, a person can remove every lid 2, 3, 4 covering a cavity 6, 7, 8 containing an odorous substance 11, 12, 13 without removing any other lids 2, 3, 4 attached onto a base 5.

Figure 6:
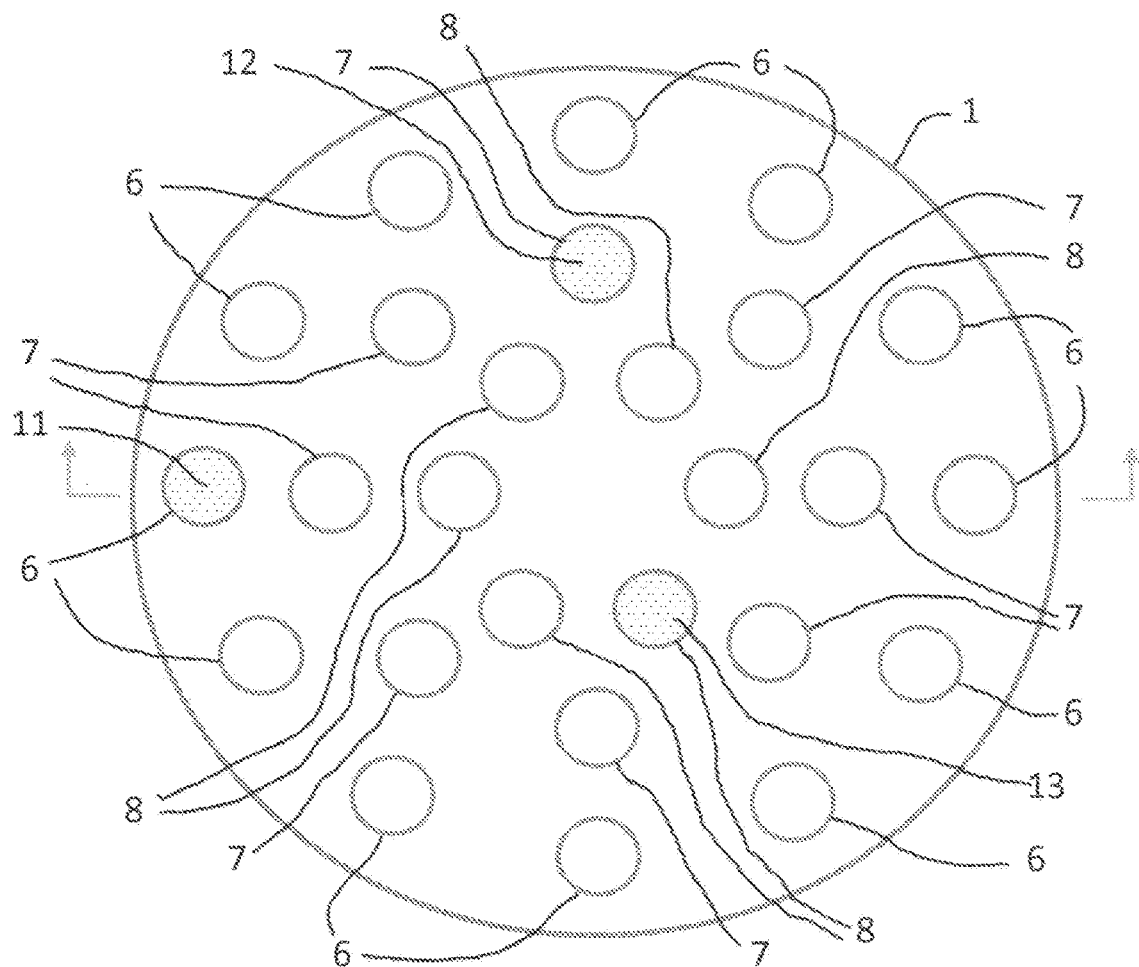
FIG. 6 depicts a top planar view of an embodiment of a base component in another embodiment of the present device.

FIG. 6 depicts a top view of another embodiment of the present device. In such embodiments, a base 5 can comprise multiple cavities 6, 7, 8 disposed in substantially concentric rings on the top surface, but in other embodiments can be arranged in any known and/or convenient configuration. As shown in FIG. 6, a base 5 can be substantially circular, but in other embodiments can be any other known and/or convenient geometry. In some embodiments, cavities 6, 7, 8 can have a substantially circular cross section, but in other embodiments can be any other known and/or convenient geometry. In other embodiments cavities 6, 7, 8 can be regions configured to accept test patches. In some embodiments a base 5 can be comprised of an injection molded or thermoformed plastic part, but in other embodiments can be produced by any other known and/or convenient method.

Figure 7:
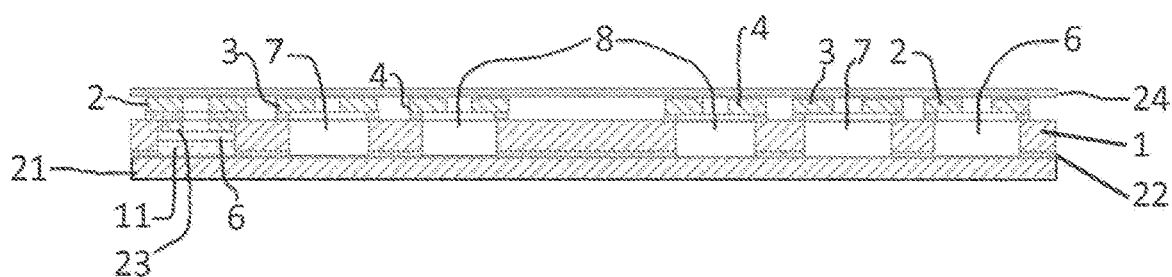
FIG. 7 depicts a side cross-sectional view of the present device.

FIG. 7 depicts a side cross-sectional view of an embodiment of the present device. To visually accentuate cavities 6, 7, 8 that contain an odorous substance 11, 12, 13 either the interior of each such cavity 6, 7, 8 or the odorous substance 11, 12, 13 or absorbent material can have one or more distinctive indicia 23, such as, but not limited to color (e.g., green). In other embodiments distinctive indicia 23 can comprise text, symbols, pattern, or any other known and/or convenient marking.

Figure 8:
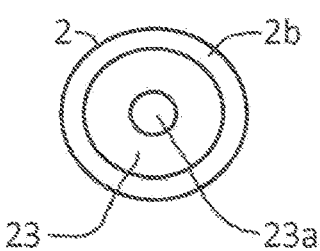
FIG. 8 depicts a bottom planar view of an embodiment of a lid component of the present device shown in FIG. 1.

FIG. 8 depicts a bottom view of a lid 2, 3 4. In some embodiments, the interior side of a lid 2, 3, 4 for those specific cavities 6, 7, 8 can have an indicium 23. Alternatively, every cavity 6, 7, 8 which does not contain an odorous substance 11, 12, 13 can comprise an interior surface with an indicium 23, such as, but not limited to the color red, and none of the cavities 6, 7, 8 enclosing an odorous substance 11, 12, 13 can comprise an interior surface with that indicia 23.

Figure 9:
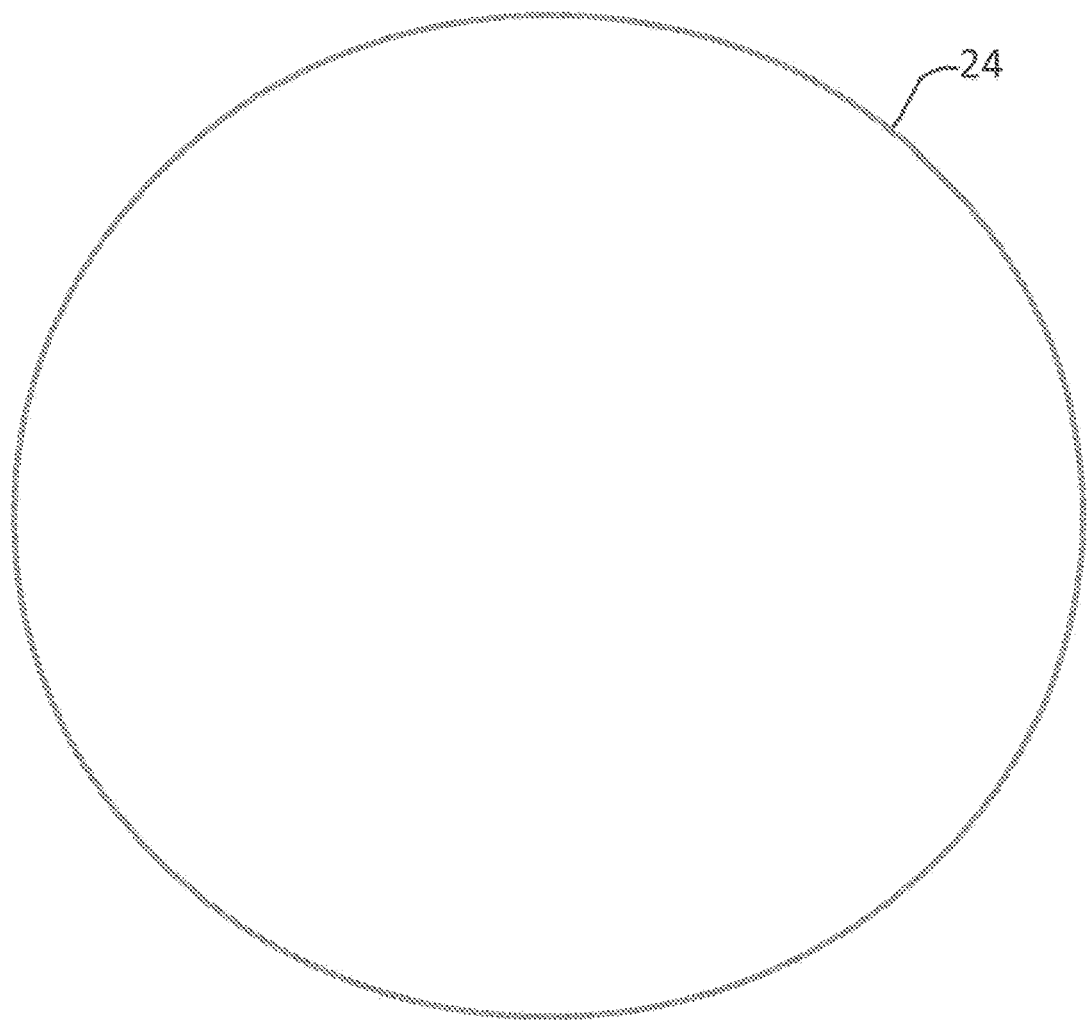
FIG. 9 depicts a top planar view of a membrane of a first embodiment of the present device.

FIG. 9 depicts a top view of a membrane of a first embodiment of the present device.

A membrane 24 can be substantially transparent, but in other embodiments can be opaque, translucent, or any other known and/or convenient degree of optical transmission. In order to prevent odor from escaping any cavity 6, 7, 8 which can enclose odorous substances 11, 12, 13 prior to commencement of the smell test, a membrane 24 can be affixed to a lid 2, 3, 4 via and an adhesive layer disposed between a membrane 24 and the top exterior face of a lid 2, 3, 4. An adhesive layer and membrane 24 can create a gas seal which prevents odor from escaping a cavity until this membrane is removed, via manual peeling, from all lids 2, 3, 4 immediately prior to commencement of a smell test.

FIG. 10 depicts a bottom view of a lid 2, 3, 4 of the present device. In some embodiments, a lid 2, 3, 4 can comprise a tab 2c extending substantially radially from the perimeter of lid 2, 3, 4, which can facilitate manual removal of a lid 2, 3, 4 by a user.

Figure 11:
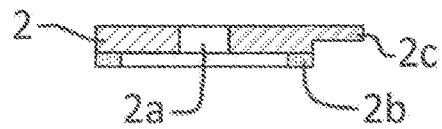
FIG. 11 depicts a side cross-sectional view of the lid shown in FIG. 10

FIG. 11 depicts a side cross-sectional view of the embodiment shown in FIG. 7. In some embodiments, a tab 2c, can extend substantially perpendicularly from the side of a lid 2, 3, 4.

Figure 12:
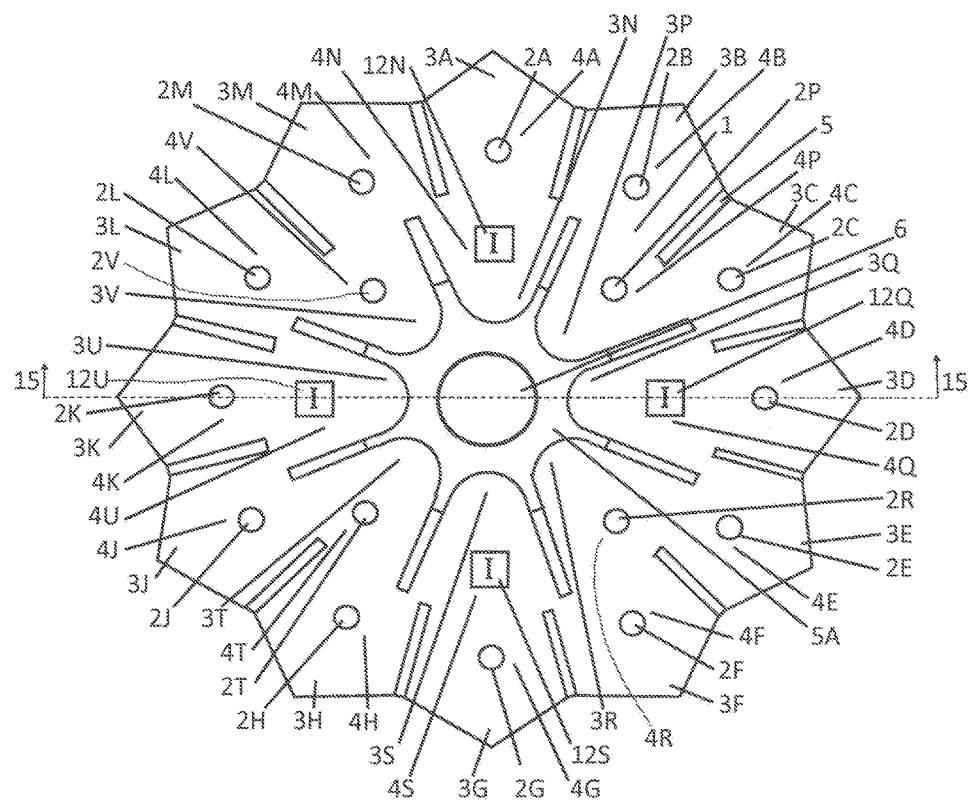
FIG. 12 depicts a top view of a first embodiment of the present device.
Figure 15:
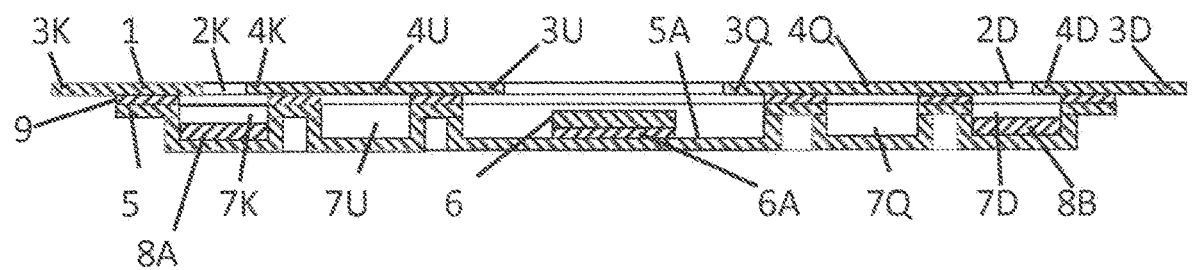
FIG. 15 depicts a side cross-sectional view of the first embodiment shown in FIG. 12.

FIG. 12 depicts a top planar view of a first embodiment of the present device. A cover 1 can be disposed onto a top surface of a base 5, as shown in FIG. 12 and FIG. 15. In some embodiments, a cover can be opaque, but in other embodiments can be transparent, translucent, or any other known and/or convenient degree of optical transmission. A cover 1 can comprise a single piece of bendable material suitable for a punching process, such as, but not limited to, aluminum foil or paperboard, or a polymer suitable for thermoforming process, such as, but not limited to, PETG, PET, PVC, styrene, polypropylene, ABS, polycarbonate, HDPE, or an opaque polymer suitable for injection molding process.

Figure 13:
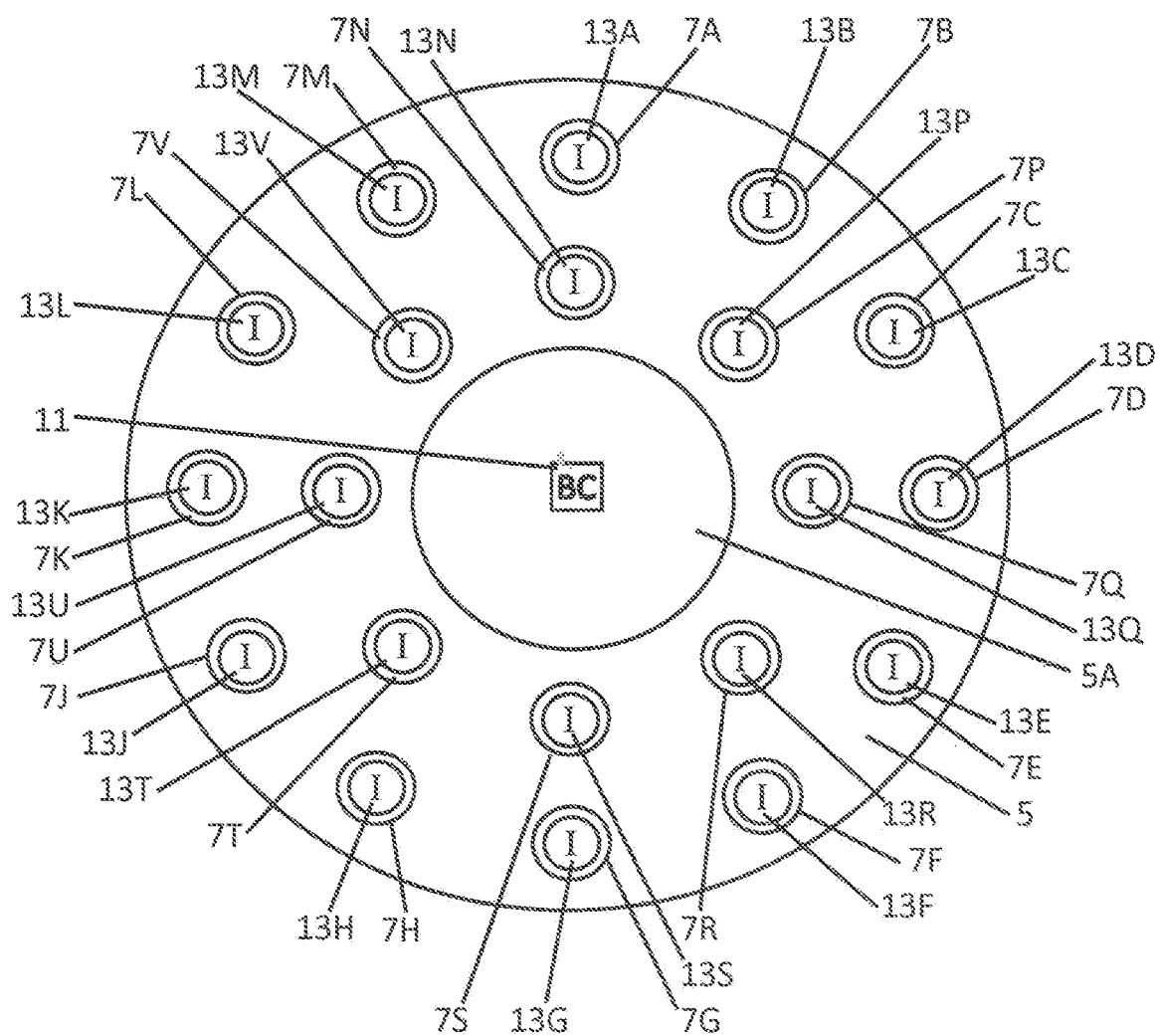
FIG. 13 depicts a top view of a base component in the first embodiment shown in FIG. 12 with indicia disposed on base.

FIG. 13 depicts a top view of a base component in the first embodiment shown in FIG. 12.

Figure 17:
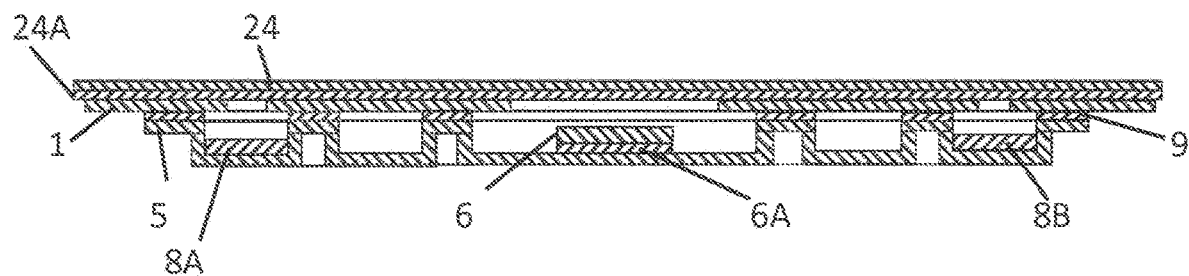
FIG. 17 depicts a side cross-sectional view of the first embodiment shown in FIG. 12.

As shown in FIG. 12 and FIG. 15, segments 4A-4V of cover 1 can each enclose corresponding cavities 7A-7V of base 5. Contiguous to each interconnected segment 4A-4V of cover 1 can be a corresponding tab 3A-3V radially disposed around the inner and outer perimeters of cover 1, as shown in FIG. 12. In order to prevent odor from escaping any cavity 7A-7V which encloses an odorous substance 8A et seq, such as, but not limited to, cavity 7K in base 5, prior to commencement of a smell test, a membrane 24, as shown in FIG. 17, can have an adhesive layer 24A disposed between a membrane 24 and a cover 1. An adhesive layer 24A and membrane 24 can create a gas seal which can prevent any odor from escaping any cavity until a membrane 24 can be removed, via manual peeling, from a cover 1 immediately prior to commencement of the smell test.

A first embodiment of a testing hardware device can incorporate means for reporting these symptoms as shown in FIG. 12 and FIG. 13. When a device is targeted for COVID-19 in the first embodiment, an orange color-coded circular indicium 13N can be disposed on an interior surface of cavity 7N, and the indicium 12N can be disposed in segment 4N, which can enclose cavity 7N and comprise the embossed or printed word FEVER. A blue color-coded circular indicium 13Q can be disposed on an interior surface of cavity 7Q, and an indicium 12Q disposed in segment 4Q, which can enclose cavity 7Q, can comprise the embossed or printed phrase NASAL CONGESTION. A purple color-coded circular indicium 13S can be disposed on an interior surface of cavity 7S, and an indicium 12S disposed in segment 4S, which encloses cavity 7S, can comprise the embossed or printed phrase DRY COUGH. Similarly, a yellow color-coded circular indicium 13U can be disposed on an interior surface of cavity 7U, and an indicium 12U disposed in segment 4U, which can enclose cavity 7U, can comprise the embossed or printed phrase SHORTNESS OF BREATH.

Alternatively, the indicia 12N, 12Q, 12S, and 12U can be printed adhesive labels, attached to exterior surface of cover 1, with corresponding symptoms printed on labels disposed on corresponding segments 4N, 4Q, 4S, and 4U of cover 1.

Figure 16:
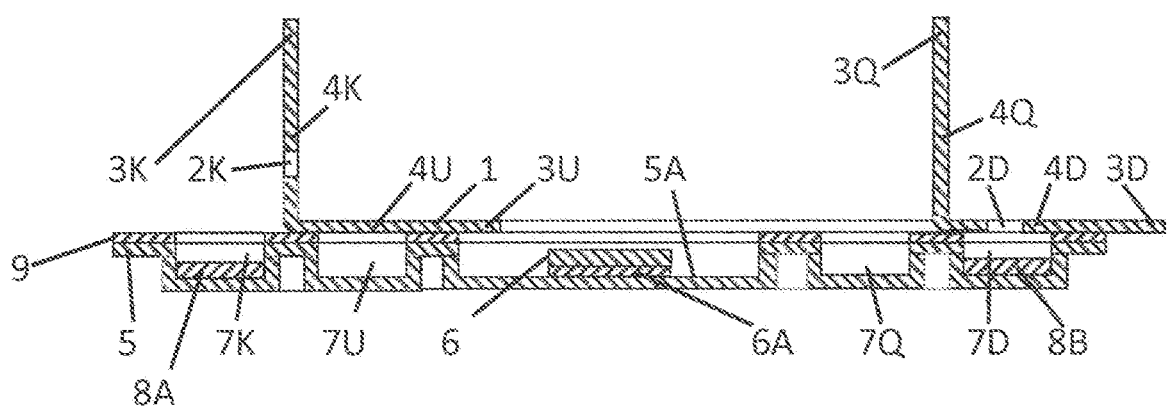
FIG. 16 depicts a side cross-sectional view of the first embodiment shown in FIG. 12.

After a person uses this hardware to test for anosmia and fever, he or she can report another symptom by manually peeling the corresponding tab 3N, 3Q, 3S, or 3U in cover 1 adjacent to the indicium 12N, 12Q, 12S, or 12U for that symptom, thereby removing the corresponding segment of cover 1 from the base 5, such as segment 4Q shown in FIG. 16. In some embodiments, a symptom can be a pre-existing impaired sense of smell.

This symptom indicium which references a pre-existing impaired sense of smell accommodates the 20% of population which already had a pre-existing impaired sense of smell prior to the COVID-19 epidemic, whereby failing this medical diagnostic device's small test does not by itself indicate that the user is likely to have COVID-19. For those users who had impaired sense of smell for at least 2 weeks, they either had a pre-existing impaired sense of smell unrelated to COVID-19, or COVID-19 may have caused this symptom, but the user is no longer contagious and may not need to self-isolate. The custom application software can reference at least some of this information in the result displayed. In the test instructions, there can be comment that this LOSS OF SMELL symptom tab should be peeled back only if loss of smell has lasted more than 2 weeks."

Figure 76:
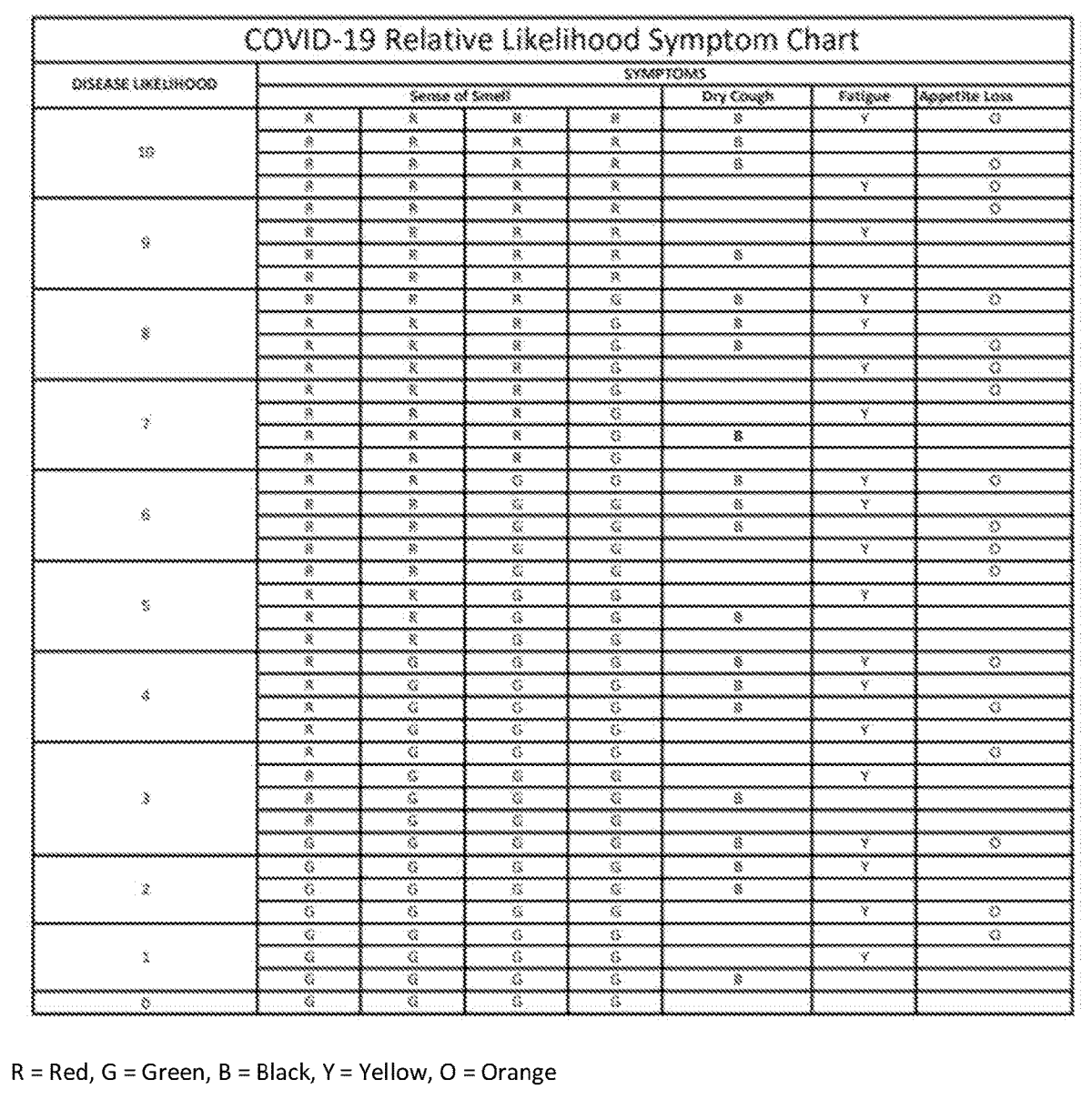

After a user has completed the smell test, the fever test, and has manually peeled applicable tabs 3N, 3Q, 3S, or 3U of opaque cover 1 to report symptoms, a first embodiment can include a symptoms chart Table 1, shown in FIG. 76 which can allow either the user, a medical professional, or someone screening people for a targeted disease to check the relative likelihood that the user's symptoms correspond to patients who have been diagnosed with that targeted disease. The person reviewing this symptom chart can locate the row in this chart which matches the all the symptoms' color codes reported and then can check the Disease Likelihood score adjacent to that row of this chart.

As a non-limiting example, based on the symptom chart in FIG. 76, if the exposed color codes visible on the test hardware match the symptom color codes in row 3 of this chart, this chart's corresponding Disease Likelihood score of 10 indicates a relatively high likelihood that the person who reported symptoms and took the smell test has the targeted disease. If a person's Disease Likelihood score is 0, based on this Table 1 shown in FIG. 76, that person can be experiencing none of the targeted symptoms, which can indicate that the person has lower likelihood of having the targeted disease. A condensed and simplified lookup table based on this symptom chart can either be a printed label with adhesive layer disposed between label and a back surface of base 5 or Table 1, shown in FIG. 76, can be a separate document provided with this test hardware.

Figure 14:
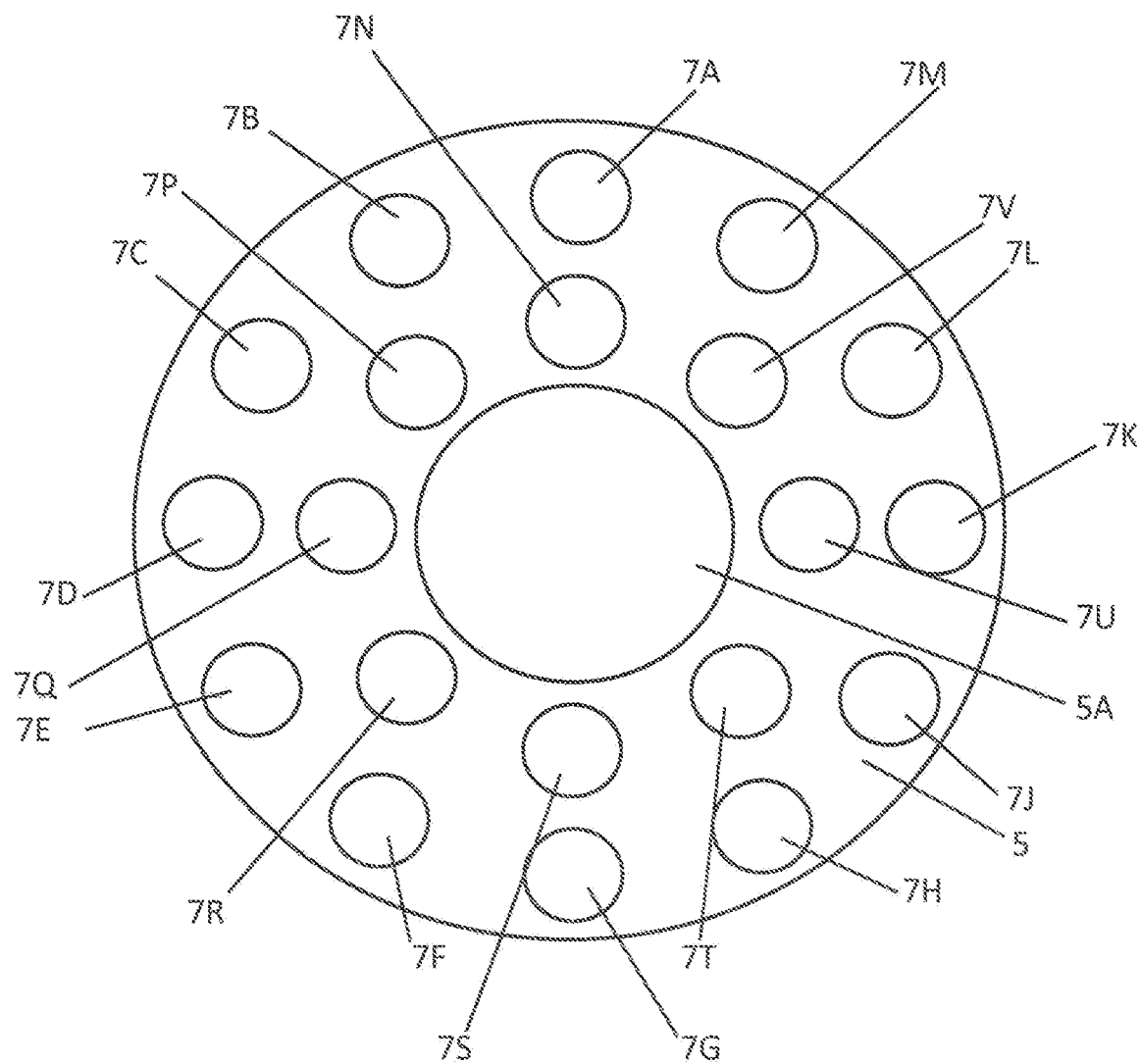
FIG. 14 depicts a top view of a first embodiment of a base component in the first embodiment shown in FIG. 12.

FIG. 14 depicts a top view of a first embodiment of a base component in the first embodiment shown in FIG. 12. As shown in FIG. 13 and FIG. 14, a series of twenty cavities 7A-7V can be configured in at least two substantially concentric rings, or any other known and/or convenient arrangement in base 5, which can be an injection-molded or thermo-formed or vacuum-formed polymer similar to polymers suitable for cover 1, or any other known and/or convenient material. As shown in FIG. 12, a cover 1 can comprise a set of openings 2A-2V that can be disposed in corresponding interconnected segments 4A-4V of cover 1, which can be each disposed contiguous to a corresponding cavity 7A-7V in base 5, as shown in FIG. 15. Such openings 2A-2V can allow odor from each cavity 7A-7V containing an odorous substance 8A et seq to escape from that cavity at a rate controlled by the diameter of the opening 2A-2V contiguous with that cavity, such as hole 2K contiguous with cavity 7K, as shown in FIG. 15.

FIG. 15 depicts a side cross-section view of the first embodiment shown in FIG. 12. An odorous substance 8A can be disposed within at least one cavity, such as cavity 7K shown in FIG. 15. Each such odorous substance 8A can be in a liquid form, a solid form, a gas form, a sol form, an aerosol form, a gel form, or hybrid form. A suitable hybrid form can comprise an absorbent material, such as, but not limited to, a porous solid, a sponge-like material, or a cotton ball, infused with liquid that emits an odor. An absorbent material can prevent the liquid from spilling out of the cavity. As an option, one or more different odorous substances 8A can be disposed in one or more other cavities in base 5, such as odorous substance 8B disposed within cavity 7D shown in FIG. 15. As shown in FIG. 15, an adhesive layer 9 can be disposed between cover 1 and base 5, which can structurally attach these two components and provide an odor seal that can prevent odor from escaping between these two components wherever an odorous substance is disposed within a cavity.

In order to test whether a person has lost the sense of smell, he or she can sniff near each opening 2A-2V in cover 1 and then manually peel corresponding tab 3A-3V in cover 1 adjacent to an opening 2A-2V where he or she smells an odor, thereby removing the corresponding segment 4A-4V of cover 1 from a base 5, as shown in FIG. 16. In some embodiments adhesive layer 9 can comprise material which ensures that the maximum peel force required for manually peeling one segment of cover 1 from base 5 can be in the range of 5.25±2.75 oz., but in other embodiments can be in any other known and/or convenient range. In order to pass this sense of smell test, a person can manually peel a corresponding tab 3A-3V in cover 1 to uncover each cavity enclosing an odorous substance 8A et seq in base 5, such as manually peeling tab 3K inward to uncover odorous substance 8A within cavity 7K shown in FIG. 16, without manually peeling any tabs 3A-3V that uncover cavities 7A-7V in base 5 which do not contain any odorous substance.

FIG. 15 depicts a side cross-sectional view of the first embodiment shown in FIG. 12. Since an elevated body temperature can often be associated with many illnesses, this test hardware can also comprise a simple means for detecting a fever. As shown in FIG. 12 and FIG. 15, base 5 can include a pocket 5A for storage of a removable fever indicator patch 6. A fever indicator patch 6 can comprise material that changes to red or any other known and/or convenient color whenever forehead skin reaches temperature corresponding with body temperature of 100° F. or higher. Similar technology can already be incorporated into forehead thermometer strips available in the market, although such thermometer strips do not provide a simple fever/no fever visual indication. Alternatively, this fever indicator can be a conventional thermometer, a forehead thermometer strip or any other known and/or convenient device. As shown in FIG. 15, an adhesive layer 6A can be disposed between a fever indicator 6 and pocket 5A surface. This fever indicator can be manually removed from pocket 5A and temporarily placed onto a person's forehead for fever check. When a fever indicator 6 is placed onto a person's forehead, adhesive layer 6A on back side of fever indicator 6 can temporarily adhere to the skin.

In some embodiments, adhesive layer 24A can comprise material that can ensure that the maximum peel force required for manually peeling sealing membrane 24 off from cover 1 can be in the range of 1.25±0.750 oz. In addition, in some embodiments the material in adhesion layer 24A and surface treatments of membrane 24 and cover 1 can be selected to ensure that the adhesion between adhesion layer 24A and membrane 24 can be greater than the adhesion between adhesion layer 24A and cover 1.

FIG. 17 depicts a side cross-sectional view of the first embodiment shown in FIG. 12.

Figure 18:
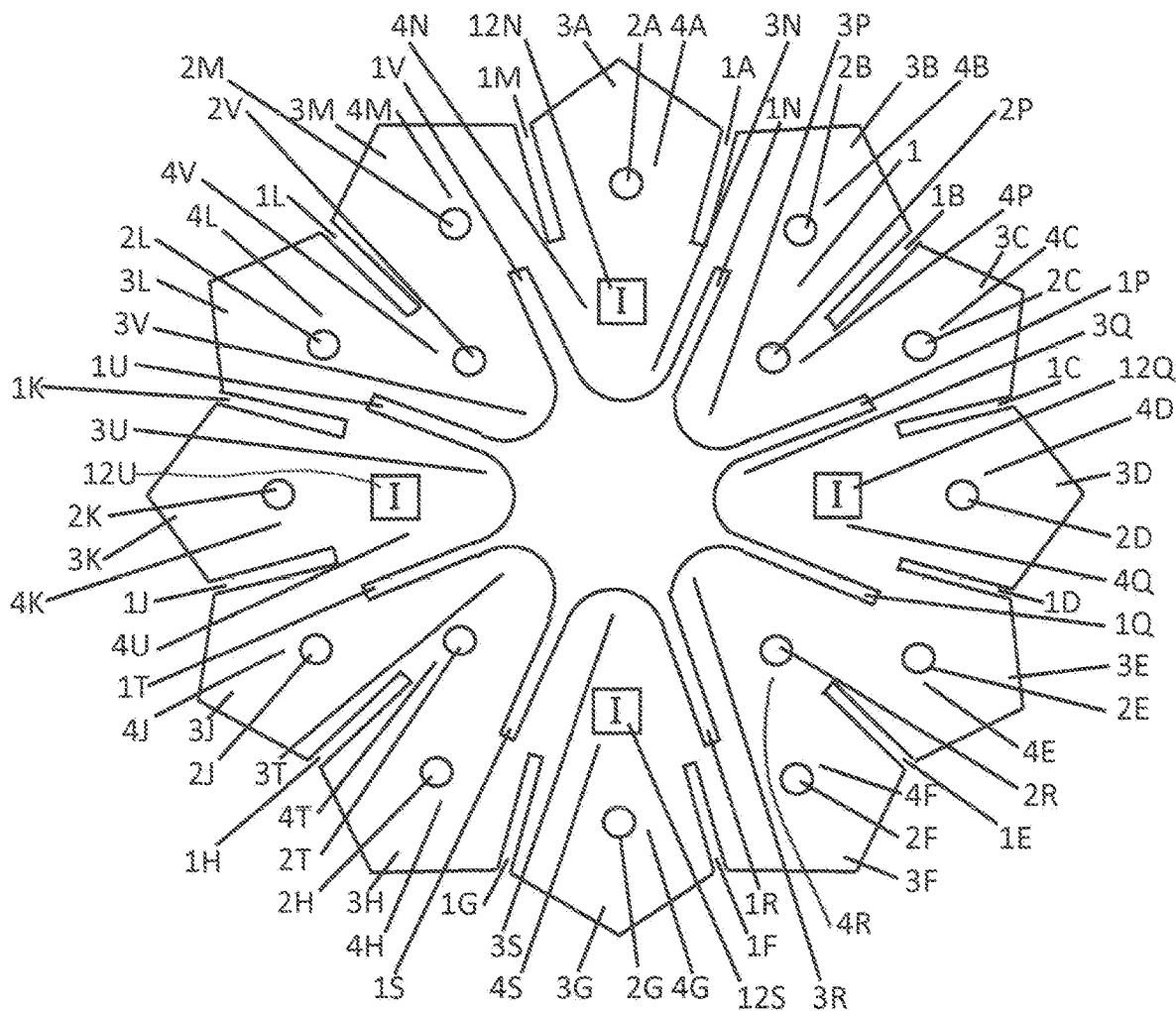
FIG. 18 depicts a top view of a cover of a first embodiment of the present device.

FIG. 18 depicts a top planar view of a cover of a first embodiment of the present device. As shown in FIG. 18, there can be gaps 1A-1V between adjacent segments 4A-4V of cover 1. These gaps can allow a person to manually remove a particular segment of cover 1 from a corresponding cavity in base 5, such as segment 4K shown in FIG. 16, without unintentionally removing an adjacent segment, such as segment 4L, from an adjacent cavity in base 5. The spacing between adjacent openings 2A-2V can be optimized to ensure that a person without anosmia can consistently and accurately distinguish which through hole from which the odor is emanating, which depends on the spacing between a person's nostrils, the diameter of each opening 2A-2V, and how pungent the odor.

The cover 1 of the first embodiment is shown in FIG. 18.

In a first embodiment of this test hardware device, each cavity in base 5 without an odorous substance inside can comprise color-coded circular indicium (symbolized as "I" enclosed within a circle) in FIG. 13, such as 13A, 13B, 13C, 13E, 13F, 13G, 13H, 13J, 13L, 13M, 13N, 13P, 13Q, 13R, 13S, 13T, 13U, and 13V) disposed on an interior surface of a cavity 7A-V. Each color-coded circular indicium can be a monochromatic color-filled circle disposed inside a corresponding cavity via a printing process, a multiple-shot injection molding process using 2-6 polymers of different colors, a colored dye or pigment dispensing process, secondary placement of a color-coded circular label comprising adhesive in contact with interior surface of each cavity, or any other known and/or convenient method. If each odorous substance, such as substance 8A and substance 8B shown in FIG. 15, comprises a clear gel-like material, this material can be dispensed into each corresponding cavity, such as, but not limited to cavity 7K and cavity 7D, and each of these two cavities can have a green color-coded circular indicium, such as 13K and 13D in FIG. 13, disposed on an interior surface. Alternatively, each odorous substance can comprise an added green dye or added green pigment, which can function as a circular green color-coded circular indicium inside the corresponding cavity.

In some embodiments, a first color can be red, a second color can be green, a third color can be black, a fourth color can be yellow, a fifth color can be orange, a sixth color can be purple, a seventh color can be cyan, an eighth color can be blue, a ninth color can be medium gray, and a tenth color can be light gray. Or any other known and/or desired colors.

When this circular green indicium is visible inside two exposed cavities following the smell test, this can indicate that the user does not have anosmia. In this first embodiment, circular red color-coded circular indicia 13A, 13B, 13C, 13E, 13F, 13G, 13H, 13J, 13L, 13M, 13P, 13R, 13T, 13V can be disposed in a subset of the cavities in base 5, such as cavities 7A, 7B, 7C, 7E, 7F, 7G, 7H, 7J, 7L, 7M, 7P, 7R, 7T, 7V shown in FIG. 13, which, in some embodiments, an odorous substance is absent. When this circular red indicium is visible inside one or two exposed cavities following the smell test, this can indicate that the user does have anosmia.

The remaining cavities 7N, 7Q, 7S, and 7U can each comprise a unique color-coded circular indicium disposed on an interior surface, which can be used to indicate the presence of other key symptoms of a targeted disease. In addition to anosmia, research on COVID-19 disease indicates that other common symptoms can be fever, dry cough, and shortness of breath. Based on research indicating that anosmia without nasal congestion can be strongly correlated with COVID-19 disease, the presence or absence of nasal congestion can be another symptom which can be monitored.

Figure 19:
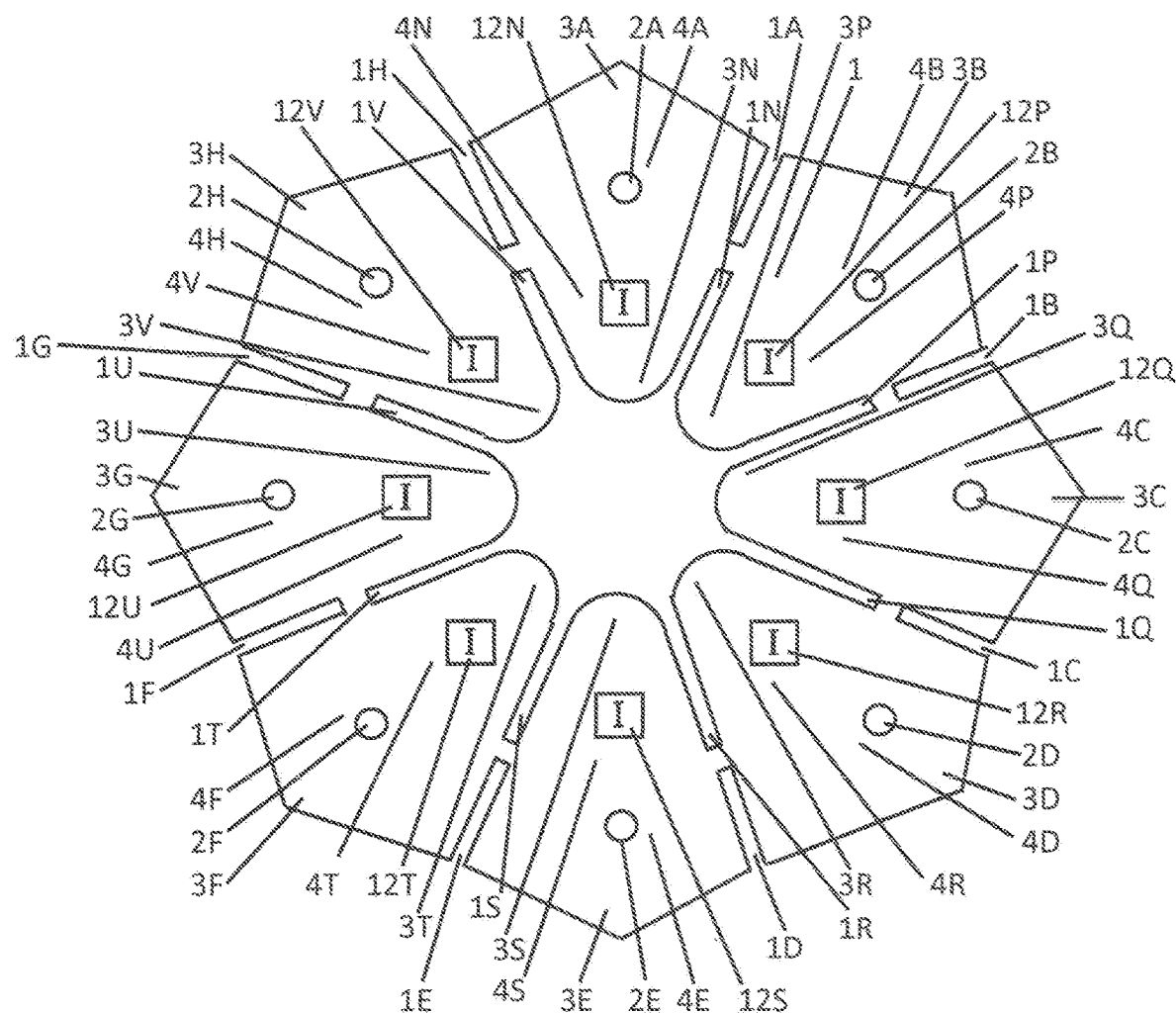
FIG. 19 depicts a top view of a cover of a second embodiment of the present device.
Figure 20:
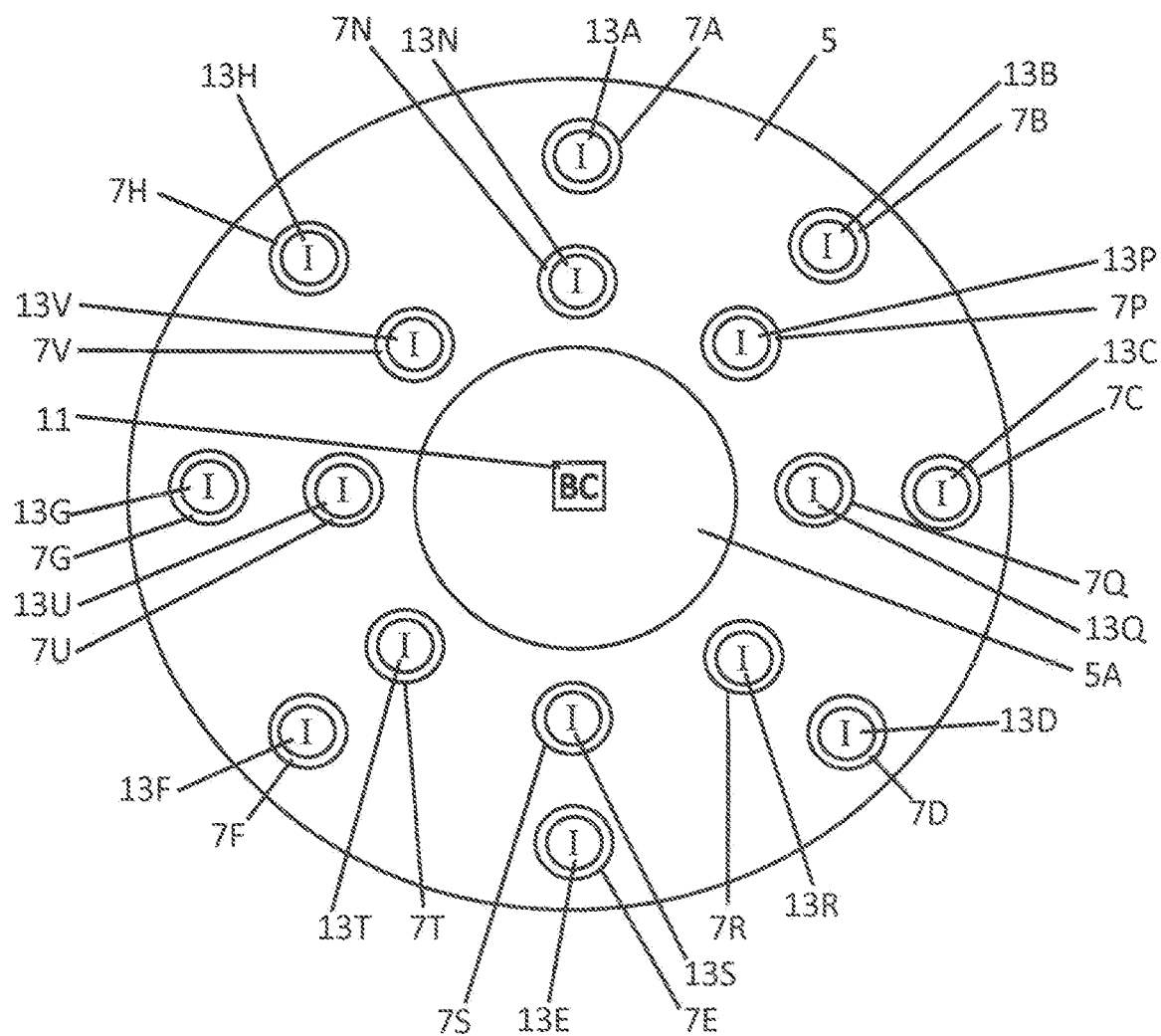
FIG. 20 depicts a top view of a base component of a second embodiment of the present device.

FIG. 19 depicts a top planar view of a cover in a second embodiment of the device FIG. 20 depicts a top planar view of a base in a second embodiment of the device. The embodiment shown in FIG. 20 can have plurality of, such as, but not limited to, 8 cavities 7A, 7B, 7C, 7D, 7E, 7F, 7G, and 7H equidistantly disposed from the center of base 5, with odorous substance 8A, 8B, 8C, and 8D disposed within four cavities 7C, 7E, 7G, and 7 H, but in other embodiments can have any other known and/or convenient configuration. In other embodiments, there can be multiple versions of this base 5 with odorous substance 8A, 8B, 8C, and 8D disposed within a plurality of, such as, but not limited to, four other cavities instead, as discussed in the description of the first embodiment shown in FIG. 12, FIG. 13, FIG. 14, and FIG. 15.

In the second embodiment shown in FIG. 19 and FIG. 20, each odorous substance 8A, 8B, 8C, and 8D can be different, and each cavity with odorous substance disposed within can have a corresponding indicium 13C, 13E, 13G, and 13H disposed within, which can comprise a mixture of a green dye or green pigment and the corresponding odorous substance. In an alternate embodiment, this green color-coded circular indicium can be disposed directly onto interior surface of corresponding cavity if the odorous substance within the cavity can be transparent. Similarly, each cavity 7A, 7B, 7D, and 7F without odorous substance disposed within can have red color-coded circular indicium 13A, 13B, 13D, and 13F disposed directly onto interior surface of corresponding cavity in base 5.

As shown in FIG. 20, there can be eight additional cavities 7N, 7P, 7Q, 7R, 7S, 7T, 7U, and 7V equidistantly disposed from the center of base 5, and each of these cavities can have a unique color-coded circular indicium 13N, 13P, 13Q, 13R, 13S, 13T, 13U, and 13V disposed on an interior surface of the corresponding cavity. Each of these eight cavities 7N, 7P, 7Q, 7R, 7S, 7T, 7U, and 7V in base 5 can be disposed contiguous with the interior surface of a corresponding segment 4N, 4P, 4Q, 4R, 4S, 4T, 4U, and 4V of cover 1, whereby each of these cavities in base 5 can be enclosed by a corresponding segment of opaque cover 1. As shown in FIG. 19 there can be unique symptom indicium 12N, 12P, 12Q, 12R, 12S, 12T, 12U, and 12V disposed on the exterior surface of each corresponding segment 4N, 4P, 4Q, 4R, 4S, 4T, 4U, and 4V of opaque cover 1.

Figure 21:
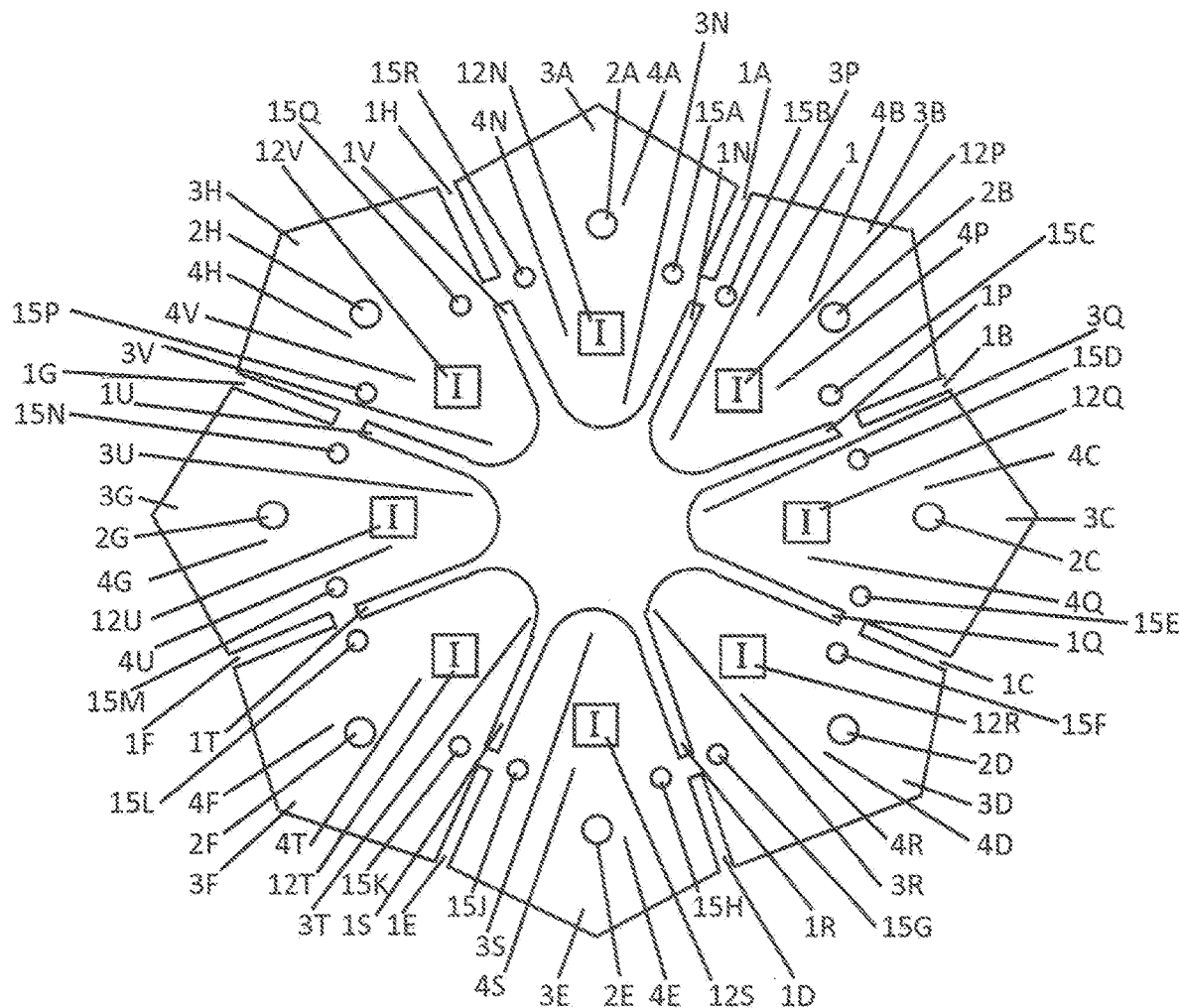
FIG. 21 depicts a top view of a cover of a third embodiment of the present device.

FIG. 21 depicts a top view of a cover 1 of a third embodiment of the present device. In the embodiment shown in FIG. 23, FIG. 22 and FIG. 21, when the test hardware can be targeted for COVID-19, a blue-green color-coded circular indicium 13P can be disposed on an interior surface of cavity 7P, and the symptom indicium 12P disposed in segment 4P, which can enclose cavity 7P, can comprise the embossed or printed word CHILLS. A grey color-coded circular indicium 13R can be disposed on an interior surface of cavity 7R, and the symptom indicium 12R disposed in segment 4R, which encloses cavity 7R, can comprise the embossed or printed phrase MUSCLE PAIN. A black color-coded circular indicium 13T can be disposed on an interior surface of cavity 7T, and the symptom indicium 12T disposed in segment 4T, which encloses cavity 7T, can comprise the embossed or printed word FATIGUE. A brown color-coded circular indicium 13V can be disposed on an interior surface of cavity 7V, and the symptom indicium 12V disposed in segment 4V, which encloses cavity 7V, can comprise the embossed or printed phrase SORE THROAT.

Figure 22:
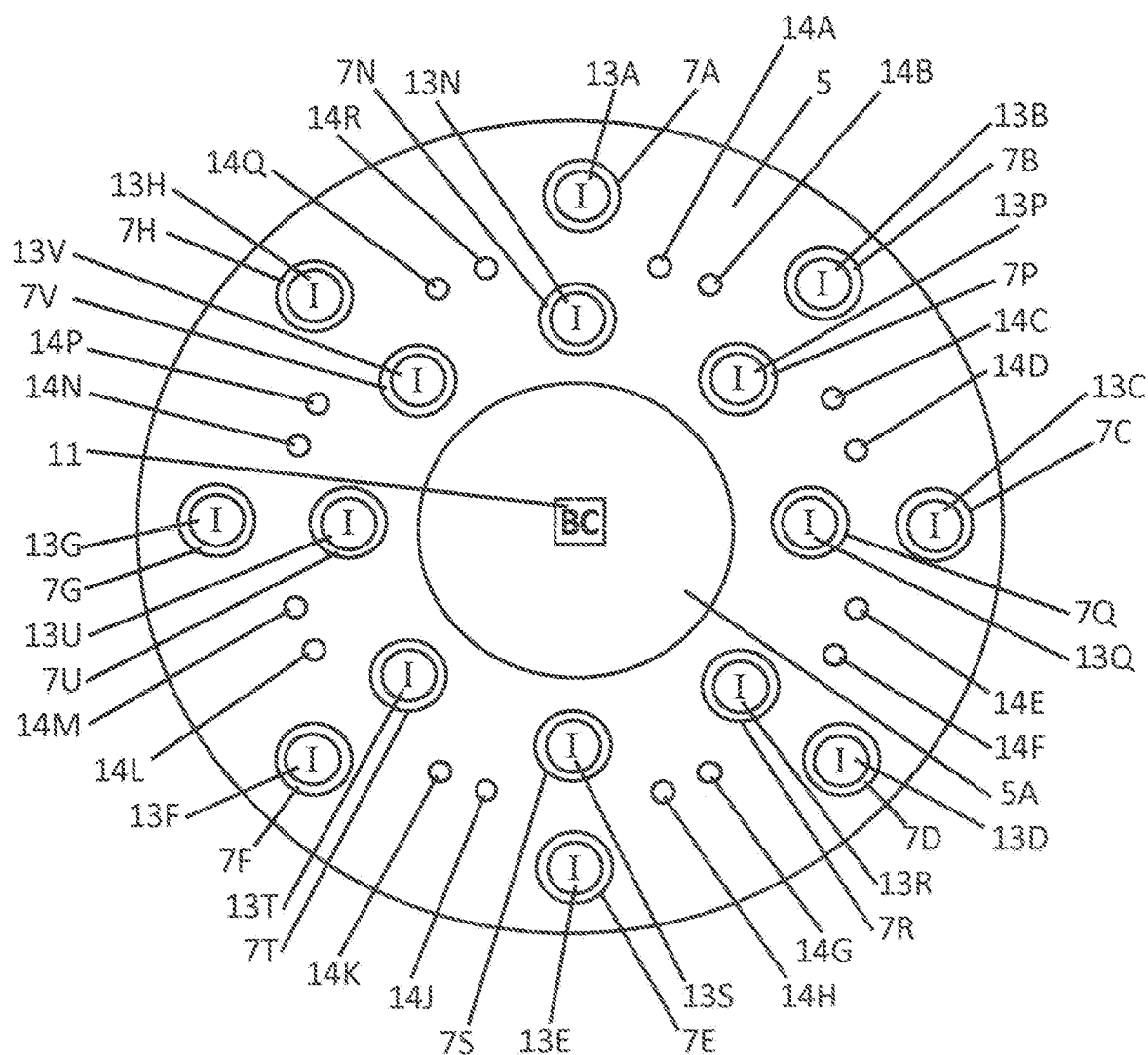
FIG. 22 depicts a top view of a base of a third embodiment of the present device.

FIG. 22 depicts a top planar view of a base of a third embodiment.

Figure 23:
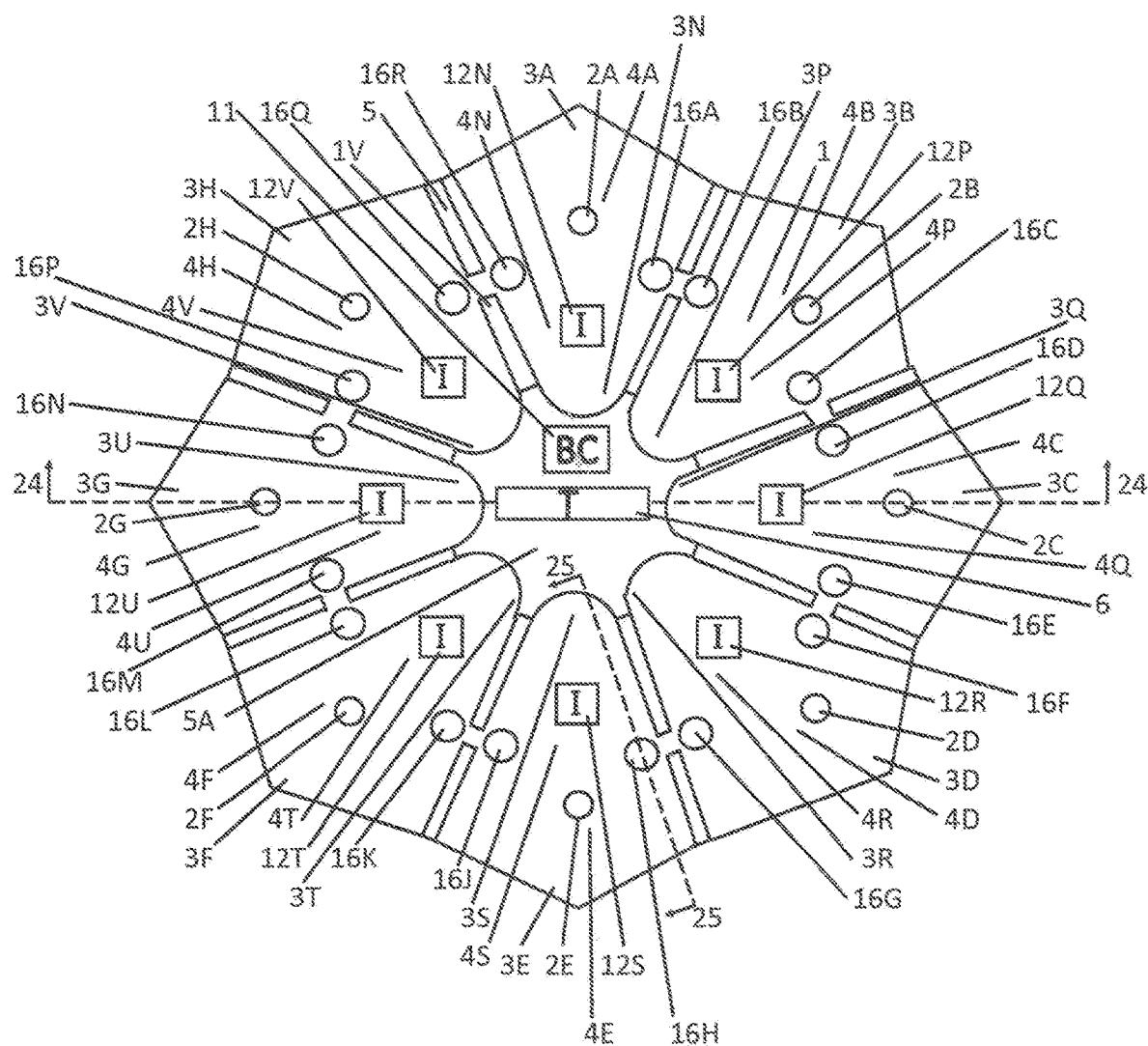
FIG. 23 depicts a top view of a third embodiment of the present device.

FIG. 23 depicts a top view of a third embodiment of the present device. As shown in FIG. 23, there can be a unique serial number 11 (symbolized as BC enclosed within rectangle) disposed on pocket 5A of base 5. This can be a conventional bar code representing a unique serial number for the test hardware, which can be printed directly onto a surface of pocket 5A or which can be a bar code printed onto an adhesive label disposed on a surface of pocket 5A. Alternately this embodiment can simply comprise a unique serial number printed conventionally with alphanumeric characters.

Figure 24:
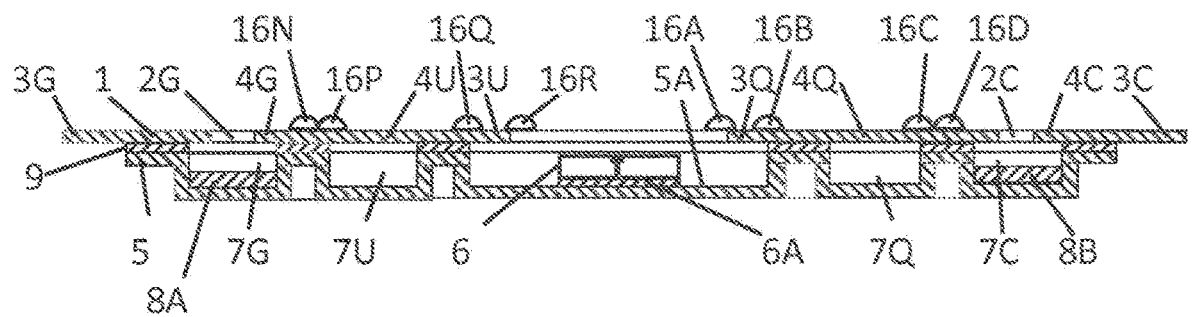
FIG. 24 depicts a side cross-sectional view of a third embodiment of the present device.

FIG. 24 depicts a side cross-sectional view of the third embodiment shown in FIG. 23.

Figure 25:
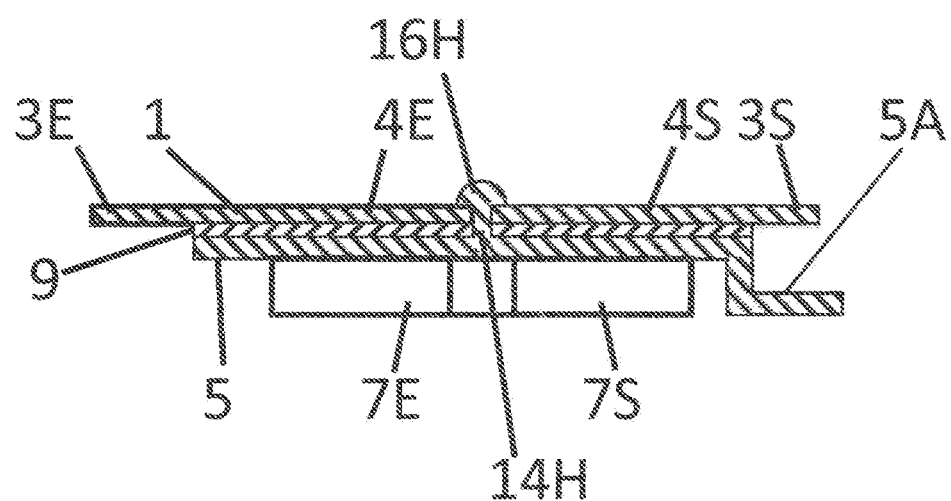
FIG. 25 depicts an enlarged side cross-sectional view of a portion of third embodiment of the present device.

FIG. 25 depicts an enlarged side cross-sectional view of a portion of a third embodiment of the present device. FIG. 25, as well as FIG. 24, illustrate the structure of this test hardware following production assembly. Although there are sixteen heat stake features which can structurally connect base 5 with cover 1, adhesive layer 9 can be disposed between base 5 and cover 1, as shown in FIG. 24 and FIG. 25. As noted with other embodiments, an adhesive layer 9 can serve as an odor seal between cavities in base 5 and cover 1, and this layer can ensure that each interconnected segment 4A, 4B, 4C, 4D, 4E, 4F, 4G, 4H, 4N, 4P, 4Q, 4R, 4S, 4T, 4U, 4V of cover 1 fully encloses each corresponding cavity of base 5, as shown in FIG. 24, until some segments of cover 1 are manually peeled away from surface of base 5. In this embodiment, each odorous substance 8A, 8B, 8C, and 8D can comprise an absorbent solid material, such as felt, propylene glycol, and an odorant fluid or other odorant material, similar to the Sniffin' Sticks® test. This absorbent solid material can also comprise green dye and be formed as a circular disk, which can be disposed inside four cavities of base 5, such as, but not limited to, cavity 7G and cavity 7C shown in FIG. 24. Each felt disk can function as a green color-coded circular indicium.

As noted in other embodiments of this test hardware, if each odorous substance is transparent and colorless, then the green color-coded circular indicium can alternately be green ink or other green pigment disposed directly onto the circular interior surface of four cavities of base 5, such as, but not limited to, cavities 7C, 7E, 7G, and 7H shown in FIG. 24. During assembly of the test hardware, a transparent odorous substance 8A, 8B, 8C, and 8D can be subsequently dispensed into these four corresponding cavities, thereby covering each green color-coded circular indicium 13C, 13E, 13G, and 13H. As shown in FIG. 23 and FIG. 24, an optional conventional digital or analog body temperature thermometer 6 (symbolized as T enclosed within rectangle) can be attached to pocket 5A of base 5, with an adhesive layer 6A disposed between thermometer 6 and pocket 5A of base 5. The adhesive layer's surface area and material can be selected to ensure that the peel force required for manually removing thermometer 6 from base 5 can be in the range of 5 oz±3 oz.

FIG. 21, FIG. 22, FIG. 23, FIG. 24, and FIG. 25 depict a third embodiment that can include the same design features and/or can be comprised of similar materials as the second embodiment shown and described in relation to FIG. 19 and FIG. 20, as well as conventional heat stake features which can structurally attach base 5 to cover 1. As shown in FIG. 22, there can be sixteen cylindrical bosses 14A, 14B, 14C, 14D, 14E, 14F, 14G, 14H, 14J, 14K, 14L, 14M, 14N, 14P, 14Q, and 14R disposed perpendicular to the top surface of base 5. These bosses 14A-14R can be integrally molded features of base 5. After injection molding of base 5, during assembly these bosses 14A-14R can be inserted into openings 15A, 15B, 15C, 15D, 15E, 15F, 15G, 15H, 15J, 15K, 15L, 15M, 15N, 15P, 15Q, and 15R of cover 1, shown in FIG. 22 and FIG. 21. Following insertion of these bosses through these holes in cover 1, a production heat staking tool can apply compression force at elevated temperature to the protruding ends of all bosses simultaneously to form dome heat stake heads 16A, 16B, 16C, 16D, 16E, 16F, 16G, 16H, 16J, 16K, 16L, 16M, 16N, 16P, 16Q, and 16R shown in FIG. 24 and FIG. 25, using a conventional heat staking process. An enlarged cross-sectional view of dome heat stake head 16H and cylindrical boss 14H of base 5 is shown in FIG. 25.

Figure 26:
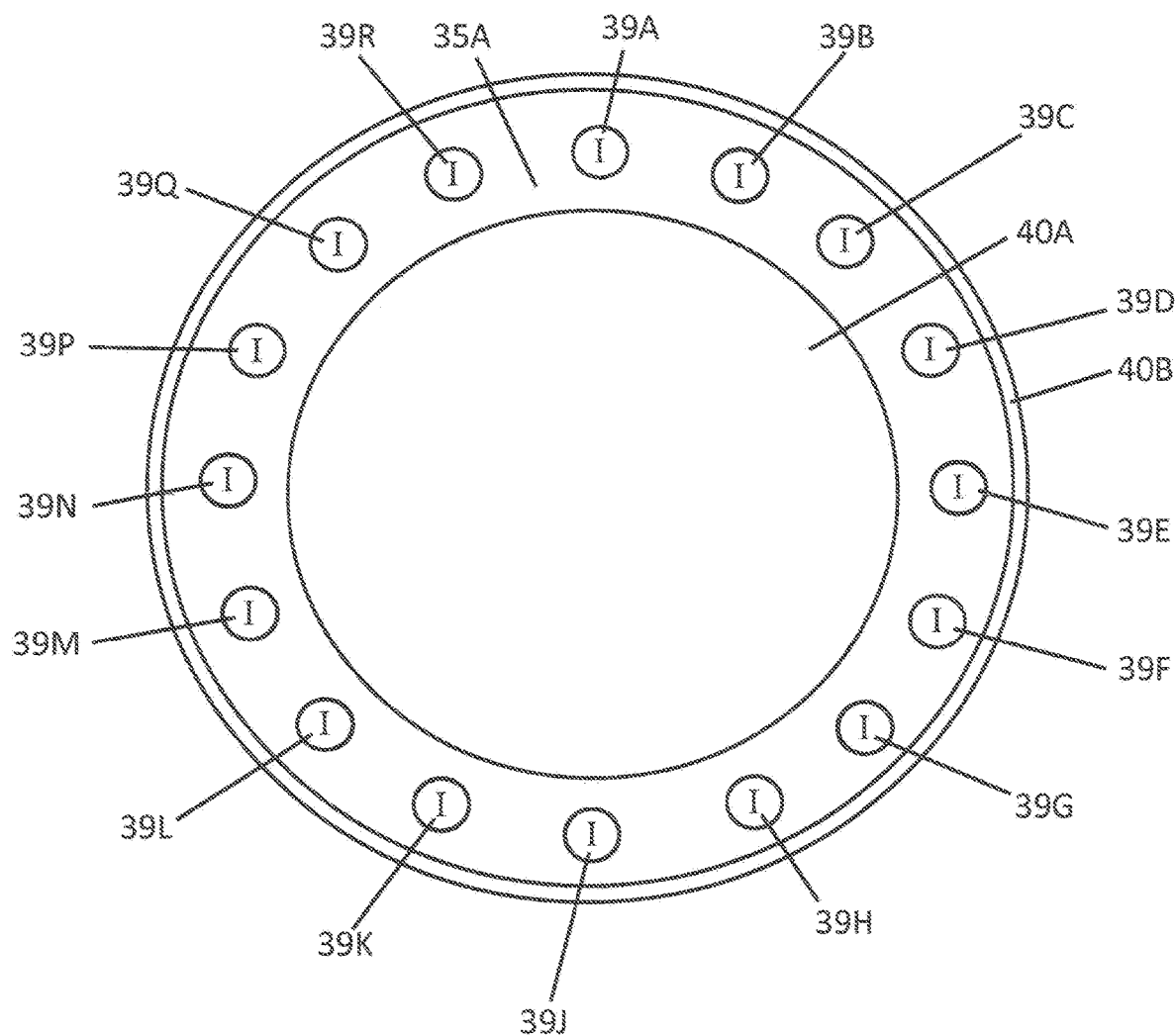
FIG. 26 depicts a top view of a posterior base component of a fourth embodiment of the present device.

FIG. 26 depicts a top view of a posterior base component of a fourth embodiment of the present device. As shown in FIG. 26 top view of posterior base 35A, a set of eight posterior base color-coded circular smell test indicium (symbolized as "I" enclosed within a circle) 39A, 39C, 39E, 39G, 39J, 39L, 39N, and 39Q can be printed on a top surface of posterior base 35A. Four posterior base color-coded circular smell test indicium 39A, 39E, 39J, and 39Q can comprise green ink or green pigment, and each green color-coded circular smell test indicium can be disposed behind corresponding anterior base segments 34A, 34E, 34J, and 34Q. Four other posterior base color-coded circular smell test indicium 39C, 39G, 39L, and 39N can comprise red ink or red pigment, and each red color-coded circular smell test indicium can be disposed behind corresponding anterior base segments 34C, 34G, 34L, and 34N.

In addition to these eight, posterior base color-coded circular smell test indicia, there can be a second set of posterior base color-coded circular indicium (symbolized as I enclosed within a circle) 39B, 39D, 39F, 39H, 39K, 39M, 39P, and 39R printed on a top surface of posterior base 35A. In this embodiment, posterior base color-coded circular indicium 39B can be black, posterior base color-coded circular indicium 39D can be yellow, posterior base color-coded circular indicium 39F can be orange, posterior base color-coded circular indicium 39H can be light grey, posterior base color-coded circular indicium 39K can be purple, posterior base color-coded circular indicium 39M can be cyan, posterior base color-coded circular indicium 39P can be blue, and posterior base color-coded circular indicium 39R can be medium grey. In other embodiments indicium can be any other known and/or convenient color or pattern.

Figure 30:
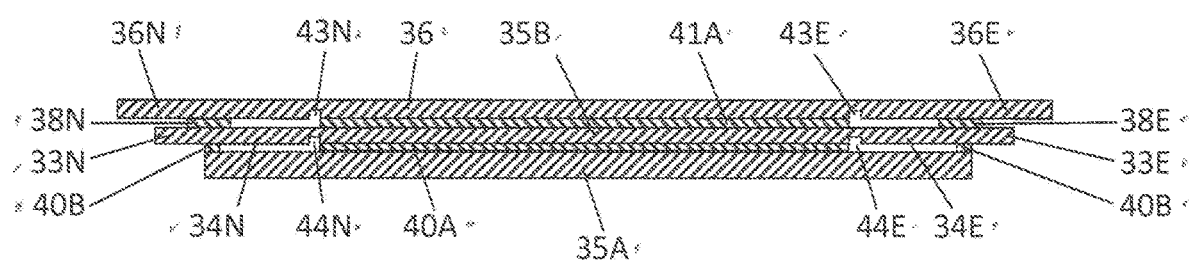
FIG. 30 depicts a side cross-sectional view of a fourth embodiment of the present device.

This second set of posterior base color-coded circular indicium can be disposed behind corresponding anterior base segments 34B, 34D, 34F, 34H, 34K, 34M, 34P, and 34R. All sixteen posterior base color-coded circular indicium can be printed on posterior base 35A equidistantly spaced apart, and these can provide indication regarding illness symptoms, age, and gender of the user when these can be visible. As shown in FIG. 26 and FIG. 30, there can be a circular adhesive layer 40A and an annular adhesive layer 40B disposed between a posterior base 35A and an anterior base 35B. A circular adhesive layer 40A can structurally attach posterior base 35A and anterior base 35B, and this layer's material can be selected to ensure a minimum peel force of approximately 1 pound required to separate posterior base 35A and anterior base 35B. An annular adhesive layer 40B structurally attaches the perimeter of posterior base 35A to each of anterior base segments 34A, 34B, 34C, 34D, 34E, 34F, 34G, 34H, 34J, 34K, 34L, 34M, 34N, 34P, 34Q, and 34R. The force required to manually peel any anterior base segment off the posterior base 35A can be less than 8 ounces and greater than the force required to manually peel any cover tab off a corresponding anterior base segment. In addition, the surface treatment, finish, and materials of this embodiment can be selected such that the adhesion of annular adhesive layer 40B to posterior base 35A can be greater than the adhesion of annular adhesive layer 40B to any anterior base segment.

The anterior base 35B material can be similar to one of the materials listed as options for the cover 36 in this embodiment or any other known and/or convenient material. The posterior base 35A material can also be similar to one of these materials listed as options for the cover 36 in this embodiment, or any other known and/or convenient material, although the stiffness of the posterior base 35A can be greater than the stiffness of cover 36 and anterior base 35B, in order to limit warpage of posterior base 35A during manual peeling of cover tabs and during manual peeling of anterior base segments. The posterior base 35A potentially can comprise a stiffer grade of paperboard, such as binder's board, or paperboard with a greater thickness, in the range of 0.040 in.-0.125 in. (0.0825 in.±0.0425 in).

Figure 27:
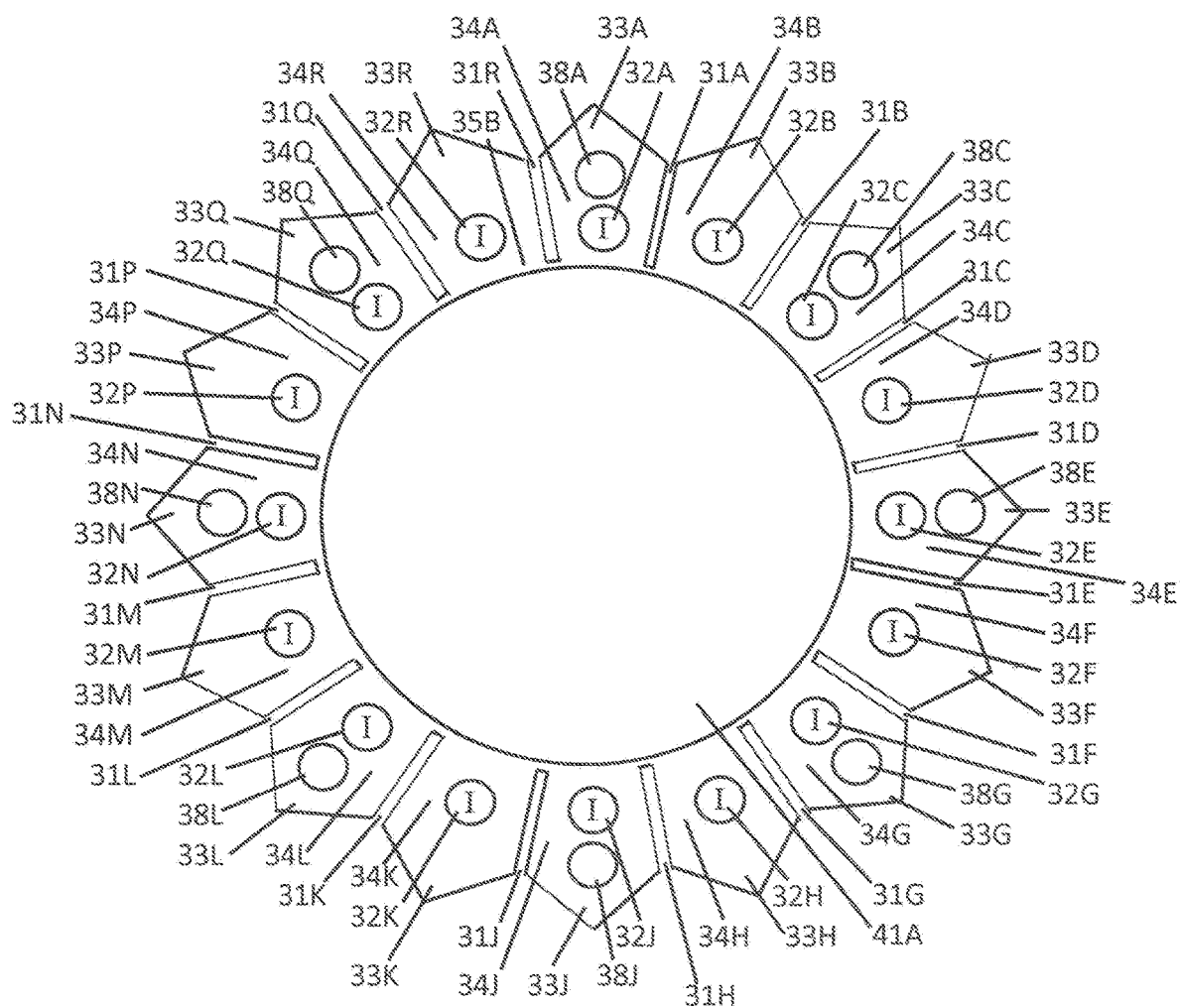
FIG. 27 depicts a top view of an anterior base component of fourth embodiment of the present device.

FIG. 27 depicts a top view of an anterior base component of fourth embodiment of the present device.

As shown in FIG. 27 top view of the anterior base 35B, eight anterior base indicia (symbolized as "I" enclosed within a circle) 32A, 32C, 32E, 32G, 32J, 32L, 32N, and 32Q can be printed or embossed on corresponding anterior base segments 34A, 34C, 34E, 34G, 34J, 34L, 34N, 34Q. Each anterior base indicium 32A, 32C, 32E, 32G, 32J, 32L, 32N, and 32Q can provide an indication that a user can sniff that area. This indicium can simply comprise the word SNIFF or a simple visual representation of a nose or nostrils, as non-limiting examples. As also shown in FIG. 27, anterior base indicium 32B, 32D, 32F, 32H, 32K, 32M, 32P, and 32R can be printed or embossed on corresponding anterior base segments 34B, 34D, 34F, 34H, 34K, 34M, 34P, and 34R.

Figure 28:
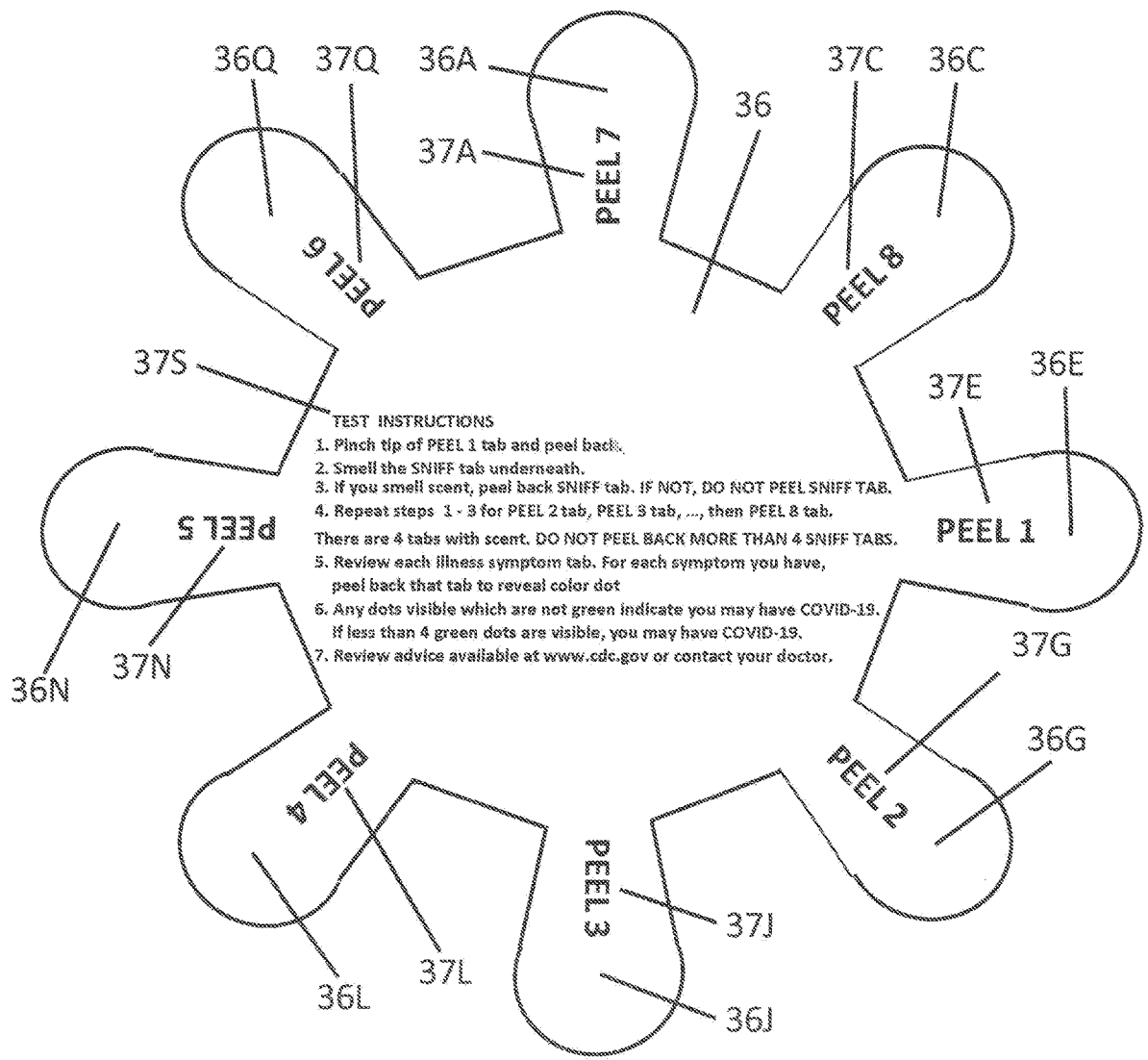
FIG. 28 depicts a top view of a cover of a fourth embodiment of the present device.
Figure 29:
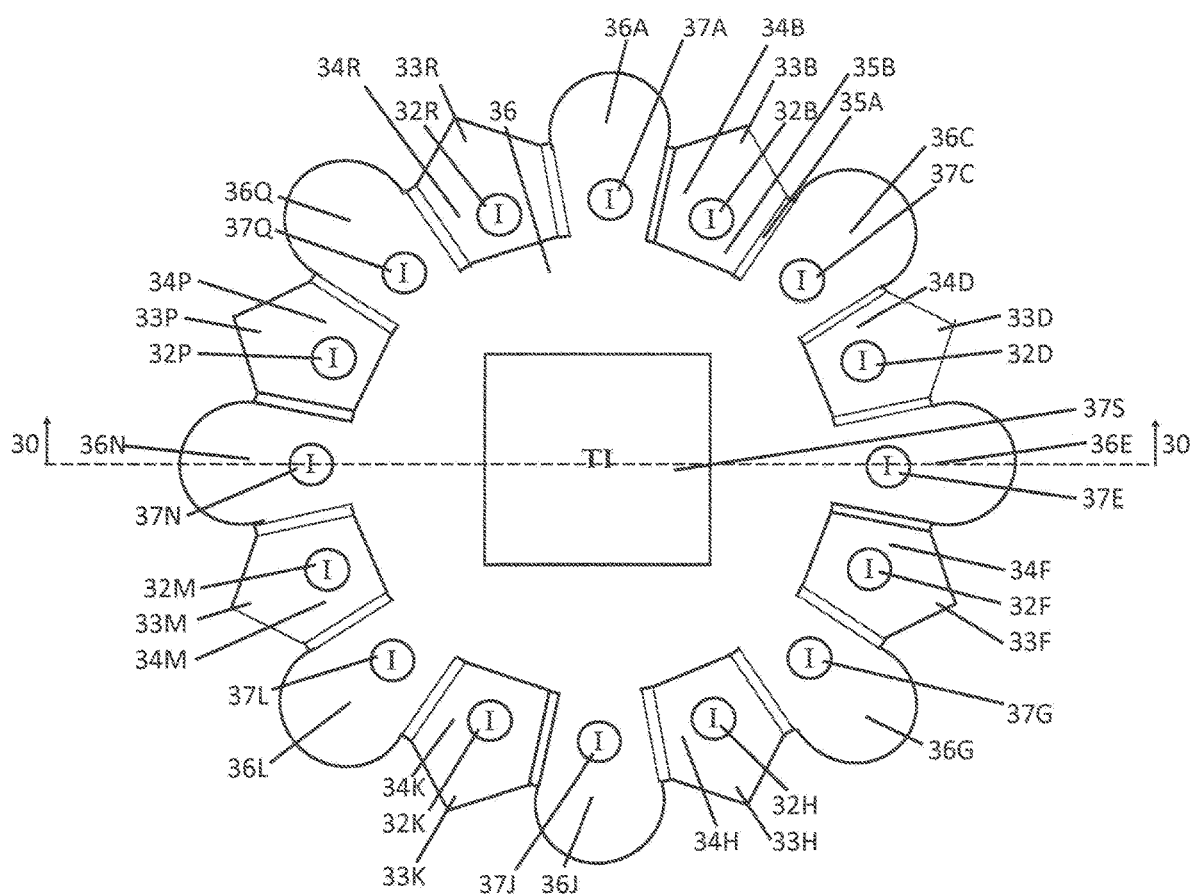
FIG. 29 depicts a top view of a fourth embodiment of the present device.

FIG. 28 depicts a top view of a cover of a fourth embodiment of the present device. In the embodiment shown in FIG. 28, these eight radially aligned tabs can be spaced 45° apart and can be integral to cover 36. Each cover tab indicium 37A, 37C, 37E, 37G, 37J, 37L, 37N, and 37Q can include an identification number which can be referenced in test instructions 37S (symbolized as TI enclosed within a square) which can be printed or embossed onto a top surface of cover 36, as shown in FIG. 29 and FIG. 28. Cover tab Indicium 37A can comprise the phrase PEEL 7, cover tab indicium 37C can comprise the phrase PEEL 8, cover tab indicium 37E can comprise the phrase PEEL 1, cover tab indicium 37G can comprise the phrase PEEL 2, cover tab indicium 37J can comprise the phrase PEEL 3, cover tab indicium 37L can comprise the phrase PEEL 4, cover tab indicium 37N can comprise the phrase PEEL 5, cover tab indicium 37Q can comprise the phrase PEEL 6.

FIG. 29 depicts a top view of a fourth embodiment of the present device. As shown in FIG. 29, a fourth embodiment can simply comprise three manufactured components, as well as one or more odorous substances disposed onto a base. A cover 36 can be disposed onto a top surface of anterior base 35B, as shown in FIG. 29 top view and FIG. 30 cross-section view. A cover 36 can comprise a single piece of bendable material suitable for a punching process, such as paperboard (e.g., folding boxboard, for which the thickness can be in the range of 0.025±0.015 in., which can be capable of being scored and bending without fracture) or any other known and/or convenient material. For cover 36, alternate materials can be used instead, such as, but not limited to, paper having a thickness in the range of 0.0055±0.0045 in., aluminum foil, a polymer suitable for thermoforming process, such as PETG, PET, PVC, styrene, polypropylene, ABS, polycarbonate, HDPE, or a polymer suitable for injection molding process, or any other known and/or convenient material. As shown in FIG. 28 and FIG. 29 top view, cover tab indicium (symbolized as I enclosed within a circle) 37A, 37C, 37E, 37G, 37J, 37L, 37N, and 37Q can be printed or embossed onto a top surface of corresponding cover tabs 36A, 36C, 36E, 36G, 36J, 36L, 36N, and 36Q which can extend radially from cover 36.

FIG. 30 depicts a side cross-sectional view of a fourth embodiment of the present device.

Figure 31:
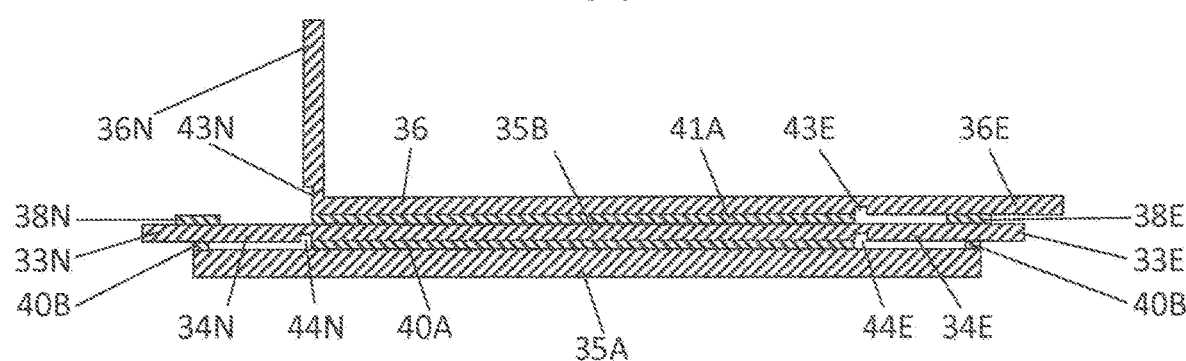
FIG. 31 depicts a side cross-sectional view of a fourth embodiment of the present device.

FIG. 31 depicts a side cross-sectional view of a fourth embodiment of the present device.

Figure 32:
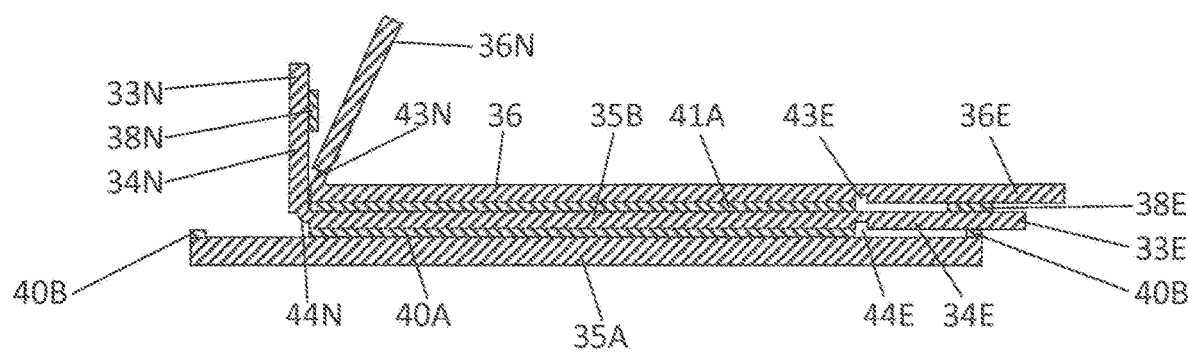
FIG. 32 depicts a side cross-sectional view of a fourth embodiment of the present device.

FIG. 32 depicts a side cross-sectional view of a fourth embodiment of the present device.

Figure 33:
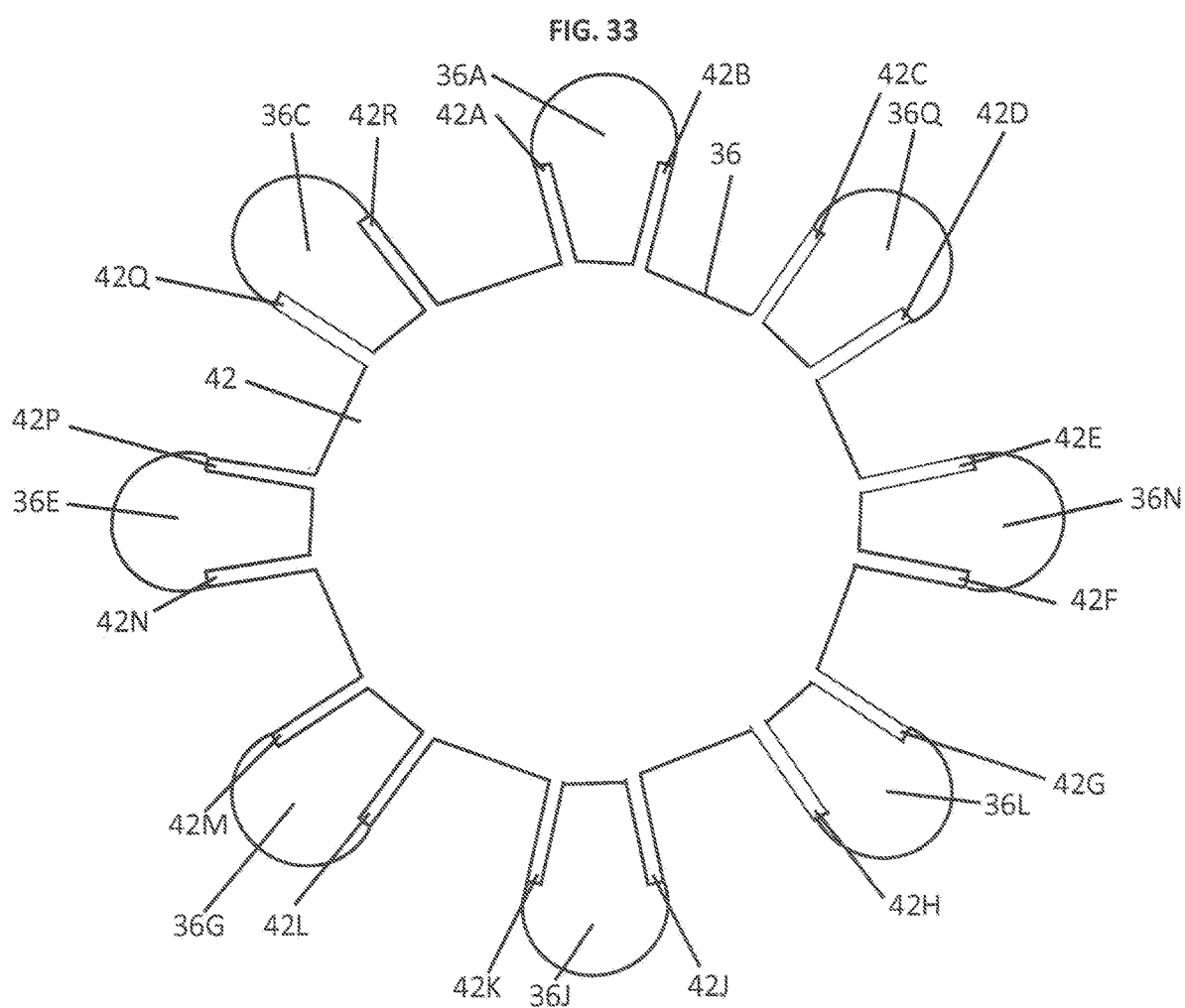
FIG. 33 depicts a bottom view of a cover of a fourth embodiment of the present device.

FIG. 33 depicts a bottom view of a cover of a fourth embodiment of the present device. As shown in FIG. 33, first adhesive layer 42 can include narrow adhesive strips 42A, 42B, 42C, 42D, 42E, 42F, 42G, 42H, 42J, 42K, 42L, 42M, 42N, 42P, 42Q, and 42R which can extend radially on the posterior surface of corresponding cover tabs 36A, 36C, 36E, 36G, 36J, 36L, 36N, 36Q. These narrow adhesive strips can increase the force required to manually peel these cover tabs off corresponding anterior base segments 34A, 34C, 34E, 34G, 34J, 34L, 34N, and 34Q. The force required to manually peel a cover tab off a corresponding anterior base segment can be in the range of approximately 2.25 oz.±1.75 oz., and the first adhesive layer material and shape can be selected accordingly.

Figure 34:
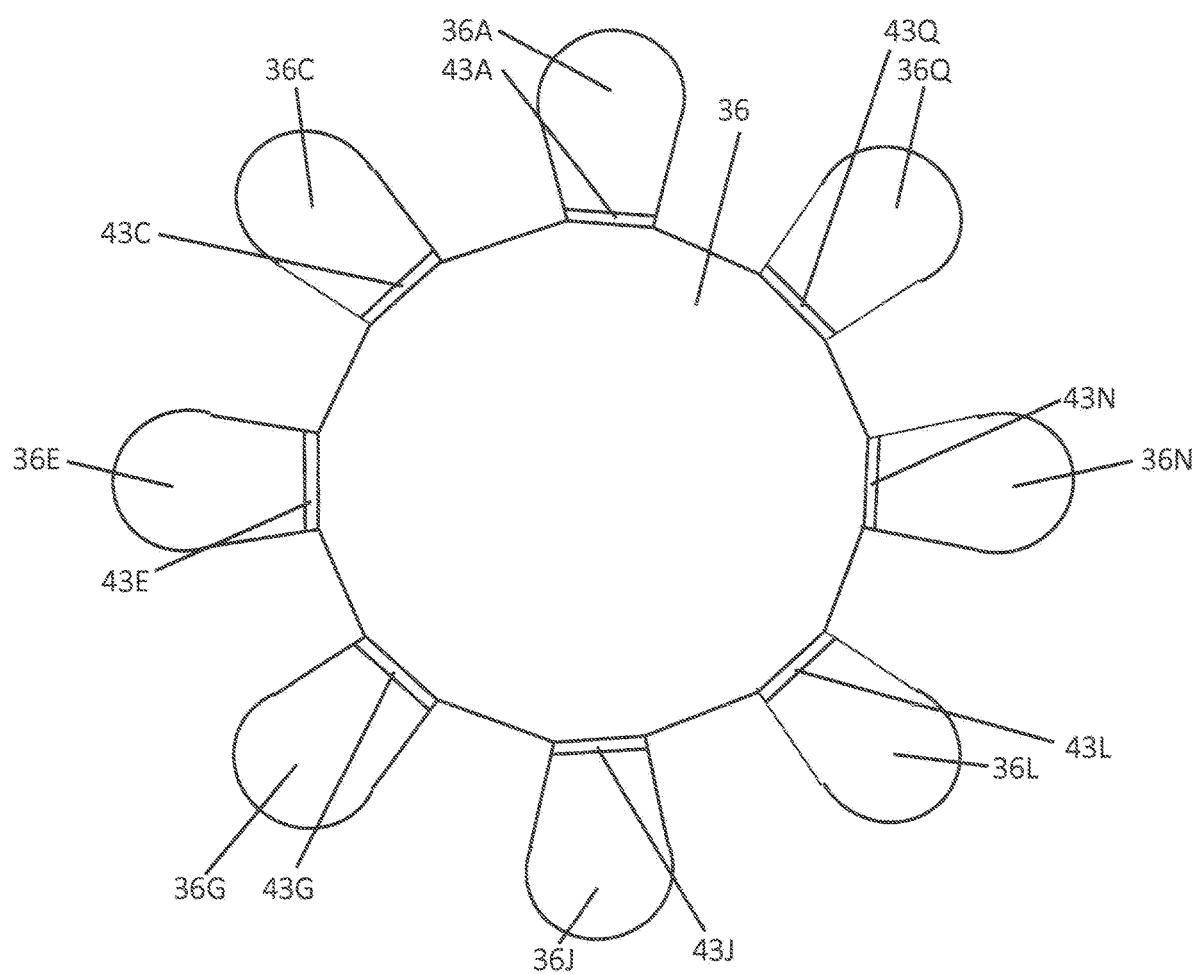
FIG. 34 depicts a bottom view of a cover of a fourth embodiment of the present device.

FIG. 34 depicts a bottom view of cover 36 of fourth embodiment of the present device. As shown in FIG. 34, the bottom surface of cover 36 can comprise cover grooves 43A, 43C, 43E, 43G, 43J, 43L, 43N, and 43Q disposed between corresponding cover tabs 36A, 36C, 36E, 36G, 36J, 36L, 36N, 36Q and the circular central portion of cover 36. Cover groove 43N and cover groove 43E of cover 36 are shown in FIG. 30 sectional view as well. Each cover groove 43A, 43C, 43E, 43G, 43J, 43L, 43N, and 43Q can decrease the force required to manually peel a corresponding cover tab 36A, 36C, 36E, 36G, 36J, 36L, 36N, and 36Q away from anterior base 35B, as shown in FIG. 31 cross-section view of cover tab 36N. As shown in this figure, once cover tab 36N has been manually peeled away from anterior base 35B, smell test substance patch 38N can be exposed.

There can be eight smell test substance patches 38A, 38C, 38E, 38G, 38J, 38L, 38N, and 38Q disposed equidistantly spaced apart on eight corresponding anterior base segments 34A, 34C, 34E, 34G, 34J, 34L, 34N, and 34Q. An additional eight anterior base segments 34B, 34D, 34F, 34H, 34K, 34M, 34P, and 34R can be disposed between these anterior base segments. There can be sixteen anterior base tabs 33A, 33B, 33C, 33D, 33E, 33F, 33G, 33H, 33J, 33K, 33L, 33M, 33N, 33P, 33Q, and 33R that can be contiguous with the outer edge of sixteen corresponding anterior base segments 34A, 34B, 34C, 34D, 34E, 34F, 34G, 34H, 34J, 34K, 34L, 34M, 34N, 34P, 34Q, and 34R, with anterior base gaps 31A, 31B, 31C, 31D, 31E, 31F, 31G, 31H, 31J, 31K, 31L, 31M, 31N, 31P, 31Q, and 31R separating these anterior base segments, as shown in FIG. 27 top view.

Figure 35:
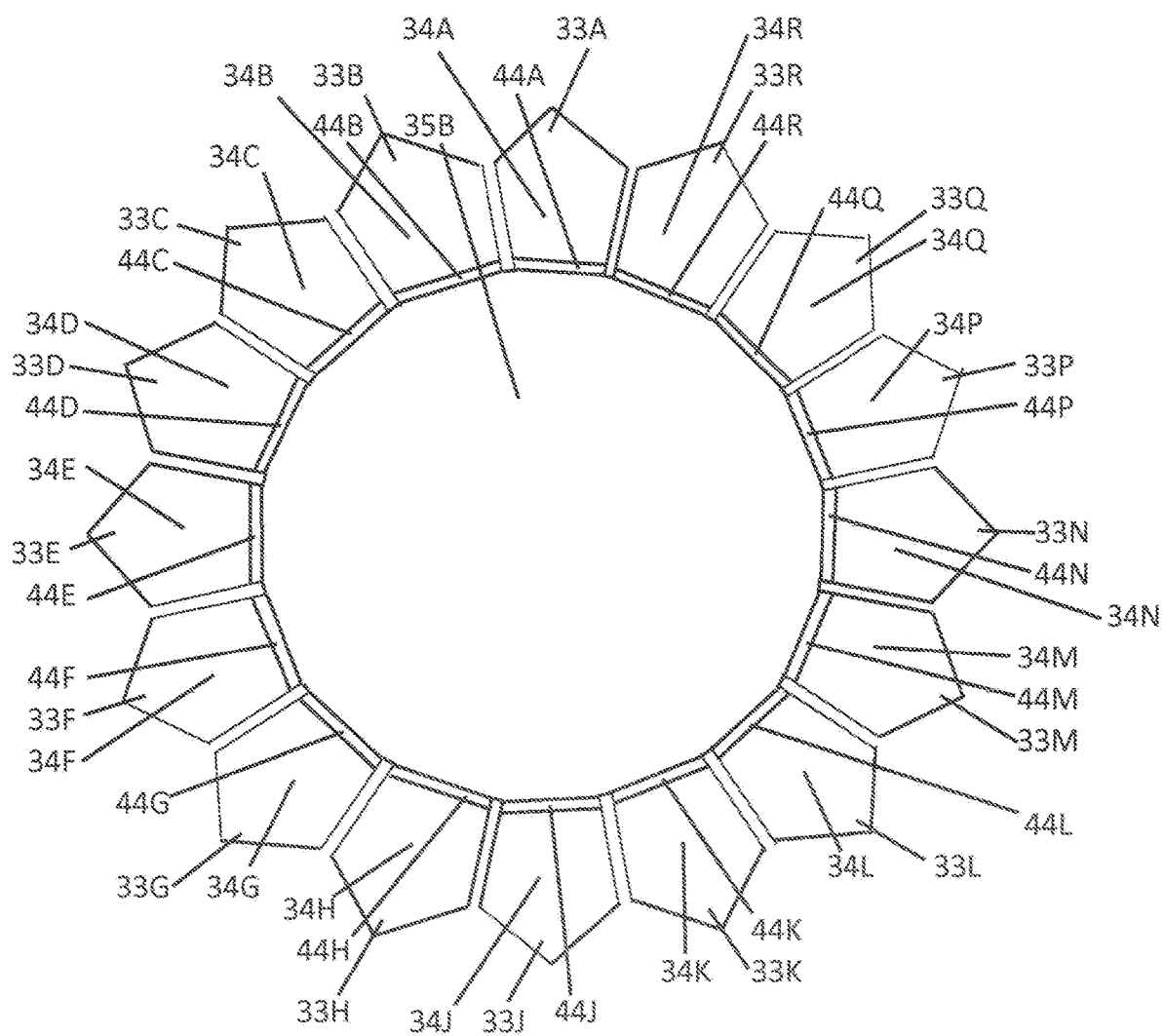
FIG. 35 depicts a bottom view of an anterior base of a fourth embodiment of the present device.

FIG. 35 depicts a bottom view of an anterior base of a fourth embodiment of the present device. As shown in FIG. 35, bottom view of anterior base 35B, there can be anterior base grooves 44A, 44B, 44C, 44D, 44E, 44F, 44G, 44H, 44J, 44K, 44L, 44M, 44N, 44P, 44Q and 44R that can be disposed at the interior perimeter of corresponding anterior base segments 34A, 34B, 34C, 34D, 34E, 34F, 34G, 34H, 34J, 34K, 34L, 34M, 34N, 34P, 34Q, and 34R. Each anterior base groove 44A, 44B, 44C, 44D, 44E, 44F, 44G, 44H, 44J, 44K, 44L, 44M, 44N, 44P, 44Q, and 44R can decrease the force required to manually peel corresponding anterior base tabs 33A, 33B, 33C, 33D, 33E, 33F, 33G, 33H, 33J, 33K, 33L, 33M, 33N, 33P, 33Q, and 33R away from posterior base 35A, as shown in FIG. 32 cross-section assembly view with anterior base tab 33N, anterior base segment 34N peeled away from posterior base 35A.

In this fourth embodiment, smell test substance patches 38A, 38E, 38J, and 38Q can each comprise a unique odorous substance, and smell test substance patches 38C, 38G, 38L, and 38N can all comprise an odorless substance. Numerous companies such as International Fragrances and Flavors® and Scentisphere® create odorous substances disposed on peel and sniff cards, labels, or stickers, known by brand names such as Lift'nSmell™ and Scent-A-Peel®, and certain odorous substances available from such companies can be suitable for these smell test substance patches 34A-R.

The material and surface treatment of cover tabs and anterior base segments can be selected to ensure that the adhesion between each smell test substance patch and the corresponding anterior base segment can be greater than the adhesion between each smell test substance patch and the corresponding cover tab, to ensure that when any cover tab 36A, 36C, 36E, 36G, 36J, 36L, 36N, 36Q is manually peeled away from the corresponding anterior base segment, each smell test substance patch 38A, 38C, 38E, 38G, 38J, 38L, 38N, 38Q can maintain its adherence to the corresponding anterior base segment. As shown in FIG. 27, FIG. 30, FIG. 32, and FIG. 31, first adhesive layer 41A can be disposed between the anterior base 35B and the cover 36. This first adhesive layer 41A can have sufficient adhesion to both an anterior base 35B and a cover 36 to ensure that force required to manually peel cover 36 off of anterior base 35B can be greater than approximately one pound. As shown in FIG. 27, first adhesive layer 41A can have a circular perimeter, and this layer can structurally attach a cover 36 to the anterior base 35B. Alternatively, a first adhesive layer 42 can be disposed between a cover 36 and an anterior base 35B instead to structurally attach these two components, as shown in FIG. 33.

Each of these eight anterior base indicia represents one of eight factors which impact a person's likelihood of having a particular disease, based on medical research. For example, in the May 2020 journal Nature Medicine, researchers discuss the symptoms with the strongest correlation to COVID-19 disease. Based on this journal article, impairment of sense of smell, taste have the strongest correlation to COVID-19 disease. Using a mathematical model, the researchers were able to predict with nearly 80 percent accuracy whether a person was likely to have Covid-19 based on their age, sex and a combination of four symptoms: loss of taste or smell, persistent cough, fatigue and loss of appetite.

In this fourth embodiment, anterior base indicium 32B can comprise the printed or embossed phrase PERSISTENT COUGH, anterior base indicium 32D can comprise the printed or embossed word FATIGUE, anterior base indicium 32F can comprise the printed or embossed phrase LOSS OF APPETITE, anterior base indicium 32H can comprise the printed or embossed phrase MALE, anterior base indicium 32K can comprise the printed or embossed phrase AGE 20-39, anterior base indicium 32M can comprise the printed or embossed phrase AGE 40-59, anterior base indicium 32P can comprise the printed or embossed phrase AGE 60-79, and anterior base indicium 32R can comprise the printed or embossed phrase AGE 80+.

It should be noted that although the cover 36 can be oriented in FIG. 30 and FIG. 29 such that the bottom surface of cover tab 36E can be disposed contiguous with smell test substance patch 38E, this cover 36 alternately can be oriented such that cover tab 36E can be disposed contiguous with any one of the other seven smell test substance patches 38A, 38C, 38G, 38J, 38L, 38N, or 38Q instead. Thus, cover tab indicium 37E, which can comprise the printed or embossed phrase PEEL 1, can correspond to a different smell test substance patch than 38E. In mass production of this fourth embodiment, there can be up to eight different variations of the cover 36 orientation assembled and distributed. Since this test hardware can be used daily to screen people at their workplace, school, or any other known and/or convenient location, multiple variations of this test hardware can be manufactured. This can make it impossible for a person to memorize the relative positions of smell test substance patches with an odor, in order to consistently pass a smell test regardless of whether or not that person develops anosmia or impaired sense of smell eventually.

If posterior base 35A comprises a thermoplastic material instead of paperboard, there can be 4-16 cylindrical bosses disposed perpendicular or in any other known and/or convenient geometry to top surface of posterior base 35A, and these bosses can be integrally molded features of posterior base 35A. After injection molding of posterior base 35A, during assembly these bosses can be inserted into corresponding holes of anterior base 35B and cover 36. Following insertion of these bosses through these holes in anterior base 35B and cover 36, a production heat staking tool can apply compression force at elevated temperature to the protruding ends of all bosses simultaneously to form dome heat stake heads, using a conventional heat staking process or any other known and/or convenient process. Such heat stake features can structurally attach posterior base 35A, anterior base 35B, and cover 36, similar to the heat stake features in the third embodiment. These heat stake features can potentially eliminate the need for circular adhesive layer 40A and first adhesive layer 41A described in the fourth embodiment.

Each posterior base color-coded circular indicium 39A, 39B, 39C, 39D, 39E, 39F, 39G, 39H, 39J, 39K, 39L, 39M, 39N, 39P, 39Q, and 39R disposed on this thermoplastic posterior base 35A can be printed onto the base surface or can be created via a multi-shot injection molding process using thermoplastic polymers of different colors, which is a known process in the plastics molding industry, or any other known and/or convenient process.

The fourth embodiment test instructions 37S shown in FIG. 29 can be disposed on the anterior (top) surface of a cover 36 and can comprise the following text, which can be relevant for COVID-19 disease:
1. Pinch outer tip of PEEL 1 tab and peel back.
2. Smell the SNIFF tab underneath.
3. If you smell scent, peel back SNIFF tab until color dot is fully visible. IF NOT, DO NOT PEEL SNIFF TAB.
4. Repeat steps 1-3 for PEEL 2 tab, PEEL 3 tab, . . . , then PEEL 8 tab. There are 4 tabs with scent. DO NOT PEEL BACK MORE THAN 4 SNIFF TABS TO REVEAL ADDITIONAL COLOR DOTS.
5. Review each illness symptom tab. For each symptom you have, peel back tab until color dot is fully visible.
6. If you are male, peel back MALE tab until color dot is fully visible. NOTE THERE IS NO FEMALE TAB.

7. Select AGE tab with your age range and peel back tab until color dot is fully visible.
8. If there are any red, orange, yellow, or black dots visible, you may have COVID-19. Unless there are 4 green dots visible, you may have COVID-19.
9. Activate COVID-19 symptom checker app on your smart phone, then use phone camera to photograph all visible color dots. This app will estimate likelihood you have COVID-19.

Note that the eight PEEL tabs can be 36A, 36C, 36E, 36G, 36J, 36L, 36N, 36Q in FIG. 29, the eight SNIFF tabs can be 33A, 33C, 33E, 33G, 33J, 33L, 33N, 33Q, the three symptom tabs can be 33B, 33D, 33F, the four AGE tabs can be 33K, 33M, 33P, 33R, and the MALE gender tab can be 33H in FIG. 27 and FIG. 29. It should be noted that the test instructions 37S, the symptoms tabs, the gender tab, and the age tabs can be modified as appropriate for other illnesses.

Figure 36:
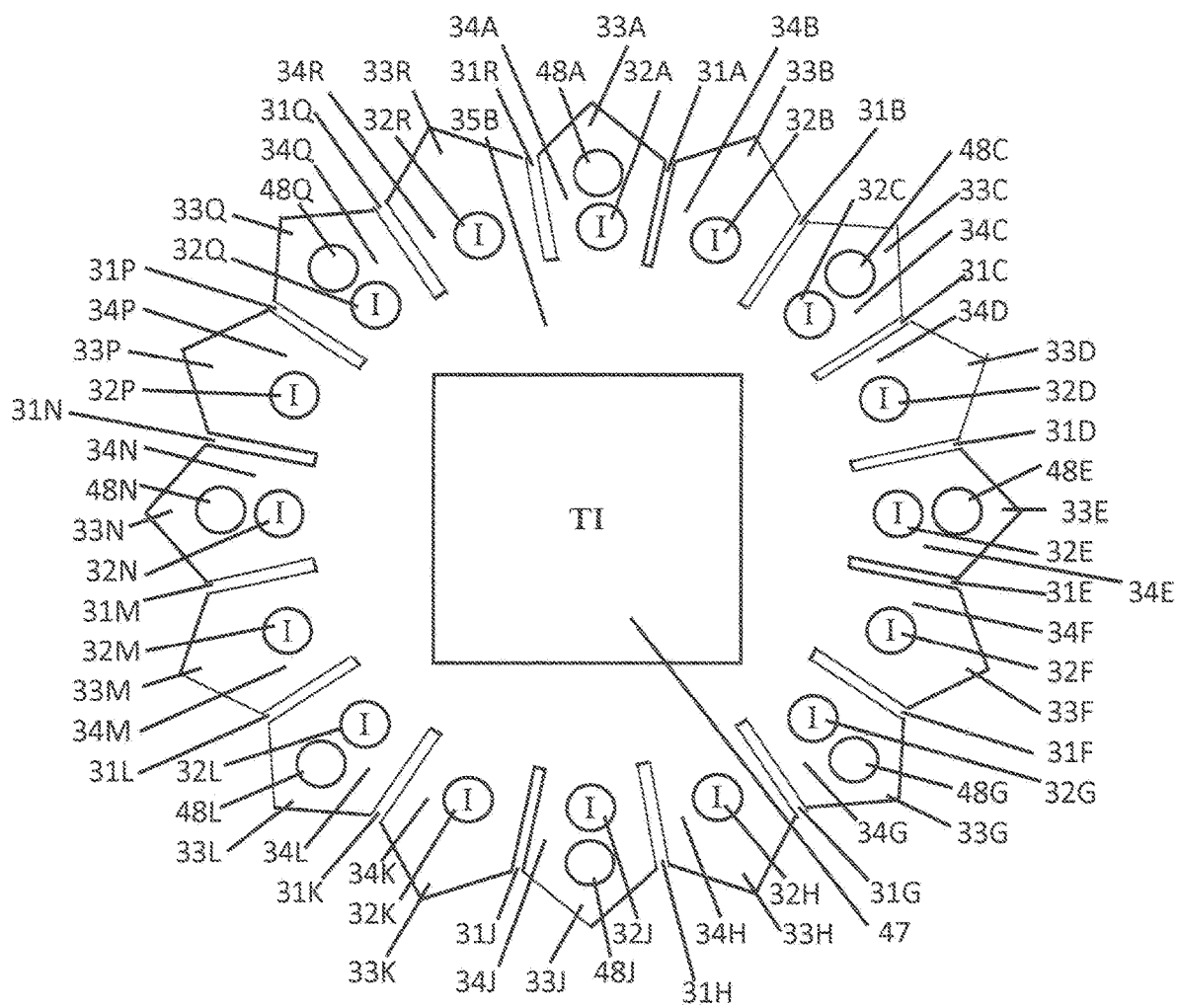
FIG. 36 depicts a top view of an anterior base of a fifth embodiment of the present device.

FIG. 36 depicts a top view of an anterior base of a fifth embodiment of the present device.

Figure 37:
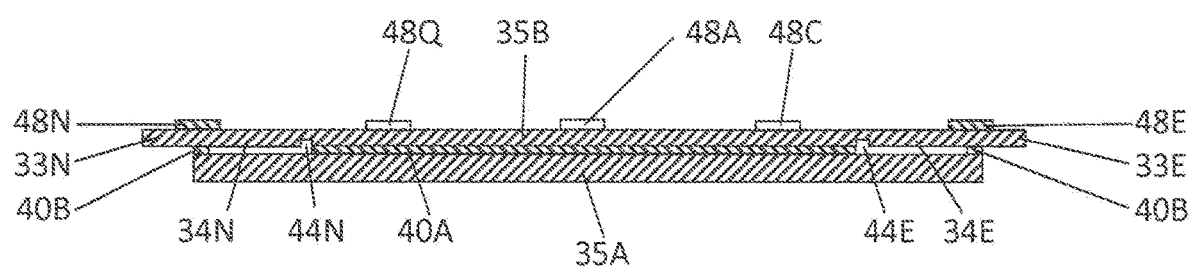
FIG. 37 depicts a side cross-sectional view of a fifth embodiment of the present device.

FIG. 37 depicts a side cross-sectional view of a fifth embodiment of the present device. As shown in FIG. 36 and FIG. 37, eight smell test substance patches 48A, 48C, 48E, 48G, 48J, 48L, 48N, and 48Q can be disposed on a top surface of anterior base 35B, which replace the peel and sniff substances disposed on this base in the fourth embodiment shown in FIG. 26. In this fifth embodiment shown in FIG. 39, smell test substance patches 48A, 48E, 48J, and 48Q can each comprise a unique odorous substance, and smell test substance patches 48C, 48G, 48L, and 48N can all comprise an odorless substance. The anterior base indicium 32A can comprise the printed or embossed word SNIFF 7, anterior base indicium 32C can comprise the printed or embossed word SNIFF 8, anterior base indicium 32E can comprise the printed or embossed word SNIFF 1, anterior base indicium 32G can comprise the printed or embossed word SNIFF 2, anterior base indicium 32J can comprise the printed or embossed word SNIFF 3, anterior base indicium 32L can comprise the printed or embossed word SNIFF 4, anterior base indicium 32N can comprise the printed or embossed word SNIFF 5, and anterior base indicium 32Q can comprise the printed or embossed word SNIFF 6.

Figure 38:
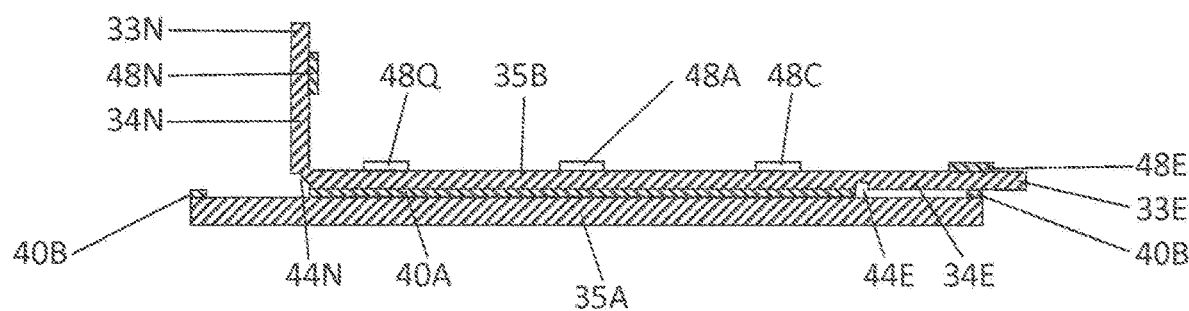
FIG. 38 depicts a side cross-sectional view of a fifth embodiment of the present device.

FIG. 38 depicts a side cross-sectional view of a fifth embodiment of the present device. A difference between anterior base 35B in this fifth embodiment can be that the test instructions 47 printed on anterior base 35B comprise different text than the test instructions 37S printed on cover 36. As shown in FIG. 38 cross section view, a user can manually peel an anterior base segment such as 34N away from posterior base 35A if the user smells an odor from corresponding smell test substance patch 48N. Other than these differences described in this paragraph, anterior base 35B in this fifth embodiment can comprise the same features, design, and materials as this base in the fourth embodiment.

Figure 39:
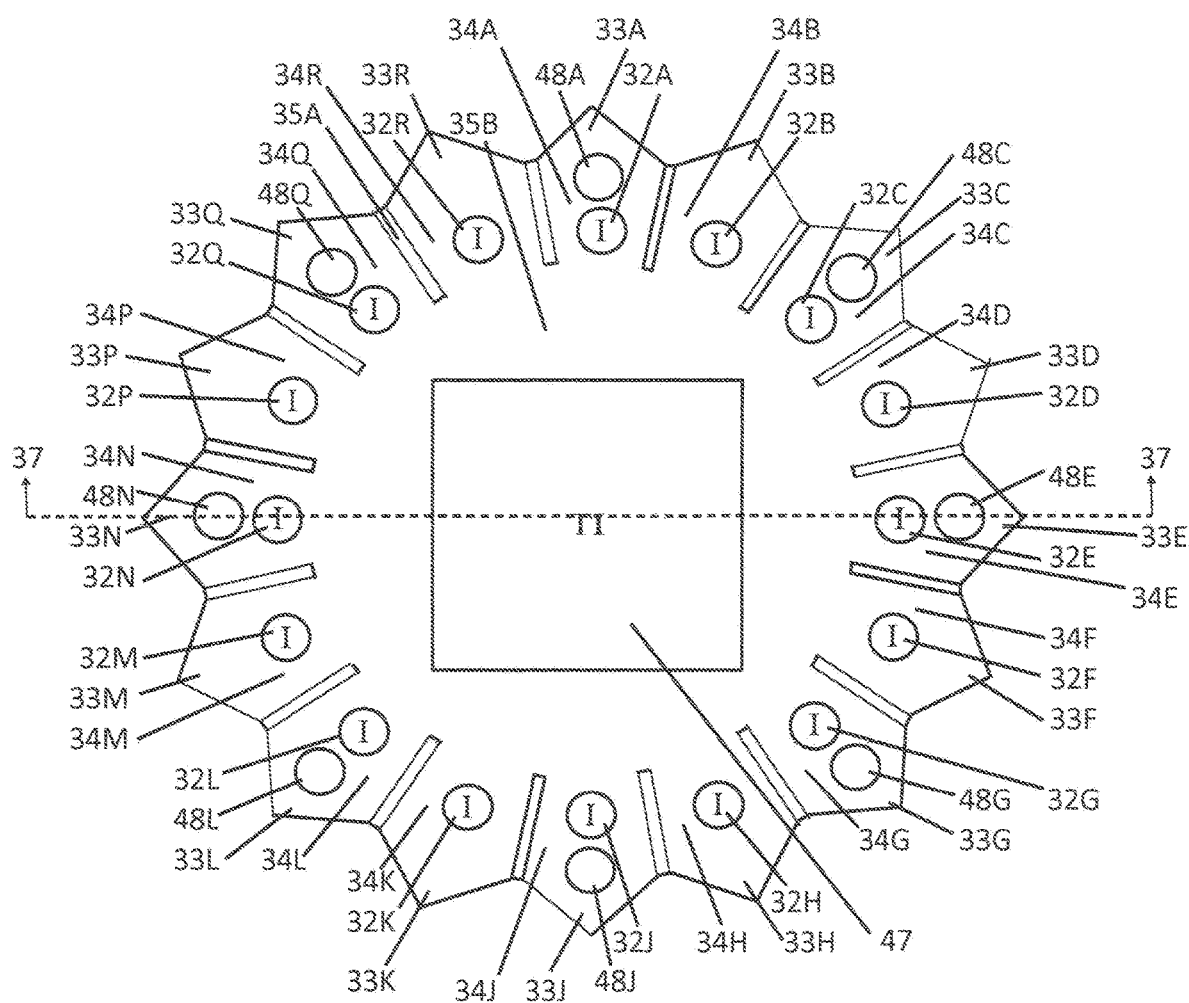
FIG. 39 depicts a top view of a fifth embodiment of the present device.

FIG. 39 depicts a top view of a fifth embodiment of the present device. A fifth embodiment shown in FIGS. 39 and 37 can comprise posterior base 35A and anterior base 35B, similar to the fourth embodiment, although there is no cover 36, unlike the fourth embodiment. In this fifth embodiment, posterior base 35A can be identical to this base in the fourth embodiment, comprising the same features, design, and materials. The primary difference between this fifth embodiment and the fourth embodiment is that the eight smell test substance patches 48A, 48C, 48E, 48G, 48J, 48L, 48N, and 48Q comprise scratch and sniff substances comparable or identical to the substances used in the Smell Identification Test™ (olfactory testing) available from Sensonics International.

Additionally, in "peel and sniff" sampling systems an aroma is released by physically separating two strips of film, paper or other material between which micro encapsulated fragrance has been deposited. Separation of the strips ruptures the microcapsules containing the fragrance, thereby releasing the aroma. In "scratch and sniff" sampling systems an aroma is released when paper, film or other material, to which the micro-encapsulated fragrance has been applied, is scratched or rubbed. The friction generated by the scratching or rubbing ruptures the walls of the microcapsules containing the fragrance, thereby releasing the aroma. Some smell test substance patches disclosed in drawings and descriptions of the various embodiments herein can comprise comparable or identical micro-encapsulated odorous substances or microcapsules containing odorous substances. Other smell test substance patches disclosed in drawings and descriptions of the various embodiments herein can comprise comparable or identical micro-encapsulated odorless substances or microcapsules containing odorless substances. Smell test substance patches in these various embodiments can comprise at least one material which has adhesion properties as well.

The fifth embodiment test instructions 47 shown in FIG. 39 and FIG. 36 can comprise the following text, which can be relevant for COVID-19 disease:

1. Scratch and sniff the substance patch on SNIFF 1 tab.
2. If you smell scent, peel back SNIFF 1 tab until color dot is fully visible. IF NOT, DO NOT PEEL SNIFF TAB.
3. Repeat steps 1 & 2 for SNIFF 2 tab, SNIFF 3 tab, . . . , then SNIFF 8 tab. There are 4 tabs with scent. DO NOT PEEL BACK MORE THAN 4 SNIFF TABS TO REVEAL ADDITIONAL COLOR DOTS.
4. Review each illness symptom tab. For each symptom you have, peel back tab until color dot is fully visible.
5. If you are male, peel back MALE tab until color dot is fully visible. NOTE THERE IS NO FEMALE TAB.
6. Select AGE tab with your age range and peel back tab until color dot is fully visible.
7. If there are any red, orange, yellow or black dots visible, you may have COVID-19. Unless there are 4 green dots visible, you may have COVID-19.
8. Activate COVID-19 symptom checker app on your smart phone, if available, then use phone camera to photograph all visible color dots. This app will estimate likelihood you have COVID-1.

Note that the eight SNIFF tabs can be 33A, 33C, 33E, 33G, 33J, 33L, 33N, and 33Q, the three symptom tabs can be 33B, 33D, and 33F, the four AGE tabs can be 33K, 33M, 33P, and 33R, and the MALE gender tab can be 33H in FIG. 39. It should be noted that the test instructions 47, the symptoms tabs, the gender tab, and the age tabs can be modified as appropriate for other illnesses. It should be noted that the relative positions of some or all of the four smell test substance patches with odor and the four smell test substance patches without odor can be swapped. Any such changes in relative positions of these smell test substance patches can be accompanied by corresponding changes in the green and red color-coded circular indicium positions on posterior base 35A.

Figure 40:
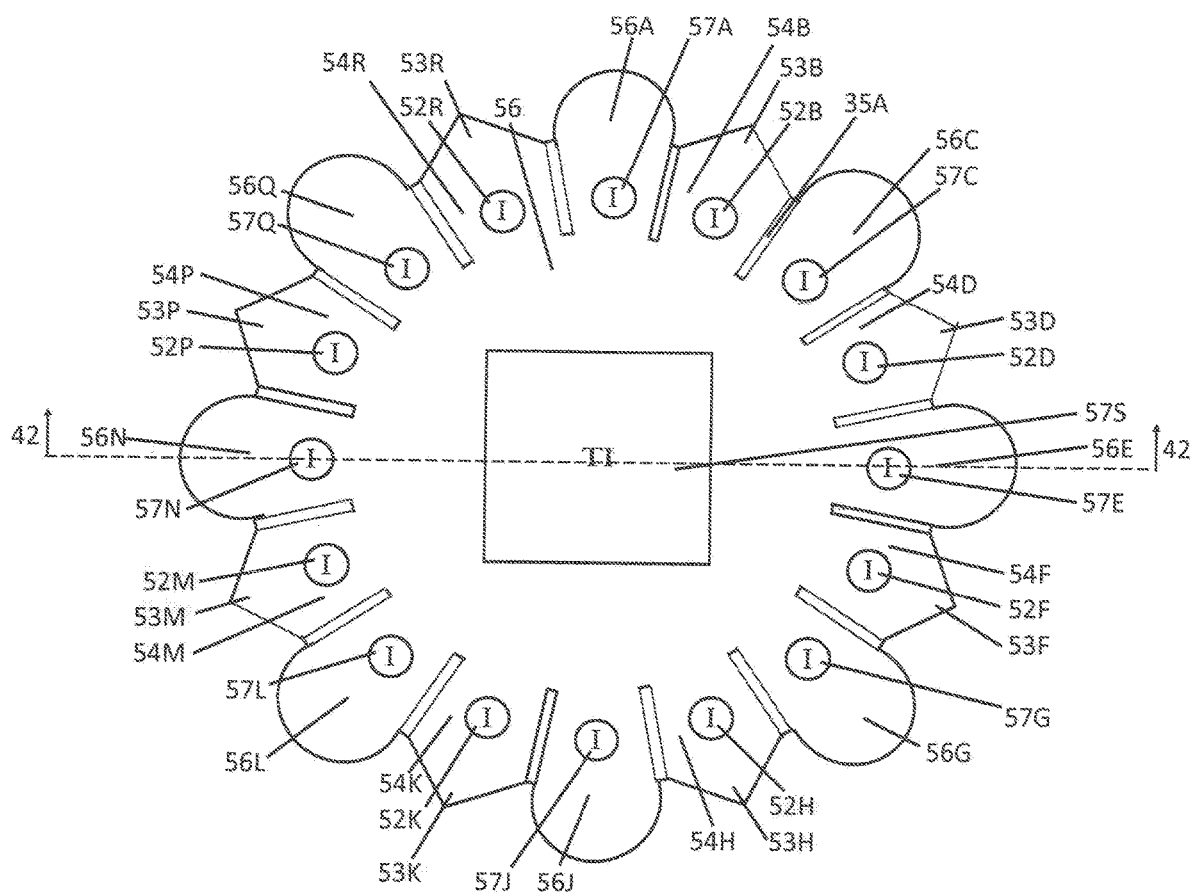
FIG. 40 depicts a top view of a sixth embodiment of the present device.

FIG. 40 depicts a top view of a sixth embodiment of the present device. As shown in FIG. 40, each anterior cover tab 56A, 56C, 56E, 56G, 56J, 56L, 56N, and 56Q can have a corresponding anterior cover tab indicium 57A, 57C, 57E, 57G, 57J, 57L, 57N, and 57Q disposed on an anterior cover tab. Each anterior cover tab indicium 57A, 57C, 57E, 57G, 57J, 57L, 57N, and 57Q can include an identification number which can be referenced in test instructions 57S (symbolized as TI enclosed within a square), which can be printed or embossed onto a top surface of an opaque anterior cover 56, as shown in FIG. 40.

As shown in FIG. 40, opaque anterior cover 56 can comprise anterior cover tabs 53B, 53D, 53F, 53H, 53K, 53M, 53P, and 53R which can be disposed contiguous to corresponding anterior cover tab segment 54B, 54D, 54F, 54H, 54K, 54M, 54P, and 54R. Anterior cover tabs 53B, 53D, 53F, 53H, 53K, 53M, 53P, and 53R in this sixth embodiment have comparable design and function as corresponding anterior base tabs 33B, 33D, 33F, 33H, 33K, 33M, 33P, and 33R in the fourth embodiment discussed earlier. As shown in FIG. 40 top assembly view, opaque anterior cover 56 can also comprise anterior cover indicium 52B, 52D, 52F, 52H, 52K, 52M, 52P, and 52R which can be disposed on corresponding anterior cover tab segment 54B, 54D, 54F, 54H, 54K, 54M, 54P, and 54R. These anterior cover indicia can be printed or embossed on the top surface of the corresponding anterior cover tab segment 54B, 54D, 54F, 54H, 54K, 54M, 54P, and 54R, and each anterior cover indicium 52B, 52D, 52F, 52H, 52K, 52M, 52P, and 52R in this sixth embodiment can comprise an identical word or phrase as the corresponding anterior base indicium 32B, 32D, 32F, 32H, 32K, 32M, 32P, and 32R in the fourth embodiment described earlier.

Figure 41:
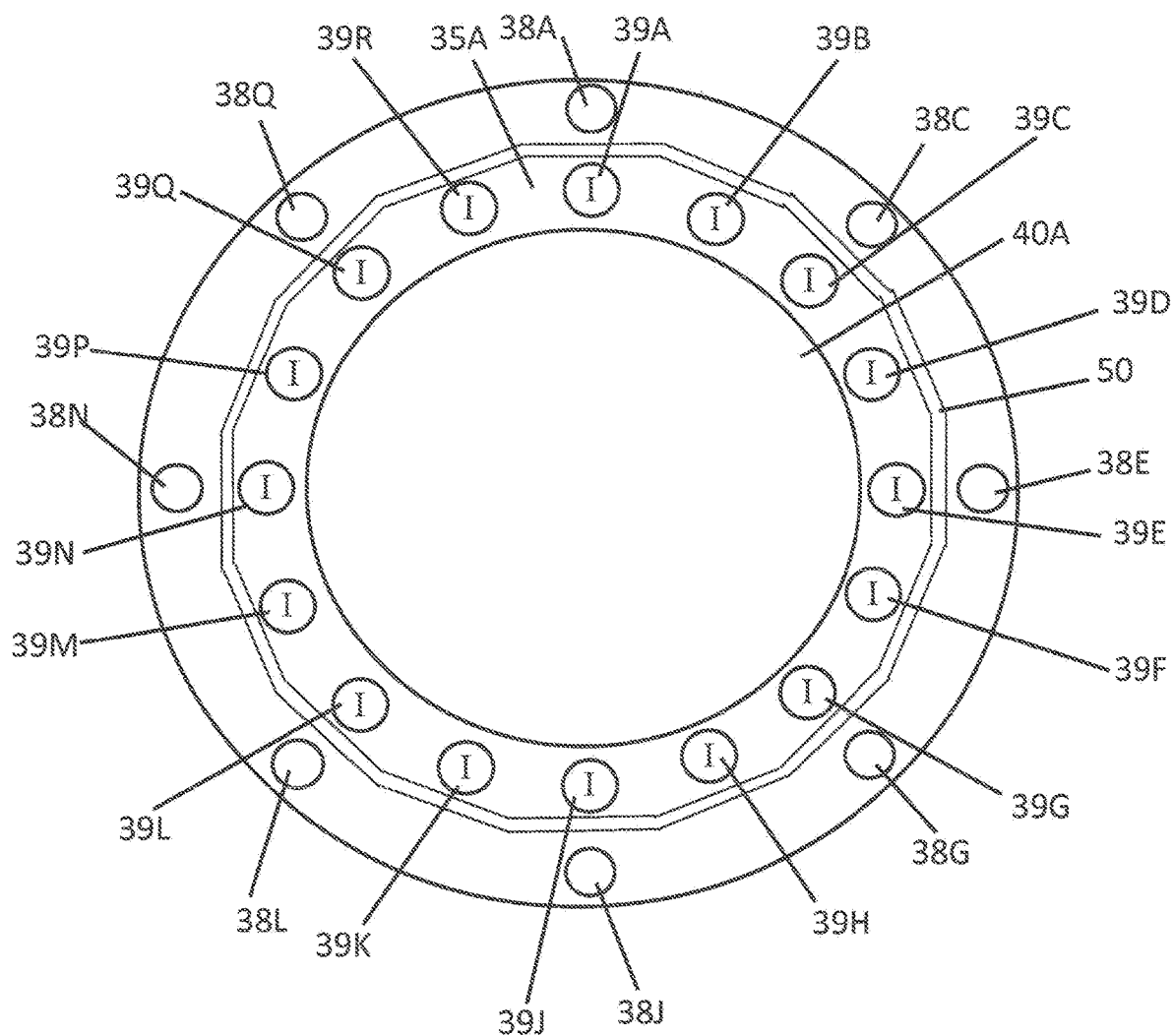
FIG. 41 depicts a top view of a posterior base component of a sixth embodiment of the present device.

FIG. 41 depicts a top view of a posterior base component of a sixth embodiment of the present device. As shown in FIG. 41, eight smell test substance patches 38A, 38C, 38E, 38G, 38J, 38L, 38N, and 38Q can be disposed equidistantly spaced apart on top surface of posterior base 35A, equidistance from the center of this base, or in any other known and/or convenient configuration. These eight smell test substance patches can be substantially identical in function, design, and materials to the eight smell test substance patches in the fourth embodiment, although these eight smell test substance patches in the fourth embodiment can be disposed on anterior base 35B instead.

As shown in FIG. 41, each of the eight smell test substance patches 38A, 38C, 38E, 38G, 38J, 38L, 38N, and 38Q can be radially aligned with a corresponding posterior base color-coded circular indicium 39A, 39C, 39E, 39G, 39J, 39L, 39N, and 39Q also disposed on posterior base 35A. As shown in FIG. 41, a circular adhesive layer 40A and a polygonal adhesive ring 50 can structurally attach posterior base 35A and opaque anterior cover 56. An opaque anterior cover 56 can comprise features similar to some fourth embodiment features of anterior base 35B and features similar to some fourth embodiment features of cover 36. As shown in FIG. 40 top assembly view of sixth embodiment and FIG. 45 bottom view of opaque anterior cover 56, this opaque anterior cover 56 comprises anterior cover tabs 56A, 56C, 56E, 56G, 56J, 56L, 56N, and 56Q which can extend radially from opaque anterior cover 56. These eight radially aligned tabs can be spaced approximately 45° apart and can be integral to opaque anterior cover 56 or in any other known and/or convenient configuration.

Anterior cover tab indicium 57A can comprise the phrase PEEL 7, anterior cover tab indicium 57C can comprise the phrase PEEL 8, anterior cover tab indicium 57E can comprise the phrase PEEL 1, anterior cover tab indicium 57G can comprise the phrase PEEL 2, anterior cover tab indicium 57J can comprise the phrase PEEL 3, anterior cover tab indicium 57L can comprise the phrase PEEL 4, anterior cover tab indicium 57N can comprise the phrase PEEL 5, anterior cover tab indicium 57Q can comprise the phrase PEEL 6. The bottom surface of each anterior cover tab 56A, 56C, 56E, 56G, 56J, 56L, 56N, and 56Q can be contiguous with a corresponding smell test substance patch 38A, 38C, 38E, 38G, 38J, 38L, 38N, and 38Q, such as anterior cover tab 56E and smell test substance patch 38E shown in FIG. 42 cross section assembly view.

Figure 42:
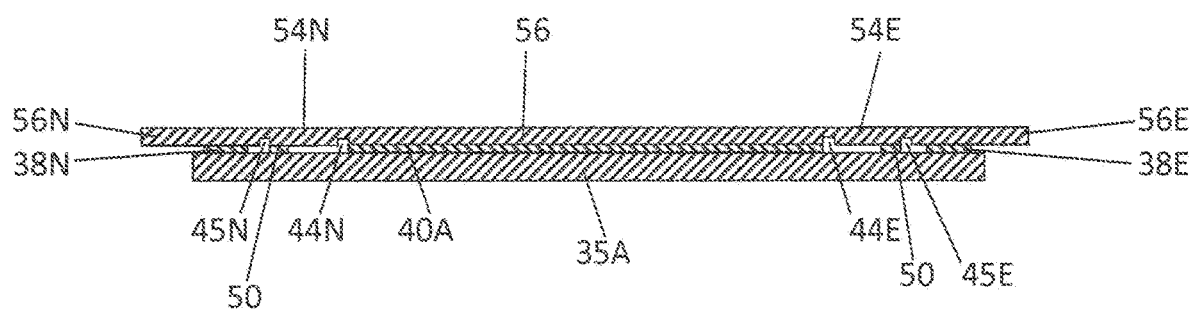
FIG. 42 depicts a side cross-sectional view of a sixth embodiment of the present device.

FIG. 42 depicts a side cross-sectional view of a sixth embodiment of the present device. A sixth embodiment shown in FIGS. 40 and 42 comprises two manufactured components—posterior base 35A and an opaque anterior cover 56. In this sixth embodiment, posterior base 35A can be identical to this base in the fourth embodiment, comprising similar features, design, and materials, with minor exceptions. The posterior base color-coded circular indicium 39A, 39B, 39C, 39D, 39E, 39F, 39G, 39H, 39J, 39K, 39L, 39M, 39N, 39P, 39Q, 39R and circular adhesive layer 40A disposed on this posterior base 35A can be identical to the fourth embodiment in function, design, colors, and materials, as shown in FIG. 41 top view of posterior base 35A. A polygonal adhesive ring 50 shown in FIG. 41 can be identical in function and materials to an annular adhesive layer 40B in the fourth embodiment, although there can be a minor difference in shape between these two adhesive layers.

Figure 43:
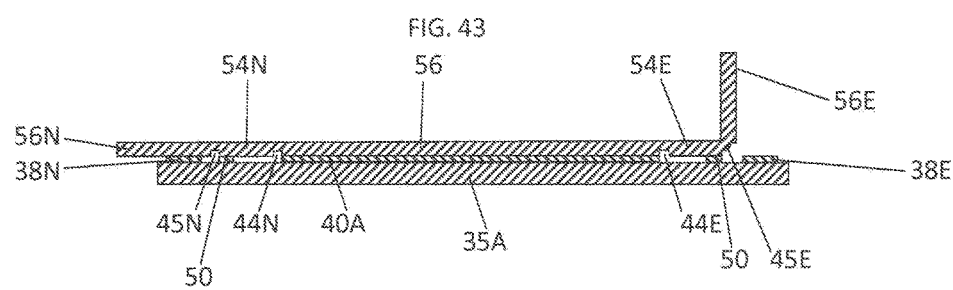
FIG. 43 depicts a side cross-sectional view of a sixth embodiment of the present device.

FIG. 43 depicts a side cross-sectional view of a sixth embodiment of the present device. FIG. 43 depicts an embodiment of an approximate position of anterior cover tab 56E which has been manually (or otherwise) peeled back sufficiently such that smell test substance patch 38E is visible.

Figure 44:
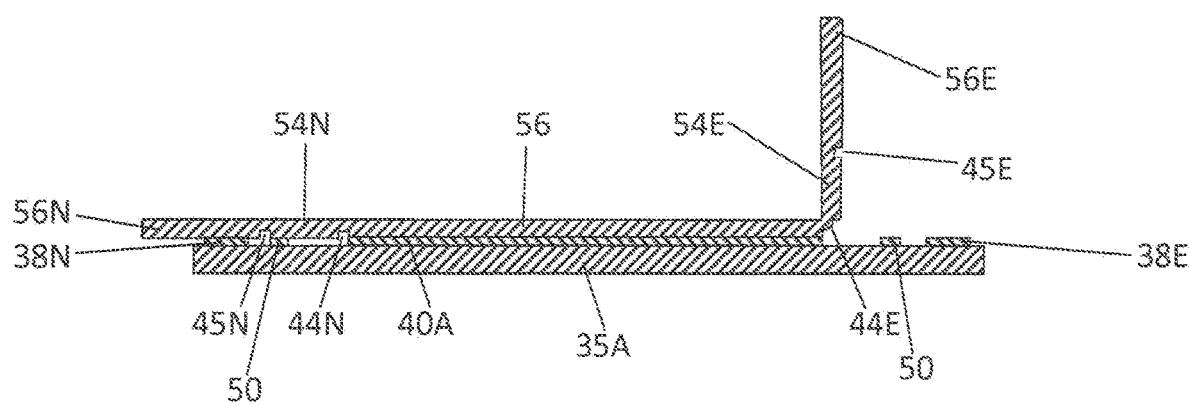
FIG. 44 depicts a side cross-sectional view of a sixth embodiment of the present device.

FIG. 44 depicts a side cross-sectional view of a sixth embodiment of the present device. Similarly FIG. 44 depicts an embodiment of an approximate position of anterior cover tab 56E which has been manually (or otherwise) peeled back sufficiently such that the posterior base color-coded circular indicium 39E is visible. It should be noted that the test instructions 57S, the symptoms tabs, the gender tab, and the age tabs can be modified as appropriate for other illnesses.

Figure 45:
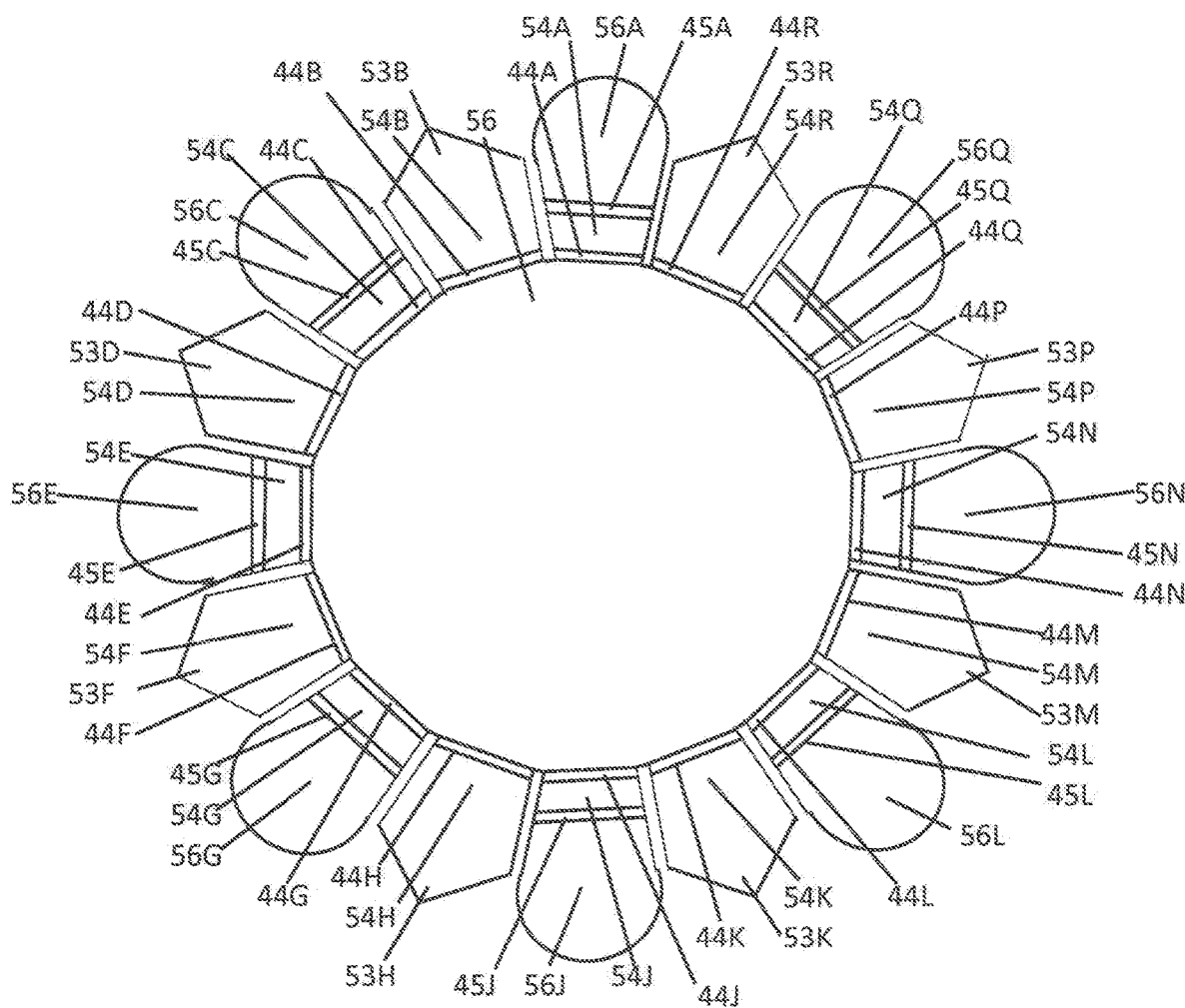
FIG. 45 depicts a bottom view of an anterior cover component of a sixth embodiment of the present device.

FIG. 45 depicts a bottom view of an anterior cover component of a sixth embodiment of the present device. As shown in FIG. 45, opaque anterior cover 56 can comprise sixteen anterior cover grooves 44A, 44B, 44C, 44D, 44E, 44F, 44G, 44H, 44J, 44K, 44L, 44M, 44N, 44P, 44Q, and 44R, which can be each disposed at the inward edge of a corresponding anterior cover tab segment 54A, 54B, 54C, 54D, 54E, 54F, 54G, 54H, 54J, 54K, 54L, 54M, 54N, 54P, 54Q, and 54R. Each of these sixteen anterior cover tab segments can extend radially outward from the central portion of opaque anterior cover 56, and each of anterior cover grooves 44A, 44B, 44C, 44D, 44E, 44F, 44G, 44H, 44J, 44K, 44L, 44M, 44N, 44P, 44Q, and 44R can decrease the bending force required to manually peel the corresponding anterior cover tab segment 54A, 54B, 54C, 54D, 54E, 54F, 54G, 54H, 54J, 54K, 54L, 54M, 54N, 54P, 54Q, and 54R away from posterior base 35A, as shown in FIG. 44 cross section assembly view with anterior cover tab segment 54E peeled away from posterior base 35A.

As shown in FIG. 45, each anterior cover tab 56A, 56C, 56E, 56G, 56J, 56L, 56N, and 56Q can comprise the corresponding anterior cover tab segment as well as a corresponding secondary anterior cover tab groove 45A, 45C, 45E, 45G, 45J, 45L, 45N, and 45Q, which can be disposed between the corresponding anterior cover tab segment and the distal portion of the corresponding anterior cover tab 56A, 56C, 56E, 56G, 56J, 56L, 56N, and 56Q. Each secondary anterior cover tab groove can decrease the bending force required to manually peel the distal portion of the corresponding anterior cover tabs 56A, 56C, 56E, 56G, 56J, 56L, 56N, and 56Q away from posterior base 35A, as shown in FIG. 43 cross section assembly view with the distal portion of anterior cover tab 56E peeled away from posterior base 35A.

This sixth embodiment's opaque anterior cover 56, which can include all features shown in FIG. 45, can comprise the same material as described in the fourth embodiment's anterior base 35B. This sixth embodiment can be manufactured using the same fabrication and assembly processes as described for the fourth embodiment earlier, or any other known and/or convenient process. If posterior base 35A comprises a thermoplastic material instead of paperboard, there can be 4-16 cylindrical bosses disposed substantially perpendicular to top surface of posterior base 35A, and these bosses can be integrally molded features of posterior base 35A. After injection molding of posterior base 35A, during assembly these bosses can be inserted into corresponding openings of opaque anterior cover 56. Following insertion of these bosses through these holes in opaque anterior cover 56, a production heat staking tool can apply compression force at elevated temperature to the protruding ends of all bosses simultaneously to form dome heat stake heads, using a conventional heat staking process or any other known and/or convenient process. Such heat stake features can structurally attach posterior base 35A and opaque anterior cover 56, similar to the heat stake features in the third embodiment described earlier. These heat stake features can potentially eliminate the need for circular adhesive layer 40A.

It should be noted that the relative positions of some or all of the four smell test substance patches with odor and the four smell test substance patches without odor can be swapped. Any such changes in relative positions of these smell test substance patches can be accompanied by corresponding changes in the green and red color-coded circular indicium positions on posterior base 35A. For example, there can be eight versions of this sixth embodiment manufactured, with these smell test substance patch positions swapped. In some alternate embodiments, the positions of all of the smell test substance patches can remain the same on the posterior base 35A, and the positions of some or all of the anterior cover tab indicium 57A, 57C, 57E, 57G, 57J, 57L, 57N, 57Q and the test instructions 57S disposed on opaque anterior cover 56 can be rotated clockwise, relative to the center of posterior base 35A, either 0°, 45°, 90°, 135°, 180°, 225°, 270°, or 315° from their positions (and or by any other known, convenient and/or desired angle) shown in FIG. 40, thereby creating at least eight versions of this sixth embodiment.

The sixth embodiment test instructions 57S shown in FIG. 40 can comprise the following text, which can be relevant for COVID-19 disease:

1. Pinch outer tip of PEEL 1 tab and peel back enough until a circular scent patch is fully visible.
2. Sniff very close to the scent patch.
3. If you smell scent, peel back PEEL 1 tab further until color dot is fully visible underneath. IF NOT, DO NOT PEEL TAB FURTHER
4. Repeat steps 1-3 for PEEL 2 tab, PEEL 3 tab, . . . , then PEEL 8 tab. There are 4 tabs with scent. DO NOT PEEL BACK MORE THAN 4 TABS FURTHER TO REVEAL ADDITIONAL COLOR DOTS.
5. Review each illness symptom tab. For each symptom you have, peel back tab until color dot is fully visible.
6. If you are male, peel back MALE tab until color dot is fully visible. NOTE THERE IS NO FEMALE TAB.
7. Select AGE tab with your age range and peel back tab until color dot is fully visible.
8. If there are any red, orange, yellow, or black dots visible, you may have COVID-19. Unless there are 4 green dots visible, you may have COVID-19.
9. Activate COVID-19 symptom checker app on your smart phone, if available, then use phone camera to photograph all visible color dots together. This app will estimate likelihood you have COVID-19.

Note that the eight PEEL tabs can be anterior cover tabs 56A, 56C, 56E, 56G, 56J, 56L, 56N, 56Q in FIG. 40, the three symptom tabs can be anterior cover tabs 53B, 53D, 53F, the four AGE tabs can be anterior cover tabs 53K, 53M, 53P, 53R, and the MALE gender tab can be anterior cover tab 53H in FIG. 40.

Figure 46:
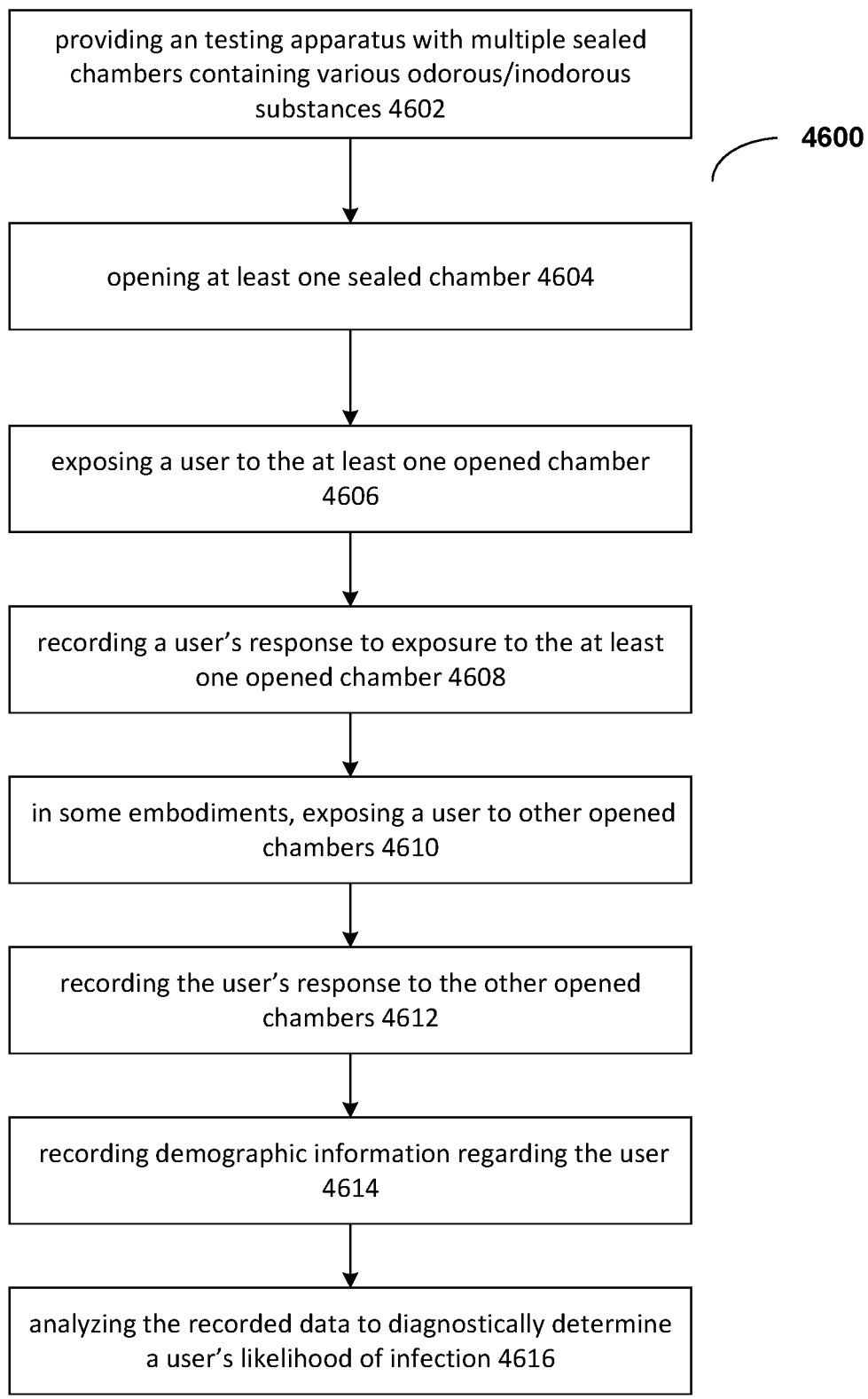
FIG. 46 depicts a flow chart of a method using the present device

FIG. 46 depicts a flow diagram of a method for using 4600 the present disease screening system. In some embodiments, the present system can be used by performing the following steps, providing an testing apparatus with multiple sealed chambers (which can comprise hollowed chambers, scratch-and-sniff type regions, peel-and-sniff type regions and/or any other known convenient and/or desired mechanism adapted and configured to allow a user to selectively sense an odor) containing various odorous or inodorous substances 4602, opening, exposing or activating at least one sealed chamber 4604, exposing a user 4606 to the at least one opened chamber; recording a user's response to exposure to the at least one opened, exposed or activated chamber 4608; in some embodiments, exposing a user to other opened, exposed or activated chambers 4610; recording the user's response to the other opened, exposed or activated chambers 4612; recording demographic information regarding the user 4614 and analyzing the recorded data to diagnostically determine a user's likelihood of infection 4616.

Figure 47:
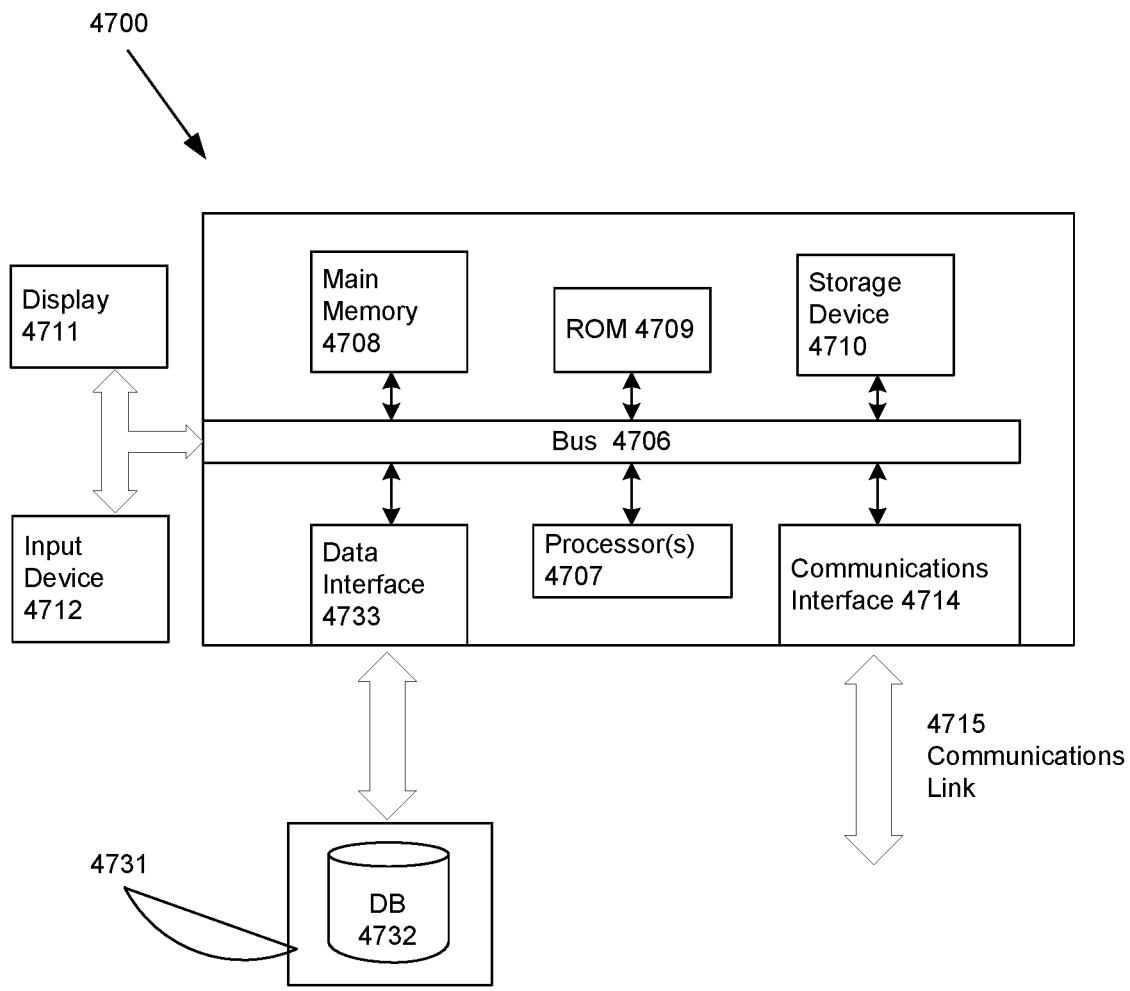
FIG. 47 depicts a schematic drawing of an embodiment of a computer system used in the present device.

FIG. 47 depicts a schematic drawing of an embodiment of a computer system used in the present device. The execution of the sequences of instructions required to practice the embodiments can be performed by a computer system 4700 as shown in FIG. 47. In an embodiment, execution of the sequences of instructions is performed by a single computer system 4700. According to other embodiments, two or more computer systems 4700 coupled by a communication link 4715 can perform the sequence of instructions in coordination with one another. Although a description of only one computer system 4700 will be presented below, however, it should be understood that any number of computer systems 4700 can be employed to practice the embodiments.

A computer system 4700 according to an embodiment will now be described with reference to FIG. 47, which is a block diagram of the functional components of a computer system 4700. As used herein, the term computer system 4700 is broadly used to describe any computing device that can store and independently run one or more programs.

Each computer system 4700 can include a communication interface 4714 coupled to the bus 4706. The communication interface 4714 can provide two-way communication between computer systems 4700. The communication interface 4714 of a respective computer system 4700 transmits and receives electrical, electromagnetic or optical signals, that include data streams representing various types of signal information, e.g., instructions, messages and data. A communication link 4715 links one computer system 4700 with another computer system 4700. For example, the communication link 4715 can be a LAN, in which case the communication interface 4714 can be a LAN card, or the communication link 4715 can be a PSTN, in which case the communication interface 4714 can be an integrated services digital network (ISDN) card or a modem, or the communication link 4715 can be the Internet, in which case the communication interface 4714 can be a dial-up, cable or wireless modem. In some embodiments, test result data can automatically be transmitted to a website which tracks disease data, such as www.cdc.gov. Many wireless devices, including newer mobile models, include software that determines location of the phone. Such location data together with the diagnostic data can be used to detect/determine where COVID-19 or other similar disease hot spots may be developing. This could be particularly valuable in geographic areas where virus detection tests already in use are not yet readily available for mass screening of many people in a geographic area. Moreover, in some embodiment that include interface 4714, two-way communications between computer systems can apply. In alternate embodiments that include interface 4714, one-way communications between computer systems can apply, such as if a mobile computing device with interface 4714 and can transmit user data to www.cdc.gov or another applicable website.

A computer system 4700 can transmit and receive messages, data, and instructions, including program, i.e., application, code, through its respective communication link 4715 and communication interface 4714. Received program code can be executed by the respective processor(s) 4707 as it is received, and/or stored in the storage device 4710, or other associated non-volatile media, for later execution.

In an embodiment, the computer system 4700 operates in conjunction with a data storage system 4731, e.g., a data storage system 4731 that contains a database 4732 that is readily accessible by the computer system 4700. The computer system 4700 communicates with the data storage system 4731 through a data interface 4733. A data interface 4733, which is coupled to the bus 4706, transmits and receives electrical, electromagnetic or optical signals, that include data streams representing various types of signal information, e.g., instructions, messages and data. In embodiments, the functions of the data interface 4733 can be performed by the communication interface 4714.

Computer system 4700 includes a bus 4706 or other communication mechanism for communicating instructions, messages and data, collectively, information, and one or more processors 4707 coupled with the bus 4706 for processing information. Computer system 4700 also includes a main memory 4708, such as a random access memory (RANI) or other dynamic storage device, coupled to the bus 4706 for storing dynamic data and instructions to be executed by the processor(s) 4707. The main memory 4708 also can be used for storing temporary data, i.e., variables, or other intermediate information during execution of instructions by the processor(s) 4707.

The computer system 4700 can further include a read only memory (ROM) 4709 or other static storage device coupled to the bus 4706 for storing static data and instructions for the processor(s) 4707. A storage device 4710, such as a magnetic disk or optical disk, can also be provided and coupled to the bus 4706 for storing data and instructions for the processor(s) 4707.

A computer system 4700 can be coupled via the bus 4706 to a display device 4711, such as, but not limited to, a cathode ray tube (CRT) or a liquid-crystal display (LCD) or light-emitting diode (LED) monitor, for displaying information to a user. An input device 4712, e.g., alphanumeric, other keys, camera or any other known, convenient and/or desired input device can be coupled with the bus 4706 for communicating information and/or command selections to the processor(s) 4707.

According to one embodiment, an individual computer system 4700 performs specific operations by their respective processor(s) 4707 executing one or more sequences of one or more instructions contained in the main memory 4708. Such instructions can be read into the main memory 4708 from another computer-usable medium, such as the ROM 4709 or the storage device 4710. Execution of the sequences of instructions contained in the main memory 4708 causes the processor(s) 4707 to perform the processes described herein. In alternative embodiments, hard-wired circuitry can be used in place of or in combination with software instructions. Thus, embodiments are not limited to any specific combination of hardware circuitry and/or software.

The term "computer-usable medium," as used herein, refers to any medium that provides information or is usable by the processor(s) 4707. Such a medium can take many forms, including, but not limited to, non-volatile, volatile and transmission media. Non-volatile media, i.e., media that can retain information in the absence of power, includes the ROM 4709, CD ROM, magnetic tape, and magnetic discs. Volatile media, i.e., media that cannot retain information in the absence of power, includes the main memory 4708. Transmission media includes coaxial cables, copper wire and fiber optics, including the wires that comprise the bus 4706. Transmission media can also take the form of carrier waves, i.e., electromagnetic waves that can be modulated, as in frequency, amplitude or phase, to transmit information signals. Additionally, transmission media can take the form of acoustic or light waves, such as those generated during radio wave and infrared data communications.

Figure 49:
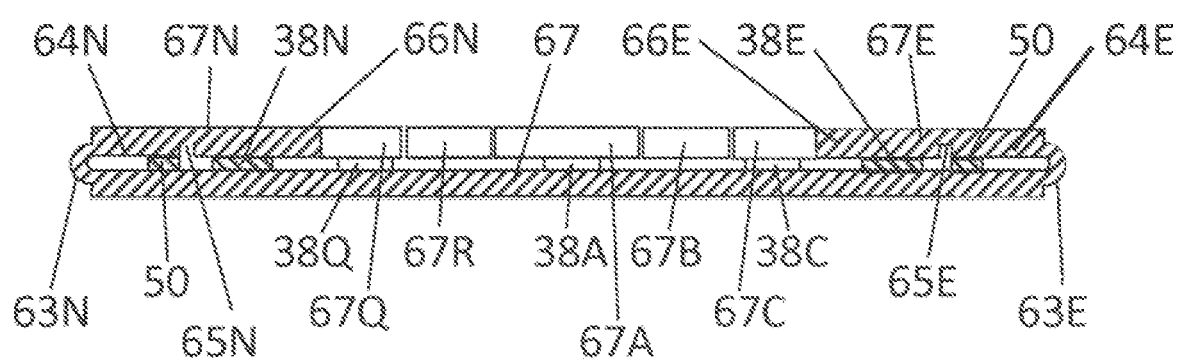
FIG. 49 depicts a side cross-sectional view of a seventh embodiment of the present device.

FIG. 49 depicts a side cross-sectional view of a seventh embodiment of the present device. In some embodiments, each of the eight smell test substance patches 38A, 38C, 38E, 38G, 38J, 38L, 38N, and 38Q can be contiguous with both the top surface of the posterior base/anterior cover 67 and the surface of the corresponding distal base/cover tab region 66A, 66C, 66E, 66G, 66J, 66L, 66N, and 66Q, as shown in FIG. 49. Again, in some embodiments, the surface finish or treatment of the distal base/cover tab regions can be different than the surface finish or treatment of the circular central region of the posterior base/anterior cover 67 such that whenever a distal base/cover tab region is manually (or otherwise) peeled away from the circular central region of the posterior base/anterior cover 67, the adhesion between any smell test substance patch and the circular central region of the posterior base/anterior cover 67 is greater than the adhesion between the any smell test substance patch and the corresponding distal base/cover tab region. This surface finish or treatment difference can aid in ensuring that any smell test substance patch remain attached to the circular central region of the posterior base/anterior cover 67 after one or more distal base/cover tab regions is manually (or otherwise) peeled away. This seventh embodiment can be manufactured using many of the same fabrication and assembly processes as described for the sixth embodiment, herein.

FIG. 49 depicts a side cross-sectional view of a seventh embodiment of the present device.

Figure 50:
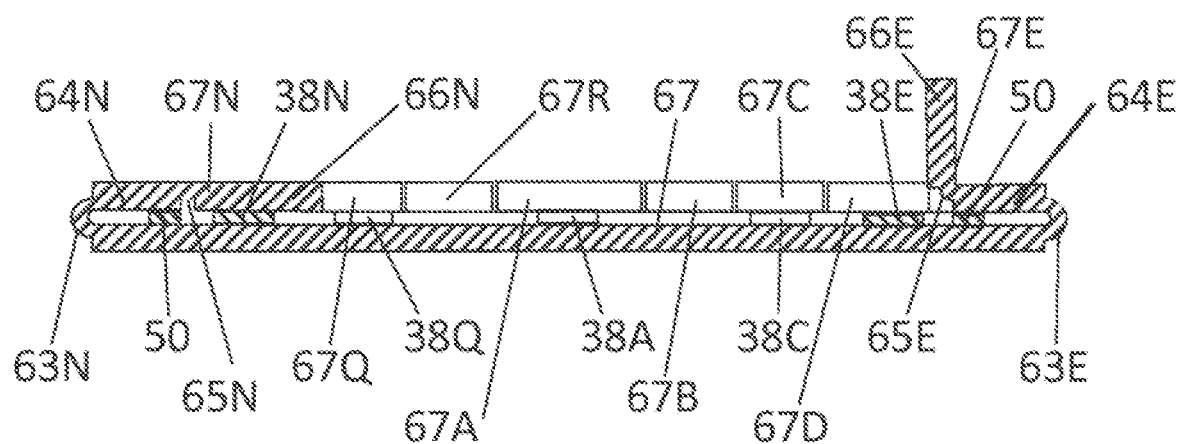
FIG. 50 depicts a side cross-sectional view of a seventh embodiment of the present device.

FIG. 50 depicts a side cross-sectional view of a seventh embodiment of the present device.

Figure 51:
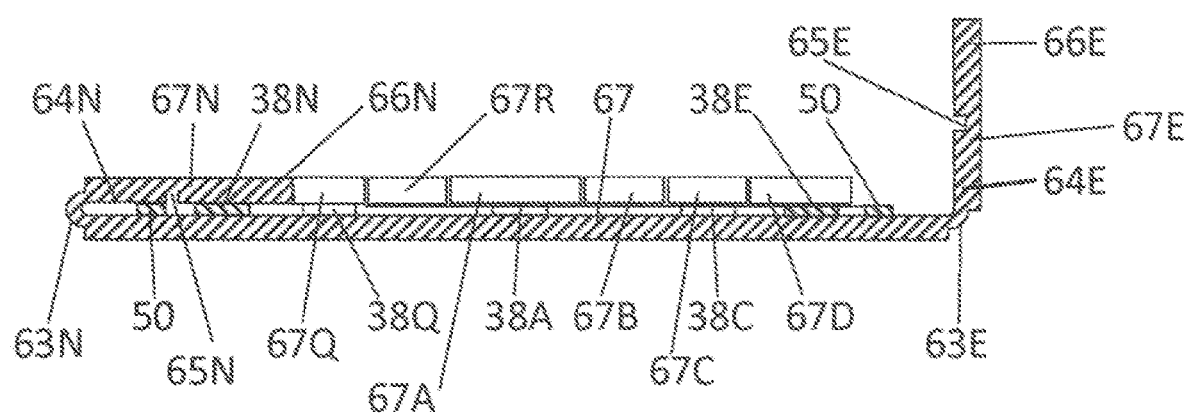
FIG. 51 depicts a side cross-sectional view of a seventh embodiment of the present device.

FIG. 51 depicts a side cross-sectional view of a seventh embodiment of the present device.

Figure 52:
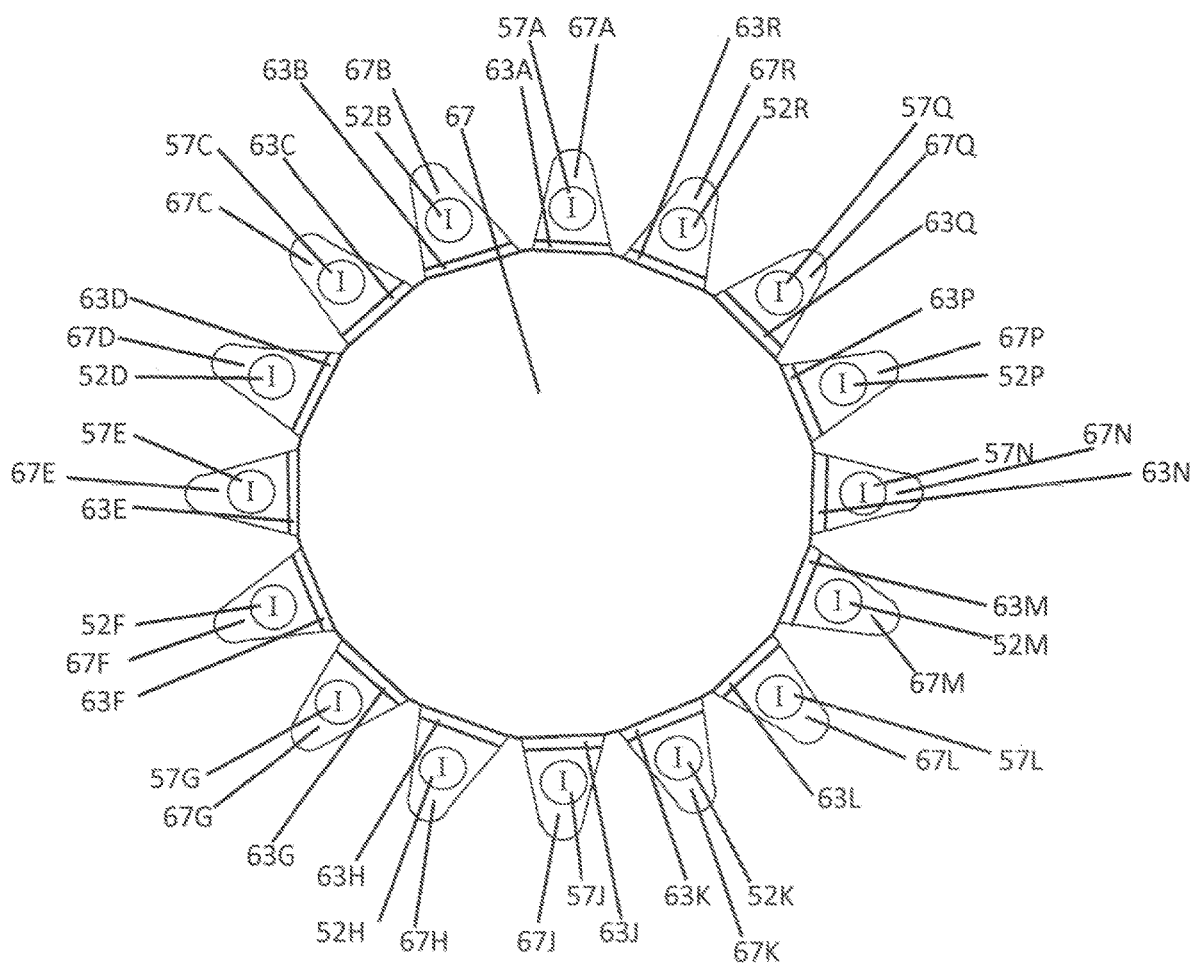
FIG. 52 depicts a bottom view of a posterior base/anterior cover component of a seventh embodiment of the present device prior to folding operation during manufacturing.

FIG. 52 depicts a bottom view of a posterior base/anterior cover component of a seventh embodiment of the present device prior to folding operation during manufacturing. As depicted in FIG. 52, sixteen base/cover tabs 67A, 67B, 67C, 67D, 67E, 67F, 67G, 67H, 67J, 67K, 67L, 67M, 67N, 67P, 67Q, and 67R can extend radially from the central portion of posterior base/anterior cover 67 and each can have a corresponding primary base/cover tab groove 63A, 63B, 63C, 63D, 63E, 63F, 63G, 63H, 63J, 63K, 63L, 63M, 63N, 63P, 63Q, and 63R disposed contiguous with the inner border of each base/cover tab. These sixteen base/cover tabs, or a portion thereof, can be integral with the posterior base/anterior cover 67, and they can each extend radially outward from the substantially circular central region of the posterior base/anterior cover 67. In some embodiments, each of these sixteen base/cover tabs can comprise a corresponding proximal base/cover tab region 64A, 64B, 64C, 64D, 64E, 64F, 64G, 64H, 64J, 64K, 64L, 64M, 64N, 64P, 64Q, and 64R and a corresponding distal base/cover tab region 66A, 66B, 66C, 66D, 66E, 66F, 66G, 66H, 66J, 66K, 66L, 66M, 66N, 66P, 66Q, and 66R, with a corresponding secondary base/cover tab groove 65A, 65B, 65C, 65D, 65E, 65F, 65G, 65H, 65J, 65K, 65L, 65M, 65N, 65P, 65Q, and 65R disposed between the distal region and proximal region of each base/cover tabs 67A, 67B, 67C, 67D, 67E, 67F, 67G, 67H, 67J, 67K, 67L, 67M, 67N, 67P, 67Q, and 67R, as shown in FIG. 52 and FIG. 53.

Figure 53:
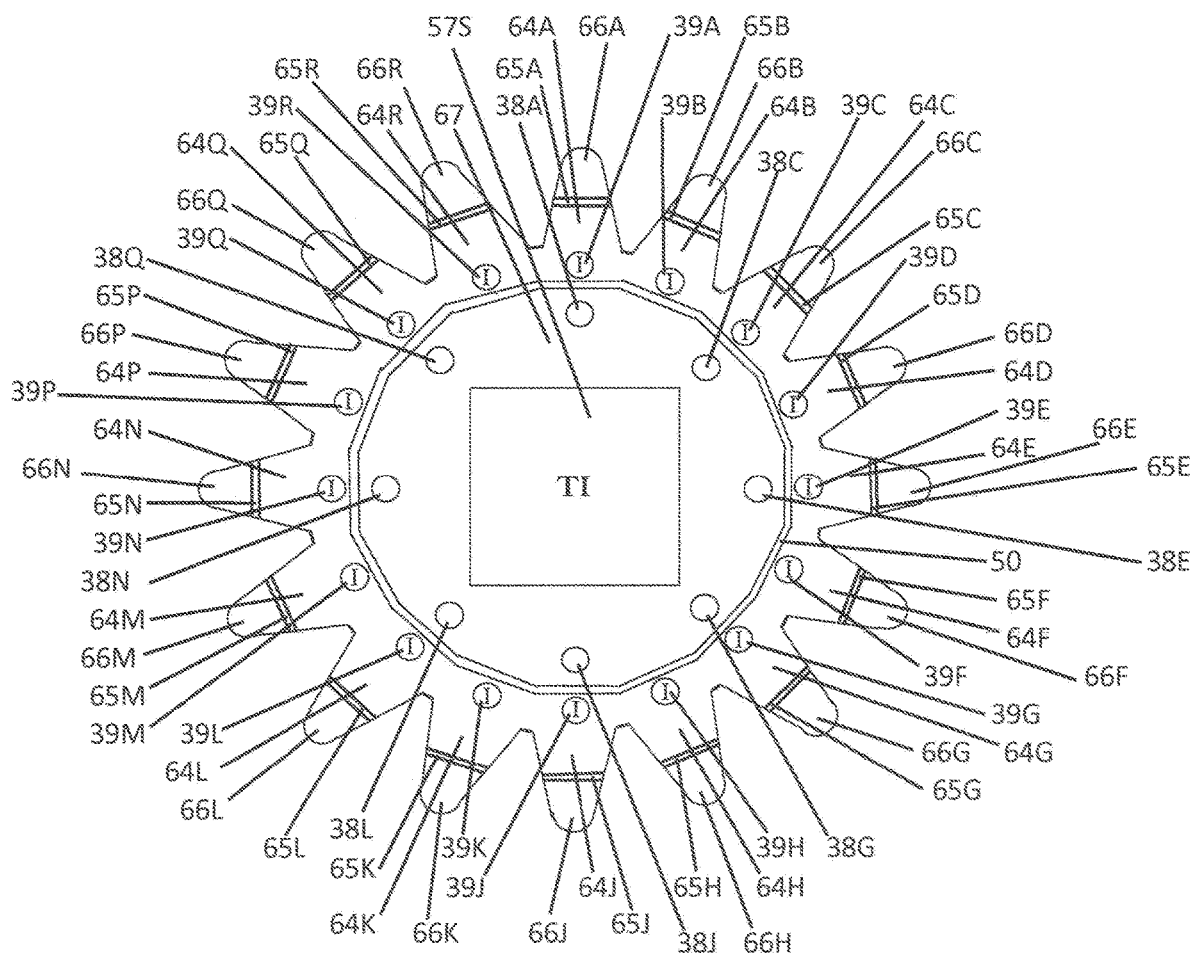
FIG. 53 depicts a top view of a seventh embodiment of the present device prior to folding operation during manufacturing.

FIG. 53 depicts a top view of a seventh embodiment of the present device prior to folding operation during manufacturing. As depicted in FIG. 53, in some embodiments, eight smell test substance patches 38A, 38C, 38E, 38G, 38J, 38L, 38N, and 38Q can be disposed equidistantly spaced apart on the top surface of posterior base/anterior cover 67, equidistant from the center of this component. However, in alternate embodiments, any known, convenient and/or desired spacing can be employed. Moreover, in still further alternate embodiments any known, convenient and/or desired quantity of smell test substance patches can be employed. In the embodiment depicted in the seventh embodiment, the eight smell test substance patches can be identical in function, design, and materials to the eight smell test substance patches disposed on the posterior base 35A in the sixth embodiment. As depicted in FIG. 53, each of the eight smell test substance patches 38A, 38C, 38E, 38G, 38J, 38L, 38N, and 38Q can be radially aligned with a corresponding posterior base color-coded circular indicium 39A, 39C, 39E, 39G, 39J, 39L, 39N, and 39Q, with a polygonal adhesive ring 50 disposed between the posterior base color-coded circular indicium and the eight smell test substance patches.

As depicted in FIG. 52, base/cover tab 67A, 67C, 67E, 67G, 67J, 67L, 67N, and 67Q can each have a corresponding anterior cover tab indicium 57A, 57C, 57E, 57G, 57J, 57L, 57N, and 57Q disposed on that base/cover tab, identical or substantially similar to the indicia shown in FIG. 40 of the sixth embodiment. In some embodiments, each anterior cover tab indicium 57A, 57C, 57E, 57G, 57J, 57L, 57N, and 57Q can comprise an identification number which is referenced in test instructions 57S (symbolized as TI enclosed within a square), which can be printed or embossed onto the top surface of posterior base/anterior cover 67, as shown in FIG. 54.

As depicted in FIG. 52, posterior base/anterior cover 67 comprises anterior cover indicium 52B, 52D, 52F, 52H, 52K, 52M, 52P, and 52R which can be disposed on corresponding base/cover tabs 67B, 67D, 67F, 67H, 67K, 67M, 67P, and 67R. In some embodiments, the anterior cover indicium can be printed or embossed on the surface of the corresponding base/cover tabs 67B, 67D, 67F, 67H, 67K, 67M, 67P, and 67R as shown in FIG. 52 and FIG. 54 and each anterior cover indicium 52B, 52D, 52F, 52H, 52K, 52M, 52P, and 52R in this embodiment can comprise identical word(s) or phrase(s) to the corresponding anterior base indicium 32B, 32D, 32F, 32H, 32K, 32M, 32P, and 32R in the fourth embodiment as more fully described herein.

FIG. 53 depicts a top view of a seventh embodiment of the present device prior to folding operation during manufacturing.

Figure 48:
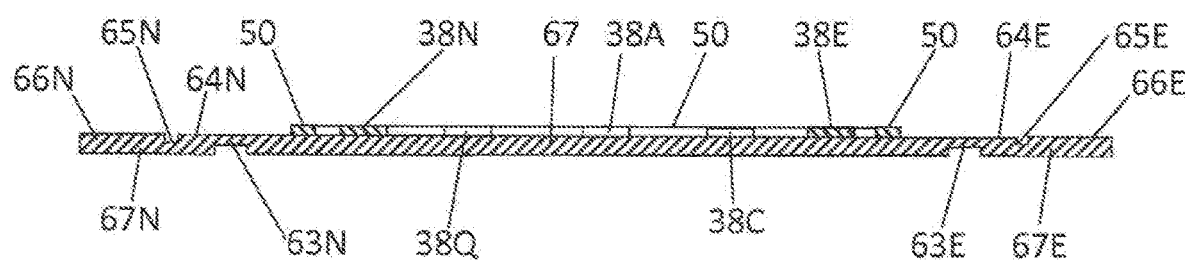
FIG. 48 depicts a side cross-sectional view of a posterior base/anterior cover component of a seventh embodiment of the present device, after deposition of smell test patches and adhesive, prior to folding operation during manufacturing.
Figure 54:
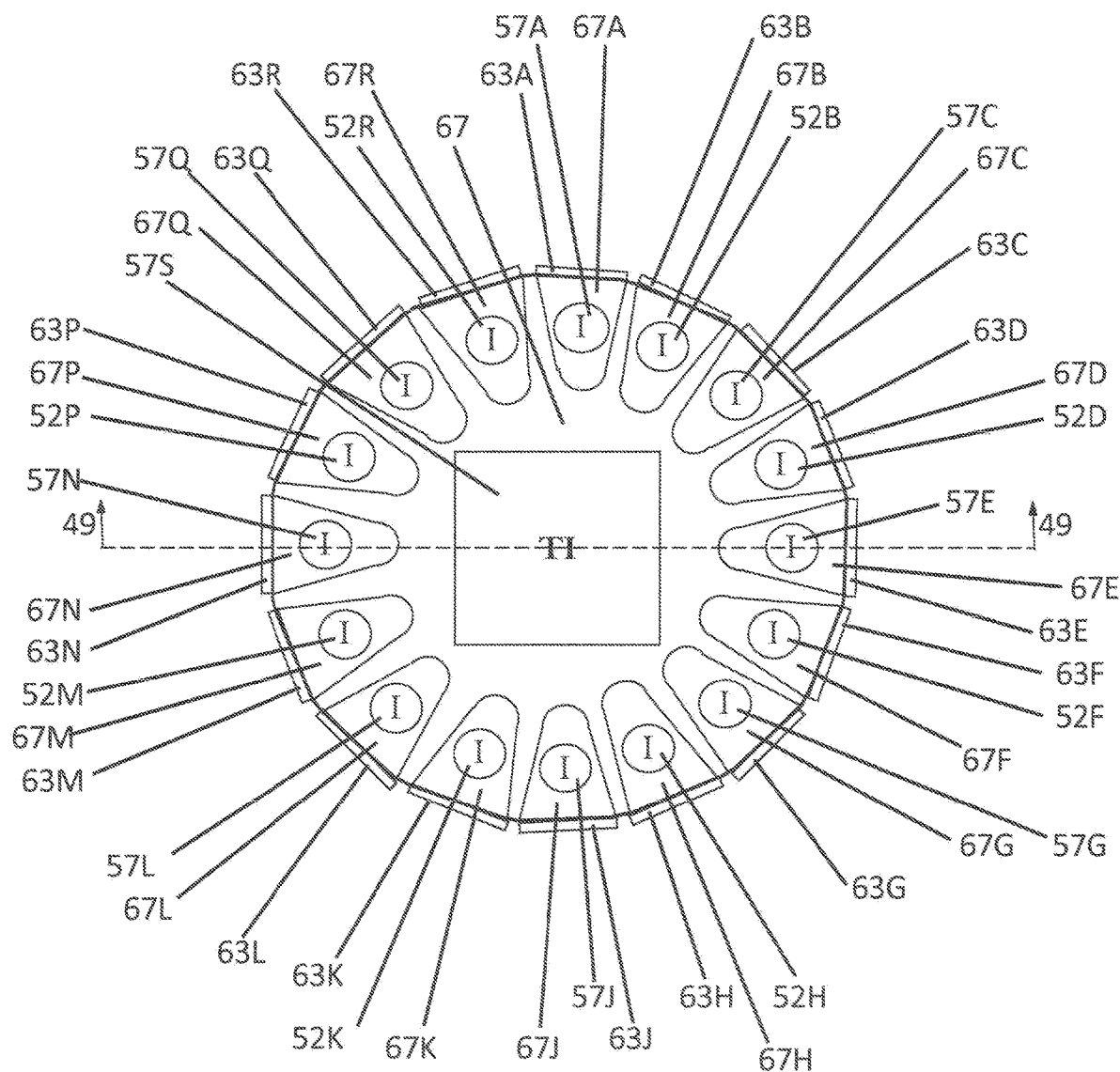
FIG. 54 depicts a top view of a seventh embodiment of the present device.

FIG. 54 depicts a top view of a seventh embodiment of the present device. A seventh embodiment depicted in FIG. 54 top assembly view and FIG. 49 cross section view, can comprise one manufactured component—posterior base/anterior cover 67. The seventh embodiment can comprise many of the same features as the sixth embodiment, with similar functionality, and comprise similar or identical design, colors, indicia, and materials. In some embodiments of the seventh embodiment, prior to final assembly, the posterior base color-coded circular indicium 39A, 39B, 39C, 39D, 39E, 39F, 39G, 39H, 39J, 39K, 39L, 39M, 39N, 39P, 39Q, 39R, the polygonal adhesive ring 50, and test instructions 57S can be disposed on a top surface of the posterior base/anterior cover 67, as shown in FIG. 53 top view and FIG. 48 cross section view of posterior base/anterior cover 67 prior to base/cover tabs bending process.

In some embodiments, the primary base/cover tab grooves and the secondary base/cover tab grooves can reduce the force required to bend each base/cover tab into the positions shown in FIG. 49, FIG. 50, and FIG. 51 cross section views, each groove effectively functioning as a hinge similar to the anterior cover grooves and the secondary anterior cover tab grooves in the sixth embodiment In some further embodiments, anterior cover tab indicium 57A can comprise the phrase PEEL 7, anterior cover tab indicium 57C can comprise the phrase PEEL 8, anterior cover tab indicium 57E can comprise the phrase PEEL 1, anterior cover tab indicium 57G can comprise the phrase PEEL 2, anterior cover tab indicium 57J can comprise the phrase PEEL 3, anterior cover tab indicium 57L can comprise the phrase PEEL 4, anterior cover tab indicium 57N can comprise the phrase PEEL 5, and anterior cover tab indicium 57Q can comprise the phrase PEEL 6.

In some embodiments of the seventh embodiment, after initial fabrication of the posterior base/anterior cover 67, which can comprise paperboard punching process, groove-making or scoring or creasing process, indicia printing process, and smell test substance patch, adhesive screen printing or dispensing processes, the sixteen base/cover tabs 67A, 67B, 67C, 67D, 67E, 67F, 67G, 67H, 67J, 67K, 67L, 67M, 67N, 67P, 67Q, and 67R can be folded via automated bending process into the positions depicted in FIGS. 49 and 54. In some embodiments, the polygonal adhesive ring 50 can be contiguous with both the top surface of the posterior base/anterior cover 67 and the surface of the proximal base/cover tab region 64A, 64B, 64C, 64D, 64E, 64F, 64G, 64H, 64J, 64K, 64L, 64M, 64N, 64P, 64Q, and 64R, and the polygonal adhesive ring 50 can couple the proximal base/cover tab regions with the posterior base/anterior cover 67 as depicted in FIGS. 49 and 54.

Additionally, in some embodiments, the polygonal adhesive ring 50 can comprise adhesion properties identical or similar to polygonal adhesive ring 50 as described in the sixth embodiment. In some embodiments, the surface finish or treatment of the proximal base/cover tab regions can be different than the surface finish or treatment of the circular central region of the posterior base/anterior cover 67 such that whenever a proximal base/cover tab region is manually peeled away from the circular central region of the posterior base/anterior cover 67, the adhesion between the polygonal adhesive ring 50 and the circular central region of the posterior base/anterior cover 67 is greater than the adhesion between the polygonal adhesive ring 50 and any proximal base/cover tab region. In some embodiments, the surface finish or treatment difference can aid the polygonal adhesive ring 50 in remaining attached to the circular central region of the posterior base/anterior cover 67 after one or more proximal base/cover tab regions is peeled away.

The seventh embodiment test instructions 57S depicted in FIG. 53 and FIG. 54 can comprise the following text, which is relevant for COVID-19 disease:

1. Pinch outer tip of PEEL 1 tab and peel back enough until a circular scent patch is fully visible.
2. Sniff very close to the scent patch.
3. If you smell scent, peel back PEEL 1 tab further until color dot is fully visible underneath. IF NOT, DO NOT PEEL TAB FURTHER
4. Repeat steps 1-3 for PEEL 2 tab, PEEL 3 tab, . . . , then PEEL 8 tab. There are 4 tabs with scent. DO NOT PEEL BACK MORE THAN 4 TABS FURTHER TO REVEAL ADDITIONAL COLOR DOTS.
5. Review each illness symptom tab. For each symptom you have, peel back tab until color dot is fully visible.
6. If you are male, peel back MALE tab until color dot is fully visible. NOTE THERE IS NO FEMALE TAB.
7. Select AGE tab with your age range and peel back tab until color dot is fully visible.
8. If there are any red, orange, yellow, or black dots visible, you may have COVID-19. Unless there are 4 green dots visible, you may have COVID-19.
9. Activate COVID-19 symptom checker app on your smart phone, if available, then use phone camera to photograph all visible color dots together. This app will estimate likelihood you have COVID-19.

In some embodiments, the eight PEEL tabs can be base/cover tab 67A, 67C, 67E, 67G, 67J, 67L, 67N, and 67Q in FIG. 54, the three symptom tabs can be base/cover tab 67B, 67D, 67F, the four AGE tabs can be base/cover tab 67K, 67M, 67P, 67R, and the MALE gender tab can be base/cover tab 67H in FIG. 54. FIG. 50 depicts the approximate position of base/cover tab 67E after the tab is peeled back enough that smell test substance patch 38E is visible. Similarly, FIG. 51 depicts the approximate position of base/cover tab 67E after the tab is peeled back enough that posterior base color-coded circular indicium 39E is fully visible. It should be noted that the test instructions 57S, the symptoms tabs, the gender tab, and the age tabs can be modified as appropriate for other illnesses.

Figure 55:
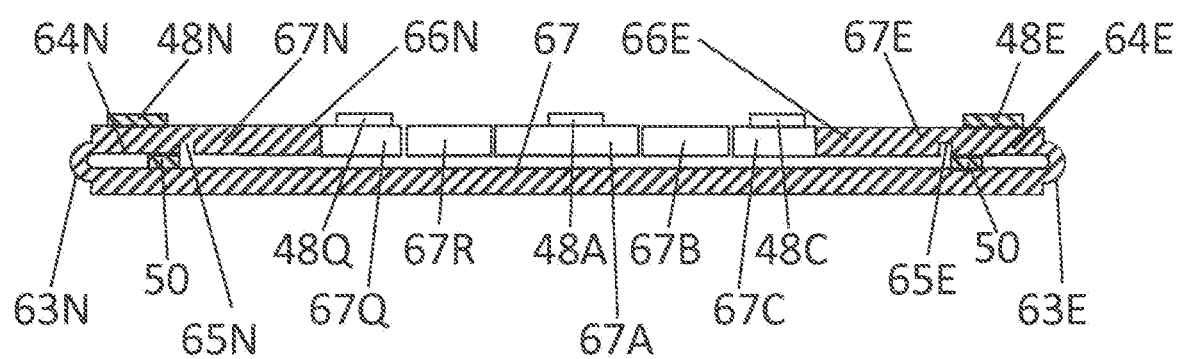
FIG. 55 depicts a side cross-sectional view of an eighth embodiment of the present device.

FIG. 55 depicts a side cross-sectional view of an eighth embodiment of the present device.

Figure 56:
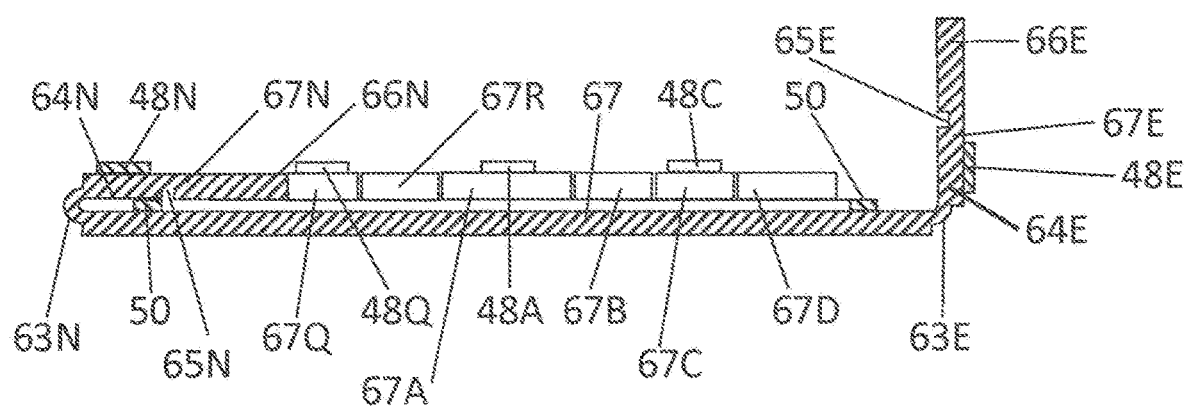
FIG. 56 depicts a side cross-sectional view of an eighth embodiment of the present device.

FIG. 56 depicts a side cross-sectional view of an eighth embodiment of the present device.

Figure 57:
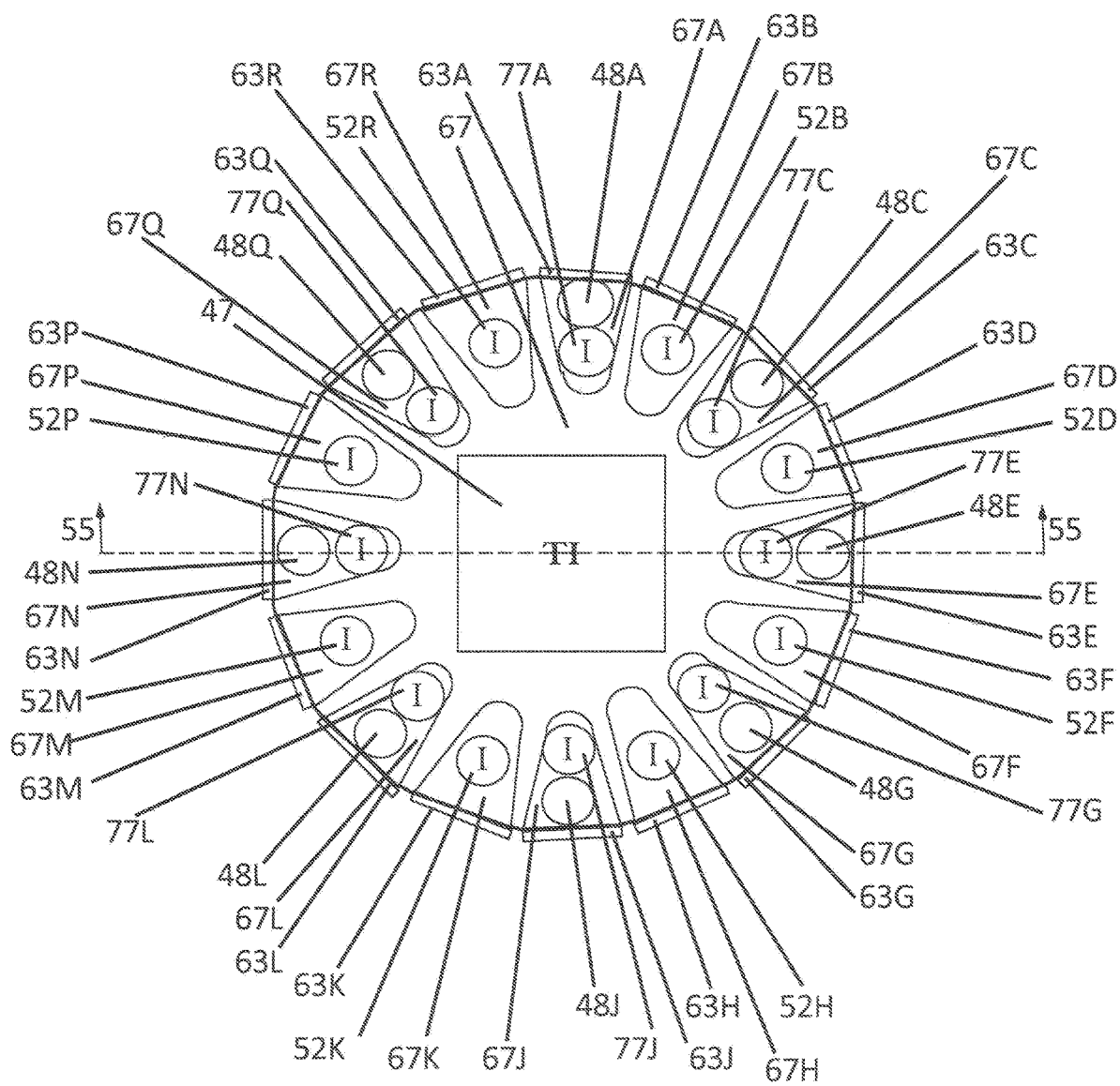
FIG. 57 depicts a top view of an eighth embodiment of the present device.

FIG. 57 depicts a top view of an eighth embodiment of the present device.

An eighth embodiment depicted in FIGS. 55 and 57 can comprise one manufactured component—posterior base/anterior cover 67. The eighth embodiment can comprise many of the same features as the seventh embodiment, with similar functionality, and comprise similar and/or identical design, colors, indicia, and materials. In some embodiments, the eighth embodiment can comprise eight smell test substance patches 48A, 48C, 48E, 48G, 48J, 48L, 48N, and 48Q disposed on posterior base/anterior cover 67, as shown in FIG. 57 and FIG. 55. These smell test substance patches 48A, 48C, 48E, 48G, 48J, 48L, 48N,48Q can comprise scratch and sniff substances comparable and/or identical to the substances used in the Smell Identification Test™ (olfactory test) available from Sensonics International, and these patches can be substantially identical and/or identical to the eight smell test substance patches 48A, 48C, 48E, 48G, 48J, 48L, 48N, and 48Q in the fifth embodiment.

In some embodiments, such as, by way of non-limiting example, the eighth embodiment, the eight smell test substance patches 48A, 48C, 48E, 48G, 48J, 48L, 48N, and 48Q in the eighth embodiment can all be exposed and visible before any base/cover tabs 67A, 67B, 67C, 67D, 67E, 67F, 67G, 67H, 67J, 67K, 67L, 67M, 67N, 67P, 67Q, and 67R have been manually peeled by a user, as shown in FIG. 57. In some embodiments, such as, by way of non-limiting example, the eighth embodiment can comprise primary anterior cover tab indicium 77A, 77C, 77E, 77G, 77J, 77L, 77N, and 77Q, each disposed on a corresponding base/cover tab 67A, 67C, 67E, 67G, 67J, 67L, 67N, and 67Q. In the embodiment depicted in relation to the eighth embodiment, the primary anterior cover tab indicium 77A can comprise the printed or embossed word SNIFF 7, primary anterior cover tab indicium 77C can comprise the printed or embossed word SNIFF 8, primary anterior cover tab indicium 77E can comprise the printed or embossed word SNIFF 1, primary anterior cover tab indicium 77G can comprise the printed or embossed word SNIFF 2, primary anterior cover tab indicium 77J can comprise the printed or embossed word SNIFF 3, primary anterior cover tab indicium 77L can comprise the printed or embossed word SNIFF 4, primary anterior cover tab indicium 77N can comprise the printed or embossed word SNIFF 5, and primary anterior cover tab indicium 77Q can comprise the printed or embossed word SNIFF 6.

Figure 58:
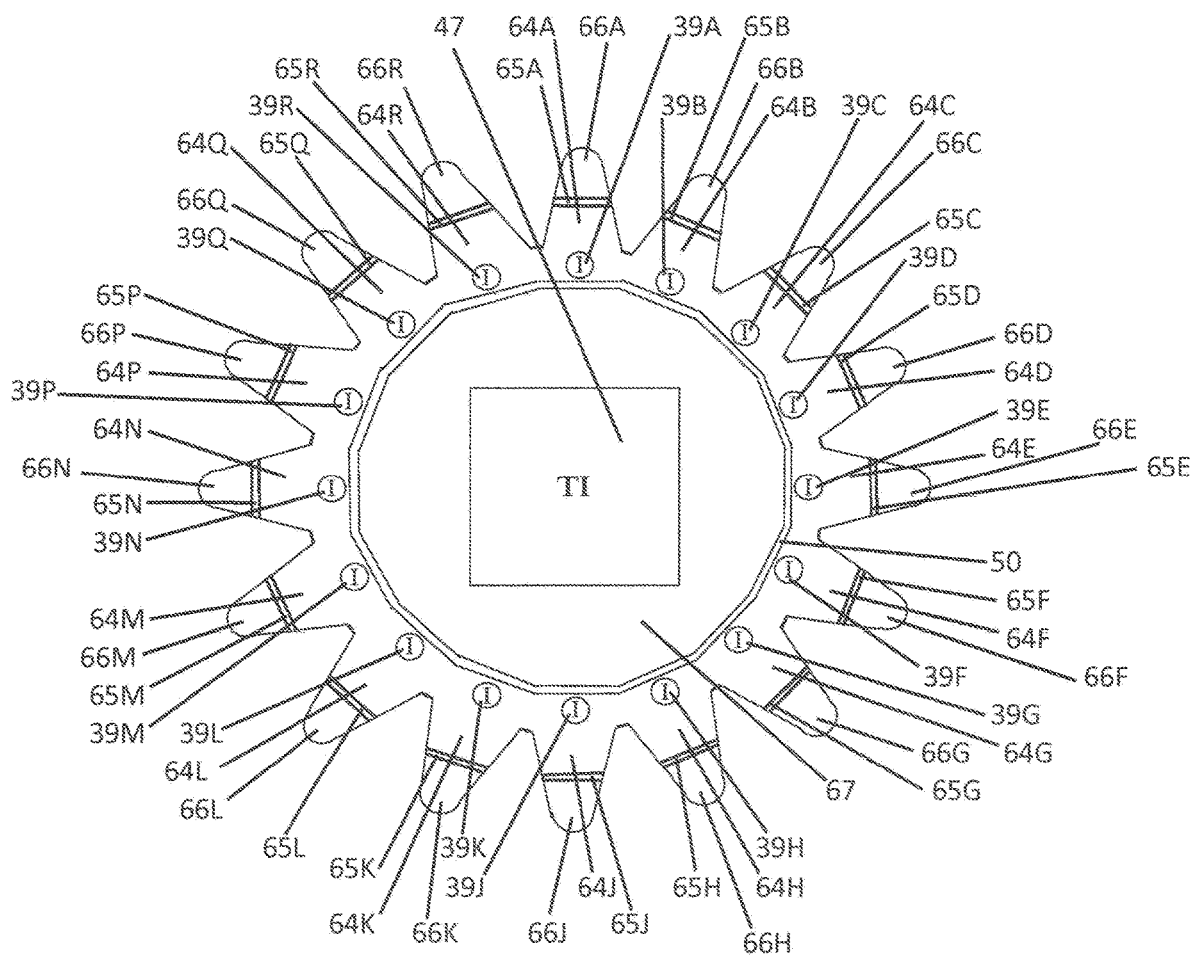
FIG. 58 depicts a top view of an eighth embodiment of the present device prior to folding operation during manufacturing.

FIG. 58 depicts a top view of an eighth embodiment of the present device prior to folding operation during manufacturing.

Figure 59:
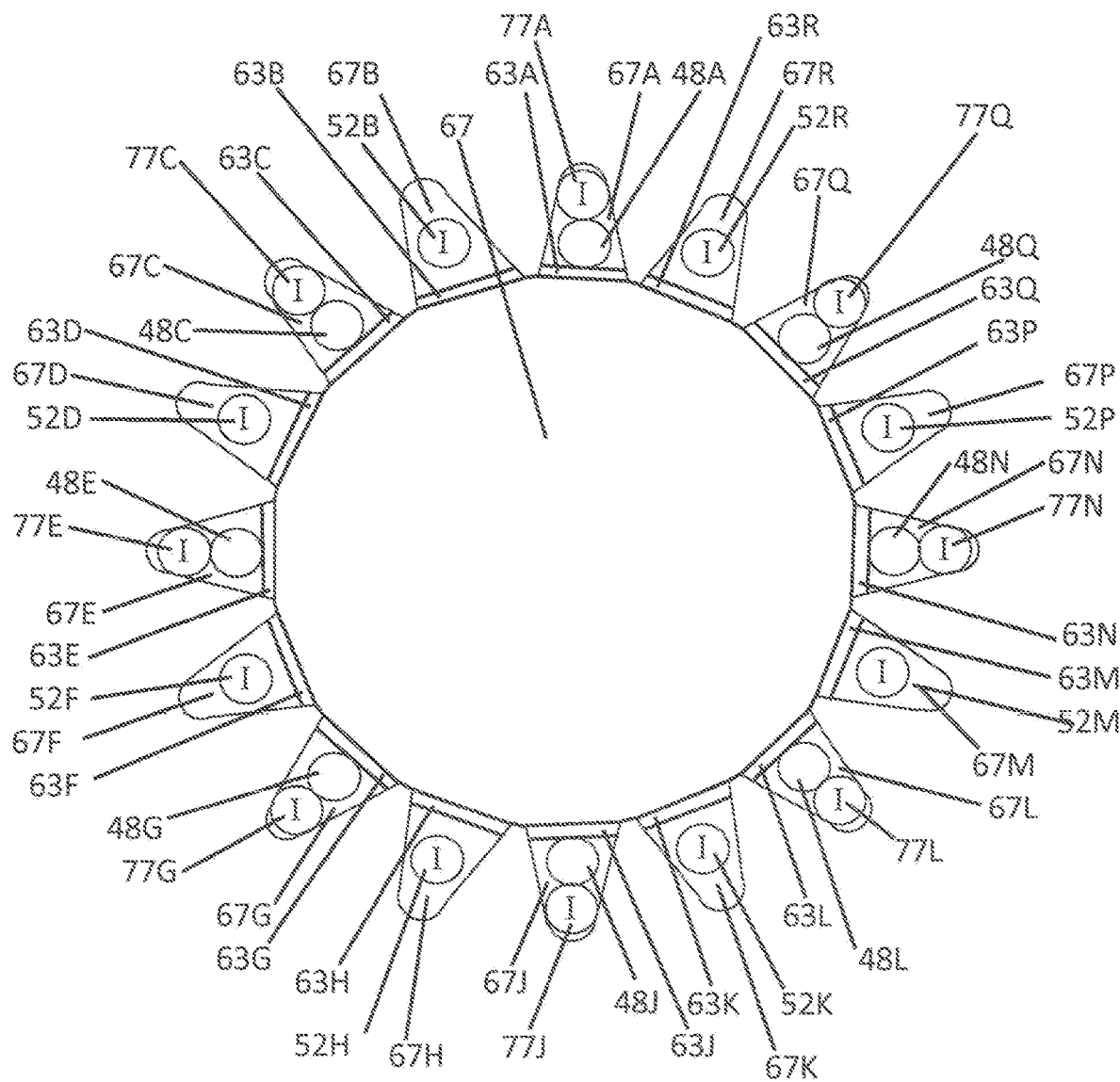
FIG. 59 depicts a bottom view of an eighth embodiment of the present device prior to folding operation during manufacturing.

FIG. 59 depicts a bottom view of an eighth embodiment of the present device prior to folding operation during manufacturing.

Figure 60:
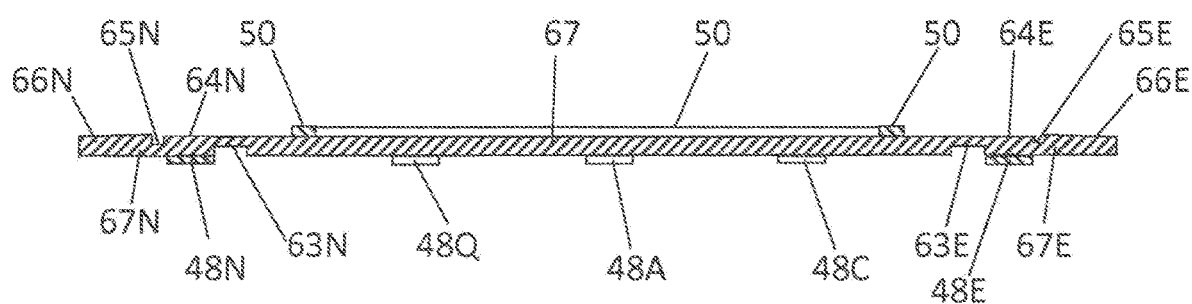
FIG. 60 depicts a side cross-sectional view of an eighth embodiment of the present device prior to folding operation during manufacturing.

FIG. 60 depicts a side cross-sectional view of the eighth embodiment prior to folding operation during manufacturing.

FIGS. 58, 59, and 60 illustrate the eighth embodiment posterior base/anterior cover 67 prior to an automated bending process. In embodiments which comprise paperboard, initial fabrication can comprise a paperboard punching process, groove-making or scoring or creasing process, indicia printing process, and smell test substance patch, adhesive screen printing or dispensing processes. Subsequently, the sixteen base/cover tabs 67A, 67B, 67C, 67D, 67E, 67F, 67G, 67H, 67J, 67K, 67L, 67M, 67N, 67P, 67Q, and 67R can be folded via automated bending process into the positions depicted in FIGS. 57 and 55.

While FIG. 60 illustrates eight smell test substance patches 48A, 48C, 48E, 48G, 48J, 48L, 48N, and 48Q as disposed on posterior base/anterior cover 67 prior to such an automated bending process, alternately these smell test substance patches can be disposed onto posterior base/anterior cover 67 following the automated bending process instead. In some embodiments, the fabrication and assembly processes for the eighth embodiment can be comparable and/or identical to the fabrication and assembly processes for the seventh embodiment as disclosed herein. Additionally, in some embodiments, the design, materials, indicia, colors, functions, adhesion properties, surface finishes, surface treatments of the elements in this eighth embodiment can be comparable and/or identical to the design, materials, indicia, colors, functions, adhesion properties, surface finishes, surface treatments of some or all the elements in the seventh embodiment, as disclosed herein.

The eighth embodiment test instructions 47, disposed on top surface of posterior base/anterior cover 67 as shown in FIG. 57 and FIG. 58 top view, can comprise the following text, which can be relevant for COVID-19 disease:
1. Scratch and sniff the substance patch on SNIFF 1 tab.
2. If you smell scent, peel back SNIFF 1 tab until color dot is fully visible. IF NOT, DO NOT PEEL SNIFF TAB.
3. Repeat steps 1 & 2 for SNIFF 2 tab, SNIFF 3 tab, . . . , then SNIFF 8 tab. There are 4 tabs with scent. DO NOT PEEL BACK MORE THAN 4 SNIFF TABS TO REVEAL ADDITIONAL COLOR DOTS.
4. Review each illness symptom tab. For each symptom you have, peel back tab until color dot is fully visible.
5. If you are male, peel back MALE tab until color dot is fully visible. NOTE THERE IS NO FEMALE TAB.
6. Select AGE tab with your age range and peel back tab until color dot is fully visible.
7. If there are any red, orange, yellow or black dots visible, you may have COVID-19. Unless there are 4 green dots visible, you may have COVID-19.
8. Activate COVID-19 symptom checker app on your smart phone, if available, then use phone camera to photograph all visible color dots. This app will estimate likelihood you have COVID-19.

These test instructions 47 can be comparable to the test instructions in the fifth embodiment. In some embodiments, the eight SNIFF tabs can be 67A, 67C, 67E, 67G, 67J, 67L, 67N, and 67Q, the three symptom tabs can be 67B, 67D, and 67F, the four AGE tabs can be 67K, 67M, 67P, and 67R, and the MALE gender tab can be 67H in FIG. 57. FIG. 56 assembly cross section view illustrates the approximate position of SNIFF 1 base/cover tab 67E if the user peels this tab back enough that posterior base color-coded circular indicium 39E is fully visible, per the test instructions 47 step 2. In some embodiments, the test instructions 47, the symptoms tabs, the gender tab, and the age tabs can be modified as appropriate for other illnesses. Additionally, in some embodiments, the relative positions of some or all of the four smell test substance patches with odor and the four smell test substance patches without odor can be swapped. Any such changes in relative positions of these smell test substance patches can be accompanied by corresponding changes in the green and red color-coded circular indicium positions on posterior base/anterior cover 67.

Figure 61:
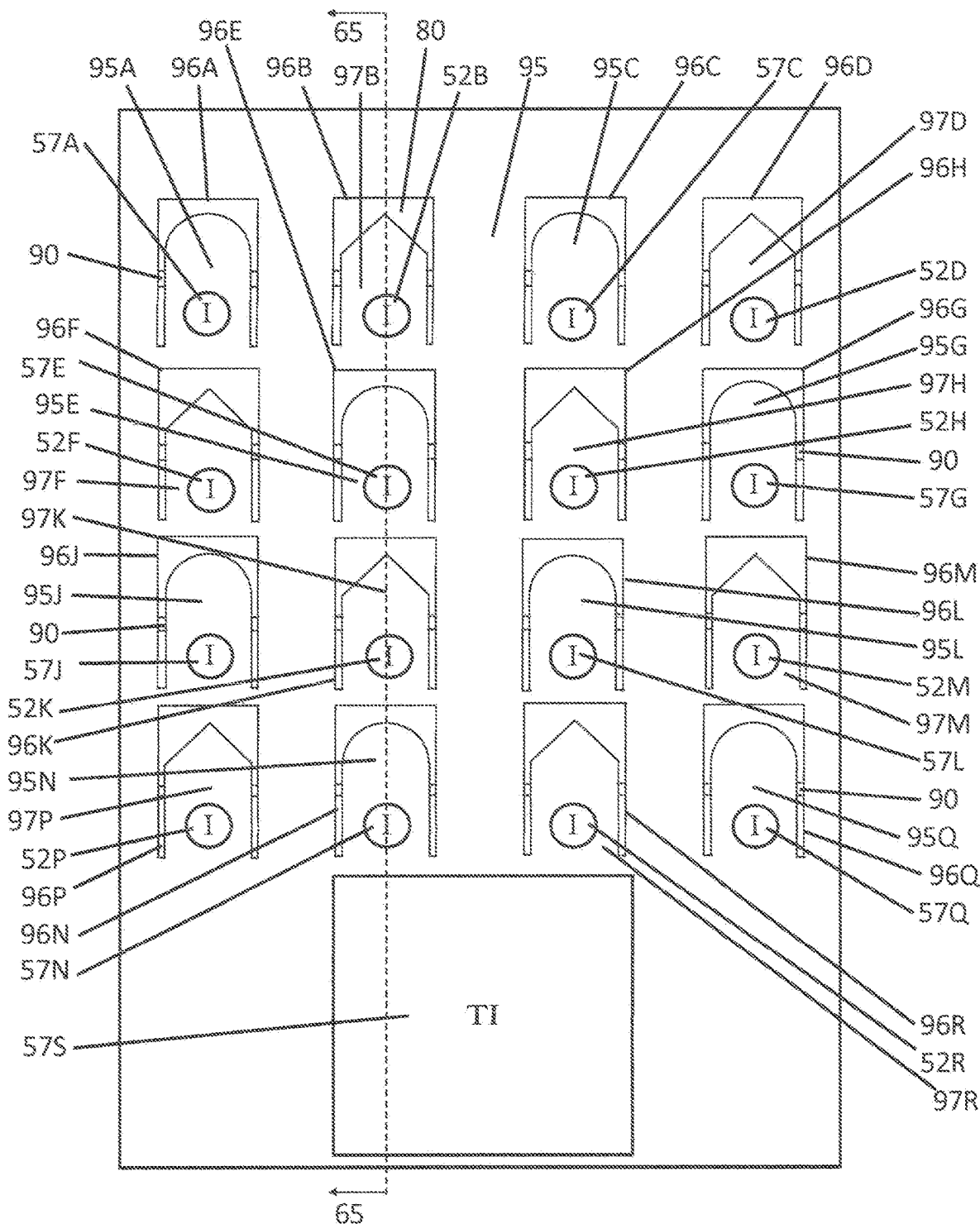
FIG. 61 depicts a top view of a ninth embodiment of the present device.

FIG. 61 depicts a top view of a ninth embodiment of the present device. A ninth embodiment shown in FIG. 61 top assembly view and FIG. 65 cross section assembly view comprises two manufactured components—rectangular posterior base 80 and a rectangular opaque anterior cover 95. The ninth embodiment can be comparable to the sixth embodiment, comprising many similar and/or identical features, indicia, and materials, although these embodiments can have different form as shown in respective figures. In addition, similar or identical manufacturing processes used in production for the sixth embodiment can be used in production for this ninth embodiment.

In some embodiments, the eight PEEL tabs can be smell test cover tabs 95A, 95C, 95E, 95G, 95J, 95L, 95N, and 95Q in FIG. 61, the three symptom tabs can be auxiliary cover tabs 97B, 97D, 97F, the four AGE tabs can be auxiliary cover tabs 97K, 97M, 97P, 97R, and the MALE gender tab can be auxiliary cover tab 97H in FIG. 61.

Figure 63:
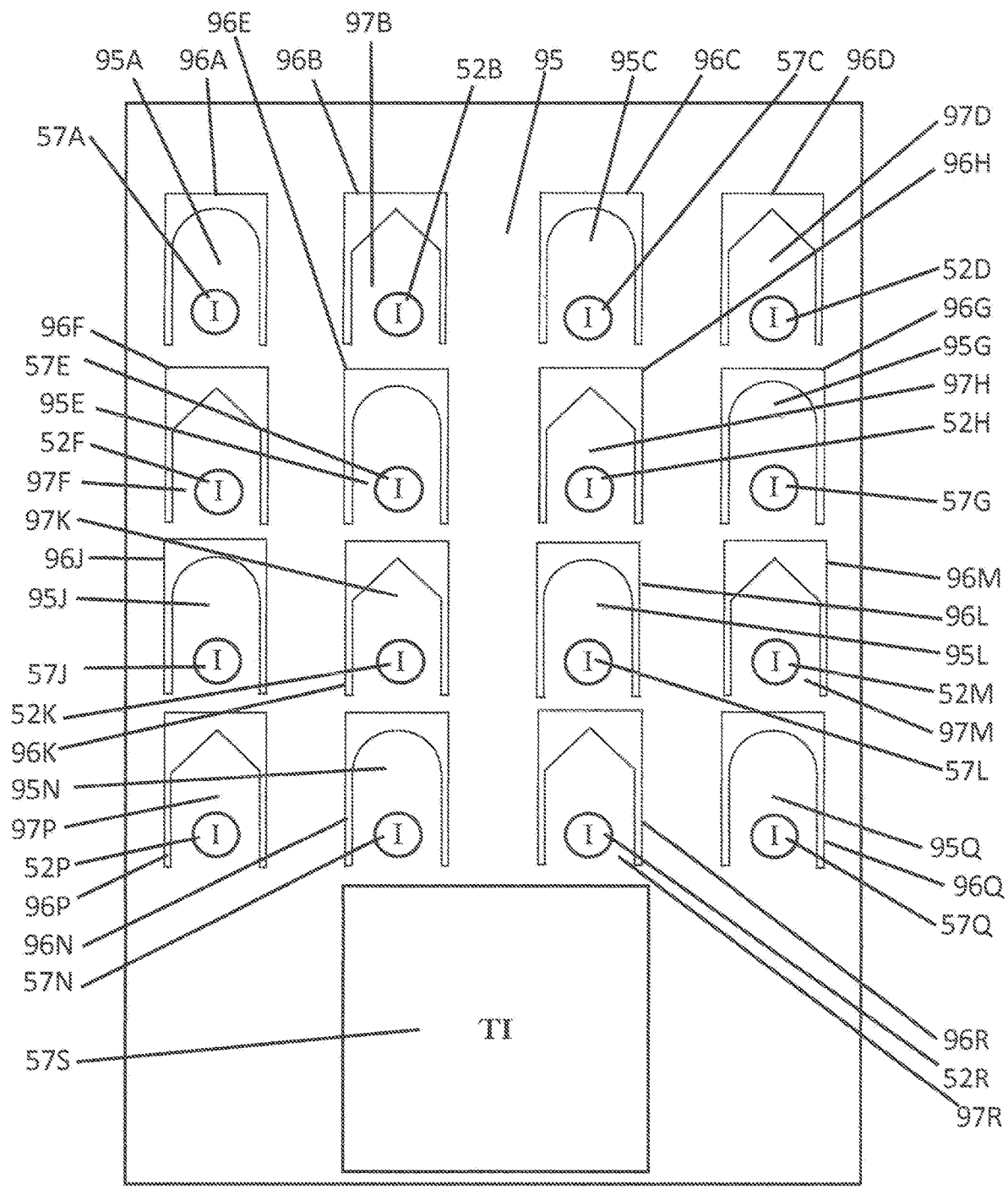
FIG. 63 depicts a top view of a rectangular anterior cover of a ninth embodiment of the present device.

The rectangular opaque anterior cover 95 can comprise eight auxiliary cover tabs 97B, 97D, 97F, 97H, 97K, 97M, 97P, and 97R which can be integral elements of this component disposed within eight corresponding auxiliary rectangular cover openings 96B, 96D, 96F, 96H, 96K, 96M, 96P, and 96R in this component, as shown in FIG. 63. In some embodiments, the eight auxiliary cover tabs can be functionally equivalent to the set of eight anterior cover tabs 53B, 53D, 53F, 53H, 53K, 53M, 53P, and 53R as described in relation to the sixth embodiment, and the design of these tabs can be similar. As shown in FIG. 63, each of the eight auxiliary cover tabs 97B, 97D, 97F, 97H, 97K, 97M, 97P, and 97R can have a corresponding anterior cover tab indicium 52B, 52D, 52F, 52H, 52K, 52M, 52P, and 52R disposed on it. Each of the anterior cover tab indicia 57A, 57C, 57E, 57G, 57J, 57L, 57N, 57Q, 52B, 52D, 52F, 52H, 52K, 52M, 52P, and 52R in this ninth embodiment can comprise identical or substantially similar word or phrase printed on the cover tab as the corresponding anterior cover tab indicium in the sixth embodiment disclosed earlier.

Figure 62:
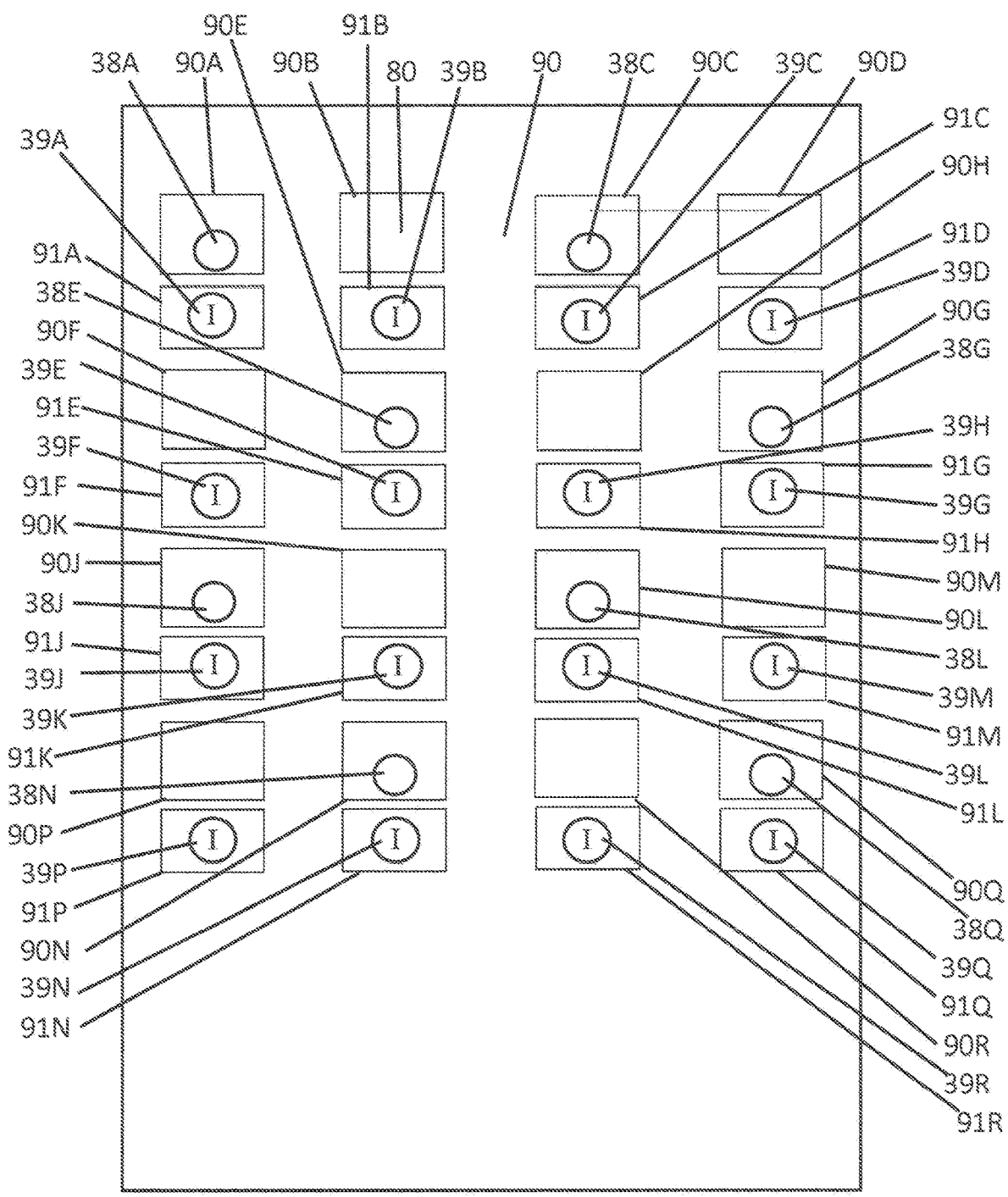
FIG. 62 depicts a top view of a rectangular posterior base component of a ninth embodiment of the present device, with an adhesive layer disposed on top surface.

FIG. 62 depicts a top view of a rectangular posterior base component of a ninth embodiment of the present device, with an adhesive layer disposed on top surface.

FIG. 63 depicts a top view of a rectangular anterior cover of a ninth embodiment of the present device. In the ninth embodiment, the rectangular opaque anterior cover 95 comprises a set of smell test cover tabs 95A, 95C, 95E, 95G, 95J, 95L, 95N, and 95Q which can be integral elements of this component disposed within a set of corresponding rectangular cover openings 96A, 96C, 96E, 96G, 96J, 96L, 96N, and 96Q in this component, as shown in FIG. 63. This set of eight smell test cover tabs can be functionally equivalent to the set of eight anterior cover tabs 56A, 56C, 56E, 56G, 56J, 56L, 56N, and 56Q in the sixth embodiment, and the design of these tabs can be similar. As shown in FIG. 63, each smell test cover tab 95A, 95C, 95E, 95G, 95J, 95L, 95N, and 95Q can have a corresponding anterior cover tab indicium 57A, 57C, 57E, 57G, 57J, 57L, 57N, and 57Q disposed on it. Each anterior cover tab indicium 57A, 57C, 57E, 57G, 57J, 57L, 57N, and 57Q can include an identification number which can be referenced in test instructions 57S, which can be printed or embossed onto top surface of the rectangular opaque anterior cover 95, as shown in FIG. 63.

In some embodiments, the test instructions 57S (symbolized as TI enclosed within a square) disposed on top surface of rectangular opaque anterior cover 95, shown in FIG. 61 and in FIG. 63 top view of rectangular opaque anterior cover 95, can comprise the same text as the test instructions 57S disposed on top surface of opaque anterior cover 56 in the sixth embodiment. The ninth embodiment can be used by similar and/or identical steps as when operating the sixth embodiment disclosed earlier. As shown in FIG. 62 top view of rectangular posterior base 80, this ninth embodiment can further comprise eight smell test substance patches 38A, 38C, 38E, 38G, 38J, 38L, 38N, and 38Q, which can be identical and/or substantially similar to the sixth embodiment's smell test substance patches, although these eight smell test substance patches can be aligned in rows and columns disposed on top surface of the rectangular posterior base 80.

The ninth embodiment can further comprise eight posterior base color-coded circular smell test indicia (symbolized as an "I" enclosed within a circle) 39A, 39C, 39E, 39G, 39J, 39L, 39N, and 39Q which can be printed on a top surface of rectangular posterior base 80, each disposed adjacent to a corresponding smell test substance patch 38A, 38C, 38E, 38G, 38J, 38L, 38N, and 38Q, as shown in FIG. 62. The eight, posterior base color-coded circular smell test indicia can be similar and/or identical to the of eight posterior base color-coded circular smell test indicia in the sixth embodiment. In some embodiments the device can further comprise a second set of posterior base color-coded circular indicium (symbolized as an "I" enclosed within a circle) 39B, 39D, 39F, 39H, 39K, 39M, 39P, and 39R printed on a top surface of the rectangular posterior base 80, which can be identical and/or substantially similar to the second set of posterior base color-coded circular indicium in the sixth embodiment. In such embodiments, the corresponding colors of these sixteen color-coded circular indicia in this ninth embodiment can be identical or substantially similar to corresponding colors of the sixteen color-coded circular indicia in the sixth embodiment, described earlier.

Figure 65:
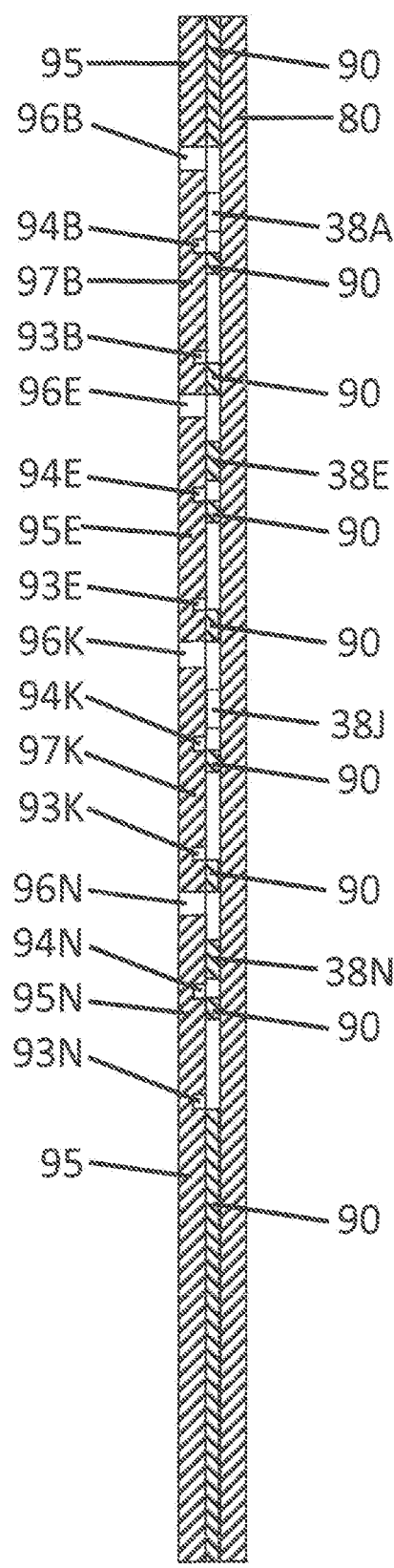
FIG. 65 depicts a side cross-sectional view of a ninth embodiment of the present device.

In still further alternate embodiments, rectangular adhesive layer 90 can comprise a fourth set of rectangular openings 91B, 91D, 91F, 91H, 91K, 91M, 91P, and 91R, with corresponding posterior base color-coded circular indicium 39B, 39D, 39F, 39H, 39K, 39M, 39P, and 39R disposed within each opening. As shown in FIG. 62, all these rectangular openings in adhesive layer 90 can be oriented in a matrix of rows and columns. This rectangular adhesive layer 90 can be disposed between the top surface of the rectangular posterior base 80 and the bottom surface of the rectangular opaque anterior cover 95, as shown in FIG. 65, and this rectangular adhesive layer 90 can structurally attach these two components together, which is comparable in function to the circular adhesive layer 40A in the sixth embodiment. In addition, each of eight smell test substance patches 38A, 38C, 38E, 38G, 38J, 38L, 38N, and 38Q can be contiguous with both the top surface of the rectangular posterior base 80 and the bottom surface of the rectangular opaque anterior cover 95, as shown in FIG. 65.

Figure 64:
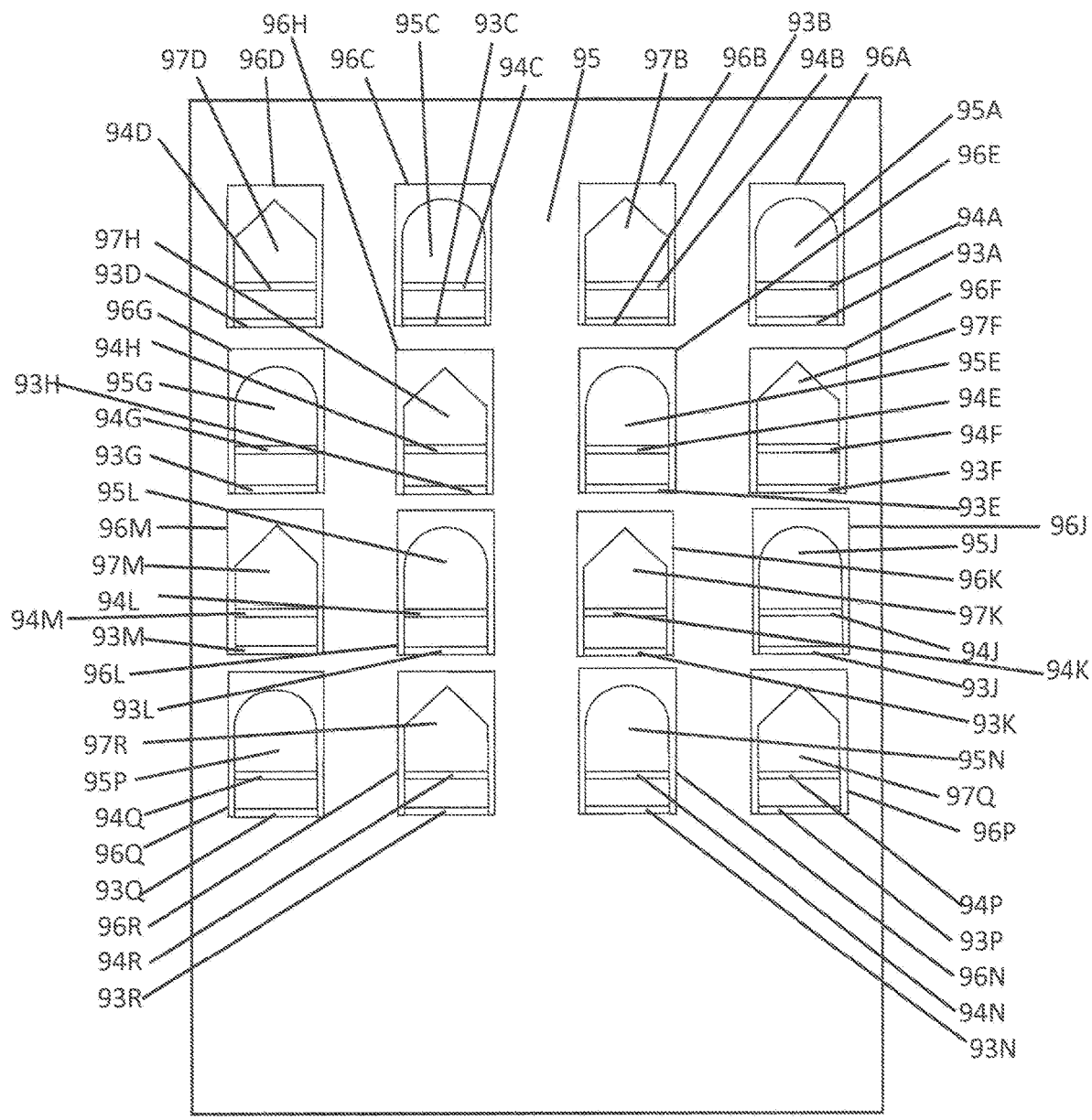
FIG. 64 depicts a bottom view of a rectangular anterior cover of a ninth embodiment of the present device.

As shown in FIG. 64 bottom view of rectangular opaque anterior cover 95, each of the eight smell test cover tabs 95A, 95C, 95E, 95G, 95J, 95L, 95N, and 95Q can have a corresponding distal cover tab groove 94A, 94C, 94E, 94G, 94J, 94L, 94N, and 94Q disposed on bottom surface of cover tab, adjacent to edge of adhesive layer 90. Additionally, in some embodiments, each of the eight smell test cover tabs 95A, 95C, 95E, 95G, 95J, 95L, 95N, and 95Q can have a corresponding proximal cover tab groove 93A, 93C, 93E, 93G, 93J, 93L, 93N, and 93Q disposed on bottom surface of cover tab, adjacent to edge of adhesive layer 90 at inner border of cover tab. Also shown in FIG. 64 bottom view of rectangular opaque anterior cover 95, in some embodiments each of the eight auxiliary cover tabs 97B, 97D, 97F, 97H, 97K, 97M, 97P, and 97R can have a corresponding distal cover tab groove 94B, 94D, 94F, 94H, 94K, 94M, 94P, and 94R disposed on bottom surface of cover tab, adjacent to edge of adhesive layer 90. Additionally, in some embodiments, each of the eight auxiliary cover tabs 97B, 97D, 97F, 97H, 97K, 97M, 97P, and 97R can have a corresponding proximal cover tab groove 93B, 93D, 93F, 93H, 93K, 93M, 93P, and 93R disposed on bottom surface of cover tab, adjacent to edge of adhesive layer 90 at inner border of cover tab.

FIG. 65 depicts a side cross-sectional view of a ninth embodiment of the present device. As shown in FIG. 62 and in FIG. 65, there can be a rectangular adhesive layer 90 disposed on top surface of rectangular posterior base 80. However, in alternate embodiments, the adhesive layer can have any known, convenient and/or desired geometry. In some embodiments, rectangular adhesive layer 90 can comprise a first set of rectangular openings 90A, 90C, 90E, 90G, 90J, 90L, 90N, 90Q, and a corresponding smell test substance patch 38A, 38C, 38E, 38G, 38J, 38L, 38N, and 38Q can be disposed within each opening. In some embodiments, rectangular adhesive layer 90 can further comprise a second set of rectangular openings 90B, 90D, 90F, 90H, 90K, 90M, 90P, and 90R without corresponding smell test substance patches disposed within these openings. In addition, this rectangular adhesive layer 90 can comprise a third set of rectangular openings 91A, 91C, 91E, 91G, 91J, 91L, 91N, and 91Q, with corresponding posterior base color-coded circular smell test indicium 39A, 39C, 39E, 39G, 39J, 39L, 39N, and 39Q disposed within each opening.

Figure 66:
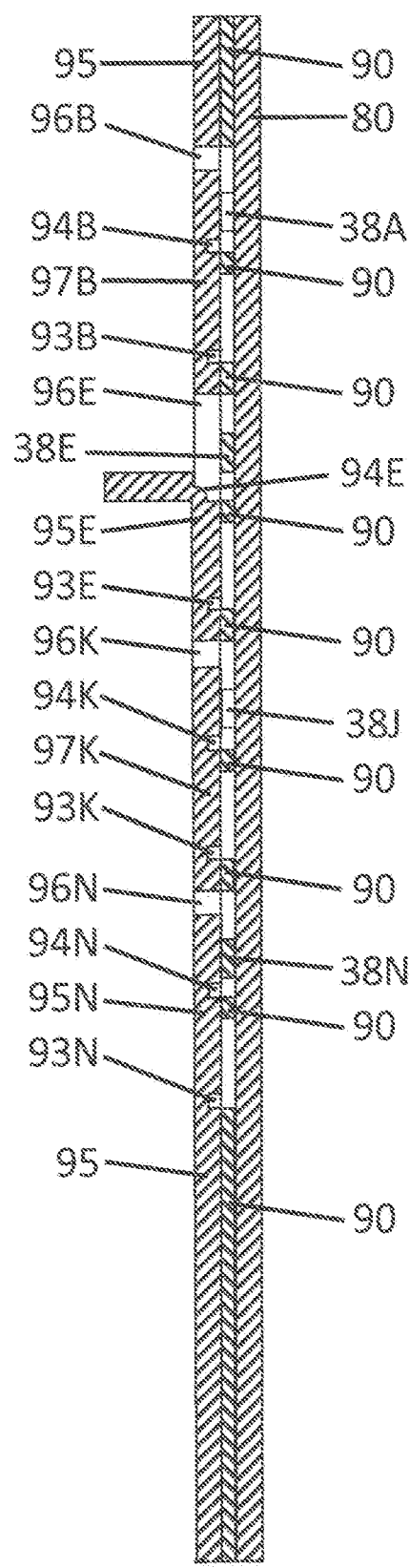
FIG. 66 depicts a side cross-sectional view of a ninth embodiment of the present device.
Figure 67:
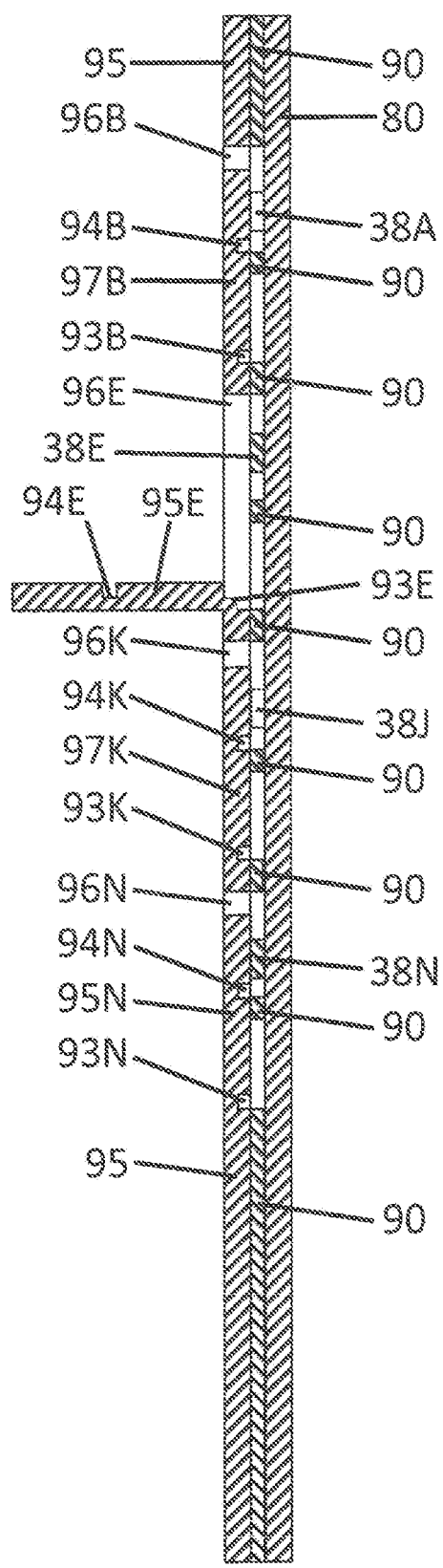
FIG. 67 depicts a side cross-sectional view of a ninth embodiment of the present device.

FIG. 66 depicts a ninth embodiment of a position of smell test cover tab 95E which has been mechanically peeled back sufficiently such that smell test substance patch 38E is visible. Similarly FIG. 67 depicts an embodiment of an approximate position of smell test cover tab 95E which has been mechanically peeled back sufficiently such that the posterior base color-coded circular indicium 39E is visible. In some alternate embodiments, the test instructions 57S, the symptoms tabs, the gender tab, and the age tabs can be modified as appropriate for other illnesses. Additionally, in some alternate embodiments, the relative positions of some or all of the four smell test substance patches with odor and the four smell test substance patches without odor can be swapped. Any such changes in relative positions of these smell test substance patches can be accompanied by corresponding changes in the green and red color-coded circular indicium positions on rectangular posterior base 80.

In some embodiments, the design, materials, indicia, colors, functions, adhesion properties, surface finishes, surface treatments of the elements in this ninth embodiment can be similar or identical to the design, materials, indicia, colors, functions, adhesion properties, surface finishes, surface treatments of some or all the elements in the sixth embodiment, as disclosed herein.

FIG. 67 depicts a side cross-sectional view of a ninth embodiment of the present device.

The function of each of these proximal cover tab grooves and each of these distal cover tab grooves in this ninth embodiment can be substantially similar and/or identical to the function of the cover tab grooves shown in FIG. 45 of the sixth embodiment. These proximal cover tab grooves and these distal cover tab grooves can reduce the force required to manually bend each cover tab into the positions shown in FIG. 66 and FIG. 67 cross section assembly views, whereby each groove effectively functions as a hinge similar to the anterior cover tab grooves and the secondary anterior cover tab grooves in the sixth embodiment. As shown in FIG. 66, the distal cover tab groove 94E can reduce the force to mechanically bend the smell test cover tab 95E into the position shown in this figure, which is step 1 of the test instructions 57S. As shown in FIG. 67, the proximal cover tab groove 93E can reduce the force to mechanically bend the smell test cover tab 95E into the position shown in this figure, which is step 3 of the test instructions 57S. These test instructions 57S can comprise the following text, comparable to the sixth embodiment test instructions, which can be relevant for COVID-19 disease:

1. Pinch outer tip of PEEL 1 tab and peel back enough until a circular scent patch is fully visible.
2. Sniff very close to the scent patch.
3. If you smell scent, peel back PEEL 1 tab further until color dot is fully visible underneath. IF NOT, DO NOT PEEL TAB FURTHER.
4. Repeat steps 1-3 for PEEL 2 tab, PEEL 3 tab, . . . , then PEEL 8 tab. There are 4 tabs with scent. DO NOT PEEL BACK MORE THAN 4 TABS FURTHER TO REVEAL ADDITIONAL COLOR DOTS.
5. Review each illness symptom tab. For each symptom you have, peel back tab until color dot is fully visible.
6. If you are male, peel back MALE tab until color dot is fully visible. NOTE THERE IS NO FEMALE TAB.

7. Select AGE tab with your age range and peel back tab until color dot is fully visible.
8. If there are any red, orange, yellow, or black dots visible, you may have COVID-19. Unless there are 4 green dots visible, you may have COVID-19.
9. Activate COVID-19 symptom checker app on your smart phone, if available, then use phone camera to photograph all visible color dots together. This app will estimate likelihood you have COVID-19.

Figure 68A:
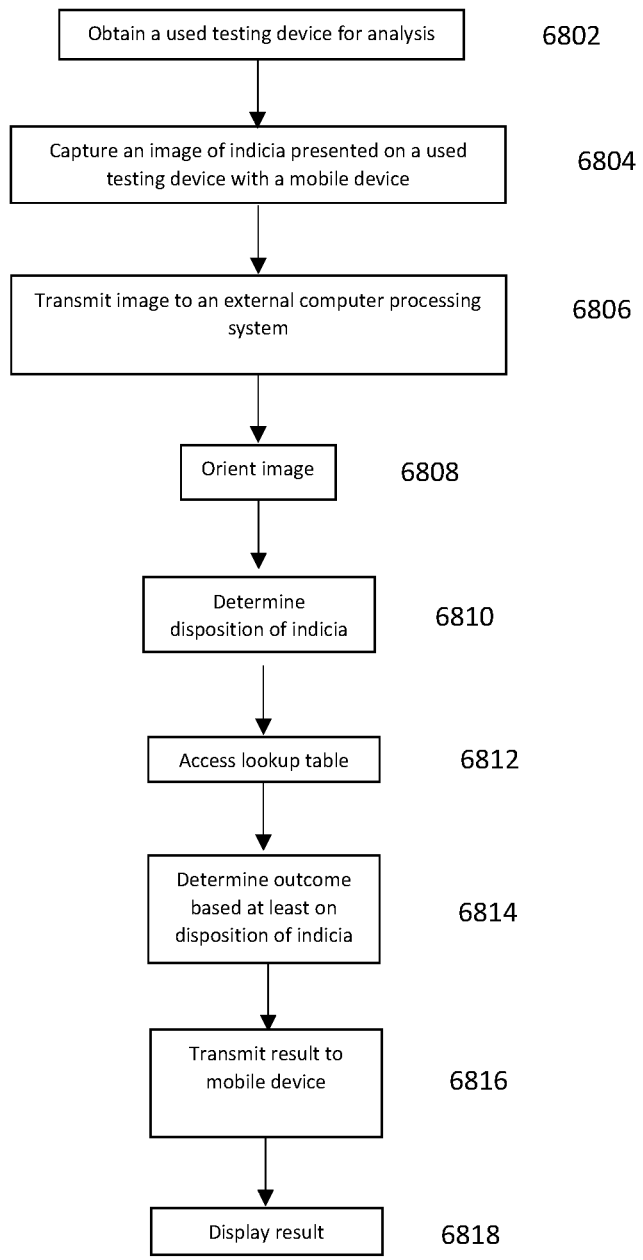
FIGS. 68*a*-68*d* depict flow charts of embodiments of methods using the present system.

FIG. 68a depicts a flow chart of an embodiment of a method using the present system. As shown in FIG. 68a, a method can comprise the following steps. A user can obtain a used testing device (i.e., smell test has been completed) 6802 and capture an image of indicia presented on a used testing device with a mobile device 6804. The mobile device can transmit the image to an external computer processing system 6806. An external processing system can orient the image 6808 and determine the disposition of the indicia on the testing device 6810. Using a lookup table 6812, the processing system can determine the test results based at least upon the disposition of the indicia 6814. The processing system can transmit this result to a mobile device 6816, which can display this result 6818 on a mobile device. In some embodiments, a result can be a set of data obtained from analysis of said indicia for an organization, whereby a business, school, hospital, transportation hub, disease monitoring center, or any other type of organization has access to said set of data, which can be transmitted from mobile device comprising this processing system.

In some embodiments, said result can include at least one phrase regarding symptoms of a targeted disease present, based on analysis of said indicia. In other embodiments, said result can further comprise at least one phrase regarding likelihood of targeted disease based on symptoms present. Said result can include at least one phrase regarding demographics information, based on analysis of said indicia. In some embodiments, said result can include an error message when analysis of said indicia indicates at least one extra indicium. In some embodiments, said result can include an error message when analysis of said indicia indicates at least one missing indicium.

In some embodiments, a method can also comprise the step of comparing the presence of an indicium which corresponds to a substance that stimulates the trigeminal nerve, the presence of at least one indicium which corresponds to at least one non-odorous substance, and the presence of at least one indicium which corresponds to at least one odorous substance 7502 when determining the disposition of said indicia and displaying said result.

Figure 68B:
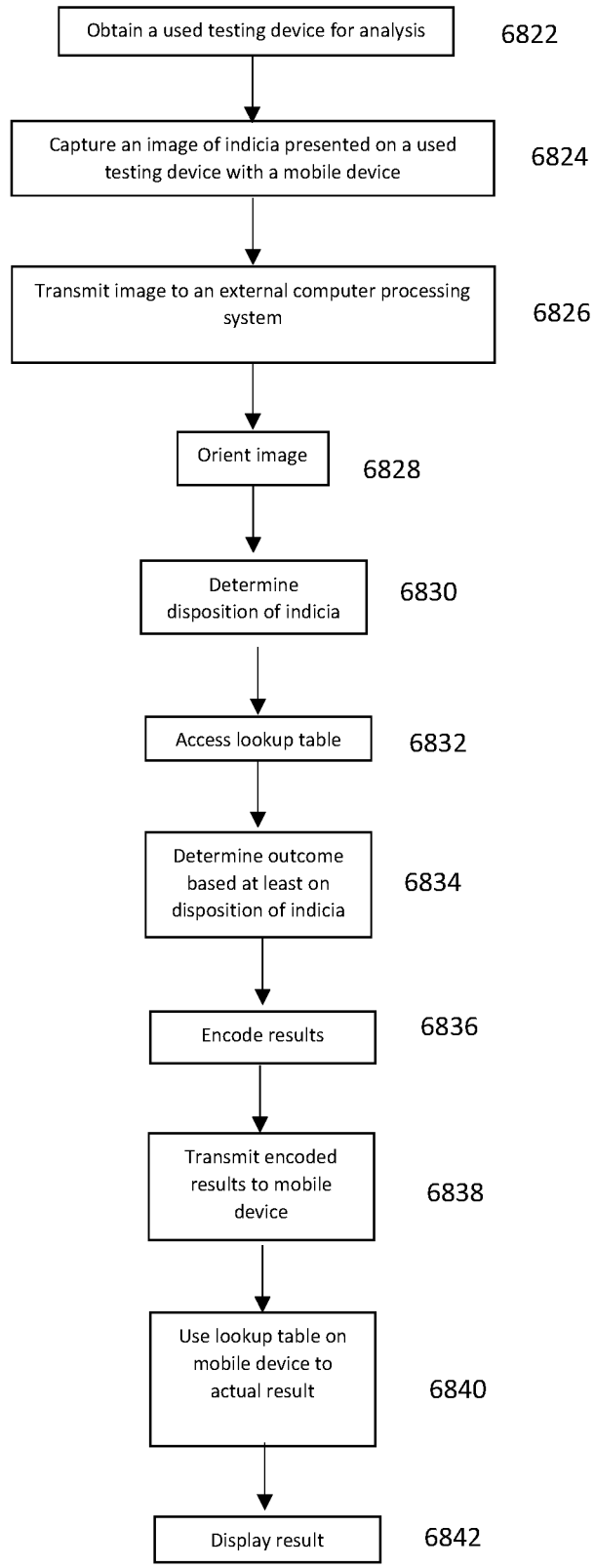

FIG. 68b depicts a flow chart of an embodiment of an alternative method using the present system. As shown in FIG. 68b, a method can comprise the following steps A user can obtain a used testing device (i.e., smell test has been completed) 6822 and capture an image of indicia presented on a used testing device with a mobile device 6824. The mobile device can transmit the image to an external computer processing system 6826. An external processing system can orient the image 6828 and determine the disposition of the indicia on the testing device 6830. Using a lookup table 6832, the processing system can determine the test results based at least upon the disposition of the indicia 6834. In such embodiments, an external processing system can encode the test results 6836 and transmit the encoded result to a mobile device 6838. A mobile device can have another lookup table to which the encoded test results can be decoded 6840 and the decoded result displayed 6842.

Figure 68C:
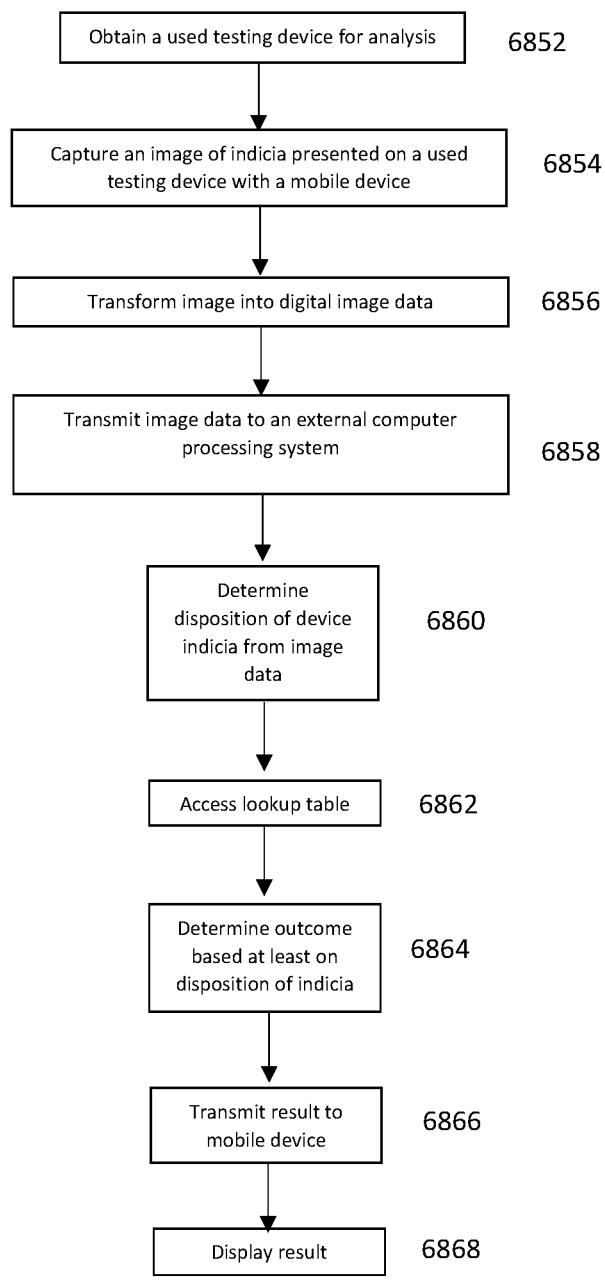

FIG. 68c depicts a flow chart of another embodiment of a method using the present system. As shown in FIG. 68c, a method can comprise the following steps. A user can obtain a used testing device (i.e., smell test has been completed) 6852 and capture an image of indicia presented on a used testing device with a mobile device 6854. A mobile device can transform an image to digital image data 6856 and transmit the digital image data to an external processing system 6858. A processing system can determine the position of device indicia from the digital image data 6860 and use a lookup table 6862 to determine a result based at least on the disposition of the device indicia 6864. This result can be transmitted to a mobile device 6866 and displayed for a user 6868.

Figure 68D:
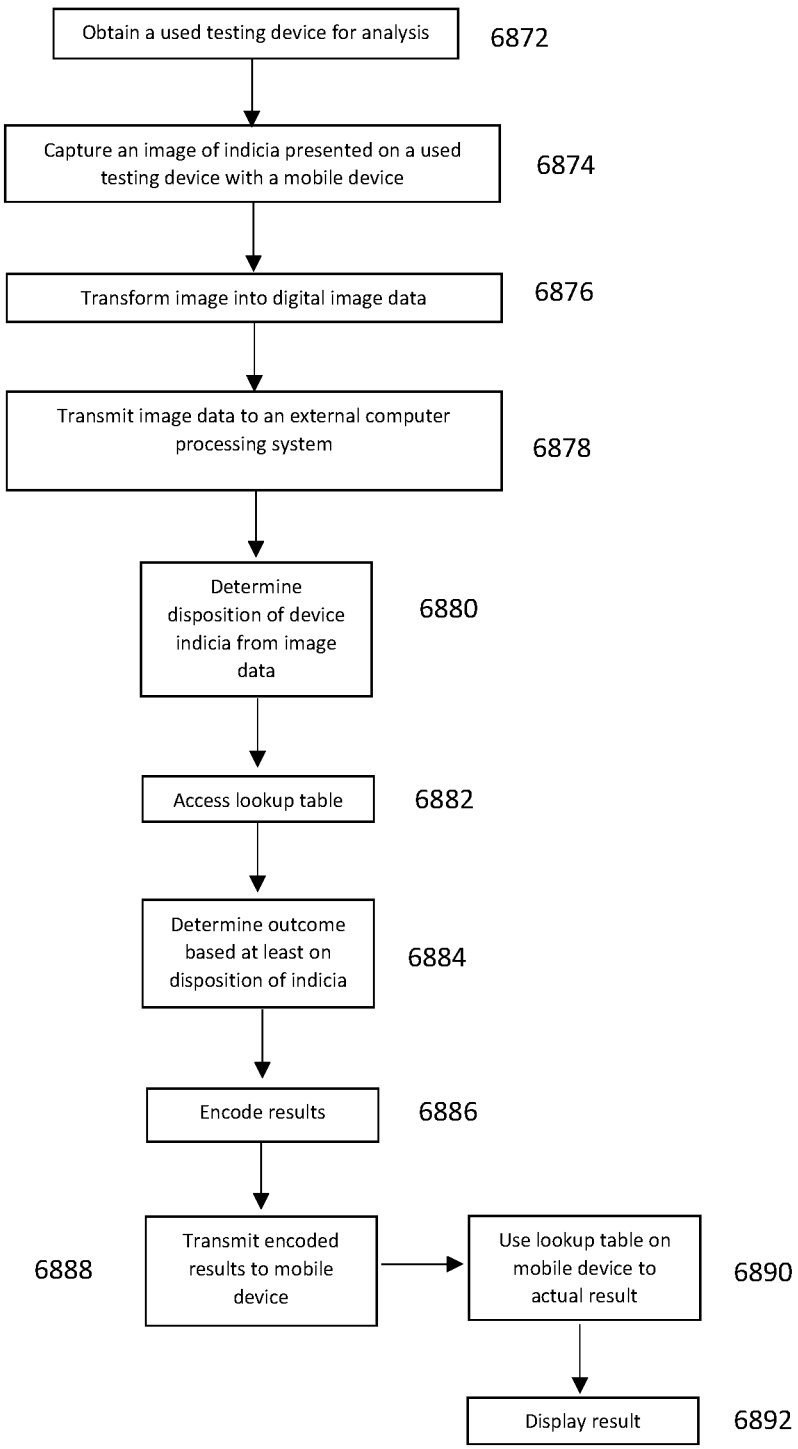

FIG. 68d depicts a flow chart of another embodiment of a method using the present system. As shown in FIG. 68d, a method can comprise the following steps. A user can obtain a used testing device (i.e., smell test has been completed) 6872 and capture an image of indicia presented on a used testing device with a mobile device 6874. A mobile device can transform an image to digital image data 6876 and transmit the digital image data to an external processing system 6878. A processing system can determine the disposition of device indicia from the digital image data 6880 and use a lookup table 6882 to determine a result based at least on the disposition of the device indicia 6884. In such embodiments, an external processing system can encode the test results 6886 and transmit the encoded result to a mobile device 6888. A mobile device can have another lookup table to which the encoded test results can be decoded 6890 and the decoded result displayed 6892.

Figure 69A:
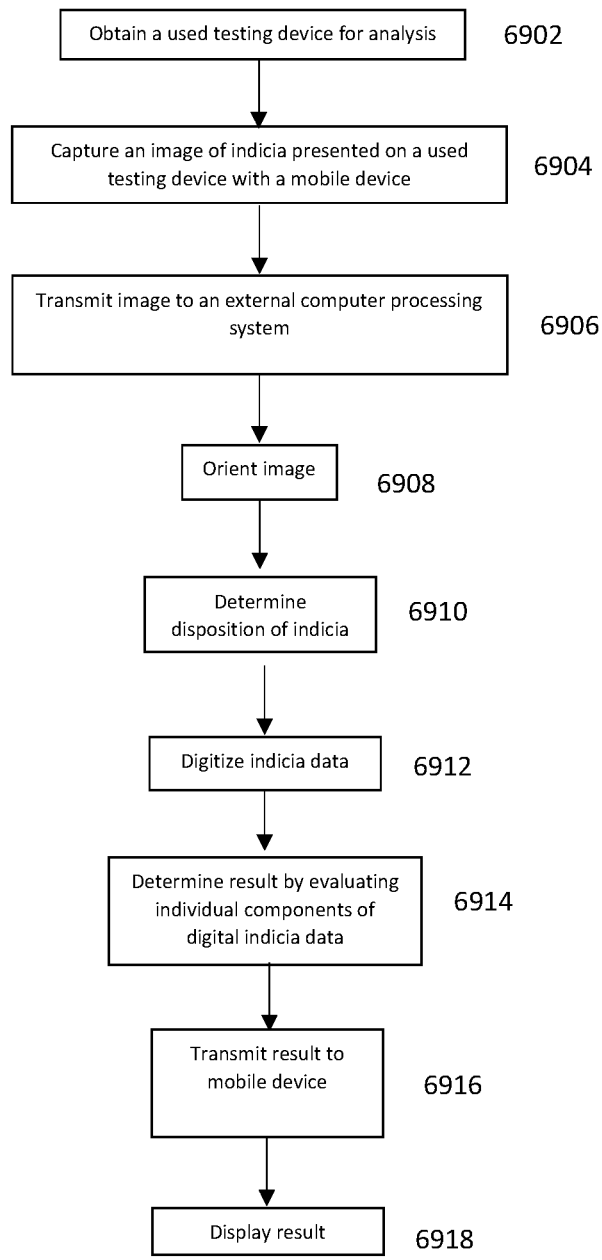
FIGS. 69*a*-69*d* depict flow charts of embodiments of methods using the present system.

FIG. 69a depicts a flow chart of an embodiment of a method using the present system. As shown in FIG. 69a, a method can comprise the following steps. A user can obtain a used testing device (i.e., smell test has been completed) 6902 and capture an image of indicia presented on a used testing device with a mobile device 6904. The mobile device can transmit the image to an external computer processing system 6906. An external processing system can orient the image 6908 and determine the disposition of the indicia on the testing device 6910. A processing system can digitize the indicia data 6912 and determine a result by evaluating individual components of digital indicia data 6914. The processing system can transmit this result to a mobile device 6916, which can display this result 6918 on a mobile device.

Figure 69B:
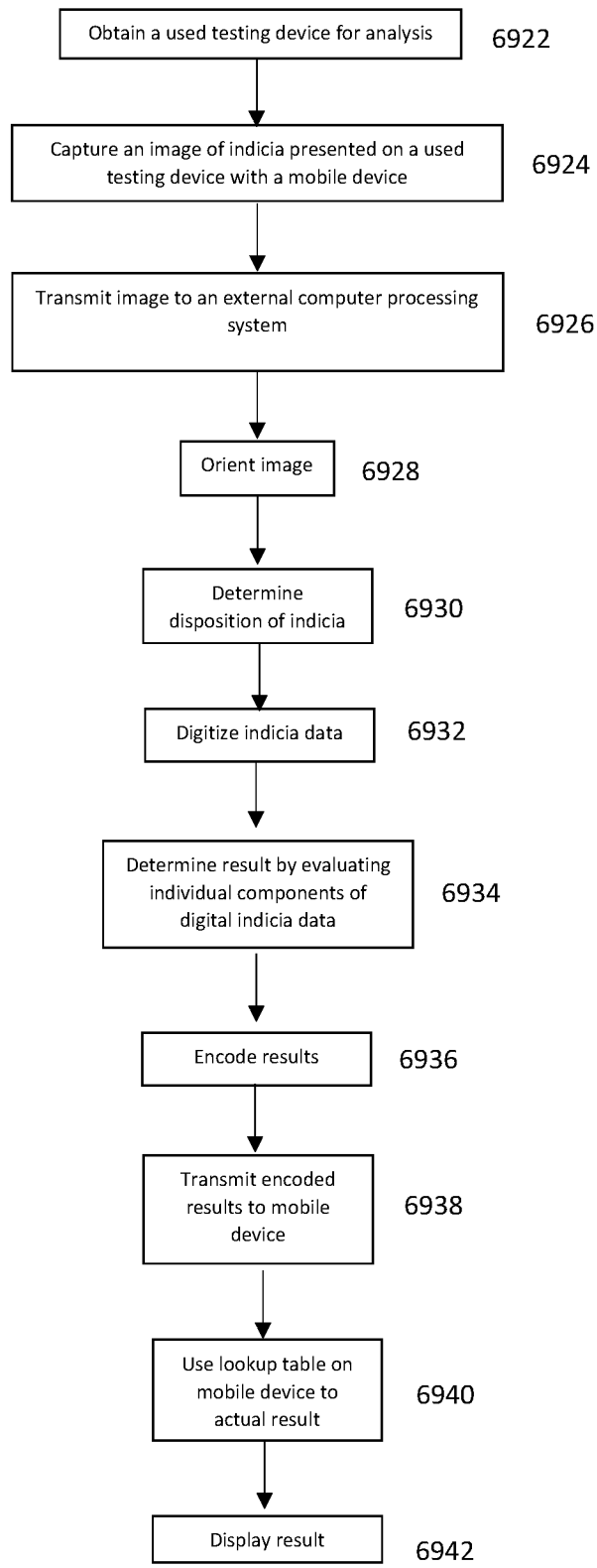

FIG. 69b depicts a flow chart of an embodiment of an alternative method using the present system. As shown in FIG. 69b, a method can comprise the following steps A user can obtain a used testing device (i.e., smell test has been completed) 6922 and capture an image of indicia presented on a used testing device with a mobile device 6924. The mobile device can transmit the image to an external computer processing system 6926. An external processing system can orient the image 6928 and determine the disposition of the indicia on the testing device 6830. A processing system can digitize the indicia data 6932 and determine a result by evaluating individual components of digital indicia data 6934. In such embodiments, an external processing system can encode the test results 6936 and transmit the encoded result to a mobile device 6938. A mobile device can have another lookup table to which the encoded test results can be decoded 6940 and the decoded result displayed 6942.

Figure 69C:
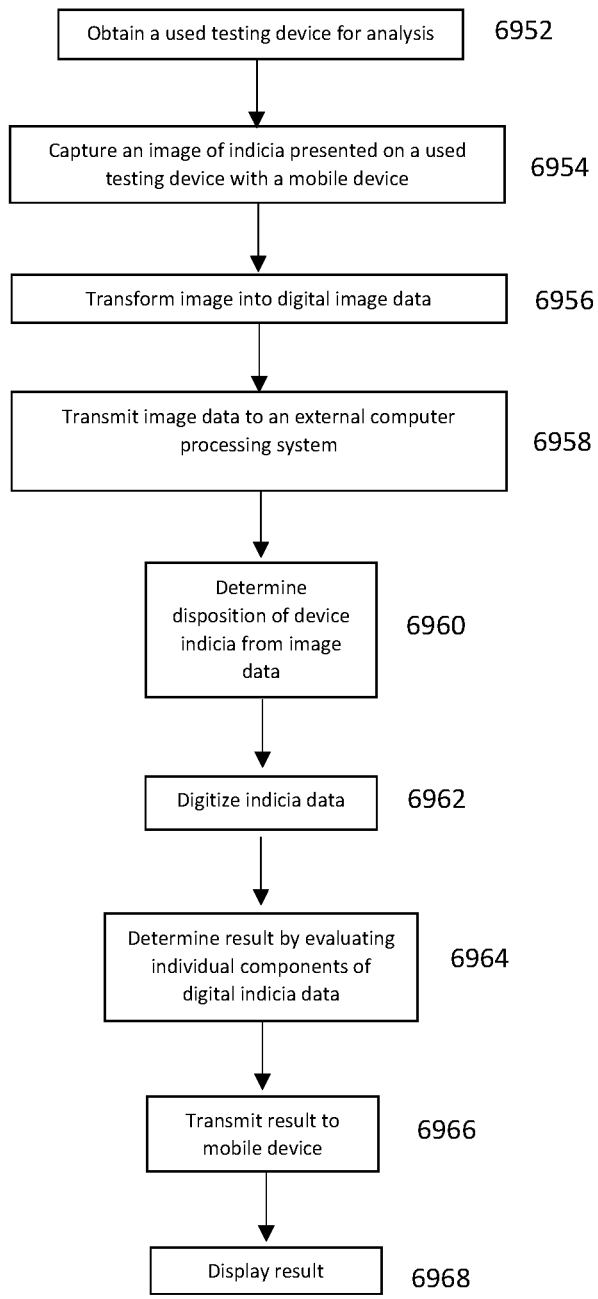

FIG. 69c depicts a flow chart of another embodiment of a method using the present system. As shown in FIG. 69c, a method can comprise the following steps. A user can obtain a used testing device (i.e., smell test has been completed) 6952 and capture an image of indicia presented on a used testing device with a mobile device 6954. A mobile device can transform an image to digital image data 6956 and transmit the digital image data to an external processing system 6958. A processing system can determine the disposition of the indicia on the testing device 6960. A processing system can digitize the indicia data 6962 and determine a result by evaluating individual components of digital indicia data 6964. This result can be transmitted to a mobile device 6966 and displayed for a user 6968.

Figure 69D:
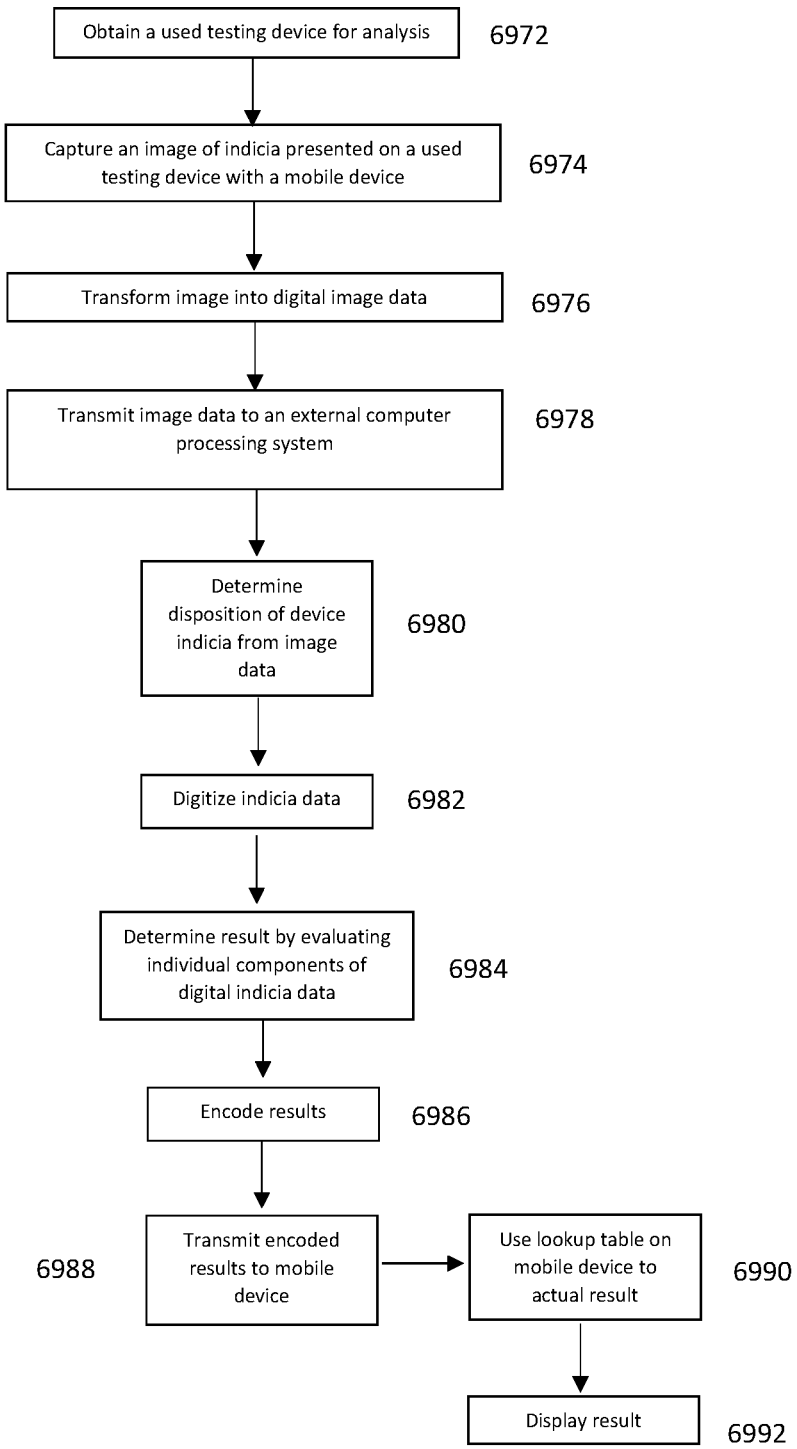

FIG. 69*d* depicts a flow chart of another embodiment of a method using the present system. As shown in FIG. 69*d*, a method can comprise the following steps. A user can obtain a used testing device (i.e., smell test has been completed) 6972 and capture an image of indicia presented on a used testing device with a mobile device 6974. A mobile device can transform an image to digital image data 6976 and transmit the digital image data to an external processing system 6978. A processing system can determine the disposition of device indicia from the digital image data 6980. A processing system can digitize the indicia data 6982 and determine a result by evaluating individual components of digital indicia data 6984. In such embodiments, an external processing system can encode the test results 6986 and transmit the encoded result to a mobile device 6988. A mobile device can have another lookup table to which the encoded test results can be decoded 6990 and the decoded result displayed 6992.

Figure 70A:
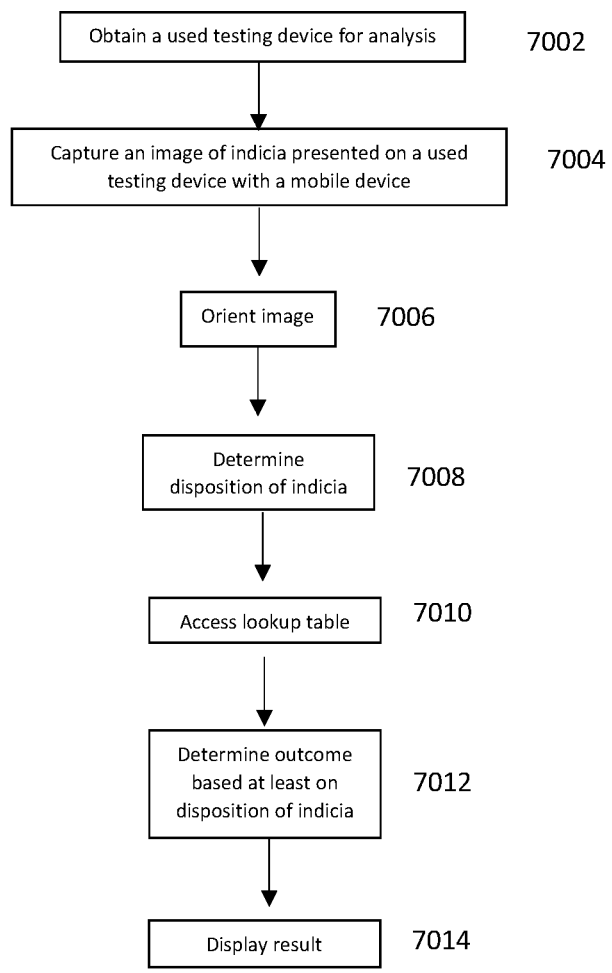

FIG. 70*a* depicts a flow chart of an embodiment of a method using the present system. As shown in FIG. 70*a*, a method can comprise the following steps. A user can obtain a used testing device (i.e., smell test has been completed) 7002 and capture an image of indicia presented on a used testing device with a mobile device 7004. A mobile device can orient the image 7006 and determine the disposition of the indicia on the testing device 7008. Using a lookup table 7010, the mobile device can determine the test results based at least upon the disposition of the indicia 7012. A mobile device can display this result 7014.

FIG. 70*b* depicts a flow chart of an embodiment of a method using the present system. As shown in FIG. 70*b*, a method can comprise the following steps. A user can obtain a used testing device (i.e., smell test has been completed) 7022 and capture an image of indicia presented on a used testing device with a mobile device 7024. The mobile device can orient the image 7026 and determine the disposition of the indicia on the testing device 7028. A mobile device can digitize the indicia data 7028 and determine a result by evaluating individual components of digital indicia data 7032. A mobile device can display this result 7034.

Figure 71:
FIG. 71 depicts a schematic of an embodiment of a method using the present system.

FIG. 71 depicts a schematic diagram of an embodiment of a communication method using the present system. As shown in FIG. 71, a mobile device 7102 comprising a camera 7104 can be wirelessly connected to a server 7106 with access to a database 7108.

Each of these embodiments disclosed can be designed to provide relevant data to a smart phone, with installed application software comprising software for analyzing a digital image created by the smart phone's internal camera. The user, a medical professional, or someone screening people for a targeted disease can use a smart phone's camera to capture a digital image of the test hardware after the user has reported relevant symptoms, as described above, and completed the smell test. The digital image created, which can include a top view of the test hardware similar to FIG. 40, can be analyzed by one or more algorithms within the application software to determine the quantity of exposed red color-coded circular indicia, green color-coded circular indicia, orange color-coded circular indicia, yellow color-coded circular indicia, blue color-coded circular indicia, and purple color-coded circular indicia, black color-coded circular indicia, medium grey color-coded circular indicia, light grey color-coded circular indicia, and cyan color-coded circular indicia, which symbolically represent the test taker's relevant disease symptoms and can include additional user information such as gender and age.

As a non-limiting example, one method for accomplishing this includes utilizing the cv2.HoughCircles function available in OpenCV, used by iOS application developers. Further details regarding utilizing this function appropriately can be available on numerous websites and blog posts, such as www.pyimageseach.com and www.stackoverflow.com. The installed application software can translate this colored-dots digital image into software code representing the user's relevant symptoms and any additional relevant user information. This application software can also include an algorithm for estimating whether the user has the targeted disease based on a software code representing the user's relevant symptoms and any additional relevant user information. Moreover, in some embodiments, indicia can have differing shapes or symbols. Moreover, in some embodiments, symbols can be bar codes or QR codes or other symbols mentioned already in detailed description. In embodiments in which indicia are differentiated by shape or symbol rather than by color, custom application software can include a pattern recognition component for differentiating by the indicium's shape or symbol in a digital image, in order to generate code to represent relevant symptoms & demographic information for the user. In some embodiments, custom application software can analyze input data from said medical diagnostic testing device after use, create a set of output information relevant to a targeted disease based on analysis of said input data, display a first subset of the output information, and send a second subset of the output information to an organization via suitable transmission means.

As noted earlier in May 2020 Nature Medicine journal, researchers reported developing a mathematical model which predicts with nearly 80 percent accuracy whether a person was likely to have Covid-19 based on their age, sex and a combination of four symptoms: loss of taste or smell, persistent cough, fatigue, and loss of appetite. By combining iOS features such as cv2.HoughCircles to analyze a digital image of the test hardware with a mathematic model for analyzing relevant symptoms and other pertinent user information, custom application software installed in a smart phone can analyze whether color dots exposed on test hardware indicate that the user probably has the targeted disease such as COVID-19, and this application software can notify a user accordingly via a smart phone's display screen.

Although the fourth, fifth, sixth, seventh, eighth, and ninth embodiments do not comprise indicia disposed on three additional corresponding symptom tabs with the phrase SHORTNESS OF BREATH or the word FEVER or the word RASH, alternate embodiments can comprise one or more additional symptoms tabs with the phrase SHORTNESS OF BREATH, the word FEVER, the word RASH, the phrase ABDOMINAL PAIN, the word HEADACHE, the phrase CHEST PAIN, the word DIARRHEA, the word CONFUSION, the word HOARSENESS, and/or any other known, convenient and/or desired indicia respectively printed on these tabs.

FIGS. 72A*i*-72AC*ii* depicts a lookup table used to determine a test result. In some embodiments, image data can be digitized and compared with a table of symptoms to determine the likelihood of a person having a target disease.

In one embodiment of this smart phone application software, color-coded circular indicia data can be compared with a target disease symptoms lookup table, such as the table in FIGS. 72Ai-72ACii within the application software to determine a target disease's relative likelihood. This application software lookup table can be digitally analogous to the symptom chart in Table 1, shown in FIG. 76. Subsequently this application software can send an appropriate disease likelihood notification for display via a smart phone's screen. This disease likelihood notification displayed on a smart phone screen can include a numerical score, comparable to the scores in the symptom chart in Table 1, shown in FIG. 76, and/or a verbal description as shown in the lookup table in FIGS. 72Ai-72ACii. This disease likelihood score can also be a percentage probability of the target disease, which can be displayed via a smart phone's screen as a test result. The notification displayed on the phone screen can include recommendations regarding next steps based on the disease likelihood, such as, but not limited to, self-imposed isolation from other people for 21 days, get medical diagnostic test as soon as possible, go to medical center for immediate treatment, retake the symptom test daily, etc., based on applicable recommendations by the Centers for Disease Control and/or other medical experts knowledgeable in the targeted disease.

Although some embodiments of the custom application software can use the Target Disease Symptoms Lookup Table in FIGS. 72Ai-72ACii to determine the disposition of the indicia in the digital image of the used medical diagnostic test device and then display a result based on lookup table, alternatively this can be accomplished by analysis of each indicium in the digital image, which is comparable to FIG. 74 flow chart:

1. Store a unique identification code corresponding with a used test device.
2. Determine the total number of first color circular indicia in a digital image of this used test device and store this quantity with the identification code corresponding with this used test device.
3. Determine the total number of second color circular indicia in a digital image of this used test device and store this quantity with the identification code corresponding with this used test device.
4. Determine the number of third color circular indicia in a digital image of this used test device and store this quantity with the identification code corresponding with this used test device.
5. Determine the number of fourth color circular indicia in a digital image of this used test device and store this quantity with the identification code corresponding with this used test device.
6. Determine the number of fifth color circular indicia in a digital image of this used test device and store this quantity with the identification code corresponding with this used test device.
7. Determine the number of sixth color circular indicia in a digital image corresponding with this used test device and store this quantity with the identification code corresponding with this used test device.
8. Determine the number of seventh color circular indicia in a digital image of this used test device and store this quantity with the identification code corresponding with this used test device.
9. Determine the number of eighth color circular indicia in a digital image of this used test device and store this quantity with the identification code corresponding with this used test device.
10. Determine the number of ninth color circular indicia in a digital image of this used test device and store this quantity with the identification code corresponding with this used test device.
11. Determine the number of tenth color color-coded circular indicia in a digital image of this used test device and store this quantity with the identification code corresponding with this used test device.
12. If the total quantity of first color circular indicia+second color circular indicia>4, then display the result message "Retake smell test due to error." Do not continue with other steps.
13. If the total quantity of first color circular indicia+second color circular indicia<4, then display the result message "Retake smell test due to error." Do not continue with other steps.
14. If the total quantity of first color circular indicia is 0, then store and display the result message "0 signs of anosmia, which is a very common symptom of COVID-19. Other target symptoms:".
15. If the total quantity of first color circular indicia is 1, then store and display the result message "1 sign of anosmia, which is a very common symptom of COVID-19. Other target symptoms:".
16. If the total quantity of first color circular indicia is 2, then store and display the result message "2 signs of anosmia, which is a very common symptom of COVID-19. Other target symptoms:".
17. If the total quantity of first color circular indicia is 3, then store and display the result message "3 signs of anosmia, which is a very common symptom of COVID-19. Other target symptoms:".
18. If the total quantity of first color circular indicia is 4, then store and display the result message "4 signs of anosmia, which is a very common symptom of COVID-19. Other target symptoms:".
19. If the total quantity of third color circular indicia+fourth color circular indicia+fifth color circular indicia is 0, then store and display a continuation of the result message with "None".
20. If the quantity of third color circular indicia is 1, then store and display a continuation of the result message with "Cough".
21. If the quantity of fourth color circular indicia is 1, then store and display a continuation of the result message with "Fatigue".
22. If the quantity of fifth color circular indicia is 1, then store and display a continuation of the result message with "Appetite Loss".
23. If the total quantity of seventh color circular indicia+eighth color circular indicia+ninth color circular indicia is 0, then store and display a continuation of the result message with "You may have lower risk for serious symptoms than older people if you have COVID-19.".
24. If the quantity of seventh color circular indicia is 1, then store and display a continuation of the result message with "You may have a higher risk for serious symptoms than younger people if you have COVID-19."
25. If the quantity of eighth color circular indicia is 1, then store and display a continuation of the result message with "You may have a significantly higher risk for serious symptoms than younger people if you have COVID-19."
26. If the quantity of ninth color circular indicia is 1, then store and display a continuation of the result message with "You are at highest risk for serious symptoms than younger people if you have COVID-19."
27. If the quantity of tenth color circular indicia is 1, then store and display a continuation of the result message with "Based on your gender, you are at higher risk for serious symptoms than women of similar age are."
28. If the total quantity of first color circular indicia is >0 and <3, then store and display a continuation of the result message stating "You may have COVID-19 based on anosmia symptoms. As soon as possible, self-isolate, contact physician for advice, and take molecular or antigen COVID-19 test, if available."
29. If the total quantity of first color circular indicia is >2 and <5, then store and display a continuation of the result message stating "You have significant likelihood of COVID-19 based on anosmia symptoms. As soon as possible, self-isolate, contact physician for advice, and take molecular or antigen COVID-19 test, if available."
30. If the total quantity of third color circular indicia+ fourth color circular indicia+fifth color circular indicia is 3 and the quantity of first color circular indicia is 0, then store and display a continuation of the result message with "The combination of cough+fatigue+ appetite loss significantly increases likelihood you have COVID-19. As soon as possible, self-isolate, contact physician for advice, and take molecular or antigen COVID-19 test, if available."
31. If the total quantity of third color circular indicia+ fourth color circular indicia+fifth color circular indicia is 3 and the quantity of first color circular indicia is >0 and <5, then store and display a continuation of the result message with "The combination of cough+fatigue+appetite loss significantly increases likelihood you have COVID-19."
32. If the total quantity of third color circular indicia+ fourth color circular indicia+fifth color circular indicia is 2 and the quantity of first color circular indicia is 0, then store and display a continuation of the result message with "The combination of several symptoms increases likelihood you have COVID-19. As soon as possible, self-isolate, contact physician for advice, and take molecular or antigen COVID-19 test, if available."
33. If the total quantity of third color circular indicia+ fourth color circular indicia+fifth color circular indicia is 2 and the quantity of first color circular indicia is >0 and <5, then store and display a continuation of the result message with "The combination of several additional symptoms significantly increases likelihood you have COVID-19."
34. If the total quantity of third color circular indicia+ fourth color circular indicia+fifth color circular indicia is 1 and the quantity of first color circular indicia is 0, then store and display a continuation of the result message with "The presence of one symptom may indicate you have COVID-19. As soon as possible, self-isolate, contact physician for advice, and take molecular or antigen COVID-19 test, if available."
35. If the total quantity of third color circular indicia+ fourth color circular indicia+fifth color circular indicia is 1 and the quantity of first color circular indicia is >0 and <5, then store and display a continuation of the result message with "The presence of an additional symptom increases likelihood you have COVID-19."
36. If the total of all second color circular indicia is 4 and the total of all first color circular indicia+third color circular indicia+fourth color circular indicia+fifth color circular indicia is 0, then store and display a continuation of the result message with "Maintain social distancing of 6 feet minimum, wear a mask when others are present, and wash hands frequently."
37. Store and display a concluding comment "If you have any concerns about other symptoms not listed, contact your physician for advice soon. Refer to www.cdc.gov for further information regarding this disease."
38. Repeat step 1-step 37 for other people in a target population.
39. Send some or all of the data and results stored for target population to an organization, which may be a business, school, government office, transportation center, CDC, or any other organization.

In the fourth embodiment, fifth embodiment, sixth embodiment, seventh embodiment, eighth embodiment, and ninth embodiment, the circular indicia listed in these steps correspond to the following indicia colors:

The first color circular indicia correspond to red color-coded circular indicia in these embodiments.

The second color circular indicia correspond to green color-coded circular indicia in these embodiments.

The third color circular indicia correspond to black color-coded circular indicia in these embodiments.

The fourth color circular indicia correspond to yellow color-coded circular indicia in these embodiments.

The fifth color circular indicia correspond to orange color-coded circular indicia in these embodiments.

The sixth color circular indicia correspond to purple color-coded circular indicia in these embodiments.

The seventh color circular indicia correspond to cyan color-coded circular indicia in these embodiments.

The eighth color circular indicia correspond to blue color-coded circular indicia in these embodiments.

The ninth color circular indicia correspond to medium grey color-coded circular indicia in these embodiments.

The tenth color circular indicia correspond to light grey color-coded circular indicia in these embodiments.

Although these embodiments can comprise ten circular indicia which each corresponding to the particular color listed, each of the circular indicia can correspond with an alternative color in other variations of these embodiments.

This application software can initiate transmission, via the internet, of a set of data which can include this symptom data, as well as other any other relevant, available data, such as demographics information (age, gender, etc.), along with an identification code, which can be a unique number automatically assigned by the application software or a test hardware serial number or 5 personal identification number for the user associated with this symptom data, estimated disease positivity rate data for target population tested during a given time period, and estimated change in disease positivity rate from one time period to a subsequent time period to a website which collects this symptom data. This website can be a disease tracking website such as www.cdc.gov or a website for a medical center. The personal identification number can be a person's driver's license number, employee number, student I.D. number, passport number, personal telephone number, or social security number. This personal I.D. number can be obtained by placing the appropriate personal I.D. card adjacent to the test hardware, within a smart phone camera's field of view, and then capturing this image using this camera to create a digital image. In some embodiments of this application software, some or all of this data can also be displayed on the smart phone screen.

In any of the embodiments, the odorous substance(s) can be identical to or have an odor similar to one or more odorous substances in smell tests on the market, such as the Smell Identification Test™ available from Sensonics International. Selection of the optimal odorous substance(s) for this test hardware can be determined by experimental trials of numerous substances, such as the substances used in this Smell Identification Test™ or substances from IFF (International Fragrances and Flavors) Living Technology collection, and then selecting one or more odorous substances which have lowest false negative test results and highest true positive test results associated with the targeted disease, such as COVID-19.

Dr. Dana Small at the Yale School of Medicine, who is conducting a study regarding sense of smell impairment associated with COVID-19 disease during 2020, has noted that peanut butter is a very good candidate for a COVID-19 smell test because peanut butter scent stimulates the olfactory nerve without stimulating the trigeminal nerve, unlike numerous other substances with odor such as alcohol, vanilla, mint, and coffee. Thus, the various embodiments can comprise peanut butter or an extract of peanut butter as one smell test substance/odorous substance. In addition to including scent which only stimulates the olfactory nerve for one or more of the odorous substances, some embodiments can also include scent which stimulates the trigeminal nerve for at least one of the odorous substances, such as alcohol, vanilla, mint, or coffee. Some smell test substance patches can comprise scents which only stimulate the olfactory nerve and one smell test substance patch can comprise scent which stimulates the trigeminal nerve in some embodiments. This combination of difference scents can help differentiate between significant sinus congestion and direct impairment of olfactory nerve functioning, which can improve the accuracy of the smell test. In other embodiments, every smell test substance patch can comprise substance with a different scent, and the user can identify the four smell test substance patches which match specific common smells listed in the test instructions, such as smoke, roses, peanut butter, and alcohol.

During 2020 numerous other similar studies are ongoing to determine appropriate odorous substances useful in detecting olfactory impairment caused by COVID-19. Members of the Association for Chemoreception Sciences have created a working group, the Global Consortium for Chemosensory Research, to help pool expertise and resources for other researchers. The American Academy of Otolaryngology—Head and Neck Surgery has developed a tool for clinicians as well. In the various embodiments disclosed, the adhesive layers, odorous substances, and smell test substance patches can be disposed onto the surfaces of the test hardware via numerous methods commonly used in manufacturing industry, such as automated dispensing, screen printing, and spraying processes, or any other known and/or convenient process.

As presented herein, some embodiments can comprise grooves which can reduce the force required to bend elements of the embodiments. Although grooves are specifically mentioned in some embodiments, embodiments which comprise paperboard, such paperboard can be creased or scored to essentially create a hinge, with same or similar functionality as a groove. Scoring is a well-known industry technique whereby paperboard stiffness along a line is reduced in order to aid in folding and/or bending—press scores (litho scoring) and old-style folding machine scores are two non-limiting such examples. As used herein, scoring references selectively weakening the paperboard sheet to aid in folding and as used herein creasing refers to the internal delamination of a paperboard sheet by compression along a line where folding is convenient and/or desired. In some non-limiting, exemplary embodiments, creasing can be accomplished by either a platen method (both sheet and die board are flat), or a rotary method (paperboard passes between cylinders or wraps around a cylinder). In alternate embodiments, alternate materials which plastically deform without fracturing when bent beyond a given angle, which can be less than 90 degrees, absent any grooves, scores, or creases in that component. Such materials as aluminum foil or certain polymer films or paper can be used for the cover component without any grooves, scores, or creases incorporated.

Although the various embodiments shown in the figures herein comprise at least one odorous substance, other embodiments can comprise indicium with the phrase "LOSS OF SMELL" or an equivalent phrase disposed on a cover tab, with a red color-coded circular indicium disposed behind that cover tab on base, without comprising any odorous substance. Alternate embodiments can comprise neither odorous substances nor any indicium which references loss of smell, which may not be relevant for some target diseases. Additionally, in alternate embodiments, one or more of the smell test substance patches can have equal adhesion to both the cover tab and the base.

Although many embodiments described comprise a set of color-coded circular indicia, the shape of these indicia can be changed to a polygon such as square, pentagon, triangle, or any other known and/or convenient shape in other embodiments. If these indicia all share a common shape in the embodiment, they can also be color-coded to visually differentiate each indicium. Alternatively, if these indicia all share a common color such as black in the embodiment, each indicium in the embodiment can comprise a unique shape (such as, but not limited to circle, triangle, square, pentagon, hexagon, heptagon, octagon, etc.) to visually differentiate each indicium. In other embodiments, each indicium can comprise a unique symbol such as, but not limited to +, −, *, # instead. Moreover, in some embodiments not shown, circular, colored indicia may be replaced by QR codes or bar codes which represent different symptoms or other information (demographic information, test hardware serial number, etc.).

It should be noted that although the odorous substance 8A and the odorous substance 8B can be disposed within cavity 7K and cavity 7D respectively, as shown in FIG. 15 and FIG. 16 of the first embodiment, each odorous substance can be disposed within any of the cavities 7A-7V of base 5. Since this test hardware can be used daily to screen people at their workplace, school, etc., ideally multiple variations of this test hardware can be manufactured, each with odorous substance(s) disposed in different cavities. This will make it impossible for a person to memorize the relative positions of one or more cavities containing an odorous substance inside in order to consistently pass this smell test regardless of whether or not that person develops anosmia eventually. In some embodiments, the number of different odorous substances disposed within cavities of base 5 can be limited to decrease the duration of the smell test. The first embodiment of this test hardware comprises two different odorous substances, each disposed in separate cavities of base 5, although this number can be increased, if necessary, in order to consistently differentiate between people who experience anosmia caused by the targeted disease, such as COVID-19, and people who do not experience anosmia caused by this disease. Each of the embodiments can have odorous substances disposed in a variety of positions not shown in the figures of this patent.

In order to visually distinguish any cavities in base 5 which contain an odorous substance, such as cavity 7K shown in FIG. 15, either an interior surface of each such cavity or the odorous substance itself can have a distinctive color, such as, but not limited to, green, or the interior side of the opaque cover's corresponding segment enclosing that particular cavity, such as, but not limited to, segment 4K in FIG. 15, can have such a distinctive color. Alternately, every cavity in base 5 which does not contain an odorous substance can comprise an interior surface with a distinctive color, such as, but not limited to red, or the interior side of the opaque cover's corresponding segment enclosing that particular cavity, such as, but not limited to, segment 4U in FIG. 15, can have such a distinctive color, and none of the cavities in base 5 enclosing an odorous substance, such as cavity 7K and cavity 7D, can comprise an interior surface with that same distinctive color.

In the foregoing specification, the embodiments have been described with reference to specific elements thereof. It will, however, be evident that various modifications and changes can be made thereto without departing from the broader spirit and scope of the embodiments. For example, the reader is to understand that the specific ordering and combination of process actions shown in the process flow diagrams described herein is merely illustrative, and that using different or additional process actions, or a different combination or ordering of process actions can be used to enact the embodiments. The specification and drawings are, accordingly, to be regarded in an illustrative rather than restrictive sense.

It should also be noted that the present invention can be implemented in a variety of computer systems 4700. The various techniques described herein can be implemented in hardware or software, or a combination of both. Preferably, the techniques are implemented in computer programs executing on programmable computers that each include a processor, a storage medium readable by the processor (including volatile and non-volatile memory and/or storage elements), at least one input device, and at least one output device. Program code is applied to data entered using the input device to perform the functions described above and to generate output information. The output information is applied to one or more output devices. Each program is preferably implemented in a high-level procedural or object-oriented programming language to communicate with a computer system. However, the programs can be implemented in assembly or machine language, if desired. In any case, the language can be a compiled or interpreted language. Each such computer program is preferably stored on a storage medium or device (e.g., ROM or magnetic disk) that is readable by a general or special purpose programmable computer for configuring and operating the computer when the storage medium or device is read by the computer to perform the procedures described above. The system can also be considered to be implemented as a computer-readable storage medium, configured with a computer program, where the storage medium so configured causes a computer to operate in a specific and predefined manner. Further, the storage elements of the exemplary computing applications can be relational or sequential (flat file) type computing databases that are capable of storing data in various combinations and configurations.

Figure 73:
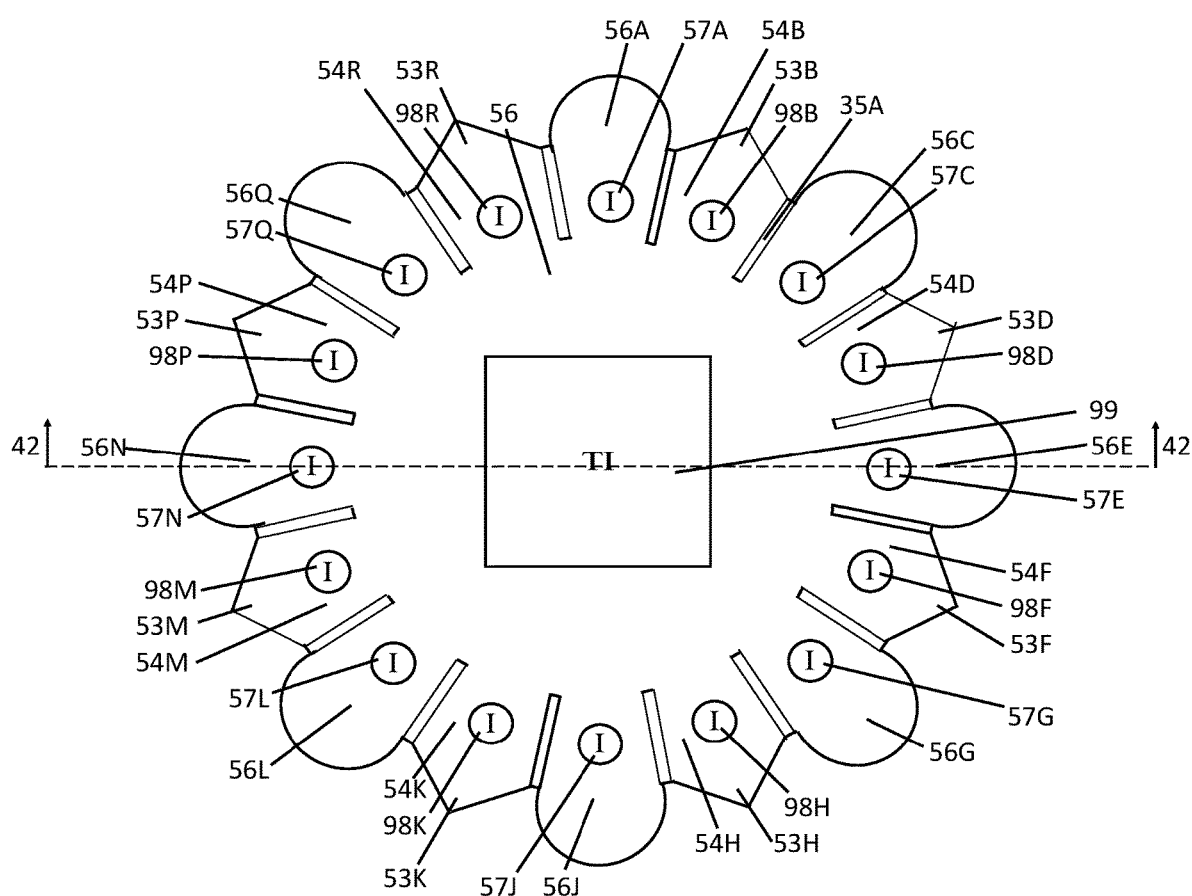
FIG. 73 depicts a top view of a tenth embodiment of the present device.
Figure 74A:
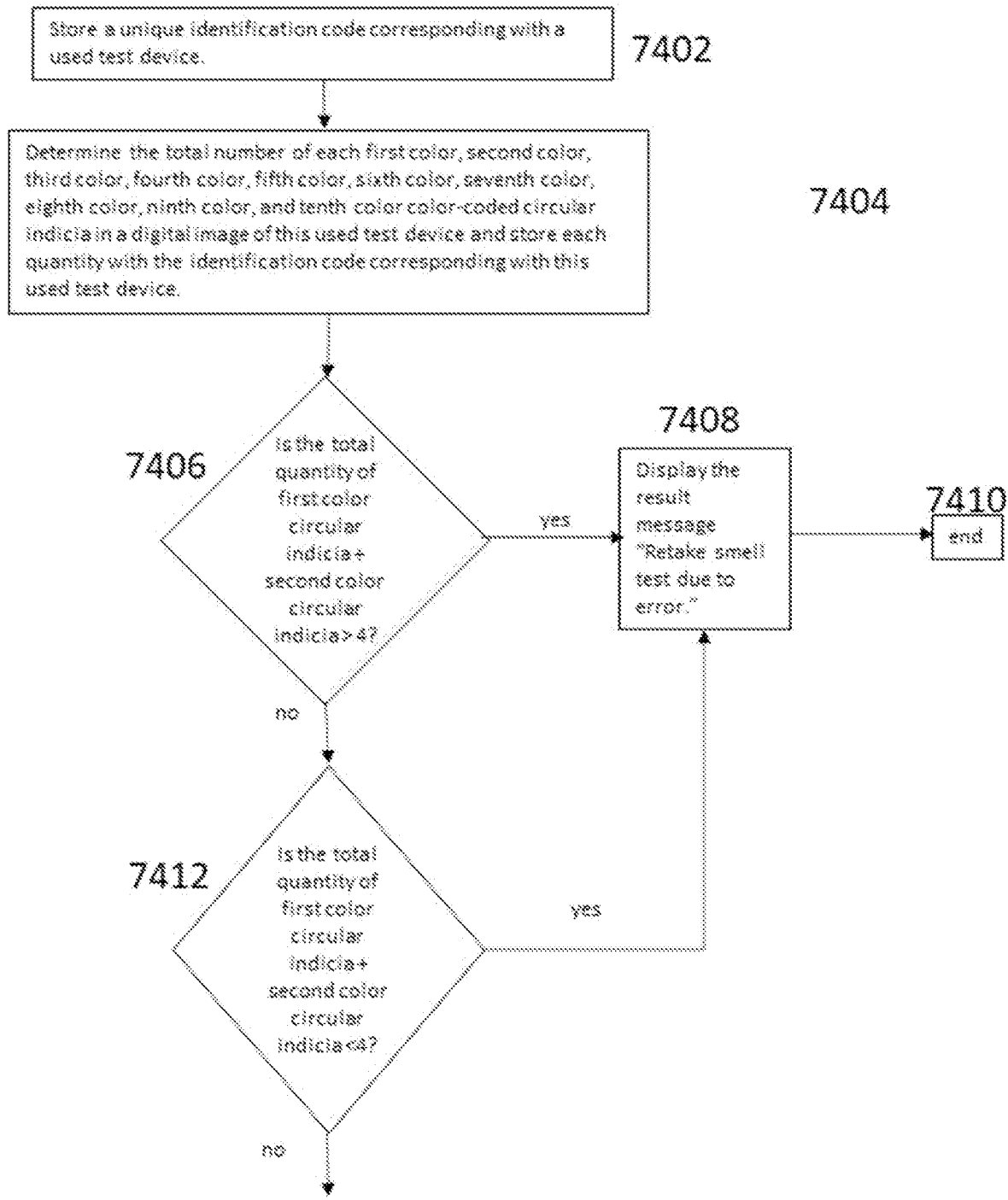
FIGS. 74*a-h* depict a flow chart of an embodiment of a method using the present system.
Figure 74B:
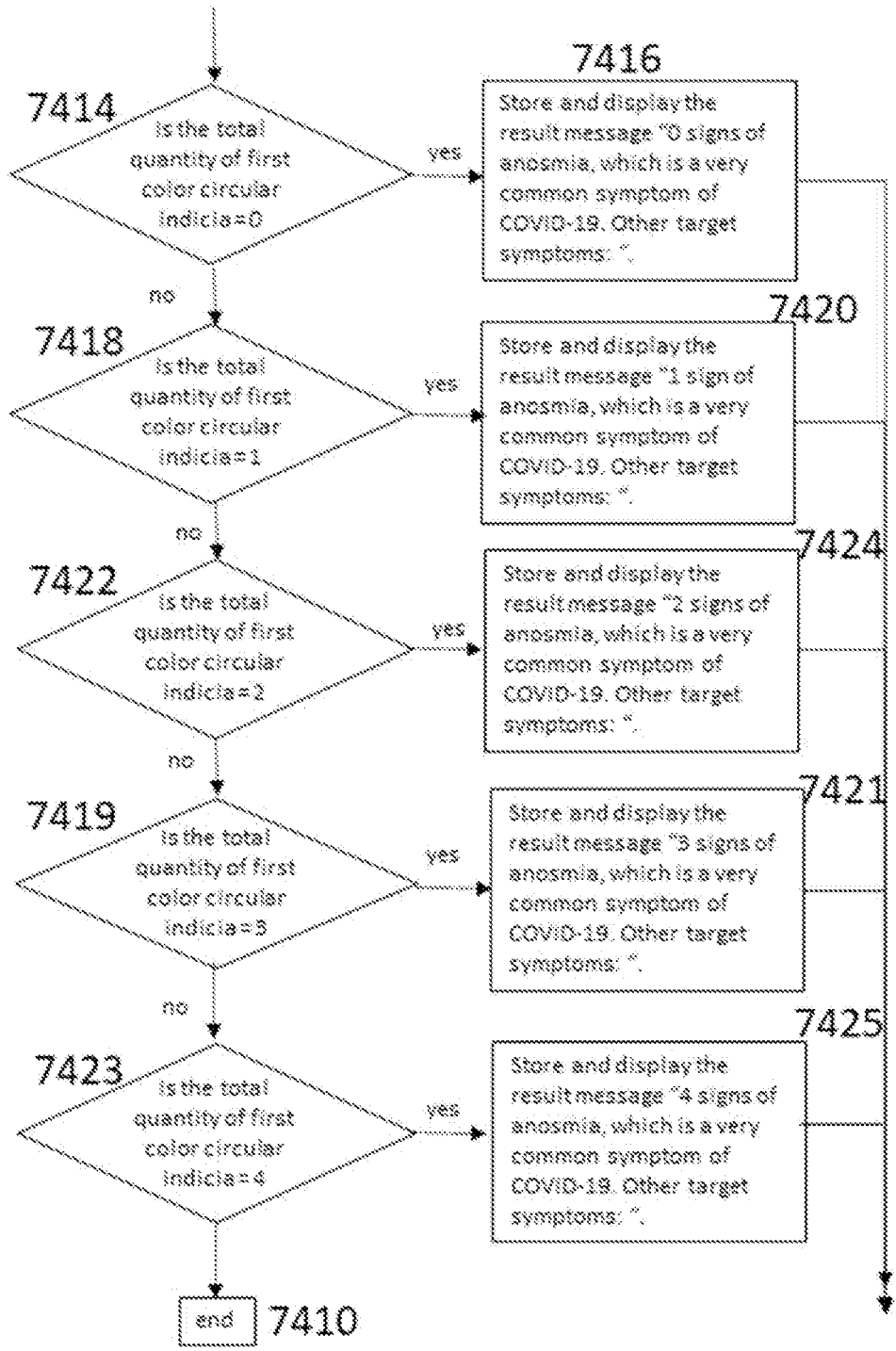
Figure 74C:
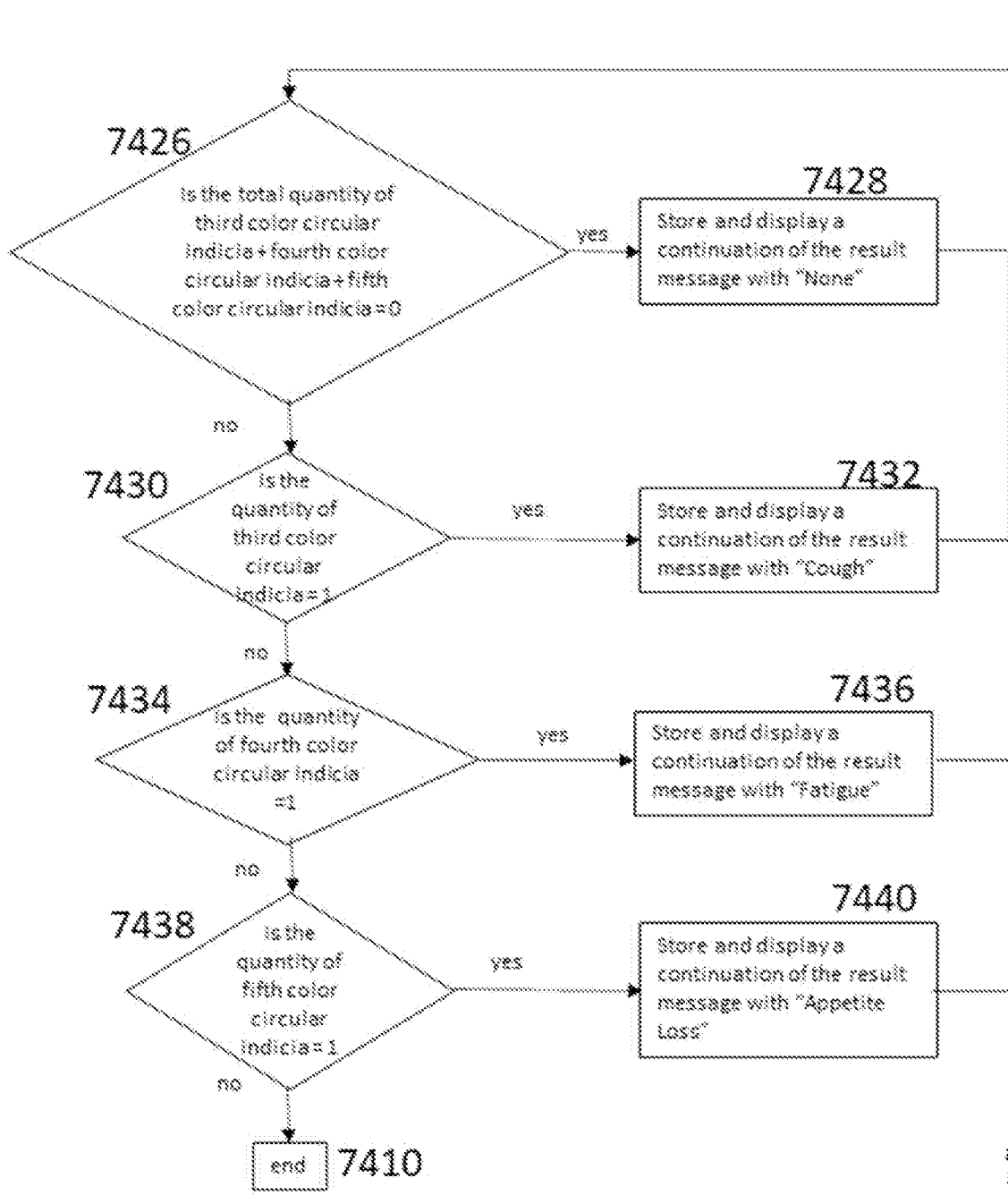
Figure 74D:
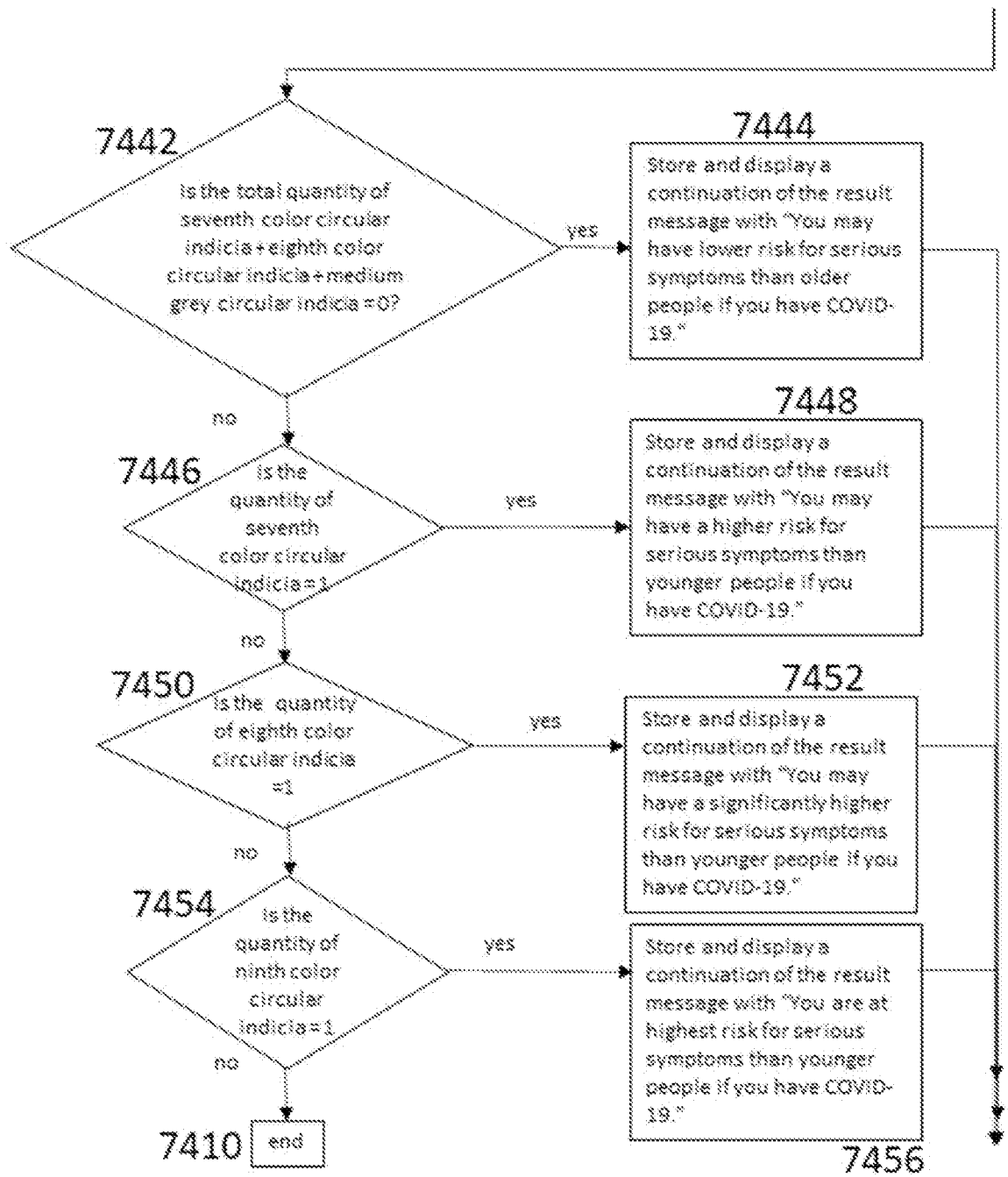
Figure 74E:
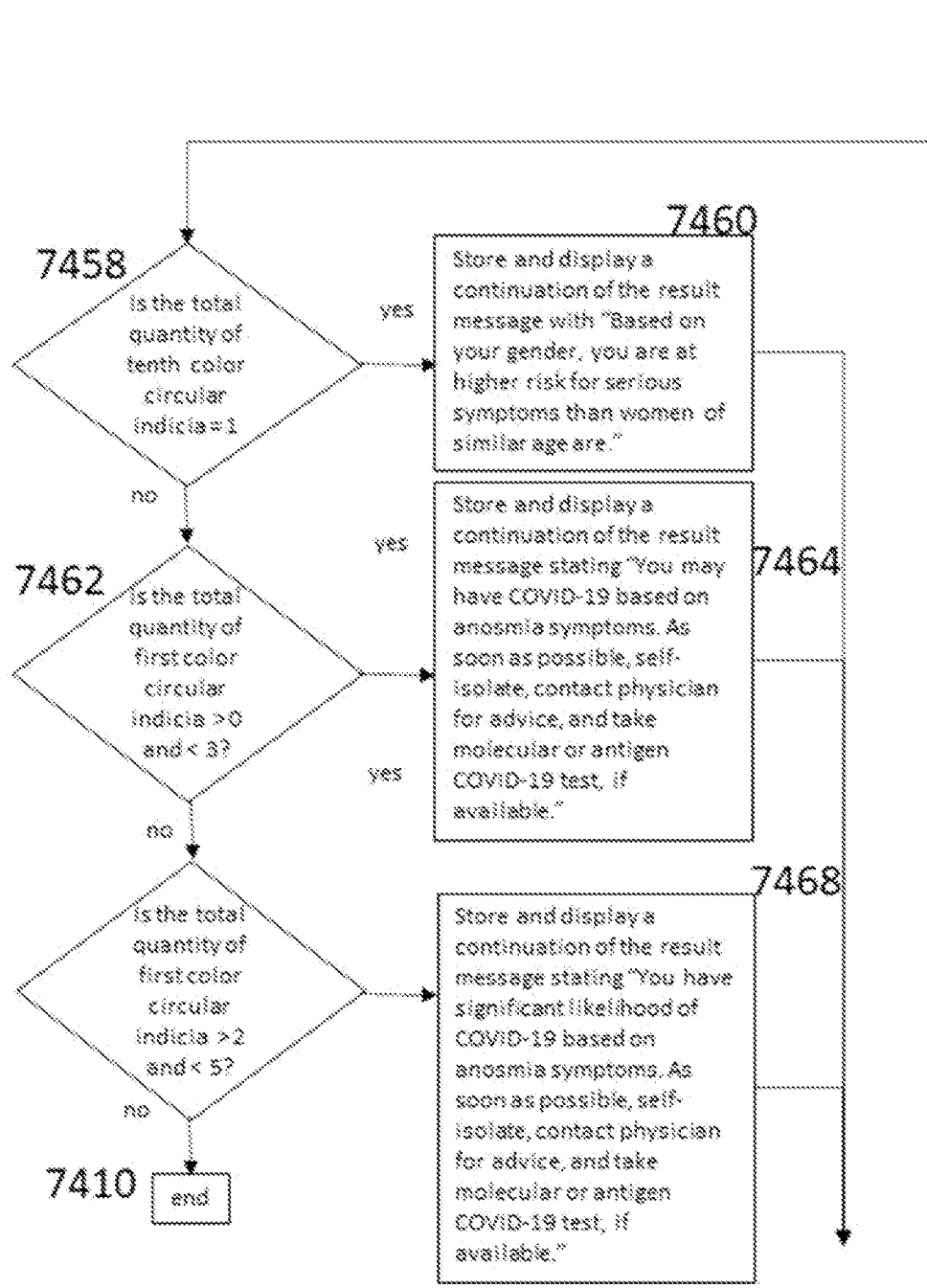
Figure 74F:
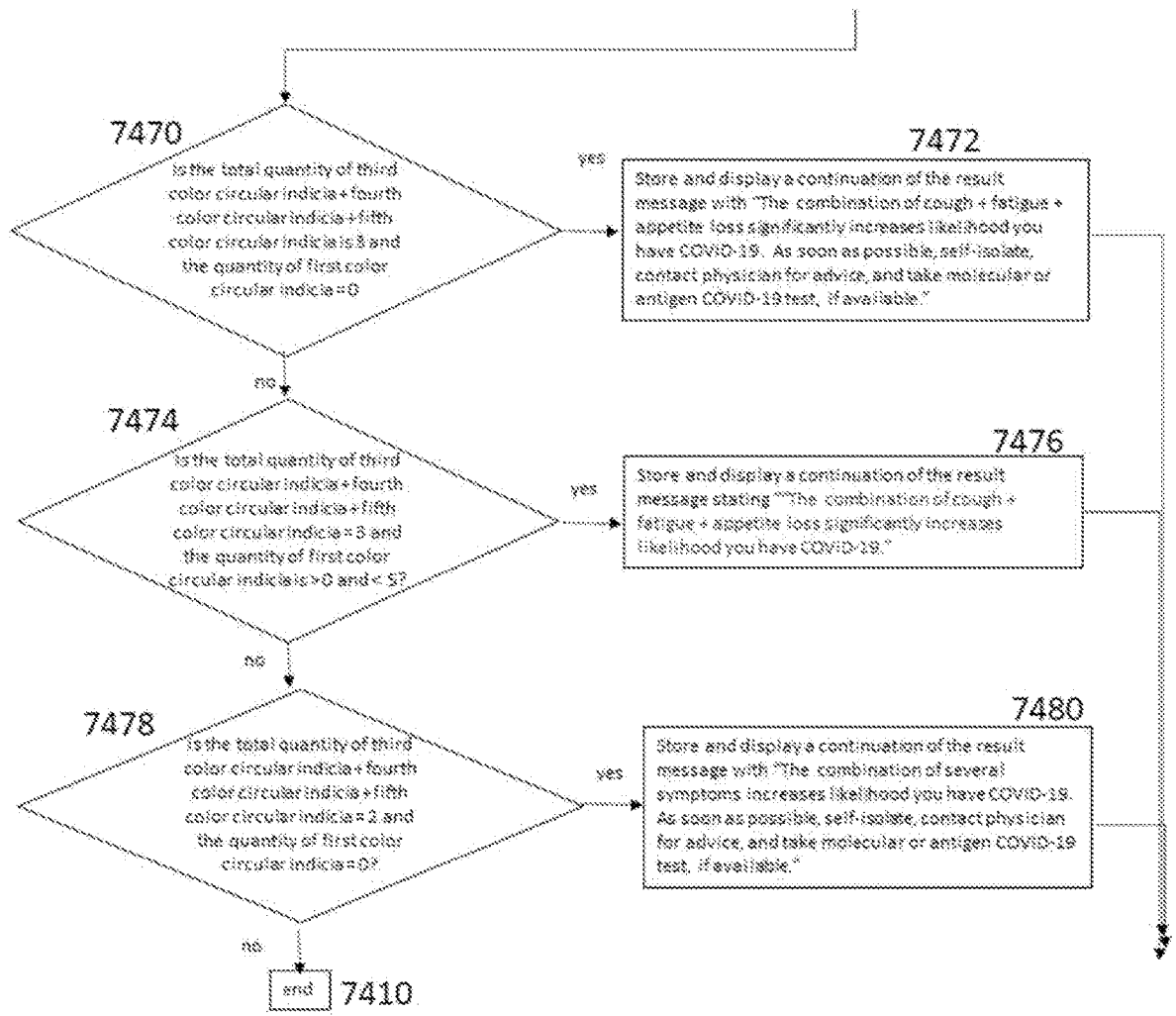
Figure 74G:
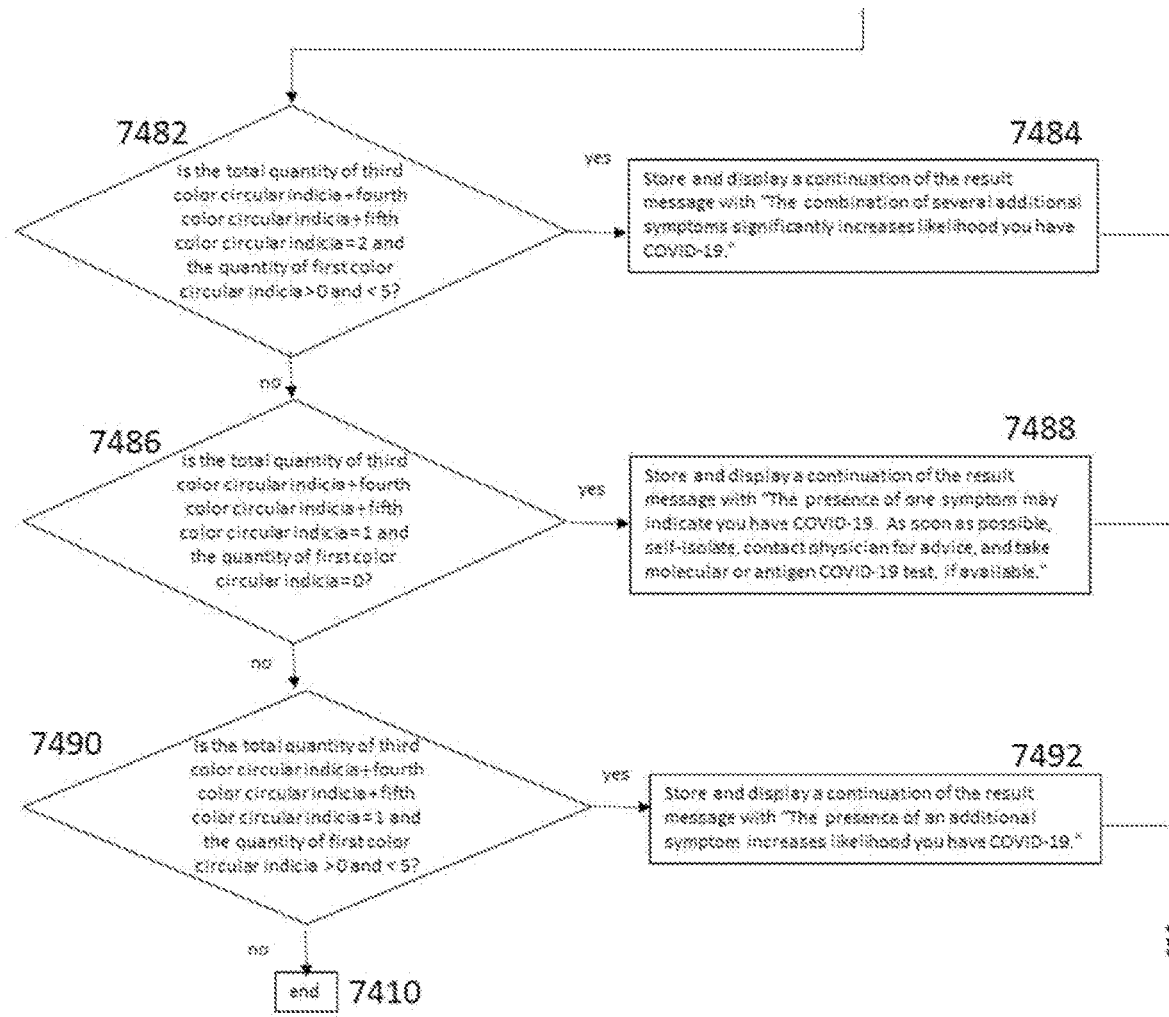
Figure 74H:
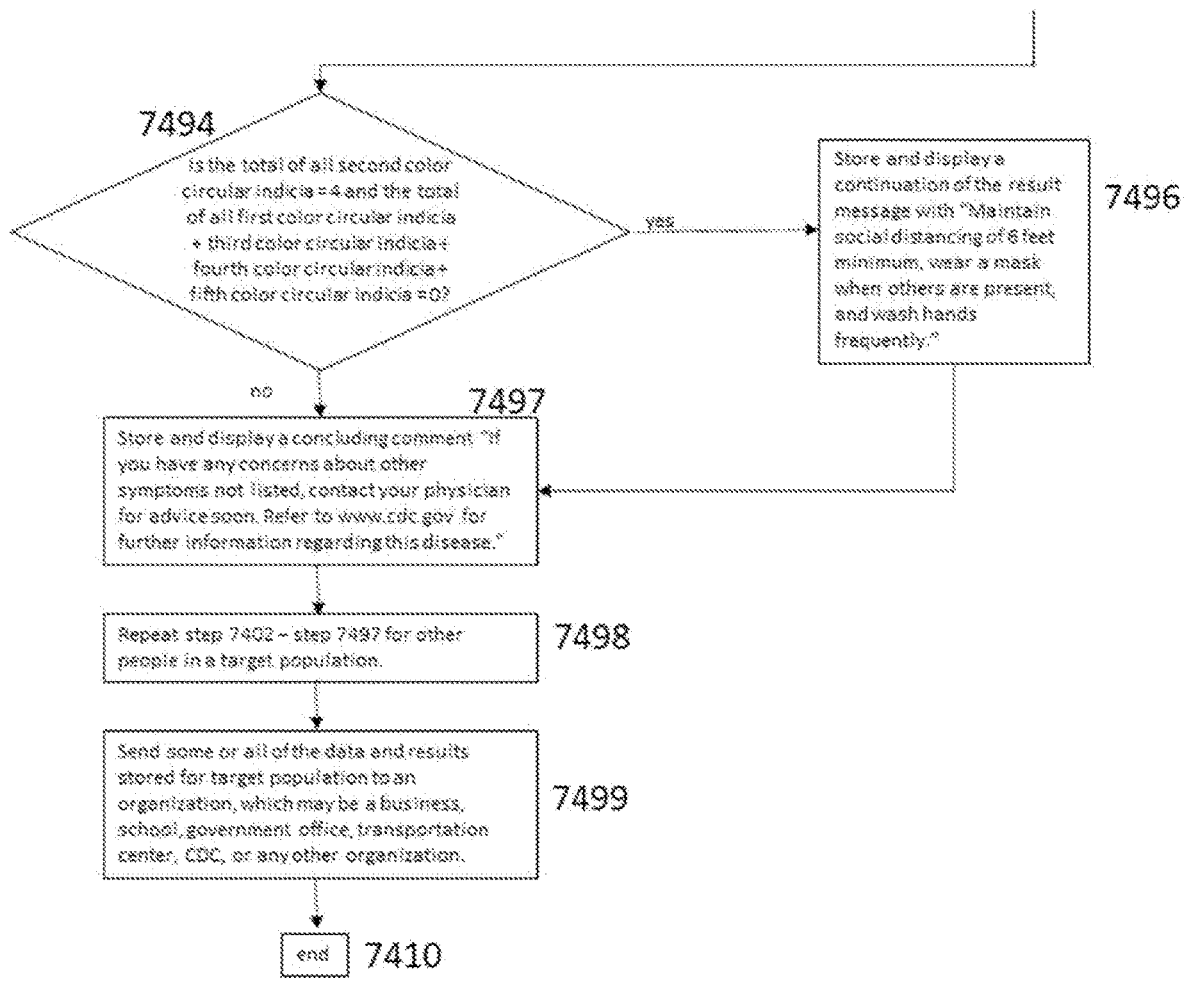

FIG. 73 depicts a tenth embodiment of the present device. A tenth embodiment shown in FIG. 73 top assembly view comprises two manufactured components—posterior base 35A and an opaque anterior cover 56. In this tenth embodiment, posterior base 35A can be identical to this posterior base 35A in the sixth embodiment, comprising similar or identical features, design, and materials. This tenth embodiment can comprise posterior base color-coded circular indicium 39A, 39B, 39C, 39D, 39E, 39F, 39G, 39H, 39J, 39K, 39L, 39M, 39N, 39P, 39Q, 39R, a polygonal adhesive ring 50, and circular adhesive layer 40A disposed on this posterior base 35A that can be identical to the sixth embodiment in function, design, colors, and materials, as shown in FIG. 41 top view of posterior base 35A.

This tenth embodiment also can comprise eight smell test substance patches 38A, 38C, 38E, 38G, 38J, 38L, 38N, and 38Q disposed equidistantly spaced apart on top surface of posterior base 35A, equidistance from the center of this base, or in any other known and/or convenient configuration. These eight smell test substance patches can be substantially identical in function, design, and materials to the eight smell test substance patches in the sixth embodiment shown in FIG. 41, and each of the eight smell test substance patches 38A, 38C, 38E, 38G, 38J, 38L, 38N, and 38Q can be radially aligned with a corresponding posterior base color-coded circular indicium 39A, 39C, 39E, 39G, 39J, 39L, 39N, and 39Q also disposed on posterior base 35A. The circular adhesive layer 40A and a polygonal adhesive ring 50 can structurally attach posterior base 35A and opaque anterior cover 56, similar to the sixth embodiment shown in FIG. 42. The opaque anterior cover 56 of this tenth embodiment, shown in FIG. 73, can comprise features similar and/or identical to the sixth embodiment features of opaque anterior cover 56. This opaque anterior cover 56 comprises anterior cover tabs 56A, 56C, 56E, 56G, 56J, 56L, 56N, and 56Q which can extend radially from opaque anterior cover 56. These eight radially aligned tabs can be spaced 45° apart and can be integral to opaque anterior cover 56 or in any other known and/or convenient configuration.

As shown in FIG. 73, each anterior cover tab 56A, 56C, 56E, 56G, 56J, 56L, 56N, and 56Q can have a corresponding anterior cover tab indicium 57A, 57C, 57E, 57G, 57J, 57L, 57N, and 57Q disposed on an anterior cover tab. Each anterior cover tab indicium 57A, 57C, 57E, 57G, 57J, 57L, 57N, and 57Q can include an identification number which can be referenced in test instructions 99 (symbolized as TI enclosed within a square), which can be printed or embossed onto a top surface of an opaque anterior cover 56, as shown in FIG. 73. Anterior cover tab indicium 57A can comprise the phrase PEEL 7, anterior cover tab indicium 57C can comprise the phrase PEEL 8, anterior cover tab indicium 57E can comprise the phrase PEEL 1, anterior cover tab indicium 57G can comprise the phrase PEEL 2, anterior cover tab indicium 57J can comprise the phrase PEEL 3, anterior cover tab indicium 57L can comprise the phrase PEEL 4, anterior cover tab indicium 57N can comprise the phrase PEEL 5, anterior cover tab indicium 57Q can comprise the phrase PEEL 6. The bottom surface of each anterior cover tab 56A, 56C, 56E, 56G, 56J, 56L, 56N, and 56Q can be contiguous with a corresponding smell test substance patch 38A, 38C, 38E, 38G, 38J, 38L, 38N, and 38Q, such as anterior cover tab 56E and smell test substance patch 38E, comparable to the sixth embodiment cross section assembly view shown in FIG. 42.

The bottom surface of opaque anterior cover 56 can comprise sixteen anterior cover grooves 44A, 44B, 44C, 44D, 44E, 44F, 44G, 44H, 44J, 44K, 44L, 44M, 44N, 44P, 44Q, and 44R, which can be each disposed at the inward edge of a corresponding anterior cover tab segment 54A, 54B, 54C, 54D, 54E, 54F, 54G, 54H, 54J, 54K, 54L, 54M, 54N, 54P, 54Q, and 54R, comparable to the sixth embodiment's opaque anterior cover 56 bottom view shown in FIG. 45. Each of these sixteen anterior cover tab segments can extend radially outward from the central portion of opaque anterior cover 56, and each of anterior cover grooves 44A, 44B, 44C, 44D, 44E, 44F, 44G, 44H, 44J, 44K, 44L, 44M, 44N, 44P, 44Q, and 44R can decrease the bending force required to manually peel the corresponding anterior cover tab segment 54A, 54B, 54C, 54D, 54E, 54F, 54G, 54H, 54J, 54K, 54L, 54M, 54N, 54P, 54Q, and 54R away from posterior base 35A, comparable to FIG. 44 cross section assembly view with anterior cover tab segment 54E peeled away from posterior base 35A in the sixth embodiment.

Comparable to the sixth embodiment's opaque anterior cover 56 shown in FIG. 45, each anterior cover tab 56A, 56C, 56E, 56G, 56J, 56L, 56N, and 56Q of the tenth embodiment can comprise the corresponding anterior cover tab segment as well as a corresponding secondary anterior cover tab groove 45A, 45C, 45E, 45G, 45J, 45L, 45N, and 45Q, which can be disposed between the corresponding anterior cover tab segment and the distal portion of the corresponding anterior cover tab 56A, 56C, 56E, 56G, 56J, 56L, 56N, and 56Q. Each secondary anterior cover tab groove can decrease the bending force required to manually peel the distal portion of the corresponding anterior cover tabs 56A, 56C, 56E, 56G, 56J, 56L, 56N, and 56Q away from posterior base 35A, comparable to the sixth embodiment FIG. 43 cross section assembly view with the distal portion of anterior cover tab 56E peeled away from posterior base 35A. As shown in FIG. 73 top assembly view, opaque anterior cover 56 can comprise anterior cover tabs 53B, 53D, 53F, 53H, 53K, 53M, 53P, and 53R which can be disposed contiguous to corresponding anterior cover tab segment 54B, 54D, 54F, 54H, 54K, 54M, 54P, and 54R. Anterior cover tabs 53B, 53D, 53F, 53H, 53K, 53M, 53P, and 53R in this tenth embodiment have comparable design and function as corresponding anterior base tabs 53B, 53D, 53F, 53H, 53K, 53M, 53P, and 53R in the sixth embodiment discussed earlier.

As shown in FIG. 73 top assembly view, opaque anterior cover 56 can also comprise anterior cover indicium 98B, 98D, 98F, 98H, 98K, 98M, 98P, and 98R which can be disposed on corresponding anterior cover tab segment 54B, 54D, 54F, 54H, 54K, 54M, 54P, and 54R. These anterior cover indicia can be printed or embossed on the top surface of the corresponding anterior cover tab segment 54B, 54D, 54F, 54H, 54K, 54M, 54P, and 54R, and each anterior cover indicium 98B, 98D, 98F, 98H, 98K, 98M, 98P, and 98R in this tenth embodiment can comprise a word or phrase that is a possible symptom or indication of dementia. The anterior cover indicium 98B can comprise the phrase BREAKING THE LAW, the anterior cover indicium 98D can comprise the phrase EATING UNUSUAL THINGS, the anterior cover indicium 98F can comprise the phrase FALLING MORE FREQUENTLY, the anterior cover indicium 98H can comprise the phrase GUM DISEASE, the anterior cover indicium 98K can comprise the phrase INABILITY TO RECOGNIZE SARCASM, the anterior cover indicium 98M can comprise the phrase COMPULSIVE BEHAVIORS, the anterior cover indicium 98P can comprise the word DEPRESSION, and the anterior cover indicium 98R can comprise the phrase OTHER MENTAL DISORDERS.

This tenth embodiment's opaque anterior cover 56, which includes all features shown in FIG. 73, can comprise the same material as described in the sixth embodiment's opaque anterior cover 56. This tenth embodiment can be manufactured using the same fabrication and assembly processes as described for the sixth embodiment earlier, or any other known and/or convenient process. It should be noted that the relative positions of some or all of the four smell test substance patches with odor and the four smell test substance patches without odor can be swapped. Any such changes in relative positions of these smell test substance patches can be accompanied by corresponding changes in the green and red color-coded circular indicium positions on posterior base 35A. For example, there can be eight versions of this tenth embodiment manufactured, with these smell test substance patch positions swapped. In some alternate embodiments, the positions of all of the smell test substance patches can remain the same on the posterior base 35A, and the positions of some or all of the anterior cover tab indicium 57A, 57C, 57E, 57G, 57J, 57L, 57N, 57Q and the test instructions 99 disposed on opaque anterior cover 56 can be rotated clockwise, relative to the center of posterior base 35A, either 0°, 45°, 90°, 135°, 180°, 225°, 270°, or 315° from their positions (and or by any other known, convenient and/or desired angle) shown in FIG. 73, thereby creating at least eight versions of this tenth embodiment. This tenth embodiment can be targeted for diseases such as dementia which sometimes manifest with symptoms discussed above.

The tenth embodiment test instructions 99 shown in FIG. 73 can comprise the following text, which can be relevant for dementia, such as Alzheimer's disease and FTD:

1. Pinch outer tip of PEEL 1 tab and peel back enough until a circular scent patch is fully visible.
2. Sniff very close to the scent patch.
3. If you smell scent, peel back PEEL 1 tab further until color dot is fully visible underneath. IF NOT, DO NOT PEEL TAB FURTHER.
4. Repeat steps 1-3 for PEEL 2 tab, PEEL 3 tab, . . . , then PEEL 8 tab. There are 4 tabs with scent. DO NOT PEEL BACK MORE THAN 4 TABS FURTHER TO REVEAL ADDITIONAL COLOR DOTS.
5. Review each illness symptom tab. For each symptom you have, peel back tab until color dot is fully visible.
6. If there are any red, orange, yellow, blue, cyan, purple, grey, or black dots visible, you may have dementia. Unless there are 4 green dots visible, you may have dementia.
7. Activate dementia symptom checker app on your smart phone, if available, then use phone camera to photograph all visible color dots together. This app will provide recommendations regarding your symptoms.

Note that the eight PEEL tabs can be anterior cover tabs 56A, 56C, 56E, 56G, 56J, 56L, 56N, 56Q, and the eight symptom tabs can be anterior cover tabs 53B, 53D, 53F, 53H, 53K, 53M, 53P, 53R, as shown in FIG. 73. FIG. 43 depicts an embodiment of an approximate position of anterior cover tab 56E which has been manually (or otherwise) peeled back sufficiently such that smell test substance patch 38E is visible. Similarly FIG. 44 depicts an embodiment of an approximate position of anterior cover tab 56E which has been manually (or otherwise) peeled back sufficiently such that the posterior base color-coded circular indicium 39E is visible. It should be noted that the test instructions 99 and the symptoms tabs can be modified as appropriate for other illnesses.

In some embodiments, the custom application software noted above can additionally analyze the input data to determine whether the target disease's estimated positivity rate and/or its basic reproduction number Ro and/or it's effective reproduction number Re is changing over time, which is particularly useful when testing a target local population daily, such as all employees entering a building where they work every workday. It should be noted that the positivity rate is the number of people who test positive for a targeted disease divided by the number of people who have been tested in a targeted population. Ro is the expected number of disease cases directly generated by one case in a target population where all individuals are susceptible to infection, whereas Re is the expected number of disease cases directly generated by one case in a target population in its current state, which already may include some infection cases.

In some embodiments, whenever this application software determines that the positivity rate and/or Ro and/or Re increases over a recent time period, such as the past 7 days, this custom application software can trigger a smart phone's screen to display a warning message noting that the target disease's incidence is increasing in that target local population. In some other embodiments, this application software can trigger the smart phone's screen to display a warning message noting that the target disease's positivity rate or reproduction number for the target local population exceeds a set target, such as 5% positivity rate or Ro=1 or Re=1, whenever this application software determines that the recent positivity rate or Ro or Re for the population being tested exceeds this target, which can be set either by an organization such as the US Centers For Disease Control, or by federal, state, or local governments, or by the business, organization, school, etc. which is testing a target local population such as employees.

Some embodiments of this custom application software can calculate an estimated disease positivity rate by first dividing the quantity of people tested who have any symptoms of anosmia ($Qa_1$), which is a very common symptom of COVID-19, by the total quantity of people in target group tested during a time period 1 ($Q_1$), in order to determine the anosmia positivity rate $Pa_1$ of this target group, based on formula $Pa_1=Qa_1/Q_1$. Then this anosmia positivity rate $Pa_1$ can be divided by an anosmia incidence factor Fa, which is the estimated number of people with newly acquired anosmia who have COVID-19 divided by the number of people with COVID-19 in the general population. This anosmia incidence factor Fa may be ~0.6 among all people with COVID-19 disease, based on some preliminary data, although this estimate may change as more data becomes available. Thus, if the anosmia positivity rate Pa=6% among a target population tested during one day, and if the general population's anosmia incidence factor Fa=0.6 for people with COVID-19, then Pa/Fa=6%/0.6=10% estimated COVID-19 disease positivity rate $P_1$ for the target group tested during time period 1, which can be one day. Some embodiments of the custom application software can use this formula $P_1=Pa_1/Fa$ to estimate the COVID-19 positivity rate $P_1$ of the target population tested during time period 1, which may be one day or any other appropriate time period. Additionally, the change in disease positivity rate over time may be estimated by comparing the disease's estimated positivity rate during time period 1 with the disease's estimated positivity rate during time period 2, where time period 2 occurs before time period 1. This can be calculated by dividing the estimated positivity rate during time period 1 ($P_1$) by the estimated positivity rate during time period 2 ($P_2$). One method for accomplishing this is by using the formula $P_1/P_2=F_2$, where $F_2$ represents the estimated COVID-19 positivity incidence factor over time. Alternatively, this can be calculated by subtracting the estimated positivity rate during time period 2 ($P_2$) from the estimated positivity rate during time period 1 ($P_1$). Instead of comparing the disease's estimated positivity rate P over time, alternatively the anosmia positivity rate Pa during time period 1 ($Pa_1$) can be compared with the anosmia positivity rate Pa during time period 2 ($Pa_2$). One method for accomplishing this is by using the formula $Pa_1/Pa_2=F_1$, where $F_1$ represents the anosmia positivity incidence factor over time. These factors $F_1$, $F_2$, Pa, $P_1$, and $P_2$ can be included in the test results displayed on a smart phone screen and/or sent via internet to an organization collecting disease test results data. In addition, $F_1$ can be compared to a set value $Z_1$, and when $F_1 \geq Z_1$, a warning message can be displayed on smart phone screen and/or sent via internet to an organization collecting disease test results data. As an example, if $Z_1=2$, and $F_1=2.3$ for the target population tested, then the custom application software can generate a warning message such as "Warning: The estimated disease positivity rate has more than doubled during the past 1 week." Similarly, if the anosmia positivity rate $Pa_1 \geq Z_2$ for a target population tested, then a warning message can be displayed on smart phone screen and/or sent via internet to an organization collecting disease test results data. As an example, if $Z_2=3\%$, and Pa=3.3% for the target population tested, then the custom application software can generate a warning message such as "Warning: The anosmia positivity rate is greater than 3%. The target population being tested should all seek medical diagnostic test for COVID-19, if available.", based on Pa. Alternatively the custom application software can generate a warning message such as "Warning: The estimated COVID-19 positivity rate is greater than 5%. The target population being tested should all seek medical diagnostic test for COVID-19, if available.", based on $P_1$.

For smaller target local populations, a single smart phone with this custom application software potentially can be used to screen the entire target population daily. For larger target local populations, multiple smart phones with this custom application software potentially can be used to screen the entire target local population daily. When multiple smart phones are used to screen the entire target local population daily, these smart phones can share applicable data, analyze this data to determine the positivity rate and/or Ro and/or Re, then display appropriate warnings as appropriate each day.

In some embodiments, a smart phone's screen can display advice relevant for every person taking the test on a particular day, such as whenever this custom application software issues a general warning message on that day. This advice can include a message that every person should submit to a molecular or antigen diagnostic test for the target disease as soon as possible, regardless of the results of test described in the various embodiments, if the positivity rate and/or Ro and/or Re has increased over set time period or if the positivity rate and/or Ro and/or Re exceeds specific target for that parameter, based on analysis by this custom application software's algorithm, which can comprise artificial intelligence.

In some embodiments, this advice can include recommendation that every person should submit to a molecular or antigen diagnostic test utilizing pool testing methodology, which combines respiratory or other bodily fluid samples from multiple people that can be a subset of target population and conducting one laboratory test on the combined pool of samples to detect the target disease as soon as possible. When such pool testing methodology is utilized, any pooled sample which tests positive for the targeted disease triggers an individual molecular or antigen diagnostic test for each person who originally submitted sample in that pool. Pool testing methodology can be appropriate when the molecular or antigen diagnostic testing cost is high and/or availability of testing for everybody in large target population is limited and/or the positivity rate is not very high.

In some embodiments this custom application software can process user-specified inputs regarding which conditions, as described above, trigger warnings that are displayed on the smart phone's screen. In addition, in some embodiments, this custom application software can process user-specified outputs, as described above, which are displayed on the smart phone's screen. When this custom application software displays notification via smart phone's screen that a person has symptoms which indicate that person may be infected with the targeted disease, some embodiments of this software may output relevant advice which is displayed on the smart phone's screen. This may comprise general statements displayed on screen such as "Contact your physician as soon as possible for advice regarding your condition." and/or "Refer to www.cdc.gov for advice regarding your condition." and/or "Proceed to nearest available diagnostic testing center for molecular or antigen diagnostic test." and/or specific recommendations listed on www.cdc.gov website, and/or any other medically appropriate advice relevant to the targeted disease.

FIGS. 74*a-h* depict a flow chart of another embodiment of a method of the present system. In some embodiments, a method can have the following steps. A computer system 4700 can store a unique identification code corresponding with a used test device 7402 and determine the total number of each first color, second color, third color, fourth color, fifth color, sixth color, seventh color, eighth color, ninth color, and tenth color color-coded circular indicia in a digital image of this used test device and store each quantity with an identification code corresponding with this used test device 7404. In some embodiments, a first color can be red, a second color can be green, a third color can be black, a fourth color can be yellow, a fifth color can be orange, a sixth color can be purple, a seventh color can be cyan, an eighth color can be blue, a ninth color can be medium gray, and a tenth color can be light gray, or any other desired colors. If a total quantity of first color circular indicia+second color circular indicia is greater than 4 7406 or less than 4 7412, a result message of "Retake smell test due to error." can be displayed 7408. A process can end 7410.

If a total quantity of first color circular indicia+second color circular indicia is not greater than 4 7406 or less than 4 7412 (i.e., equal to 4), a process can continue. If a total quantity of first color circular indicia equals 0 7414, then a computer system 4700 can store and display a result message "0 signs of anosmia, which is a very common symptom of COVID-19. Other target symptoms:" 7416 and continue. If a total quantity of first color circular indicia does not equal 0, then a process can continue. If a total quantity of first color circular indicia equals 1 7418, then a computer system 4700 can store and display a result message "1 sign of anosmia, which is a very common symptom of COVID-19. Other target symptoms:" 7420 and continue. If a total quantity of first color circular indicia does not equal 1, then a process can continue. If a total quantity of first color circular indicia equals 2 7422, then a computer system 4700 can store and display a result message "2 signs of anosmia, which is a very common symptom of COVID-19. Other target symptoms:" 7424" and continue. If a total quantity of first color circular indicia does not equal 2, process can continue. If a total quantity of first color circular indicia equals 3 7419, then a computer system 4700 can store and display a result message "3 signs of anosmia, which is a very common symptom of COVID-19. Other target symptoms: "7421 and continue. If a total quantity of first color circular indicia does not equal 3, then a process can continue. If a total quantity of first color circular indicia equals 4 7423 then a computer system 4700 can store and display a result message "4 signs of anosmia, which is a very common symptom of COVID-19. Other target symptoms:" 7425 and continue. If a total quantity of first color circular indicia does not equal 4, a process can end 7410.

If a total quantity of third color circular indicia+fourth color circular indicia+fifth color circular indicia=0 7426, then a computer system can store and display a continuation of a result message with "None" 7428 and continue. If a total quantity of third color circular indicia+fourth color circular indicia+fifth color circular indicia does not equal 0, then a process can continue. If a total quantity of third color circular indicia equals 1 7430, then a computer system 4700 can store and display a continuation of a result message with "Cough" 7432 and continue. If a total quantity of third color circular indicia does not equal 1, then a process can continue. If the total quantity of fourth color circular indicia equals 1 7434, then a computer system 4700 can store and display a continuation of a result message with "Fatigue" 7436 and continue. If a total quantity of fourth color circular indicia does not equal 1, a process can continue. If a total quantity of fifth color circular indicia equals 1 7438, then a computer system 4700 can store and display a continuation of a result message with "Appetite Loss" 7440 and continue. If a total quantity of fifth color circular indicia does not equal 1, a process can end 7410.

If a total quantity of seventh color circular indicia+eighth color circular indicia+ninth color circular indicia=0 7442, then a computer system 4700 can store and display a continuation of a result message with "You may have lower risk for serious symptoms than older people if you have COVID-19." 7444 and continue. If a total quantity of seventh color circular indicia+eighth color circular indicia+ninth color circular indicia does not equal 0, then a process can continue. If a total quantity of seventh color circular indicia equals 1 7446, then a computer system 4700 can store and display a continuation of a result message with "You may have a higher risk for serious symptoms than younger people if you have COVID-19." 7448 and continue. If a total quantity of seventh color circular indicia does not equal 1, then a process can continue. If a total quantity of eighth color circular indicia equals 1 7450, then a computer system 4700 can store and display a continuation of a result message with "You may have a significantly higher risk for serious symptoms than younger people if you have COVID-19." 7452 and continue. If a total quantity of eighth color circular indicia does not equal 1, a process can continue. If a total quantity of ninth color circular indicia equals 1 7454, then a computer system 4700 can store and display a continuation of a result message with "You are at highest risk for serious symptoms than younger people if you have COVID-19." 7456 and continue. If a total quantity of ninth color circular indicia does not equal 1, the process can end 7410.

If a total quantity of tenth color circular indicia=1 7458, then a computer system 4700 can store and display a continuation of a result message with "Based on your gender, you are at higher risk for serious symptoms than women of similar age are." 7460 and continue. If a total quantity of tenth color circular indicia does not equal 1, then a process can continue. If a total quantity of first color circular indicia is greater than 0 and less than 3, 7462, then a computer system 4700 store and display a continuation of a result message stating "You may have COVID-19 based on anosmia symptoms. As soon as possible, self-isolate, contact physician for advice, and take molecular or antigen COVID-19 test, if available." 7464 and continue. If a total quantity of first color circular indicia is not greater than 0 and less than 3, then a process can continue. If a total quantity of first color circular indicia is greater than 2 and less than 5 7466, then a computer system 4700 can store and display a continuation of a result message stating "You have significant likelihood of COVID-19 based on anosmia symptoms. As soon as possible, self-isolate, contact physician for advice, and take molecular or antigen COVID-19 test, if available." 7468 and continue. If a total quantity of first color circular indicia is not greater than 2 and less than 5, a process can end 7410.

If a total quantity of third color circular indicia+fourth color circular indicia+fifth color circular indicia is equal to 3 and a quantity of first color circular indicia equals 0 7470, then a computer 4700 system can store and display a continuation of a result message with "The combination of cough+fatigue+appetite loss significantly increases likelihood you have COVID-19. As soon as possible, self-isolate, contact physician for advice, and take molecular or antigen COVID-19 test, if available." 7472 and continue. If a total quantity of third color circular indicia+fourth color circular indicia+fifth color circular indicia is not equal to 3 or a quantity of first color circular indicia does not equal 0, then a process can continue. If a total quantity of third color circular indicia+fourth color circular indicia+fifth color circular indicia equals 3 and a quantity of first color circular indicia is greater than 0 and less than 5 7474, then a computer system 4700 can store and display a continuation of a result message stating "The combination of cough+fatigue+appetite loss significantly increases likelihood you have COVID-19." 7476 and continue. If a total quantity of third color circular indicia+fourth color circular indicia+fifth color circular indicia does not equal 3 or a quantity of first color circular indicia is not greater than 0 and less than 5, then a process can continue. If a total quantity of third color circular indicia+fourth color circular indicia+fifth color circular indicia equals 2 and a quantity of first color circular indicia equals 0 7478, then a computer system 4700 can store and display a continuation of a result message with "The combination of several symptoms increases likelihood you have COVID-19. As soon as possible, self-isolate, contact physician for advice, and take molecular or antigen COVID-19 test, if available." 7480 and continue. If a total quantity of third color circular indicia+fourth color circular indicia+fifth color circular indicia does not equal 2 or a quantity of first color circular indicia does not equal 0, a process can end 7410.

If a total quantity of third color circular indicia+fourth color circular indicia+fifth color circular indicia is equal to 2 and a quantity of first color circular indicia is greater than 0 and less than 5 7482, then a computer 4700 system can store and display a continuation of s result message with "The combination of several additional symptoms significantly increases likelihood you have COVID-19."7484 and continue. If a total quantity of third color circular indicia+fourth color circular indicia+fifth color circular indicia is not equal to 2 or a quantity of first color circular indicia is not greater than 0 and less than 5, then a process can continue. If a total quantity of third color circular indicia+fourth color circular indicia+fifth color circular indicia equals 1 and a quantity of first color circular indicia equals 0 7486, then a computer system 4700 can store and display a continuation of a result message with "The presence of one symptom may indicate you have COVID-19. As soon as possible, self-isolate, contact physician for advice, and take molecular or antigen COVID-19 test, if available." 7488 and continue. If a total of third color circular indicia+fourth color circular indicia+fifth color circular indicia does not equal 1 or a quantity of first color circular indicia does not equal 0 then a process can continue. If a total quantity of third color circular indicia+fourth color circular indicia+fifth color circular indicia equals 1 and a quantity of first color circular indicia is greater than 0 and less than 5 7490, then a computer system 4700 can store and display a continuation of to result message with "The presence of an additional symptom increases likelihood you have COVID-19." 7492 and continue. If a total quantity of third color circular indicia+fourth color circular indicia+fifth color circular indicia does not equal 1 or a quantity of first color circular indicia is not greater than 0 and less than 5, a process can end 7410.

If a total of all second color circular indicia equals 4 and a total of all first color circular indicia+third color circular indicia+fourth color circular indicia+fifth color circular indicia equals 0 7494, then a computer system 4700 can store and display a continuation of a result message with "Maintain social distancing of 6 feet minimum, wear a mask when others are present, and wash hands frequently." 7496 and continue. If a total of all second color circular indicia does not equal 4 or a total of all first color circular indicia+third color circular indicia+fourth color circular indicia+fifth color circular indicia does not equal 0, a process can continue.

Figure 75:
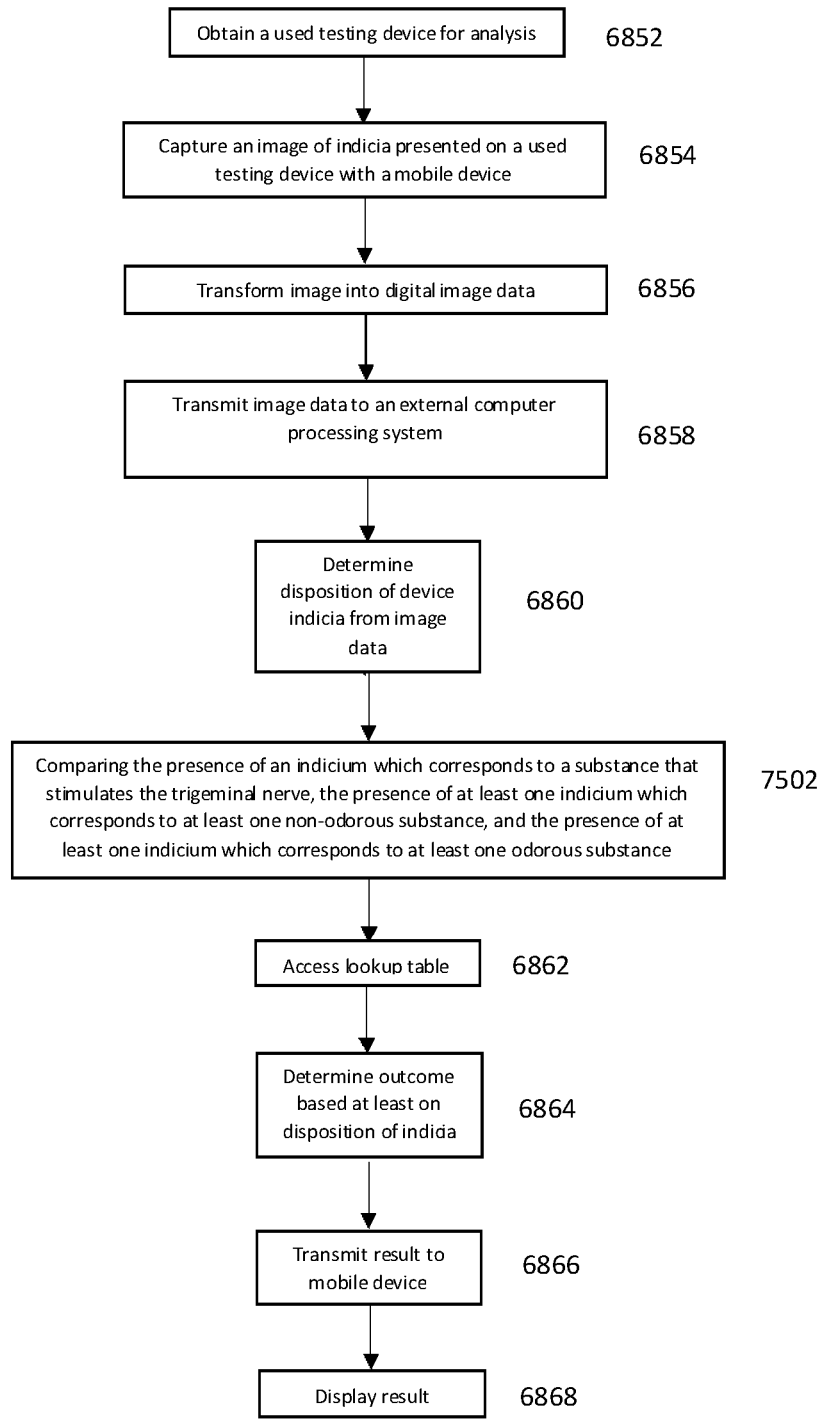
FIG. 75 depicts a flow chart of an embodiment of a method using the present system.

A computer system 4700 can store and display a concluding comment "If you have any concerns about other symptoms not listed, contact your physician for advice soon. Refer to www.cdc.gov for further information regarding this disease." 7497. A computer system 4700 can repeat step 7402-step 7497 for other people in a target population 7498. A computer system 4700 can send some or all of the data and results stored for target population to an organization, which may be a business, school, government office, transportation center, CDC, or any other organization 7499. A process can end 7410. FIG. 75 depicts a flow chart of an embodiment of a method using the present system. In such embodiments, a computer system 4700 can compare the presence of an indicium which corresponds to a substance that stimulates the trigeminal nerve, the presence of at least one indicium which corresponds to at least one non-odorous substance, and the presence of at least one indicium which corresponds to at least one odorous substance.

FIG. 76 depicts a lookup table for determining the likelihood of COVID-19 based on disposition on indicia for particular symptoms.

An alternate method for analyzing the symptom and demographics data can be based on a study reported in Nature Medicine journal. In the May 11, 2020 article Real-Time Tracking of Self-Reported Symptoms To Predict Potential COVID-19, researchers reported:

"We therefore generated a linear model for symptoms that included loss of smell and taste, fatigue, persistent cough and loss of appetite to obtain a symptoms prediction model for COVID-19:

Prediction Model=−1.32−(0.01×age)+(0.44×sex)+
(1.75×loss of smell and taste)+(0.31×severe or
significant persistent cough)+(0.49×severe
fatigue)+(0.39×skipped meals)

where all symptoms are coded as 1 if the person self-reports the symptom and 0 if not. The sex feature is also binary, with 1 indicative of male participants and 0 representing females. The obtained value is then transformed into predicted probability using exp(x)/(1+exp(x)) transformation followed by assigning cases of predicted COVID-19 for probabilities>0.5 and controls for probabilities<0.5."

"In this model, the strongest predictor was loss of smell and taste (FIG. 1a). Excluding loss of smell and taste from the model resulted in reduced sensitivity (0.33 (0.30-0.35)) but increased specificity (0.84 (0.83-0.86)). We also computed the ROC-AUC with stratification for sex and age groups and found that the results were similar in all groups, with no significant differences between strata, suggesting that our model works similarly within different sex and age groups. We validated the model in the US cohort and found an ROC-AUC of 0.76 (0.74-0.78), a sensitivity of 0.66 (0.62-0.69), a specificity of 0.83 (0.82-0.85), a positive predictive value of 0.58 (0.55-0.62) and a negative predictive value 0.87 (0.86-0.89) (FIG. 1c)."

The custom application software in some embodiments can comprise a similar mathematical model or another applicable mathematical model for predicting the probability of a target disease such as COVID-19 based on symptoms and demographics data, using the mathematical model for determining probability that a disease is present based on the quantity of circular indicia of each color in a digital image of a used test device. In embodiments of the medical diagnostic testing device which comprise indicia representing different age groups, the mathematical model can analyze the probability based on applicable age range rather than a specific age. Other variables in the custom application software's mathematical model can be similar or identical to those referenced in this journal article. It should be noted that this article's analysis was based on self-reported loss of smell in people participating in the research study, whereas the present medical diagnostic testing device comprises means for testing sense of smell. Therefore, using the present medical diagnostic testing device with a smart phone or other mobile device comprising application software with an appropriate mathematic model can increase the accuracy of the test in detecting whether or not a person has the target disease.

Figure 77:
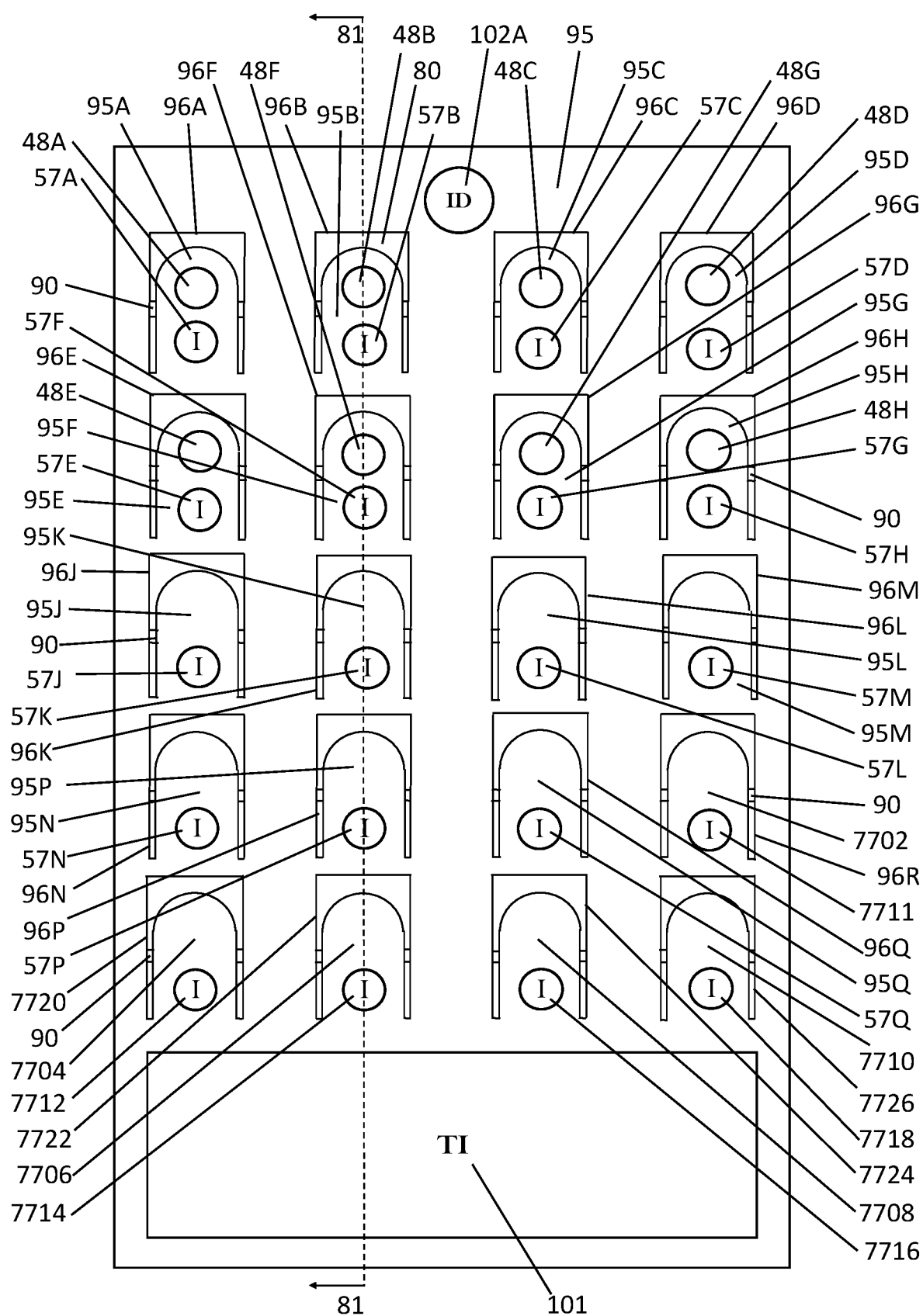
FIG. 77 depicts a top assembly view of an embodiment of the apparatus.

FIG. 77 depicts an eleventh embodiment of the present device. This eleventh embodiment shown in FIG. 77 top assembly view can comprise two manufactured components—rectangular posterior base 80 and rectangular opaque anterior cover 95. The eleventh embodiment can be comparable to the sixth embodiment, comprising many similar and/or identical features, indicia, and materials, although these embodiments can have different form as shown in respective figures. In addition, similar or identical manufacturing processes used in production for the sixth embodiment can be used in production for this eleventh embodiment. As shown in FIG. 77, there can be twenty cover tabs 95A, 95B, 95C, 95D, 95E, 95F, 95G, 95H, 95J, 95K, 95L, 95M, 95N, 95P, 95Q, 7702, 7704, 7706, 7708, and 7710. Each of these cover tabs can be disposed within a corresponding rectangular cover opening 96A, 96B, 96C, 96D, 96E, 96F, 96G, 96H, 96J, 96K, 96L, 96M, 96N, 96P, 96Q, 96R, 7720, 7722, 7724, 7726, and 7710. A rectangular adhesive layer 90 can be disposed between rectangular posterior base 80 and rectangular opaque anterior cover 95. This adhesive layer structurally couples the two manufactured components. Diagnostic test instructions 101 (symbolized by TI enclosed within a rectangle in FIG. 77) can be printed directly on the rectangular opaque anterior cover 95 or alternatively can be a printed adhesive label attached to anterior surface of the rectangular opaque anterior cover 95.

As shown in FIG. 77, a set of eight anterior smell test substance patches 48A, 48B, 48C, 48D, 48E, 48F, 48G, and 48H can be disposed on anterior surface of corresponding cover tabs 95A, 95B, 95C, 95D, 95E, 95F, 95G, and 95H. In one embodiment of a smell identification test, a first subset of these anterior smell test substance patches, such as 48A, 48B, 48C, and 48D, can each comprise a first substance with a first scent, such as peppermint. Similarly, a second subset of these anterior smell test substance patches, such as 48E, 48F, 48G, and 48H, can each comprise a second substance with a second scent, such as banana. In another embodiment of a smell identification test, each of these eight anterior smell test substance patches can comprise a substance with a different, unique odor. This set of anterior smell test substance patches can be in form of scratch and sniff substances, used in smell identification tests sold by companies such as Sensonics International, as well as other companies manufacturing scratch and sniff products. Such scratch and sniff substances can comprise an odorous substance which can be microencapsulated to retain the odor until the microencapsulated anterior smell test substance patch is scratched. Because certain diseases, such as Alzheimer's disease and some other forms of dementia, can impair a person's ability to accurately identify some scents even before significant memory impairment has begun, smell identification tests can be used to detect an early biomarker for dementia. In other embodiments, some anterior smell test substance patches such as 48A, 48D, 48F, and 48G can comprise an odorless substance, and other anterior smell test substance patches such as 48B, 48C, 48E, and 48H can comprise at least one odorous substance. In yet other embodiments, at least some of anterior smell test substance patches 48A, 48B, 48C, 48D, 48E, 48F, 48G, and 48H can comprise the same odorous substance in different concentrations, whereby the pungency of each such anterior smell test substance patch is unique. A wide variety of odorous substances are available from companies such as IFF (International Flavors and Fragrances) and Sensonics International which can be used for such smell tests. Some common scents which can be used for various embodiments are peppermint, banana, motor oil, coconut, apple, orange, cherry, watermelon, leather, cedar, pine, paint thinner, peanut, bubble gum, root beer, grass, menthol, clove, strawberry, lilac, smoke, soap, natural gas, lemon, dill pickle, fruit punch, cinnamon, pineapple, coffee, fish, rose, and licorice. In order to increase the smell test's sensitivity and/or specificity for a target disease, such as Alzheimer's, or a target family of diseases, such as dementia, smell test substances can be selected from a narrower set of scents, which people who have or are likely to develop the target illness have difficulty correctly identifying and/or detecting and/or remembering. For dementia, including Alzheimer's disease, suitable odorous substances for the smell test substance patches can include peppermint, banana, clove, fish, leather, lemon, lilac, menthol, natural gas, orange, paint thinner, peanut, pineapple, rose, smoke, soap, and strawberry scented substances. Potentially there can be a variety of embodiments with smell test substance patches comprising different sets of odorous substances, based on odor identification differences between cultures or ethnicities. In some embodiments a single odorous substance can be used for the smell test. In addition, although anterior smell test substance patches 48A, 48B, 48C, 48D, 48E, 48F, 48G, and 48H can be disposed on anterior surface of corresponding cover tabs 95A, 95B, 95C, 95D, 95E, 95F, 95G, and 95H in FIG. 77, alternatively these anterior smell test substance patches can be disposed adjacent to these corresponding cover tabs on the anterior surface of the rectangular opaque anterior cover 95 instead.

As shown in FIG. 77, a first set of anterior cover tab indicia (each symbolized by I enclosed in a circle) 57A, 57B, 57C, 57D, 57E, 57F, 57G, and 57H can be disposed on anterior surface of corresponding cover tabs 95A, 95B, 95C, 95D, 95E, 95F, 95G, and 95H. Each of these eight indicia can comprise the name of a scent. In one embodiment, anterior cover tab indicia 57A, 57B, 57C, and 57D, each comprising the name of a first scent that corresponds to the scent of one of the anterior smell test substance patches 48A, 48B, 48C, and 48D, can be disposed on corresponding cover tabs 95A, 95B, 95C, and 95D. In that embodiment, anterior cover tab indicia 57E, 57F, 57G, and 57H, each comprising the name of a second scent that corresponds to the scent of one of the anterior smell test substance patches 48E, 48F, 48G, and 48H, can be disposed on corresponding cover tabs 95E, 95F, 95G, and 95H. As shown in FIG. 77, each anterior cover tab indicium in the first set can be disposed adjacent to the anterior smell test substance patch on the corresponding cover tab 95A, 95B, 95C, 95D, 95E, 95F, 95G, and 95H respectively. In other embodiments which do not test for smell identification, the first set of anterior cover tab indicia 57A, 57B, 57C, 57D, 57E, 57F,57G, and 57H can comprise alternative phrases, such as "Smell Tab 1", "Smell Tab 2", "Smell Tab 3", "Smell Tab 4", "Smell Tab 5", "Smell Tab 6", "Smell Tab 7", and "Smell Tab 8" respectively.

The eleventh embodiment shown in FIG. 77 can comprise a second set of anterior cover tab indicia 57J, 57K, 57L, 57M, 57N, and 57P representing demographics information disposed on the anterior surface of cover tabs 95J, 95K, 95L, 95M, 95N, and 95P respectively. The anterior cover tab indicia can comprise age and gender information, as an example. Anterior cover tab indicium 57J can comprise a phrase such as "Age 60-69", anterior cover tab indicium 57K can comprise a phrase such as "Age 70-79", anterior cover tab indicium 57L can comprise a phrase such as "Age 80-89", and anterior cover tab indicium 57M can comprise a phrase such as "Age 90+". In other embodiments, such anterior cover tab indicia can comprise phrases for different age ranges between age 0 through age 120. Similarly anterior cover tab indicium 57N can comprise a word such as "Male", and anterior cover tab indicium 57P can comprise a word such as "Female". Other embodiments can comprise anterior cover tab indicia phrases specifying level of education, such as high school diploma, associate degree, BS degree, MS degree, PhD, or alternatively years of education. Another embodiment can comprise an anterior cover tab indicium phrase referencing smoker, since smoking can impair a person's olfactory abilities. Another embodiment can comprise an anterior cover tab indicium phrase referencing close relative with the target disease, which can increase the likelihood of developing the target disease if this disease is associated with one or more gene alleles, variants, or mutations, such as Alzheimer's disease.

The eleventh embodiment shown in FIG. 77 can also comprise a third set of anterior cover tab indicia representing cognitive awareness of smell identification impairment. Anterior cover tab indicium 57Q can comprise a phrase such as "No difficulty identifying scents", and anterior cover tab indicium 7711 can comprise a phrase such as "Difficulty identifying scents". When a person who has difficulty correctly identifying certain odors is not aware that he cannot correctly identify these odors, he is significantly more likely to have Alzheimer's disease. Thus, the specificity of an Alzheimer's diagnostic test can be increased if this information is included in the analysis to determine result.

Besides the anterior cover tab indicia related to olfactory sense discussed above, the eleventh embodiment shown in FIG. 77 can also include anterior cover tab indicia referencing non-olfactory biomarkers. Genes are important biomarkers for a variety of different diseases, including Alzheimer's disease. In some embodiments comprising a fourth set of anterior cover tab indicia, anterior cover tab indicium 7712 and anterior cover tab indicium 7714 can reference any two corresponding gene variants which are each either positively correlated with the target disease or are negatively correlated with the target disease, and these anterior cover tab indicia can be disposed on corresponding cover tabs 7704 and 7706. Two of the more common gene alleles which impact the likelihood of developing Alzheimer's disease are the ApoE-4 allele and the ApoE-2 allele. One copy of the ApoE-4 allele increases risk of developing Alzheimer's by two- to threefold, and two copies of ApoE-4 allele increase risk of developing Alzheimer's by eight- to twelvefold. One copy of the ApoE-2 allele decreases risk of developing Alzheimer's disease, and two copies of the ApoE-2 allele significantly decreases risk of developing Alzheimer's disease. The eleventh embodiment shown in FIG. 77 can include anterior cover tab indicium 7712 which comprises a phrase such as "ApoE-4", and anterior cover tab indicium 7714 can comprise a phrase such as "ApoE-2". When this Alzheimer's specific gene information is available and included in the analysis to determine result, the sensitivity and the specificity of an Alzheimer's diagnostic test can be increased. Other embodiments can include anterior cover tab indicia which reference at least one variant or mutation of the genes APP, PSEN1, PSEN2, ABCA7, CLU, CR1, PICALM, PLD3, TREM2, and SORL1, which are also gene biomarkers of Alzheimer's disease that can be referenced in this fourth set of anterior cover tab indicia.

The presence of other biomarkers for a target disease can also be included as a fifth set of anterior cover tab indicia on cover tabs. In the eleventh embodiment shown in FIG. 77, anterior cover tab indicium 7716 can be any applicable blood biomarker for target disease. For Alzheimer's disease, this can be a positive blood test for P-tau217, based on a minimum specified level in the blood, as one example. When the presence of this P-tau217 biomarker is available and included in the analysis to determine result, the specificity of an Alzheimer's diagnostic test can be increased significantly. There are other tau-related blood biomarkers for Alzheimer's disease, including P-Tau181, which can be referenced in this fifth set of anterior cover tab indicia. In addition, there are some microRNA molecules which are potential blood biomarkers for Alzheimer's disease, and at least one of these can be referenced in this fifth set of anterior cover tab indicia in some embodiments. In other embodiments, some or all of the biomarkers in the Dementia Blood Test Panel can be specified in this fifth set of anterior cover tab indicia on the corresponding cover tabs. This blood test panel is used to differentiate between Alzheimer's disease and other forms of dementia. This test comprises CBC, electrolytes, TSH, T4 total, vitamin B12, CRP, and sedimentation rate. In addition, abnormal levels of serum cholesterol and abnormal blood sugar levels can be other blood biomarkers associated with heart disease, diabetes, and Alzheimer's disease.

Besides tau proteins, some other proteins in brain tissue, blood, or CSF (cerebrospinal fluid) can also be a biomarker individually or as a set of proteins which is positively correlated with or negatively correlated with a target disease such as Alzheimer's disease. At least one of these proteins can be referenced by anterior cover tab indicia such as 7716. Applicable protein biomarkers referenced in the fifth set of anterior cover tab indicia can increase the sensitivity and specificity of the diagnostic device targeting a disease such as Alzheimer's disease.

In addition to olfactory biomarkers, gene biomarkers, and biomarkers in the blood or CSF, some observable symptoms, such as more frequent falling, can be early warning signs of Alzheimer's disease. In some embodiments, a sixth set of anterior cover tab indicia can reference non-olfactory warning signs of the target illness, such as observable symptoms of the target illness. In the eleventh embodiment shown in FIG. 77, anterior cover tab indicium 7718 can be a phrase describing an observable symptom of the target illness or family of diseases. If the target disease is Alzheimer's, this can be a phrase such as "Falling more frequently." Since another symptom of Alzheimer's disease can be nap lasting more than 1 hour each day or multiple naps each day, this can be a phrase such as "Daily nap longer than 1 hour or multiple naps each day" in other embodiments. As noted in the Background section of this patent, there are other early warning signs of dementia which can occur prior to significant memory impairment, such as breaking laws (stealing, trespassing, driving recklessly, etc.), eating rancid food or non-food items, changes in gait, gum disease, inability to recognize sarcasm, misplacing items more frequently, increased forgetfulness, compulsive behaviors, depression, stroke, and other untreated mental disorders, including bipolar disorder, schizophrenia, post-traumatic stress disorder, chronic stress, and ADD/ADHD. In addition, a score<25 on the Mini-Mental State Exam (MMSE) suggests possible dementia. At least one anterior cover tab indicium can comprise a phrase referencing such early warning signs of dementia in other embodiments of design shown in FIG. 77.

Figure 84A:
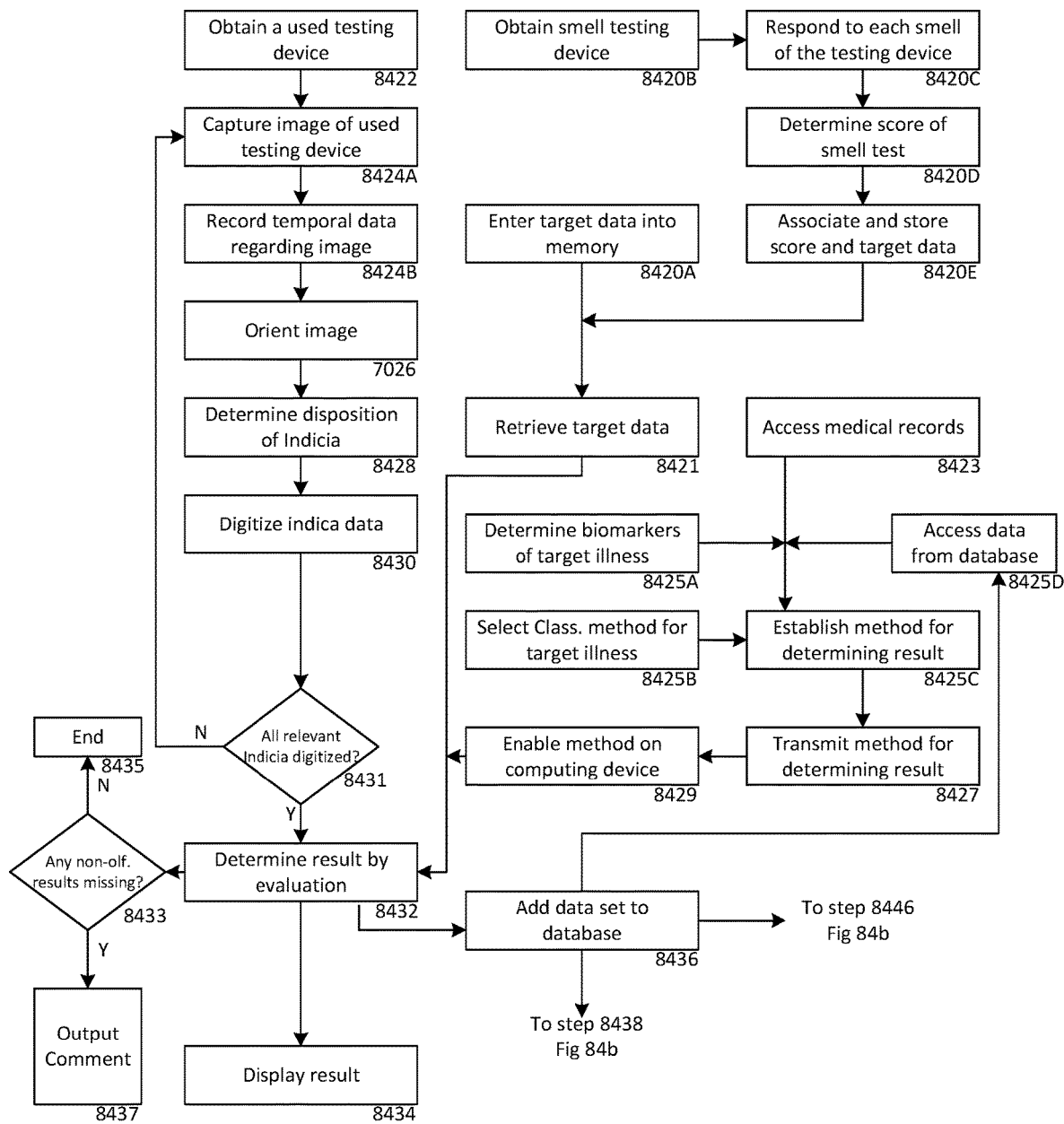
FIGS. 84*a*-84*b* depict a method flowchart for diagnosing a target illness.
Figure 84B:
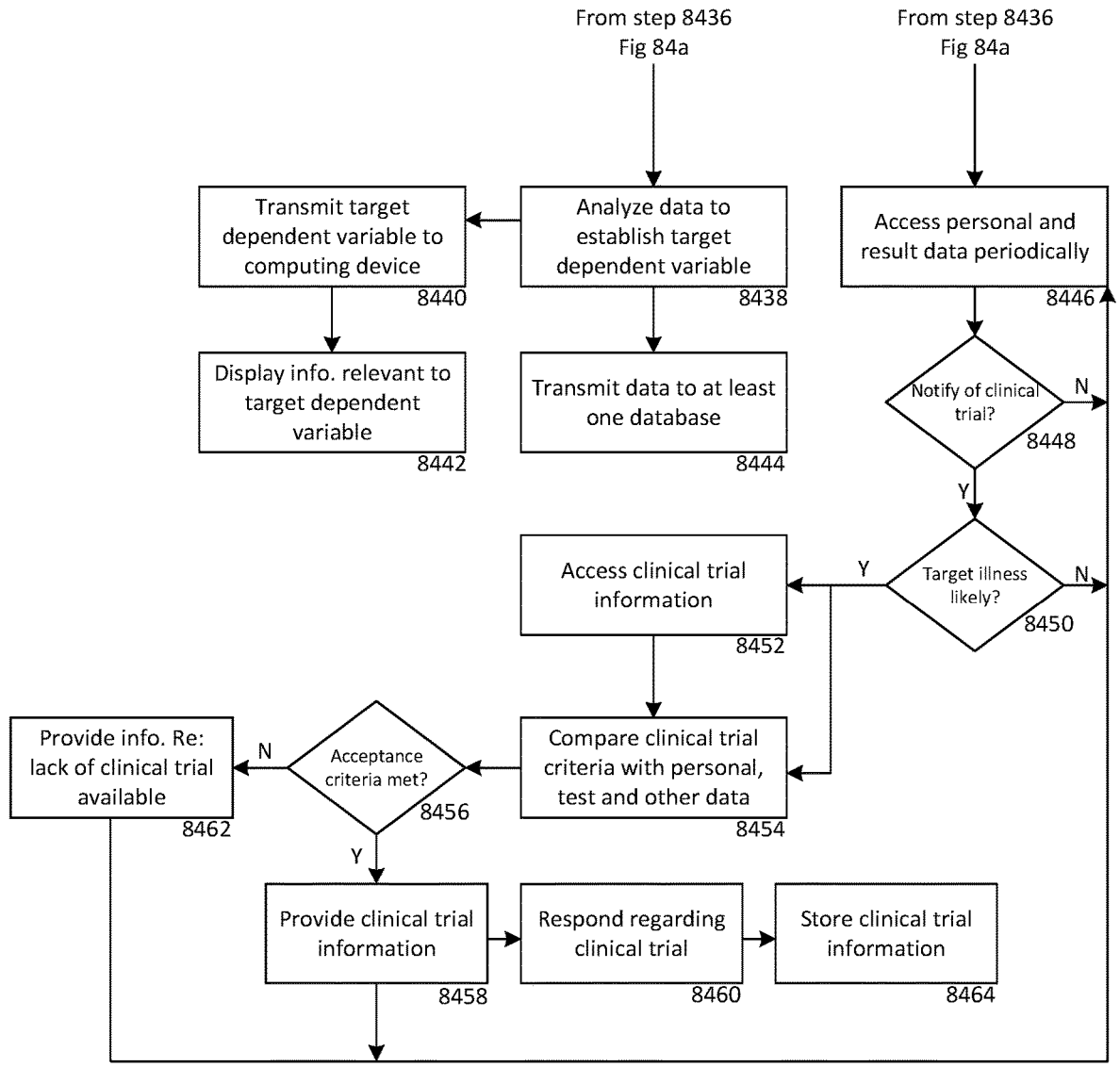

It should be noted that although there are multiple sets of anterior cover tab indicia referencing non-olfactory biomarkers (genes, tau proteins, associated diseases, symptoms, etc.) in the diagnostic device embodiments discussed, some or all the non-olfactory biomarker information alternatively can be entered in step 8420A of the method flowchart depicted in FIG. 84*a* and FIG. 84*b*, rather than manually peeling applicable cover tabs enough to expose color-coded circular indicia on the diagnostic device.

In embodiments of design shown in FIG. 77 targeting coronavirus-based diseases, such as COVID-19, at least one of such anterior cover tab indicia can comprise references to non-olfactory warning signs of the target illness such as other symptoms associated with COVID-19. Some embodiments can include anterior cover tab indicia referencing at least one symptom, such as fever, persistent cough, shortness of breath, difficulty breathing, skin rash, chills, muscle or body aches, fatigue, sore throat, loss of appetite, headache, nausea or vomiting, diarrhea, new confusion, inability to wake or stay awake, and persistent pain or pressure in the chest.

Although all the anterior cover tab indicia 57A, 57B, 57C, 57D, 57E, 57F, 57G, 57H, 57J, 57K, 57L, 57M. 57N, 57P, 57Q, 7711, 7712, 7714, 7716, and 7718 are disposed on corresponding cover tabs 95A, 95B, 95C, 95D, 95E, 95F, 95G, 95H, 95J, 95K, 95L, 95M, 95N, 95P, 95Q, 7702, 7704, 7706, 7708, and 7710 in FIG. 77, alternatively some or all of these anterior cover tab indicia can be disposed adjacent to corresponding cover tabs on anterior surface of rectangular opaque anterior cover 95 instead.

Figure 78:
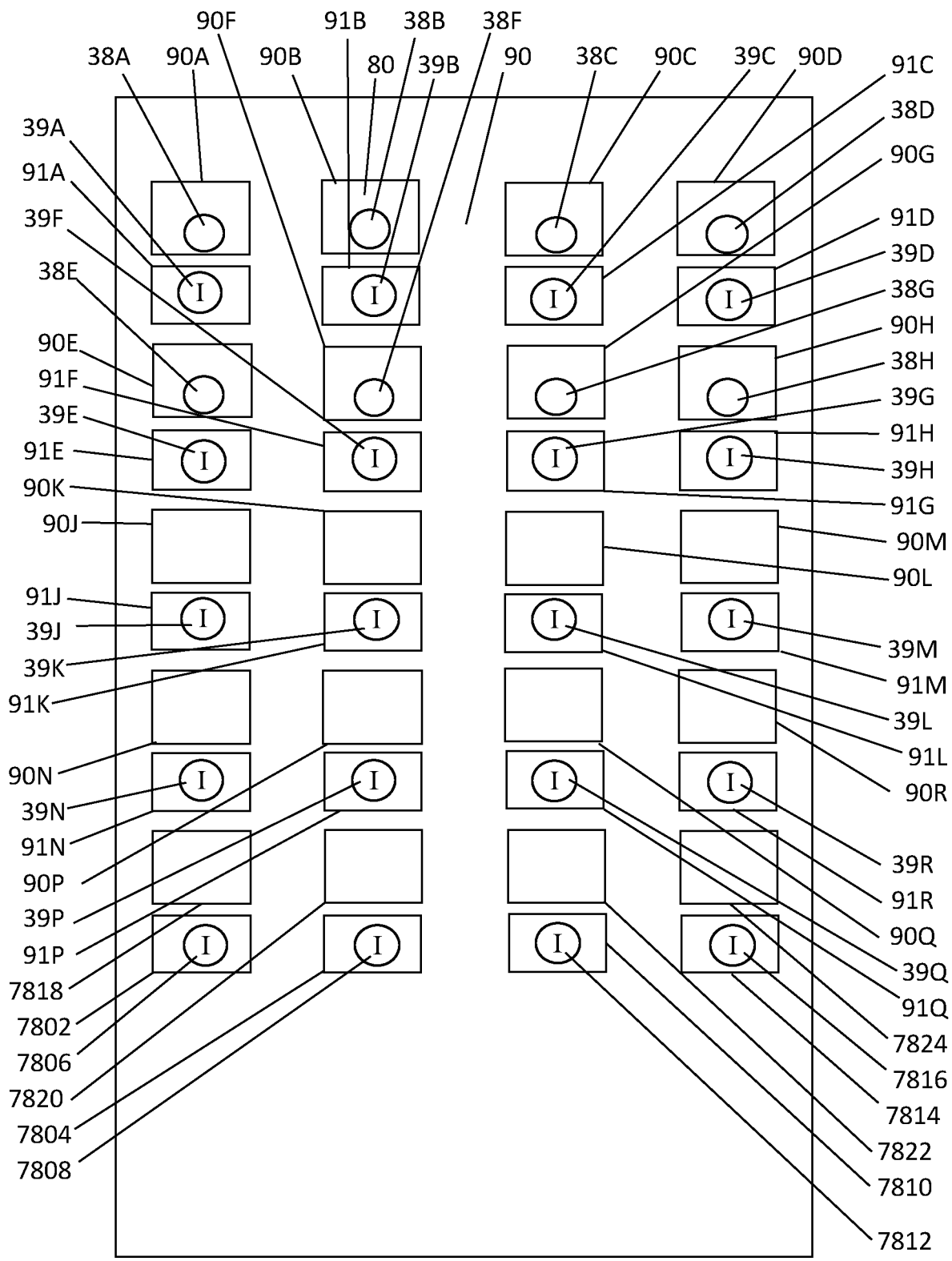
FIG. 78 depicts a top view of the rectangular posterior base, rectangular adhesive layer, and posterior smell test substance patches of the embodiment depicted in FIG. 77.

FIG. 78 of the eleventh embodiment depicts a top view of the rectangular posterior base 80 with a rectangular adhesive layer 90 disposed on anterior surface of the rectangular posterior base 80. However, in alternate embodiments, the adhesive layer can have any known, convenient and/or desired geometry. In some embodiments, rectangular adhesive layer 90 can comprise a first set of adhesive rectangular openings 90A, 90B, 90C, 90D, 90E, 90F, 90G, and 90H, and a set of posterior smell test substance patches, where corresponding posterior smell test substance patch 38A, 38B, 38C, 38D, 38E, 38F, 38G, and 38H can be disposed on the anterior surface of the rectangular posterior base 80 within each opening, as shown in FIG. 78. In one embodiment of a smell identification test, a first subset of these posterior smell test substance patches, such as 38A, 38B, 38C, and 38D, can each comprise a first substance with a first scent, such as peppermint. Similarly, a second subset of these posterior smell test substance patches, such as 38E, 38F, 38G, and 38H, can each comprise a second substance with a second scent, such as banana. In another embodiment of a smell identification test, each of these posterior smell test substance patches 38A, 38B, 38C, 38D, 38E, 38F, 38G, and 38H can comprise a substance with a different, unique odor. This set of posterior smell test substance patches can be in form of peel and sniff substances, used in scented labels sold by companies such as Scentisphere, as well as other companies manufacturing peel and sniff products. Such peel and sniff substances can comprise an odorous substance which is microencapsulated to retain the odor until the microencapsulated posterior smell test substance patch is exposed by peeling the corresponding cover tab off the anterior surface of the posterior smell test substance patch. One advantage of such peel and sniff posterior smell test substance patches is that once a cover tab is completely peeled off the anterior surface of the corresponding posterior smell test substance patch, the pungency of the posterior smell test substance patch is well controlled by the anterior surface area of the posterior smell test substance patch. By comparison, when the scratch and sniff anterior smell test substance patches 48A, 48B, 48C, 48D, 48E, 48F, 48G, and 48H on the anterior surface of the corresponding cover tabs, shown in FIG. 77, are scratched, the pungency of the odor depends on how much of the anterior surface is scratched, which can be more variable. As shown in FIG. 77-FIG. 83, both scratch and sniff smell test patches and peel and sniff smell test patches are included, allowing the user to decide which smell test option to choose. In some alternate embodiments, only the peel and sniff posterior smell test substance patches 38A, 38B, 38C, 38D, 38E, 38F, 38G, and 38H can be disposed on the device. In other alternate embodiments, only the scratch and sniff anterior smell test substance patches 48A, 48B, 48C, 48D, 48E, 48F, 48G, and 48H can be disposed on the device. In embodiments which comprise both sets of smell test substance patches, the odor of the scratch and sniff anterior smell test substance patch on the anterior surface of each cover tab can match the odor of the peel and sniff posterior smell test substance patch underneath the corresponding cover tab. In embodiments which only comprise the peel and sniff posterior smell test substance patches, such as posterior smell test substance patches 38A, 38B, 38C, 38D, 38E, 38F, 38G, and 38H, each of these posterior smell test substance patches can comprise a substance with a different, unique odor, suitable for a smell identification test to detect an early biomarker for dementia and some other diseases. In other embodiments, some posterior smell test substance patches such as 38A, 38D, 38F, and 38G can comprise an odorless substance, and other posterior smell test substance patches such as 38B, 38C, 38E, and 38H can comprise at least one odorous substance, which can be useful for detecting some other diseases such as some strains of COVID-19. In yet other embodiments, at least some of posterior smell test substance patches 38A, 38B, 38C, 38D, 38E, 38F, 38G, and 38H can comprise the same odorous substance in different concentrations, whereby the pungency of each such posterior smell test substance patch is unique, which can be useful for detecting some other diseases.

In some embodiments, such as the eleventh embodiment shown in FIG. 78, rectangular adhesive layer 90 can further comprise a second set of adhesive rectangular openings 90J, 90K, 90L, 90M, 90N, 90P, 90Q, 90R, 7818, 7820, 7822 and 7824 without corresponding posterior smell test substance patches disposed within these openings. In addition, this rectangular adhesive layer 90 can comprise a third set of adhesive rectangular openings 91A, 91B, 91C, 91D, 91E, 91F, 91G, and 91H with corresponding posterior-base color-coded circular smell test indicium 39A, 39B, 39C, 39D, 39E, 39F, 39G, and 39H disposed within each opening.

In one embodiment with a smell identification test that comprises two subsets of anterior and/or posterior smell test substance patches, each subset comprising a substance with a corresponding scent, such as peppermint scent in first subset and banana scent in second subset as noted previously, there can be two subsets of anterior cover tab indicia disposed on corresponding cover tabs. Each indicium in the first subset of anterior cover tab indicia 57A, 57B, 57C, and 57D can comprise a phrase such as "Scent 1" as well as a unique scent name. These indicia can represent four choices for this first scent. One of the four unique scent names corresponds with the scent of the four corresponding smell test substance patches, such as peppermint scent in one embodiment. Each indicium in the second subset of anterior cover tab indicia 57E, 57F, 57G, and 57H can comprise a phrase such as "Scent 2" as well as a unique scent name. These indicia can represent four choices for this second scent. One of the four unique scent names can correspond with the scent of the four corresponding smell test substance patches, such as banana scent in one embodiment. Because the four smell test substance patches in each subset have identical scent in this embodiment, alternate embodiments of such a smell identification test can comprise a single anterior or posterior smell test substance patch in each subset, in order to avoid redundancy. The four names of the scent choices referenced for each subset of anterior cover tab indicia, such as 57A, 57B, 57C, and 57D, can match the scent choices in Sensonics' Smell Identification Test (UP-SIT) or other available smell identification tests. Alternate embodiments of the present device can comprise different scent choices. The selection of appropriate smell test substances and scent choices for targeting a specific disease or family of diseases can be determined through medical research studies, machine learning methodology, and/or other known methods in the field.

In another embodiment which comprises smell identification test with 4 different choices for a first scent, such as peppermint, wherein this scent can be specified by all four anterior cover tab indicia 57A, 57B, 57C, and 57D, three of the four corresponding posterior-base color-coded circular smell test indicia 39A, 39B, 39C, and 39D can all be the same color, which represents an incorrect smell identification choice, and the other color-coded circular smell test indicium, which can be a different color, represents the correct smell identification choice for the first scent. In one embodiment of this, the correct choice for the first scent can be represented by a green posterior-base color-coded circular smell test indicium such as 39C, and the incorrect choices for the first scent can be represented by three red posterior-base color-coded circular smell test indicia such as 39A, 39B, and 39D. In this embodiment, the smell test substance patches 48C and 38C both comprise a peppermint-scented substance. In some embodiments which comprise smell identification test with 4 different choices for a second scent, such as banana, wherein this scent can be specified by all four anterior cover tab indicia 57E, 57F, 57G, and 57H, three of the four corresponding posterior-base color-coded circular smell test indicia 39E, 39F, 39G, and 39H can all be same color, which represents an incorrect smell identification choice, and the other color-coded circular smell test indicium, which can be a different color, represents the correct smell identification choice for the second scent. In one embodiment of this, the correct choice for the second scent can be represented by a green posterior-base color-coded circular smell test indicium such as 39F, and the incorrect choices for the second scent can be represented by three red posterior-base color-coded circular smell test indicia such as 39E, 39G, and 39H. In this particular embodiment, the smell test substance patches 48F and 38F both comprise a banana-scented substance. In this specific embodiment, if a person using the testing device peels one of the four cover tabs 95 with "Peppermint" indicium away from the rectangular posterior base 80 enough to fully expose a corresponding red posterior-base color-coded circular smell test indicium and also peels one of the four cover tabs 95 with "Banana" indicium away from the rectangular posterior base 80 enough to fully expose a corresponding green color-coded circular smell test indicium, these two exposed color-coded circular smell test indicia reveal an incorrect choice for the peppermint scent and a correct choice for the banana scent. Note that in such an embodiment, if there are more than two or less than two exposed color-coded circular smell test indicia, the person using the test has improperly exposed too many or too few color-coded circular smell test indicia, which is an error. In other embodiments, some anterior smell test substance patches such as 48A, 48D, 48F, and 48G can comprise an odorless substance, and other anterior smell test substance patches such as 48B, 48C, 48E, and 48H can comprise at least one odorous substance. In such embodiments, the corresponding color-coded circular smell test indicia representing the odorless anterior smell test substance patches can be represented by one color, and the color-coded circular smell test indicia representing at least one odorous anterior smell test substance patches can be represented by at least one color. In one such embodiment, the posterior-base color-coded circular smell test indicia 39A, 39D, 39F, and 39G can be red, and the posterior-base color-coded circular smell test indicia 39B, 39C, 39E, and 39H can be green. Such an embodiment requires that the person using the device only exposes the four green color-coded circular smell test indicia corresponding with an odorous smell test substance patch. His smell test score is the number of green posterior-base color-coded circular smell test indica 39 which are fully exposed, which can be score of 0-4 correct (green). If there are more than four or less than four color-coded circular smell test indicia exposed, the person using the test has improperly exposed too many or too few color-coded circular smell test indicia, which is an error. In still other embodiments where the pungency of each anterior smell test substance patch is different and the anterior smell test substance patches comprise same odorous substance in different concentrations, the color of each corresponding color-coded circular smell test indium can be the same. As one example, if the four anterior smell test substance patches 48A, 48B, 48C, and 48D all comprise the same odorous substance in different concentrations, all four corresponding posterior-base color-coded circular smell test indicia 39A, 39B, 39C, and 39D can be green. Similarly, if the four anterior smell test substance patches 48E, 48F, 48G, and 48H all comprise a second odorous substance in different concentrations, all four corresponding posterior-base color-coded circular smell test indicia 39E, 39F, 39G, and 39H can be red. In such an embodiment, the number of green color-coded circular smell test indicia and the number of red color-coded circular smell test indicia exposed during the smell test provide an odor detection threshold score for two corresponding odors. Such odor detection threshold scores can be analyzed along with other available relevant data to determine the result of test for certain target illnesses. It should be noted that although anterior smell test substance patches 48A, 48B, 48C, 48D, 48E, 48F, 48G, and 48H disposed on the anterior surface of the rectangular opaque anterior cover 95 are referenced in this paragraph, other embodiments of the present device can comprise only posterior smell test substance patches 38A, 38B, 38C, 38D, 38E, 38F, 38G, and 38H disposed on anterior surface of rectangular posterior base 80 in various configurations described in this paragraph, without any anterior smell test substance patches 48A, 48B, 48C, 48D, 48E, 48F, 48G, and 48H on the anterior surface of the corresponding cover tabs.

As shown in FIG. 78, this rectangular adhesive layer 90 can comprise a fourth set of adhesive rectangular openings 91J, 91K, 91L, 91M, 91N, and 91P, with corresponding posterior-base color-coded circular demographics indicium 39J, 39K, 39L, 39M, 39N, and 39P disposed on rectangular posterior base 80 within each adhesive rectangular opening. Each of these color-coded circular demographics indicia can be disposed behind a cover tab with a corresponding anterior cover tab indicium 57J, 57K, 57L, 57M, 57N, and 57P representing demographics information disposed on the anterior surface of cover tabs 95J, 95K, 95L, 95M, 95N, and 95P respectively. These anterior cover tab indicia can comprise age and gender information, as noted earlier. Anterior cover tab indicium 57J can comprise a phrase such as "Age 60-69", anterior cover tab indicium 57K can comprise a phrase such as "Age 70-79", anterior cover tab indicium 57L can comprise a phrase such as "Age 80-89", and anterior cover tab indicium 57M can comprise a phrase such as "Age 90+". Similarly anterior cover tab indicium 57N can comprise a word such as "Male", and anterior cover tab indicium 57P can comprise a word such as "Female". Once a person using the device has peeled the appropriate cover tabs away from the rectangular posterior base 80 according to the person's gender and age, the corresponding color-coded circular demographics indicia will be exposed. As an example, a 65-year-old man would peel the cover tab 95J labeled "Age 60-69" and the cover tab 95N labeled "Male", thereby exposing the corresponding posterior-base color-coded circular demographics indicia 39J and 39N originally hidden behind these two cover tabs.

As shown in FIG. 78, the rectangular adhesive layer 90 can comprise a fifth set of adhesive rectangular openings 91Q and 91R, with corresponding posterior-base color-coded circular olfactory identification awareness indicia 39Q and 39R disposed on rectangular posterior base 80 within each of these adhesive rectangular openings. Each of these color-coded circular olfactory identification awareness indicia is disposed behind a cover tab with a corresponding anterior cover tab indicium 57Q and 7711 representing olfactory identification awareness information disposed on the anterior surface of cover tabs 95Q and 7702 respectively. As noted earlier, in one embodiment anterior cover tab indicium 57Q can comprise a phrase such as "No difficulty identifying scents", and anterior cover tab indicium 7711 can comprise a phrase such as "Difficulty identifying scents". If a person using the device has peeled cover tab 95Q away from the rectangular posterior base 80 sufficiently to fully expose the posterior-base color-coded circular olfactory identification awareness indicium 39Q and at least one of the exposed color-coded circular smell test indicia is red color, which can indicate incorrect smell identification test choice in some embodiments, that person believes he can correctly identify smells but actually has difficulty correctly identifying at least some smells. Such a combination of exposed color-coded circular indicia on a used testing device increases the probability that person has or will develop Alzheimer's disease. Such data obtained from the used testing device, along with other relevant available data, can be analyzed by a suitable classification model to determine the probability of a target disease such as Alzheimer's disease.

As shown in FIG. 78, the rectangular adhesive layer 90 can comprise a sixth set of adhesive rectangular openings 7802 and 7804, with corresponding posterior-base color-coded circular gene variant indicia 7806 and 7808 disposed on rectangular posterior base 80 within each of these adhesive rectangular openings. Each of these color-coded circular gene variant indicia can be disposed behind a cover tab with a corresponding anterior cover tab indicium 7712 and 7714 representing gene variant information disposed on the anterior surface of cover tabs 7704 and 7706 respectively. As noted earlier, anterior cover tab indicium 7712 can comprise a phrase such as "ApoE-4", and anterior cover tab indicium 7714 can comprise a phrase such as "ApoE-2" in some embodiments. If a person using the testing device peels the cover tab 7704 with "ApoE-4" indicium away from the rectangular posterior base 80 enough to fully expose the corresponding posterior-base color-coded circular gene variant indicium 7806 representing ApoE-4 gene allele, the presence of this gene allele increases the probability that person can develop Alzheimer's disease. If instead a person fully exposes the corresponding posterior-base color-coded circular gene variant indicium 7808 representing ApoE-2 gene allele, the presence of this gene allele decreases the probability that person can develop Alzheimer's disease. It should be noted that a person can have 0, 1, or 2 copies of the ApoE-4 gene allele. Likewise, a person can have 0, 1, or 2 copies of the ApoE-2 gene allele. In addition, a person can have 0, 1, or 2 copies of the ApoE-3 gene allele, which neither increases nor decreases the probability of developing Alzheimer's disease. When a person has two copies of a particular ApoE gene allele, there are 0 copies of the two other ApoE alleles. Furthermore, people with a single copy of Klotho gene VS haplotype and also with ApoE-4 allele have ~25% lower risk of developing Alzheimer's disease than do people who have 0 or 2 copies of Klotho gene VS haplotype and have ApoE-4 allele. Based on this finding, in some embodiments of the testing device targeting Alzheimer's disease, there can be three anterior cover tab indicia referencing 0, 1, or 2 copies of the Klotho gene VS haplotype, as well as three corresponding color-coded circular gene variant indicia. Like the olfactory identification data, genetic data obtained from the used testing device, along with other relevant available data, can be analyzed by a suitable classification model to determine the probability of a target disease such as Alzheimer's disease.

As also shown in FIG. 78, the rectangular adhesive layer 90 can comprise a seventh set of at least one adhesive rectangular opening, such as 7810, with corresponding posterior-base color-coded circular blood biomarker indicium, such as 7812, disposed on rectangular posterior base 80 within such adhesive rectangular opening. Each such color-coded circular blood biomarker indicium can be disposed behind a corresponding cover tab, such as 7708, with a corresponding anterior cover tab indicium, such as 7716, representing blood biomarker information disposed on the anterior surface of at least one cover tab. Anterior cover tab indicium 7716 can be a blood biomarker for target disease. For Alzheimer's disease, this can be a positive blood test result for P-tau217, as one example. If a person using the testing device peels the cover tab 7708 with "P-tau217" indicium 7716 away from the rectangular posterior base 80 enough to fully expose the corresponding posterior-base color-coded circular blood biomarker indicium 7812 representing P-tau217, the presence of this particular blood biomarker increases the probability that person has or will develop Alzheimer's disease. When the presence of this P-tau217 biomarker is available and included in the analysis to determine result, the sensitivity and specificity of an Alzheimer's diagnostic test can be increased.

Besides blood biomarkers and gene biomarkers, there are other biomarkers associated with various diseases as well. As an example, cardiovascular disease is associated with a variety of biomarkers such as high resting heart rate, and such biomarkers may be associated with other diseases as well, including dementia. Some anterior cover tab indicia can reference such biomarkers in other embodiments of the device. Such biomarkers as high resting heart rate are non-olfactory warning signs of such diseases as dementia.

As also shown in FIG. 78, the rectangular adhesive layer 90 can comprise an eighth set of at least one adhesive rectangular opening, such as 7814, with corresponding posterior-base color-coded circular non-olfactory warning sign indicium, such as 7816, disposed on rectangular posterior base 80 within such adhesive rectangular opening. Each such color-coded circular non-olfactory warning sign indicium can be disposed behind a corresponding cover tab, such as 7710, with a corresponding anterior cover tab indicium, such as 7718, representing non-olfactory warning sign information disposed on the anterior surface of at least one cover tab, such as 7710. Anterior cover tab indicium 7718 can be an observable symptom for target illness. For Alzheimer's disease, this can be the symptom of falling more frequently, as one example. If a person using the testing device peels the cover tab 7710 with a phrase such as "Falling more frequently" indicium 7718 away from the rectangular posterior base 80 enough to fully expose the corresponding posterior-base color-coded circular non-olfactory warning sign indicium 7816 representing falling more frequently, the presence of this particular observable symptom increases the probability that person has or will develop Alzheimer's disease.

One embodiment of the device shown in FIG. 77 and FIG. 78 comprises the following set of color-coded circular indicia disposed on the rectangular posterior base 80:

Posterior-base color-coded circular smell test indicia representing correct choices: Green.
Posterior-base color-coded circular smell test indicia representing incorrect choices: Red.
Posterior-base color-coded circular demographics indicium 39J representing age 60-69: Blue-Green.
Posterior-base color-coded circular demographics indicium 39K representing age 70-79: Blue.
Posterior-base color-coded circular demographics indicium 39L representing age 80-89: Blue-Violet.
Posterior-base color-coded circular demographics indicium 39M representing age 90+: Violet.
Posterior-base color-coded circular demographics indicium 39N representing male: Yellow-Green.
Posterior-base color-coded circular demographics indicium 39P representing female: Red-Orange.
Posterior-base color-coded circular olfactory identification awareness indicium 39Q representing no awareness of smell identification problem: Red-Violet.
Posterior-base color-coded circular olfactory identification awareness indicium 39R representing awareness of smell identification problem: Yellow-Orange.
Posterior-base color-coded circular gene variant indicium 7806 representing ApoE-4 allele: Orange.
Posterior-base color-coded circular gene variant indicium 7808 representing ApoE-2 allele: Yellow.
Posterior-base color-coded circular blood biomarker indicium 7812 representing P-tau217: Black.
Posterior-base color-coded circular non-olfactory warning sign indicium 7816 representing falling frequently: Grey.

Note that there can be numerous alternative embodiments with different color-code for each color-coded circular indicium.

Figure 79:
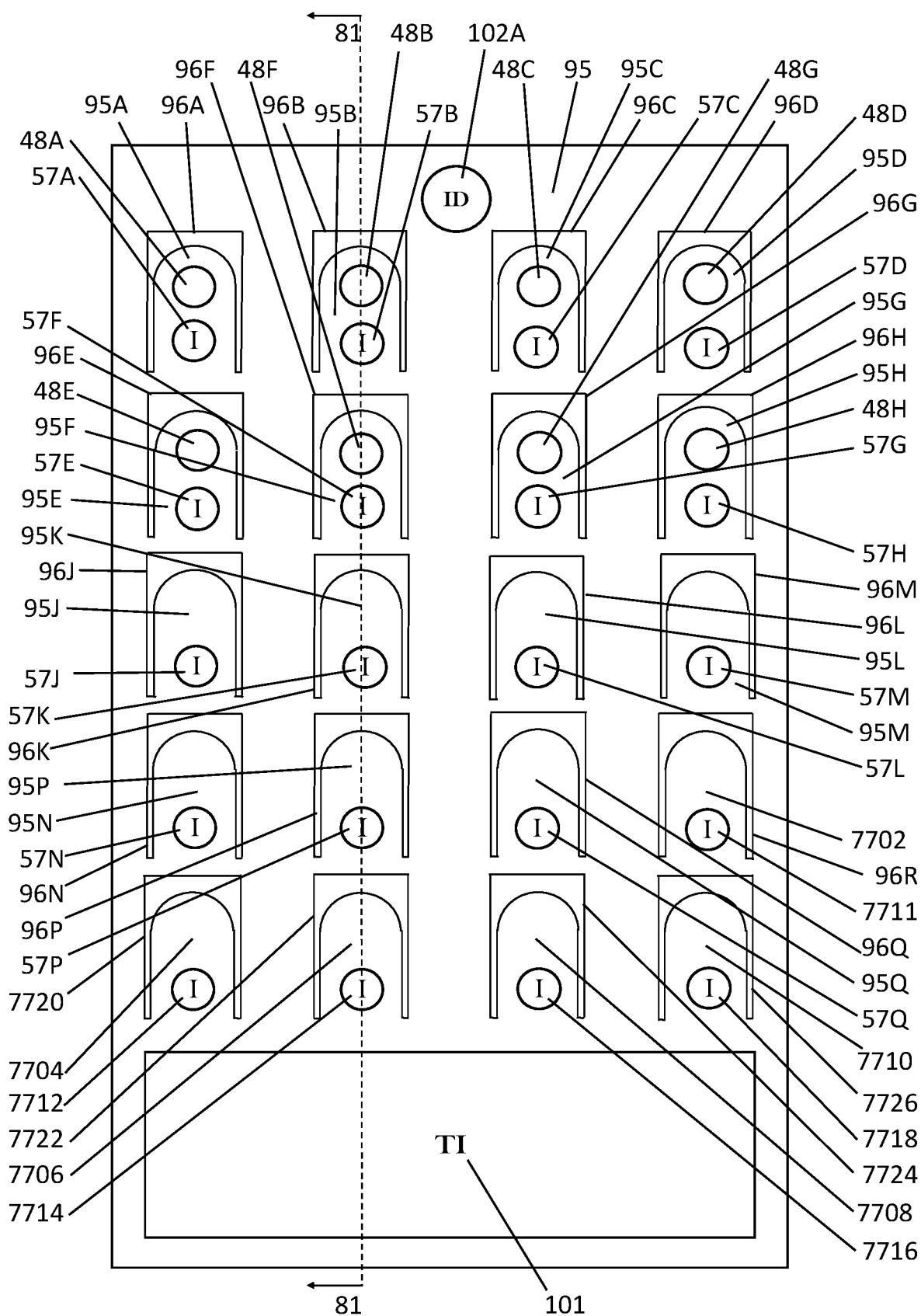
FIG. 79 depicts a top view of the rectangular opaque anterior cover of the embodiment depicted in FIG. 77.

FIG. 79 is a top view of the rectangular opaque anterior cover 95 of the eleventh embodiment. As shown, this is a substantially flat component with integral cover tabs 95A-7710 disposed within rectangular cover openings 96A-7726 and with diagnostic test instructions 101 printed on anterior surface, as described earlier. In one embodiment comprising an olfactory identification test with peel and sniff substances disposed on the anterior surface of the rectangular posterior base 80, the diagnostic test instructions 101 can comprise statements such as the following:

1. Peel the tab with your age range back enough that a color dot is fully visible.
2. Peel the tab with your gender back enough that a color dot is fully visible.
3. If you have difficulty identifying scents, peel that tab back enough that a color dot is fully visible. If you have no difficulty identifying scents, peel that alternate tab back enough that a color dot is fully visible.
4. If you have taken an ApoE gene test, peel the appropriate gene tab or tabs back enough that a color dot is fully visible, based on your gene test result.
5. If you have taken the P-tau217 blood test and your test result is positive, peel that tab back enough that a color dot is fully visible.
6. If you are falling more frequently than before, peel that tab back enough that a color dot is fully visible.
7. Partially peel back each tab labelled Scent 1, sniff each scented patch underneath, then fully peel back only the Scent 1 tab which smells most like the scent listed on that tab until a color dot is fully visible. Each scented patch underneath these tabs is the same scent.
8. Partially peel back each tab labelled Scent 2, sniff each scented patch underneath, then fully peel back only the Scent 2 tab which smells most like the scent listed on that tab until a color dot is fully visible. Each scented patch underneath these tabs is the same scent.
9. Activate the custom app on your smart phone for this diagnostic test, then use phone camera to photograph all visible color dots together. This app will estimate likelihood you have or will develop Alzheimer's disease during the next five years, and it will provide you with details regarding open clinical trials for treatments which you may be eligible for.

As noted earlier, the smell test substance patches which correspond to Scent 1 cover tabs can be peppermint scent, and the smell test substance patches which correspond to Scent 2 cover tabs can be banana scent, as one example.

In another embodiment of the device depicted in FIG. 77-FIG. 83 comprising an olfactory identification test with peel and sniff substances disposed on the anterior surface of the rectangular posterior base 80, the diagnostic test instructions 101 can comprise statements such as the following:
1. Peel the tab with your age range back enough that a color dot is fully visible.
2. Peel the tab with your gender back enough that a color dot is fully visible.
3. If you have difficulty identifying scents, peel that tab back enough that a color dot is fully visible. If you have no difficulty identifying scents, peel that alternate tab back enough that a color dot is fully visible.
4. If you have taken an ApoE gene test, peel the appropriate gene tab or tabs back enough that a color dot is fully visible, based on your gene test result.
5. If you have taken the P-tau217 blood test and your test result is positive, peel that tab back enough that a color dot is fully visible.
6. If you are falling more frequently than before, peel that tab back enough that a color dot is fully visible.
7. Partially peel back each tab labelled Peppermint, sniff each scented patch underneath, then fully peel back only the tab which smells most like peppermint until a color dot is fully visible.
8. Partially peel back each tab labelled Banana, sniff each scented patch underneath, then fully peel back only the tab which smells most like banana until a color dot is fully visible.
9. Activate the custom app on your smart phone for this diagnostic test, then use phone camera to photograph all visible color dots together. This app will estimate likelihood you have or will develop Alzheimer's disease during the next five years, and it will provide you with details regarding open clinical trials for treatments which you may be eligible for.

In one embodiment comprising an olfactory identification test with scratch and sniff substances on the anterior surface of the cover tabs, the diagnostic test instructions 101 can comprise statements such as the following:
1. Peel the tab with your age range back enough that a color dot is fully visible.
2. Peel the tab with your gender back enough that a color dot is fully visible.
3. If you have difficulty identifying scents, peel that tab back enough that a color dot is fully visible. If you have no difficulty identifying scents, peel that alternate tab back enough that a color dot is fully visible.
4. If you have taken an ApoE gene test, peel the appropriate gene tab or tabs back enough that a color dot is fully visible, based on your gene test result.
5. If you have taken the P-tau217 blood test and your test result is positive, peel that tab back enough that a color dot is fully visible.
6. If you are falling more frequently than before, peel that tab back enough that a color dot is fully visible.
7. Scratch and sniff the scented patch on each tab labelled Scent 1, then fully peel back only the Scent 1 tab which smells most like the scent listed on that tab until a color dot is fully visible. Each scented patch on these tabs is the same scent.
8. Scratch and sniff the scented patch on each tab labelled Scent 2, then fully peel back only the Scent 2 tab which smells most like the scent listed on that tab until a color dot is fully visible. Each scented patch on these tabs is the same scent.
9. Activate the custom app on your smart phone for this diagnostic test, then use phone camera to photograph all visible color dots together. This app will estimate likelihood you have or will develop Alzheimer's disease during the next five years, and it will provide you with details regarding open clinical trials for treatments which you may be eligible for.

As noted earlier, the smell test substance patches which correspond to Scent 1 cover tabs can be peppermint scent, and the smell test substance patches which correspond to Scent 2 cover tabs can be banana scent, as one example.

In another embodiment comprising an olfactory identification test with scratch and sniff substances on the anterior surface of the cover tabs, the diagnostic test instructions 101 can comprise statements such as the following:
1. Peel the tab with your age range back enough that a color dot is fully visible.
2. Peel the tab with your gender back enough that a color dot is fully visible.
3. If you have difficulty identifying scents, peel that tab back enough that a color dot is fully visible. If you have no difficulty identifying scents, peel that alternate tab back enough that a color dot is fully visible.
4. If you have taken an ApoE gene test, peel the appropriate gene tab or tabs back enough that a color dot is fully visible, based on your gene test result.
5. If you have taken the P-tau217 blood test and your test result is positive, peel that tab back enough that a color dot is fully visible.
6. If you are falling more frequently than before, peel that tab back enough that a color dot is fully visible.
7. Scratch and sniff the scented patch on each tab labelled Peppermint, then fully peel back only the tab which smells most like peppermint until a color dot is fully visible.
8. Scratch and sniff the scented patch on each tab labelled Banana, then fully peel back only the tab which smells most like banana until a color dot is fully visible.
9. Activate the custom app on your smart phone for this diagnostic test, then use phone camera to photograph all visible color dots together. This app will estimate likelihood you have or will develop Alzheimer's disease during the next five years, and it will provide you with details regarding open clinical trials for treatments which you may be eligible for.

In one embodiment comprising an olfactory detection test with peel and sniff substances disposed on the anterior surface of the rectangular posterior base 80, the diagnostic test instructions 101 can comprise statements such as the following:
1. Peel the tab with your age range back enough that a color dot is fully visible.
2. Peel the tab with your gender back enough that a color dot is fully visible.

3. If you have difficulty detecting scents, peel that tab back enough that a color dot is fully visible. If you have no difficulty detecting scents, peel that alternate tab back enough that a color dot is fully visible.
4. If you have taken target disease gene test, peel the appropriate gene tab or tabs back enough that a color dot is fully visible, based on your gene test result.
5. If you have taken target disease biomarker blood test and your test result is positive, peel that biomarker tab back enough that a color dot is fully visible.
6. If you have target disease symptom, peel that symptom tab back enough that a color dot is fully visible.
7. Partially peel back each of the eight tabs labelled "Smell Tab", sniff each smell test patch underneath, then fully peel back only tabs when you smell an odor until a color dot is fully visible.
8. Activate the custom app on your smart phone for this diagnostic test, then use phone camera to photograph all visible color dots together. This app will estimate likelihood you have or will develop target disease during the next five years, and it will provide you with details regarding open clinical trials for treatments which you may be eligible for.

In embodiments comprising an olfactory detection test having four smell test substance patches with an odorous substance and four smell test substance patches with an odorless substance, test instruction step 7 can additionally include a statement such as "There are only four Smell Tabs covering an odorous substance, so do not fully peel back more than four Smell Tabs to expose more than four color dots." If there are more than four or less than four exposed color-coded circular smell-test indicia, the test result can include an error message stating that too many or too few Smell Tabs were peeled back to expose color dots. In embodiments with a smell test comprising smell test substance patches with different pungencies, described earlier, this additional statement may not be applicable.

In one embodiment comprising an olfactory detection test with scratch and sniff substances disposed on the anterior surface of the rectangular opaque anterior cover 95, the diagnostic test instructions 101 can comprise statements such as the following:
1. Peel the tab with your age range back enough that a color dot is fully visible.
2. Peel the tab with your gender back enough that a color dot is fully visible.
3. If you have difficulty detecting scents, peel that tab back enough that a color dot is fully visible. If you have no difficulty detecting scents, peel that alternate tab back enough that a color dot is fully visible.
4. If you have taken target disease gene test, peel the appropriate gene tab or tabs back enough that a color dot is fully visible, based on your gene test result.
5. If you have taken target disease biomarker blood test and your test result is positive, peel that biomarker tab back enough that a color dot is fully visible.
6. If you have target disease symptom, peel that symptom tab back enough that a color dot is fully visible.
7. Scratch and sniff the smell test patch on each of the eight tabs labelled "Smell Tab", and fully peel back only tabs when you smell an odor until a color dot is fully visible.
8. Activate the custom app on your smart phone for this diagnostic test, then use phone camera to photograph all visible color dots together. This app will estimate likelihood you have or will develop target disease during the next five years, and it will provide you with details regarding open clinical trials for treatments which you may be eligible for.

In embodiments comprising an olfactory detection test having four smell test substance patches with an odorous substance and four smell test substance patches with an odorless substance, test instruction step 7 can additionally include a statement such as "There are only four Smell Tabs covering an odorous substance, so do not fully peel back more than four Smell Tabs to expose more than four color dots." If there are more than four or less than four exposed color-coded circular smell-test indicia, the test result can include an error message stating that too many or too few Smell Tabs were peeled back to expose color dots. In embodiments with a smell test comprising smell test substance patches with different pungencies, described earlier, this additional statement may not be applicable.

Figure 80:
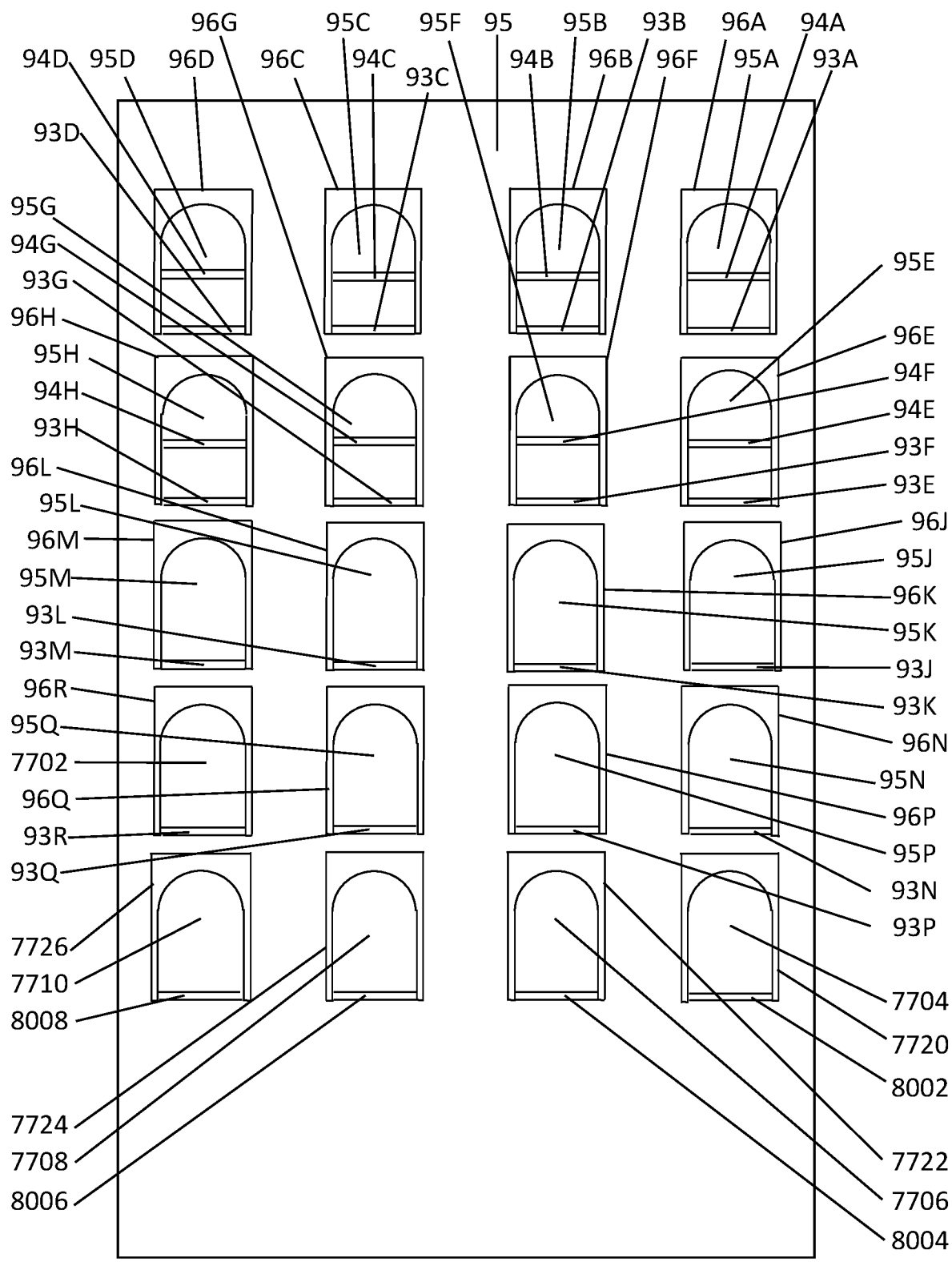
FIG. 80 depicts a bottom view of the rectangular opaque anterior cover of the embodiment depicted in FIG. 77.

As shown in FIG. 80 bottom view of rectangular opaque anterior cover 95, in some embodiments each of the eight cover tabs 95A, 95B, 95C, 95D, 95E, 95F, 95G, and 95H can have a corresponding distal cover tab groove 94A, 94B, 94C, 94D, 94E, 94F, 94G, and 94H disposed on a posterior surface of cover tab, adjacent to an edge of rectangular adhesive layer 90. Each such distal cover tab groove can decrease the bending force required to manually peel the distal portion of the corresponding cover tab away from rectangular posterior base 80, essentially functioning similar to a hinge. Additionally, in some embodiments, each of the twenty cover tabs 95A, 95B, 95C, 95D, 95E, 95F, 95G, 95H, 95J, 95K, 95L, 95M, 95N, 95P, 95Q, 7702, 7704, 7706, 7708, and 7710 can have a corresponding proximal cover tab groove 93A, 93B, 93C, 93D, 93E, 93F, 93G, 93H, 93J, 93K, 93L, 93M, 93N, 93P, 93Q, 93R, 8002, 8004, 8006, and 8008 disposed on posterior surface of cover tab, adjacent to an edge of rectangular adhesive layer 90 at inner border of cover tab. Each such proximal cover tab groove can decrease the bending force required to manually peel the proximal portion of the corresponding cover tab away from rectangular posterior base 80, also functioning similar to a hinge. As shown in FIG. 80, FIG. 81, FIG. 82, and FIG. 83, each cover tab groove can be a slot with substantially orthogonal walls. In alternate embodiments, such cover tab grooves can be U-shaped grooves, V-shaped grooves, or other appropriate form factors. When the rectangular opaque anterior cover 95 comprises paperboard or other material with similar properties, these regions of the cover tabs can be created by a scoring or creasing process, which can facilitate bending in these scored or creased regions. When the rectangular opaque anterior cover 95 comprises other materials which can be readily bent and plastically deform with minimal force, such as a sheet of aluminum alloy 0.001"-0.005" thick, scoring, creasing, or groove fabrication processes may not be necessary. When the rectangular opaque anterior cover 95 comprises a thermoplastic material, grooves can be fabricated during injection molding of the part, by thermoforming the grooves, or other known manufacturing process. In addition, such grooves can be fabricated using conventional machining processes.

It should be noted that although FIG. 77-FIG. 80 depict a rectangular form factor of the eleventh embodiment, with cover tabs aligned in rows and columns, other embodiments can have alternative form factors with similar or identical functionality, operation, and diagnostic test instructions. As an example, some embodiments can have a radial form factor, with radially-aligned cover tabs instead.

Figure 81:
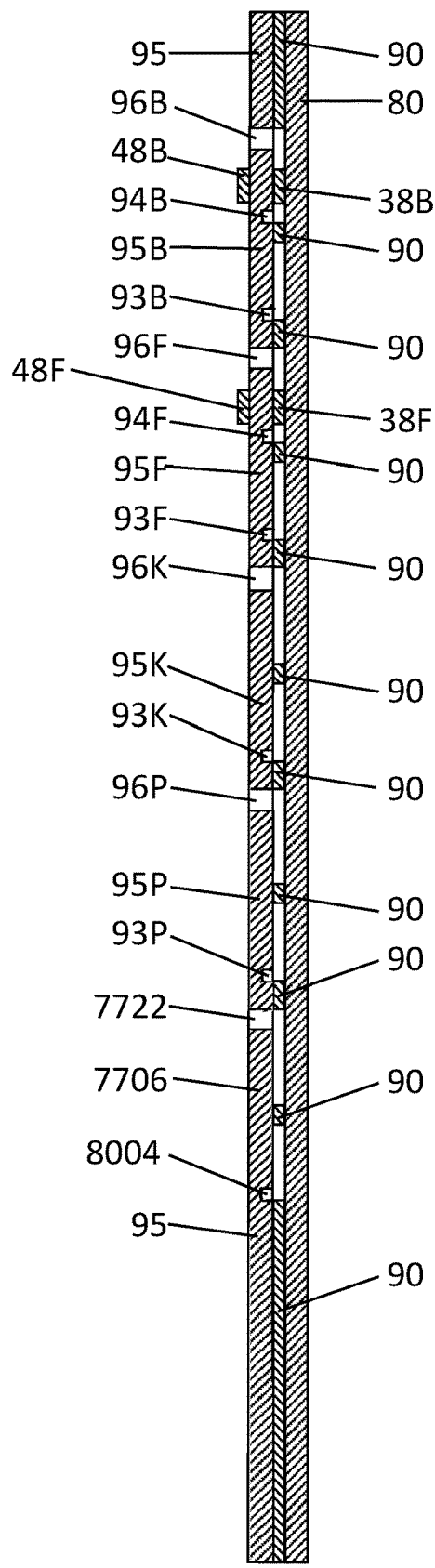
FIG. 81 depicts a side cross-section view of the embodiment depicted in FIG. 77, prior to use.

FIG. 81 depicts a side cross-sectional view of an eleventh embodiment of the present device. As also shown in FIG. 77 and in FIG. 78, there can be a rectangular adhesive layer 90 disposed on anterior surface of rectangular posterior base 80 and on posterior surface of the rectangular opaque anterior cover 95. In addition, each of eight posterior smell test substance patches 38A, 38B, 38C, 38D, 38E, 38F, 38G, and 38H can be contiguous with both the anterior surface of the rectangular posterior base 80 and the posterior surface of the rectangular opaque anterior cover 95. As shown in FIG. 81, there can be a strip of the rectangular adhesive layer 90 between its rectangular openings which is disposed adjacent to each proximal cover tab groove 93A, 93B, 93C, 93D, 93E, 93F, 93G, 93H, 93J, 93K, 93L, 93M, 93N, 93P, 93Q, 93R, 8002, 8004, 8006, and 8008, at the proximal border of each corresponding cover tab 95A, 95B, 95C, 95D, 95E, 95F, 95G, 95H, 95J, 95K, 95L, 95M, 95N, 95P, 95Q, 7702, 7704, 7706, 7708, and 7710. Similarly, there can be a strip of the rectangular adhesive layer 90 between its rectangular openings which can be disposed adjacent to each distal cover tab groove 94A, 94B, 94C, 94D, 94E, 94F, 94G, and 94H in each corresponding cover tab 95A, 95B, 95C, 95D, 95E, 95F, 95G, and 95H. In addition, there can be a strip of the rectangular adhesive layer 90 between its rectangular openings which can be disposed midspan on each cover tab 95J, 95K, 95L 95M, 95N, 95P, 95Q, 7702, 7704, 7706, 7708 and 7710, as shown in FIG. 81 and FIG. 77. Each of these adhesive layer strips disposed midspan on the posterior surface of the twenty cover tabs 95A-7710 and on the anterior surface of the rectangular posterior base 80 can be narrower than the adhesive layer strips disposed adjacent to the proximal cover tab grooves 93A-8008, at the proximal border of each corresponding cover tab 95A, 95B, 95C, 95D, 95E, 95F, 95G, 95H, 95J, 95K, 95L, 95M, 95N, 95P, 95Q, 7702, 7704, 7706, 7708 and 7710. These narrower adhesive layer strips reduce the force required when a person peels a cover tab away from the rectangular posterior base 80, removing the cover tab off the adhesive layer strip. Unlike these narrower adhesive layer strips, the wider adhesive layer strips adjacent to the proximal cover tab grooves 93A-8008 can have sufficient adhesion strength to maintain adhesion to both the rectangular posterior base 80 and to the rectangular opaque anterior cover 95 before, during, and after use without any delamination. It should be noted that although the eleventh embodiment shown in FIG. 81 comprises both posterior smell test substance patches 38A-38H and anterior smell test substance patches 48A-48H, other embodiments can comprise one set of these smell test substance patches or the other set of these smell test substance patches, depending on user preference or based on a requirement for tighter control of the pungency of each smell test substance patch, as discussed previously.

Figure 82:
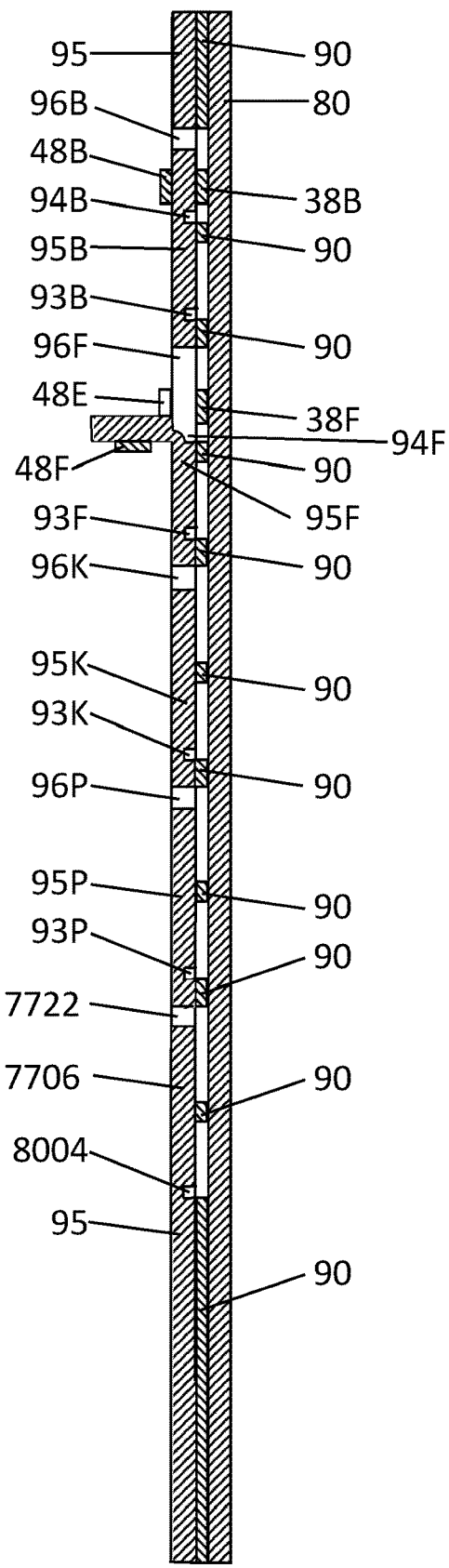
FIG. 82 depicts a side cross-section view of the embodiment depicted in FIG. 77.
Figure 83:
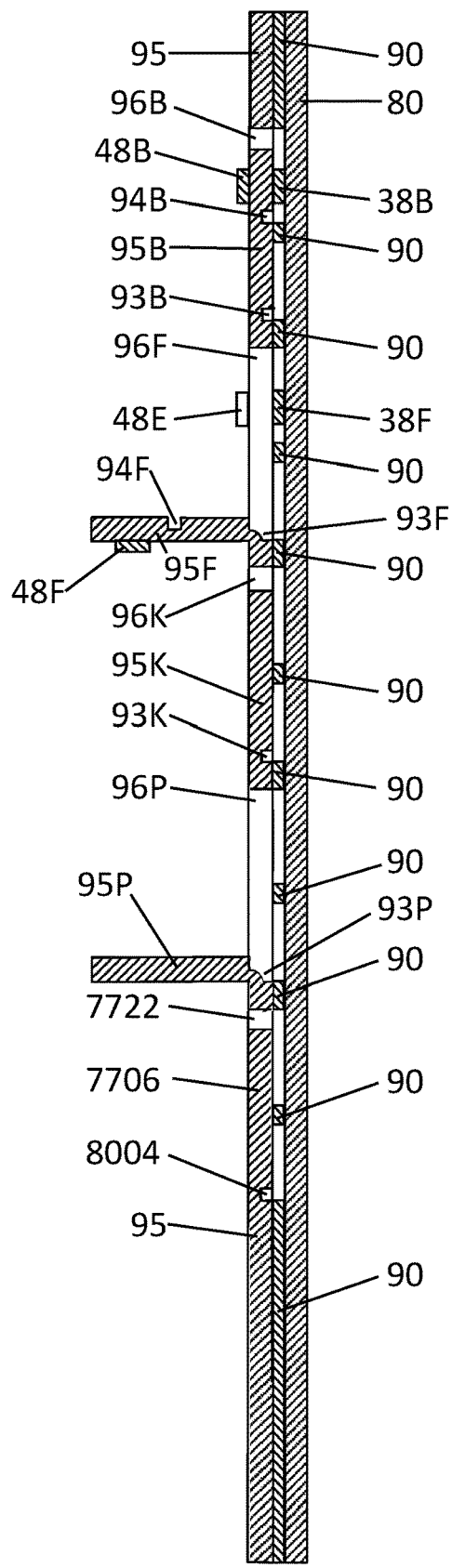
FIG. 83 depicts an alternate side cross-section view of the embodiment depicted in FIG. 77.

FIG. 82 depicts cross sectional side view of eleventh embodiment of device after distal portion of cover tab 95F has been mechanically peeled back sufficiently such that posterior smell test substance patch 38F is exposed and visible. Once a person has partially peeled this cover tab to expose this posterior smell test substance patch accordingly, he can sniff close to this smell test substance patch, per the diagnostic test instructions 101. Similarly FIG. 83 depicts cross sectional side view of eleventh embodiment of device after the entire cover tab 95F and the entire cover tab 95P have been mechanically peeled back sufficiently further such that the posterior-base color-coded circular smell test indicium 39F and the posterior-base color-coded circular demographics indicium 39P are exposed and visible. After the person has completed peeling back the relevant cover tabs to fully expose corresponding color-coded circular indicia on the rectangular posterior base 80, per the diagnostic test instructions 101, the person can activate the diagnostic test's diagnostic application software in his smart phone and then use the smart phone's camera to capture a digital image of all the exposed color-coded circular indicia on the device.

Although the eleventh embodiment shown in FIG. 77-FIG. 83 can comprise cover tabs with smell test indicia, demographics indicia, olfactory identification awareness indicia, gene variant indicia, blood biomarker indicia, and non-olfactory warning sign indicia, as already described, the twenty cover tabs shown in these figures can alternately comprise a subset of these different indicia categories instead. As one example, all twenty cover tabs can all have smell test indicia. If this embodiment comprises a smell identification test, there can be smell test substance patches with five different scents, with each row comprising four smell test substance patches with same scent. The smell test indicia disposed on the cover tabs within same row can comprise four different scent names, including one scent name which corresponds to the actual scent of the corresponding smell test substance patches within that row. In such an embodiment, the objective is to correctly identify the correct scent name for five different scents.

Although the eleventh embodiment shown in FIG. 77-FIG. 83 comprises twenty cover tabs and twenty corresponding color-coded circular indicia disposed on the rectangular posterior base 80, other similar embodiments can comprise fewer than twenty or more than twenty cover tabs and corresponding color-coded circular indicia, depending on how much input data (e.g., quantity of scent choices in the smell test, demographics data, biomarkers data, symptoms' data, etc.) is required to determine test result. In some embodiments, it can be advantageous for the diagnostic device to comprise a set of more than one rectangular opaque anterior cover 95 plus rectangular posterior base 80 assembly, which can be similar or identical in size, form factor, functionality, features, materials, and manufacturing processes. As one example, the diagnostic device can comprise a set of two rectangular opaque anterior cover 95 plus rectangular posterior base 80 assemblies shown in FIG. 77-FIG. 83. As noted earlier, there can be color-coded circular indicia with fourteen different color codes, including black and grey. Potentially these same color-coded circular indicia can be used with each rectangular opaque anterior cover 95 plus rectangular posterior base 80 assembly, such as in embodiments with a different quantity of color-coded circular smell test indicia and with all other color-coded circular indicia identical to the list of fourteen different color-coded circular indicia disclosed earlier in one example. In other embodiments, some or all the color-coded circular indicia can represent different olfactory, demographic, gene, biomarker, symptom, and other warning sign information associated with a particular rectangular opaque anterior cover 95 plus rectangular posterior base 80 assembly. In such embodiments, each rectangular opaque anterior cover 95 plus rectangular posterior base 80 assembly can have a unique assembly ID indicium (symbolized by ID enclosed in a circle) such as assembly ID indicium 102A shown in FIG. 77 and FIG. 79. Such an assembly ID indicium can be a bar code, a QR code, a color-coded circular indicium, an alphanumeric indicium, or any other indicium suitable for identifying each particular assembly. In some embodiments, each unique assembly ID indicium such as 102A can be a color-coded circular indicium which is substantially different in diameter than the other color-coded circular indicia disposed on the same rectangular opaque anterior cover 95 plus rectangular posterior base 80 assembly. In an embodiment which comprises two rectangular opaque anterior cover 95 plus rectangular posterior base 80 assemblies, one with assembly ID indicium 102A, which can be a color-coded circular indicium which is blue, and the other one with assembly ID indicium 102B, which can be a color-coded circular indicium which is purple, both of these assembly ID indicia can be substantially larger in diameter than the other color-coded circular indicia disposed on each rectangular opaque anterior cover 95 plus rectangular posterior base 80 assembly. In another embodiment, an assembly can comprise all the components of the eleventh embodiment shown in FIG. 77-FIG. 83 and described earlier, as well as a rectangular opaque posterior cover attached via an adhesive layer to posterior surface of rectangular posterior base 80. This rectangular opaque posterior cover can comprise similar or identical features as rectangular opaque anterior cover 95, with similar or identical size, shape, and quantities of features, including smell test substance patches, cover tabs, cover tab indicia, and test instructions if desired. The adhesive layer disposed between the rectangular posterior base 80 and the rectangular opaque posterior cover can also comprise similar or identical features, shape, and size as the rectangular adhesive layer 90. In addition, a unique assembly ID indicium, such as 102B, can be disposed on the posterior surface of the rectangular opaque posterior cover. In addition, there can be a corresponding color-coded circular indicium disposed on the posterior surface of rectangular posterior base 80, behind each cover tab of the rectangular opaque posterior cover. One such assembly can comprise a total of ten rows of cover tabs, which can be suitable for a smell identification test with ten different scents to be identified in one embodiment.

The diagnostic application software in the mobile device (smart phone, tablet, etc.) can include a diameter filter algorithm in addition to the circle detection and color filter algorithm(s) to recognize in a digital image the unique assembly ID indicium of each rectangular opaque anterior cover 95 plus rectangular posterior base 80 assembly in embodiments with more than one such assembly. In embodiments with more rectangular opaque anterior cover 95 plus rectangular posterior base 80 assemblies, each assembly ID indicium 102A, 102B, 102C, 102D, et cetera can be a different color. The diagnostic application software's diameter, color, and circle detection algorithm(s) can confirm when all the exposed color-coded circular indicia on every rectangular opaque anterior cover 95 plus rectangular posterior base 80 assembly have been analyzed. This is critical to ensure that the diagnostic application software's analysis includes all the relevant input data necessary for determining the result. If any critical input data, such as some smell test data, is missing, or if one of the rectangular opaque anterior cover 95 plus rectangular posterior base 80 assemblies is not detected by this diagnostic application software, the result can include an error message regarding missing input data and/or missing a rectangular opaque anterior cover 95 plus rectangular posterior base 80 assembly. A person can subsequently clear such an error message by capturing a digital image of any missing used assembly with the mobile device's camera. Once this has been completed, the diagnostic application software can complete the analysis and can determine a final result.

FIG. 84a and FIG. 84b depicts an alternate decision flowchart. Step 8420A can comprise entering target personal data into digital memory. There is available application software which allows users to transfer personal medical information to and from their Apple or Android-based smart phone, tablet, notebook computer, alternate mobile device, or desktop computer. This method can be used to quickly and conveniently enter some target personal data regarding relevant medical records information, such as medical test results, medications, and disease diagnoses, from at least one remote medical records database into digital memory in a mobile device, desktop computer, or a database server. Some such application software automatically updates this personal medical information in the mobile device or desktop computer periodically. Such target personal data can be updated shortly before using the testing device, as needed. During Step 8420A, one or more EMR (electronic medical records) for a person, such as a first EMR database and a second EMR database from different medical centers which do not share EMR data, can be stored in digital memory of a mobile device or desktop computer, which can be stored at different times than other target personal data. This other target personal data can be stored in a diagnostic database, which can also be within this digital memory. The mobile device or desktop computer can include diagnostic application software for executing some steps shown in FIG. 84a and FIG. 84b, and in some embodiments, this diagnostic application software can include this diagnostic database. The digital memory in many embodiments is used to store a relatively limited set of data, and this digital memory is typically inside a mobile device, such as a smart phone, tablet computer, or notebook computer, and it can be inside some desktop computers as well. The diagnostic database can store some data that is not included in the EMR databases. The diagnostic database can also store information regarding whether the person has awareness of an existing impaired olfactory identification ability, which can be entered during Step 8420A. In addition, some gene information, such as the presence of the ApoE-4 allele, can be also entered during Step 8420A into the diagnostic database if the gene testing was performed by a company such as 23andMe, which is independent from medical centers where the person's EMR data is stored. Some target information alternately can be entered manually using an onscreen keyboard, a touchscreen keyboard, a physical keyboard on mobile device, a separate keyboard for a desktop computer, and/or by clicking onscreen buttons on this device. Application software then can transfer this target information into memory. Target personal data can comprise name, personal ID (e.g., medical record number, Social Security number, patient ID number, employee number, school ID number, driver's license number, etc.), serial number of used testing device, demographics information (gender, age or age range or birthdate, race, ethnicity, level of education, smoking status, close relative with target disease, etc.).

In addition, this personal data can comprise any relevant biomarkers for target illness, such as levels of P-tau217 or P-tau181 in blood or cerebrospinal fluid or saliva (which can be biomarkers of Alzheimer's disease when their levels are elevated), presence or levels of other proteins in blood or cerebrospinal fluid which are either positively or negatively correlated with the target disease such as Alzheimer's disease, results of Dementia Blood Test Panel (which includes levels of CBC, electrolytes, TSH, T4 total, vitamin B12, CRP, and sedimentation rate), the presence or level of certain microRNA molecules which are positively correlated with diseases such as Alzheimer's disease, other applicable biomarkers in saliva or urine, and high resting heart rate (>80 BPM) which can also be a biomarker of some diseases such as Alzheimer's disease. A lower ratio of ABeta42/Abeta40, two isoforms of the amyloid-Beta protein that aggregate to form amyloid plaques in the brain, can be another biomarker for Alzheimer's disease as well. This personal data can also include the presence of certain gene variants related to the target disease, such ApoE-4 allele and variants, mutations of the APP, PSEN1, PSEN2, ABCA7, CLU, CR1, PICALM, PLD3, TREM2, and SORL1 genes, which are positively correlated to Alzheimer's disease, and ApoE-2 allele, which is negatively correlated to Alzheimer's disease. Since people with a single copy of Klotho gene VS haplotype and also with ApoE-4 allele have 30% lower risk of developing Alzheimer's disease than do people who have 0 or 2 copies of Klotho gene VS haplotype and have ApoE-4 allele, the number of copies of this Klotho gene VS haplotype can be included as relevant target personal data to be entered also. In addition, a cognitive function test score, such as the MMSE (Mini-Mental State Exam) score can be included as well. Target personal data entered can include relevant symptoms and early warning signs associated with the target illness. As described earlier, relevant symptoms associated with COVID-19 include fever, persistent cough, shortness of breath, difficulty breathing, skin rash, chills, muscle or body aches, fatigue, sore throat, loss of appetite, headache, nausea or vomiting, diarrhea, new confusion, inability to wake or stay awake, and persistent pain or pressure in the chest. Relevant symptoms and early warning signs associated with dementia include falling more frequently, breaking laws (stealing, trespassing, driving recklessly, etc.), eating rancid food or non-food items, changes in gait, gum disease, inability to recognize sarcasm, misplacing items more frequently, increased forgetfulness, compulsive behaviors, depression, stroke, and other untreated mental disorders, including bipolar disorder, schizophrenia, post-traumatic stress disorder, chronic stress, and ADD/ADHD. Another symptom which is an early warning sign of Alzheimer's disease is daytime napping, either daily naps lasting more than 1 hour or multiple naps each day. This symptom can be entered via an on-screen button labelled with description of this symptom or via YES on-screen button adjacent to on-screen question regarding daytime napping more than 1 hour or multiple naps each day.

Personal contact information (e.g., email address, telephone number, mailing address), input regarding personal interest in participating in relevant clinical trials (either interested, not interested, or to be determined), and other relevant personal information can also be entered. This information can be entered into digital memory within the mobile device or desktop computer by the person taking the diagnostic test and/or by an organization, such as a company which analyzes personal genetic test results and stores genetic information in remote database, such as 23andMe. Some types of target personal data can be entered using on-screen buttons, such as buttons labeled with different symptoms, male and female gender buttons, buttons labelled with different genes such as ApoE-4 allele and ApoE-2 allele, buttons labelled with different biomarkers, button which specifies difficulty identifying different scents, button which specifies no difficulty identifying different scents, buttons labelled with different age ranges, buttons labelled with different levels of education, buttons labelled with different ethnicity, buttons regarding clinical trials labelled "INTERESTED" and "NOT INTERESTED", and buttons labelled "YES", "NO", "N.A.", et cetera. In some embodiments of the testing device already described earlier, some demographics information, some symptoms information, some gene information, and/or some biomarkers information instead can be associated with indicia on the used testing device, although the indicia on used testing device can alternatively be exclusively associated with the smell test. Note that this Step 8420A can occur independent from when Step 8422 occurs.

Step 8420B can comprise obtaining a smell testing device. In some embodiments, this smell testing device can be similar or identical to the embodiment depicted in FIG. 77-FIG. 83, which can include scratch-and-sniff smell test substance patches and/or peel-and-sniff smell test substance patches described earlier. In one such embodiment, each of the twenty cover tabs 95A, 95B, 95C, 95D, 95E, 95F, 95G, 95H, 95J, 95K, 95L, 95M, 95N, 95P, 95Q, 7702, 7704, 7706, 7708, and 7710 has a corresponding anterior smell test substance patch disposed on its anterior surface, comparable to the eight anterior smell test substance patches 48A, 48B, 48C, 48D, 48E, 48F, 48G, and 48H, and/or a corresponding posterior smell test substance patch, such as 38A, 38B, 38C, 38D, 38E, 38F, 38G, and 38H, disposed between posterior surface of every cover tab and the anterior surface of the rectangular posterior base 80. In this embodiment, each corresponding anterior smell test substance patch and/or corresponding posterior smell test substance patch can comprise a unique odorous substance associated only with that particular cover tab. As noted earlier, for smell testing devices which target dementia, such as Alzheimer's disease, suitable odorous substances for the smell test substance patches can include peppermint, banana, clove, fish, leather, lemon, lilac, menthol, natural gas, orange, paint thinner, peanut, pineapple, rose, smoke, soap, and strawberry scented substances, as well as other odorous substances which people with dementia have difficulty identifying. This embodiment is suitable for a smell identification test, as discussed earlier. In some embodiments suitable for a smell detection test, similar to some embodiments discussed earlier, half of the anterior smell test substance patches, such as 48A, 48B, 48D, and 48H, and/or half of the posterior smell test substance patches, such as 38A, 38B, 38D, and 38H, can each comprise a common odorous substance, or alternately can each comprise a different, unique odorous substance.

In these embodiments suitable for smell detection test, the other half of the anterior smell test substance patches, such as 48C, 48E, 48F, and 48G, and/or the other half of the posterior smell test substance patches, such as 38C, 38E, 38F, and 38G, can each comprise a common odorless substance. In some other embodiments suitable for an odor detection threshold test, similar to some embodiments discussed earlier, half of the anterior smell test substance patches, such as 48A, 48B, 48D, and 48H, and/or half of the posterior smell test substance patches, such as 38A, 38B, 38D, and 38H, can each comprise a common odorous substance which is disposed with unique concentration in each smell test substance patch, whereby each of these smell test substance patches has a different pungency than the pungency of the smell test substance patches disposed on other cover tabs. In such odor detection threshold test embodiments, the other anterior smell test substance patches and/or other posterior smell test substance patches can comprise a common odorless substance. In the various embodiments disclosed in this paragraph, each anterior cover tab indicium 57A, 57B, 57C, 57D, 57E, 57F, 57G, 57H, 57J, 57K, 57L, 57M, 57N, 57P, 57Q, 7711, 7712, 7714, 7716, and 7718 can comprise a corresponding phrase such as "Scent 1", "Scent 2" "Scent 3", Scent 4" "Scent 5", "Scent 6", "Scent 7", "Scent 8", "Scent 9", "Scent 10", "Scent 11", "Scent 12", "Scent 13", "Scent 14", "Scent 15", "Scent 16", "Scent 17", "Scent 18", "Scent 19", and "Scent 20", although other embodiments can comprise different phrases. It should be noted that the various embodiments disclosed in this paragraph do not comprise any posterior-base color-coded circular smell test indicia, such as 39A, 39B, 39C, 39D, 39E, 39F, 39G, and 39H, nor any other color-coded circular indicia disposed on rectangular posterior base 80. Although twenty cover tabs are referenced in the various embodiments disclosed in this paragraph, other comparable embodiments of such smell identification tests, smell detection tests, and smell threshold tests can comprise fewer or more cover tabs, cover tab indicia, and smell test substance patches.

This Step 8420B can occur independently from when Step 8420A and Step 8422 occur. In some embodiments of the present invention, this smell test can be a different class of smell test, such as a smell identification test, than the testing device in Step 8422, which can be a smell detection test, as an example of such a difference. In another embodiment, the used testing device in Step 8422 can be a smell identification testing device, which was used prior to obtaining a smell memory testing device during Step 8420B, and this smell memory testing device can comprise some scents which are identical to the smell identification test and some scents which are different. During this smell memory test, a person must sniff each scent and respond whether or not he smelled that scent during the previous smell identification test. Alternatively, one of these two steps can be eliminated, along with some of the subsequent steps associated with that step. For example, if Step 8422 is eliminated, then subsequent Step 8424A, Step 8424B, Step 7026, Step 8428, Step 8430, and Step 8431 are no longer applicable. Since some people may prefer entering smell test responses via a user interface associated with a mobile device or a desktop computer, whereas other people may prefer creating an image of the used testing device with a mobile device's camera instead, both options may be provided if the same testing device is compatible with both options. In addition, it should be noted that although this patent describes numerous embodiments of smell testing devices explicitly shown in the figures, the smell testing device referenced in Step 8420B alternately can be any suitable odorous smell testing device not depicted in this patent, such as any smell identification testing device, any smell detection testing device, and any smell threshold testing device.

Step 8420C comprises responding to each smell test substance of the smell testing device. In some embodiments of diagnostic application software, smell test instructions can be displayed on a mobile device screen or an alternative computer screen, although in other embodiments, smell test instructions can be listed on the smell testing device in Step 8420B or on a separate instruction sheet. As mentioned earlier, in some embodiments of the smell testing device, a person first can scratch and sniff a smell test substance patch on an anterior surface of the smell testing device, and in other embodiments of the smell testing device, the person first can peel and sniff a smell test substance patch on the posterior base of the smell testing device. A person then can respond to each smell test substance via any suitable user interface, such as onscreen buttons, onscreen keyboard, touchscreen keyboard, or other keyboard compatible with a mobile device, desktop computer, or other computer, similar to some data entry options disclosed in Step 8420A.

After sniffing and then responding to the first smell test substance, the person can repeat these steps for each of the other smell test substances on the smell testing device. For some embodiments of a smell memory test, each response can be a binary response, such as YES or NO, or other comparable response to a question such as "Did you smell this scent during the earlier smell test?" In an alternate embodiment of a smell memory test, the responses can be selecting names of a scents from a multiple-choice list when presented with a question such as "Which of the following scents do you remember from your most recent smell test?" In such an alternate embodiment, if the most recent smell test is associated with the used testing device in Step 8422, then a second smell testing device is not necessary and Step 8420B can be skipped.

For a smell identification test, a person can respond to a multiple-choice question about each scent in the test by selecting one of the scent names listed in that multiple-choice question, or alternately the person can be asked to enter name of scent using alphanumeric keys onscreen, keypad, or keyboard. This odor identification test can comprise a question and multiple-choice answers for each scent, such as "Scent 1 smells most like: A. banana, B. fish, C. smoke, D. peanut butter", and each choice is specified on a separate onscreen button. For each scent, the person must select one of the multiple-choice onscreen buttons. In one embodiment of the smell identification test, there can be ten different scents, labelled "Scent 1", "Scent 2", "Scent 3", Scent 4", "Scent 5", "Scent 6", "Scent 7", "Scent 8", "Scent 9", and "Scent 10". The selection of such scents can be targeted for a particular disease or family of diseases, and examples of scents suitable for dementia, such as Alzheimer's disease, are referenced in Step 8420B. For a scent detection test or an odor threshold test, each response can be a binary response, such as YES or NO, or other comparable response to a question such as "Do you smell an odor?"

Step 8420D comprises scoring the number of smell test substances correctly identified and incorrectly identified. This step can be executed using application software based on inputs (user responses) from Step 8420C. This can use a simple test scoring algorithm or decision flowchart for determining whether each smell test response is correct and counting the number of correct responses. As noted previously, each smell identification test response comprises the name of a scent, which is either correct or incorrect. In the smell detection test, each response can be either the smell test substance has an odor or the substance does not have an odor, which is either correct or incorrect. In some embodiments of the smell memory test, each response can be either the smell test substance has same scent as one of the scents in the earlier smell test or the substance has a different scent than any substance in the previous smell test, and scoring comprises counting the number of correct responses. In an alternate embodiment of the smell memory test, the responses can be selecting names of scents from a list of scents, and scoring comprises counting the number of scent names which correctly correspond to scents from previous smell memory test.

In the odor threshold test, scoring comprises determining the quantity of correctly identified substances with an odor, and in some embodiments, scoring can also comprise determining the quantity of odorless substances correctly identified. With the exception of the smell identification test, the other types of smell tests can request a binary choice for each response to a scent, as noted earlier. In some embodiments of this step, the raw score (such as the number of correct responses) subsequently can be converted to an ordinal score with two categories, which can signify smell test pass/fail criteria. In one such embodiment, if the person has correctly identified at least 8 out of 10 smells correctly, this would be classified as PASS, and fewer than 8 correctly identified smells would be classified as FAIL. In some other embodiments of this step, the raw score can be converted into 3 categories. In one such embodiment, category A represents raw score between 0-4 correct, category B represents raw score between 5-7 correct, and category C represents raw score between 8-10 correct, whereby the raw test score is converted into an ordinal variable. In other embodiments of this step, the raw smell test score is not converted during this step.

Step 8420E comprises entering into memory the test score of a person who used smell testing device. In some embodiments this step can further comprise entering into this memory the date of this test together with this test score. This can be the digital memory where the target personal data in Step 8420A is stored, and this test score can be associated in this digital memory with other target personal data of person who used this smell testing device. This smell test score and the date of the smell test can be added into the diagnostic database within this digital memory. Step 8420E can occur at a different time than Step 8420A. Note that if Step 8420D occurs prior to Step 8420A, for a given person, then Step 8420E can occur prior to Step 8420A, with respect to that person, whereby a person can complete the smell test in Step 8420C prior to entry of his target personal data.

Step 8421 comprises accessing digital memory to retrieve relevant target personal data associated with the smell testing device in Step 8420C. This data can include the test score number from the smell test determined in Step 8420D. This step can include accessing data in the diagnostic database and accessing data within EMR databases, such as the first EMR database and the second EMR database stored within the digital memory, which are referenced in the detailed description of Step 8420A. This data includes available relevant target personal data for the person who used the smell testing device in Step 8420C. This digital memory can comprise memory inside a mobile device or memory external to a mobile device. Embodiments which store target personal data for a single person or for limited number of people can be memory inside the mobile device, such as RANI (random access memory), an added memory card, and other storage. Embodiments which store target personal data for many people can be memory external to the mobile device. This step can comprise accessing relevant target personal data in memory within the mobile device via diagnostic application software, or alternatively this can be accessing such data from memory in a desktop computer or a remote database via wireless internet access, a wireless network, or other means known in the industry. The remote database can be stored in a server, such as a database server or cloud storage system, which are mass storage devices. Such access potentially can occur at any time after Step 8420A and Step 8420E, including prior to Step 8422, although one logical option is to access the relevant target personal data after completing Step 8428 (Determine disposition of indicia), as shown in FIG. 84*a* and FIG. 84*b*.

In some embodiments, the diagnostic application software can automatically access the relevant target personal data when a person activates the diagnostic application software, anytime after Step 8420A and Step 8420E have been completed. Another option is to access the relevant target personal data after completing Step 8431.

Step 8422 comprises obtaining a used testing device for analysis. This used testing device has exposed indicia, and at least some of these exposed indicia corresponds to a smell test. In some embodiments of this testing device, other exposed indicia can correspond to target personal data, such as some demographics information, some symptoms information, some gene information, some biomarkers information, smell impairment awareness information, and/or other information as discussed previously. Some such indicia can correspond to information referenced in detailed description of Step 8420A, such as the presence of biomarkers which are either positively or negatively correlated with the target disease or family of diseases. In some embodiments of the testing device, all exposed indicia correspond to a smell test. In some embodiments, the smell test assesses smell identification capability, as described earlier. For smell testing devices which target dementia, such as Alzheimer's disease, suitable odorous substances for the smell test substance patches can include peppermint, banana, clove, fish, leather, lemon, lilac, menthol, natural gas, orange, paint thinner, peanut, pineapple, rose, smoke, soap, and strawberry scented substances, as well as other odorous substances which people with dementia have difficulty identifying.

In other embodiments, the smell test assesses smell detection capability, which can check for partial or complete anosmia as also described earlier. In yet other embodiments, the smell test assesses threshold level for detecting at least two different odors, as described earlier. The testing device can be any embodiment explicitly described and depicted in this patent, such as embodiment shown in FIG. 77-FIG. 83, as well as other embodiments not explicitly depicted in this patent which include a smell test and exposed indicia corresponding to this smell test.

Step 8423 comprises accessing relevant medical records data for people who have used the testing device in Step 8422 and/or in Step 8420C. Step 8423 can comprise accessing population EMR (electronic medical records) data for these people from at least one population EMR database within at least one mass storage device. In one embodiment, this step can comprise accessing a first population EMR database within a third mass storage device and accessing a second population EMR database within a fourth mass storage device. At least a portion of this data can be subsequently used during Step 8425C. This step can be executed, at least in part, by application software, either automatically or on-demand. Such data can be retrieved from a medical records database stored in memory, such as a database on a remote database server, memory in at least one desktop computer, or memory in multiple mobile devices. Relevant medical records can comprise medical data which is positively or negatively correlated with a target disease, such as Alzheimer's Disease, or family of similar diseases, such as dementia. This data can comprise same type of data as accessed in Step 8421, although the data can be updated subsequent to the original use of the testing device. This relevant medical records data can include new medical test data, new genetic data such as genetic test results for target gene alleles, variants, or mutations which are positively or negatively correlated with the presence of the target disease or family of diseases, and new diagnosis of diseases, including the target disease. This data can also include the date of target disease diagnosis, if such a diagnosis has been made by a physician.

In some embodiments, this medical records data can comprise personal genetic data in a database stored in a database server by 23andMe or similar companies. Such target data can be accessed on a fixed schedule, such as annually, or such target data can be accessed whenever new target data for each person who used the testing device is available or based on other criteria for accessing this target data. In some embodiments, the application software which executes, at least in part, this step can offer multiple options, selected by a user, for automatically accessing this data monthly, quarterly, annually, or whenever new data is available, and this application software can offer on-demand access to data upon request by a user. One option can be periodically sending users' medical records, with users' advanced permission, to a centralized medical database in a remote database server, such as the NHS patients medical records database, where the medical records for 56 million British people are stored currently. Alternately this database server can be at a medical organization, at a company which manufactures, distributes, or sells the testing device, at a company which collects genetic data such as 23andMe, or at any other organization or business. During Step 8423, relevant medical records data in this database can be accessed periodically.

Step 8424A comprises capturing an image of indicia presented on a used testing device with a mobile device. This can be a smart phone, tablet, notebook computer, any other mobile device with a camera. In some embodiments of the testing device, all the exposed indicia presented can be captured in a single image with the camera in the mobile device. In some other embodiments of the testing device, it may be necessary or desirable to capture the exposed indicia with multiple images, particularly if the testing device comprises a set of cover plus base assemblies as described earlier.

Step 8424B comprises recording temporal data regarding capturing this image. This temporal data can comprise the date when the image is captured with the mobile device. In some embodiments this temporal data can additionally comprise the time when the image is captured. Step 8424B can occur substantially at the same time as Step 8424A, although alternatively Step 8424B can occur after Step 8424A.

Step 8425A comprises determining appropriate biomarkers associated with the targeted illness. These biomarkers can include any or all of the known biomarkers specified earlier which are positively and/or negatively correlated with the targeted illness, such as ApoE-4 allele and ApoE-2 allele respectively associated with Alzheimer's disease. These biomarkers can be blood biomarkers, cerebral spinal fluid biomarkers, gene biomarkers, brain imaging biomarkers (such as visible evidence of amyloid Beta plaques and neurofibrillary tangles commonly associated with Alzheimer's disease), and other biomarkers, such as high resting heart rate>80 BPM (which is associated with Alzheimer's disease and some other diseases), abnormal blood pressure levels (which are associated with higher risk for heart disease, stroke, and Alzheimer's disease) or other symptoms of the targeted illness. Although numerous biomarkers referenced in this patent are disclosed, numerous other biomarkers are known for the diseases mentioned in this patent. Many such biomarkers are discussed in medical research journal articles. This step can include using an internet search engine to find appropriate biomarkers which are positively or negatively correlated to the target disease or family of diseases. By entering keyword phrases such as "Alzheimer's disease" and "biomarkers" into a search engine website such as www.google.com, PubMed (https://pubmed.ncbi.nim.nih.gov), PubMed Central (https://ncbi.nim.nih.gov), or any other suitable search engine, appropriate known biomarkers can be located in online research journals and in other sources accessible via the internet. This search can be executed automatically using application software at set intervals, if desired, or it can be executed, at least in part, by application software on-demand, when needed for initial development or subsequent refinement of at least one classification model during Step 8425C.

In some embodiments, the application software which executes this step can offer multiple options, selected by a user if desired, for automatically searching for applicable biomarkers weekly, monthly, quarterly, or annually, and this application software can offer on-demand search for applicable biomarkers upon request by a user. In addition, the application software can allow manual entry of known biomarkers via user interface of a mobile device or other computing device, such as a keyboard, keypad, or alternately onscreen buttons which allow selection of multiple known biomarkers, such as those referenced in this patent. If the target disease is Alzheimer's disease, there can be onscreen buttons for common known genotypes which impact the probability of developing late-on Alzheimer's, such as ApoE4/4, ApoE4/3, ApoE3/4, ApoE3/3, ApoE3/2, ApoE2/3. ApoE2/2, 0 copies of Klotho-VS haplotype, 1 copy of Klotho-VS haplotype, and 2 copies of Klotho-VS haplotype, as well as onscreen buttons for rare mutations of the genes APP, PSEN1, and PSEN2, which are strongly correlated with the development of early-onset Alzheimer's. In addition, methodologies have been developed to identify new biomarkers for diseases.

Step 8425B comprises selecting at least one relevant classification model for diagnosing or predicting likelihood of the targeted illness. Medical research journal articles reference some such classification models which have been developed to diagnose or to predict the likelihood of the targeted illness within a specified time-period, which can be during the time the diagnostic test was used or within a longer time-period, such as within 1 year, or 2 years, or X years from the time the diagnostic test was used. One such classification model for diagnosing COVID-19 likelihood is disclosed earlier in this patent. This step can include using an internet search engine to find known classification models which can diagnose or estimate probability or likelihood of a target disease or family of diseases referenced in online medical research journals and other publications. By entering keyword phrases for a target disease, such as "Alzheimer's disease", and "classification model", or a similar phrase, into a search engine website such as www.google.com, PubMed (https://pubmed.ncbi.nim.nih.gov), PubMed Central (https://ncbi.nim.nih.gov), or any other suitable search engine, appropriate known classification models can be located in online research journals and in other sources accessible via the internet. This search can be executed automatically using application software at set intervals, or it can be executed by application software on-demand, when needed. In some embodiments, the application software which executes, at least in part, this step can offer multiple options, selected by a user if desired, for automatically searching for applicable classification models weekly, monthly, quarterly, or annually, and this application software can offer on-demand search for applicable classification models upon request by a user. In addition, the application software can allow manual entry of known classification models via user interface of a mobile device or other computing device, such as a keyboard, keypad, or alternately onscreen buttons which allow selection of at least one classification model, such as one classification model referenced in this patent. Because there are multiple classification models for diagnosing or predicting the probability of some diseases, based on various biomarkers, symptoms, and demographics information, at least one classification model can be selected during this step, for further refinement during subsequent Step 8425C. It should be noted that for some diseases, there may not be an existing classification model which can be found that is appropriate or convenient. In some embodiments, this step can comprise selecting the most appropriate type of classification model for the target disease, such as logistic regression or random forest or Naïve Bayes or stochastic gradient descent or K-nearest neighbors or decision tree or support vector machine. The selection of classification method depends in part on whether the independent variables' characteristics are compatible with recommended guidelines for that method, such as whether the numeric variables should have a normal distribution, as well as dependent variable characteristics, such as whether dependent variable is a simple positive or negative diagnosis of a particular disease, or more than two classes (e.g., Alzheimer's disease, Mild Cognitive Impairment, or cognitively normal) for multi-class classification. As an example, Naïve Bayes performs well with a dependent variable comprising more than two classes. Multinomial logistic regression is also suitable for classifying more than two classes, and the numeric independent variables do not require normal distribution nor must they be continuous, making this multi-class classification model particularly suitable when an olfactory identification test score is a numeric independent variable.

Step 8425C can comprise comparing available relevant personal medical record data with result of each corresponding used testing device(s), as well as appropriate biomarkers, using machine learning methodology to refine at least one classification model for diagnosing or predicting likelihood of targeted disease or family of diseases within a specified time period, based on score(s) of smell test(s) and other relevant target personal data, and creating latest method for determining result based at least in part on the classification model(s). Initially this step can utilize machine learning methodology to develop at least one classification model to diagnose or predict the likelihood of disease within at least one time period. One such time-period can be the moment the testing device was used by a person. Alternately such a time-period can be within 1 year or within 2 years or within X years from when the testing device was used by a person. This step can include adding at least one other biomarker independent variable selected during Step 8425A into an existing classification model selected during Step 8425B, in order to increase the sensitivity and/or specificity of the classification model or to increase the accuracy of the model's estimated probability that person has target disease now or will develop target disease within a specified time period.

As one example applicable for diagnosing or predicting Alzheimer's disease, an existing classification model which simply includes the presence of 0, 1, or 2 copies of ApoE-4 gene allele, the person's age and gender can be further refined by also including the score of an olfactory identification test, the person's education level (either in total years of education, or highest educational degree achieved, such as high school diploma, associate's degree, bachelor's degree, master's degree, PhD, et cetera), the person's smoking status, the person's specific ApoE genotype (ApoE4/4 or ApoE4/3 or ApoE3/4 or ApoE3/3 or ApoE3/2 or ApoE2/3 or ApoE2/2), the presence or absence of particular mutations of APP gene, PSEN1 gene, and PSEN2 gene which cause early-onset Alzheimer's, and the presence of 0, 1, or 2 copies of the Klotho-VS haplotype, which are additional biomarkers and demographics information that can increase the sensitivity and specificity of the classification model.

Because genetic testing can be performed using a saliva sample collected at home, and the olfactory identification test can be taken at home as well, this limited set of biomarkers for Alzheimer's is suitable for a very convenient and less expensive diagnostic test. It should be noted that if there are no known diagnostic classification models which are suitable or convenient for the target disease, machine learning can be used to create a new classification model which incorporates appropriate biomarkers and demographic independent variables. Machine learning has been used for medical applications, based on a variety of methodologies to analyze data and develop and/or refine classification models for diagnosing or predicting diseases. Machine learning methodology comprises various techniques known in the industry, including machine learning problems (supervised learning, unsupervised learning, reinforcement learning), hybrid learning problems (semi-supervised learning, self-supervised learning, multi-instance learning), statistical inference (inductive learning, deductive inference, transductive learning), and learning techniques (multi-task learning, active learning, online learning, transfer learning, ensemble learning). The selection of machine learning technique depends on a variety of factors, including the input data available, the output desired, and the appropriate level of human supervision. A variety of known machine learning software tools, such as the Weka Machine Learning Workbench, can be used to develop or refine classification models for diagnosing or predicting a target disease or family of diseases during this step. Weka includes a variety of machine learning algorithms and does not require manual programing to implement machine learning, so it is more user friendly for people with a medical background, although people in the medical field have used numerous other machine learning tools as well. In addition, Weka allows pre-processing of data by simply loading a data file and then applying filters to data as appropriate, which is necessary prior to applying machine learning algorithms. Supervised machine learning is sometimes used for developing or refining a classification model for medical applications. In supervised machine learning, performance of a diagnostic classification model is supervised through evaluation against existing medical diagnoses by physicians.

Besides optimizing the accuracy of the diagnostic model, another goal of supervised machine learning can be to include biomarker independent variables in the model which are less expensive to test and/or require less time to test, such as an olfactory identification test score, rather than much more expensive, time-consuming tests such as medical imaging. There are two principal forms of supervised machine learning—classification and regression. Classification can be used for diagnosing whether or not a person has a particular disease, which is a binary classification, as one example. Logistic regression is one form of classification which can be used to determine the probability that a person has or will develop a disease within a particular time period, such as at the time of the diagnostic test or within X months or years after taking this test. Random forest is another supervised learning algorithm which can be used for medical diagnostic classification and is particularly useful for analyzing large datasets. Other supervised learning algorithms for classification are Naïve Bayes, stochastic gradient descent, K-nearest neighbors, decision tree, and support vector machine. The selection of classification method depends in part on whether the independent variables' characteristics are compatible with recommended guidelines for that method, as well as dependent variable characteristics, such as whether dependent variable is binary class (e.g., positive or negative diagnosis of a particular disease) or more than two classes (e.g., Alzheimer's disease, Mild Cognitive Impairment, or cognitively normal). As an example, Naïve Bayes algorithm performs well with a dependent variable comprising more than two classes. During the machine learning process, initially a set of training data, which can be a subset of the first set of data from Step 8425D and Step 8423, can be used to train a classification model. Subsequently during machine learning, the classification model is evaluated using validation data, which can be a subset of the second set of data from Step 8425D and Step 8423. Next during machine learning, the model is refined based on classification results from this validation data, which can include changes in independent variables, changes in type of classification model, or other changes as appropriate. This can be followed by repeating these machine learning phases sequentially at least once, using new subsets of training data and validation data each time from the first set of data and the second set of data respectively. Then the model which performs best at accurate target disease classification based on this validation step is selected, and finally the classification results are confirmed during final testing using test data, which can be the third set of data from Step 8425D and Step 8423. These machine learning steps can be executed at least in part using WEKA or other suitable machine learning tools.

After initial development of at least one suitable classification model, machine learning subsequently can be used over time to further refine the classification model for improved diagnostic accuracy and/or to change the biomarker or demographic independent variables included in the classification model. The classification models can include nominal data, such as gender, numerical data, such as age or the number of correctly identified scents in an olfactory identification test, or often both types of data for diagnosing or predicting a disease or family of diseases. One specific example of a logistic regression classification model, which is referenced earlier in this patent, estimates the probability that a person has COVID-19 based on age, gender, and several symptom biomarkers, including an olfactory test score. The format of this formula is similar to other logistic regression formulas with multiple independent variables. These independent variables in the classification model should not be strongly correlated with each other when used for logistic regression, which can be one criterion for selecting appropriate independent variables. Factors which are positively correlated with developing the target disease and the factors which are negatively correlated with developing the target disease can be included in the classification model for diagnosing or predicting the development of the target disease, such as Alzheimer's disease or COVID-19. Symptoms information, such as score of the smell test (number of correct and/or incorrect responses to the test), ignorance or awareness of existing olfactory impairment, and other symptoms of the target disease or family of diseases, can be included as independent variables in the classification model or models.

Since the inability to correctly identify certain scents is positively correlated to the probability of developing some diseases such as dementia, the score of correctly identified scents in a smell identification test can be one of the key independent variables in at least one classification model used to determine the probability or likelihood of developing such diseases. The number of correctly identified scents is inversely correlated to the probability of developing diseases such as dementia, and the inverse is also true. Similarly, since people who are unaware of existing smell identification impairment are significantly more likely to develop Alzheimer's disease, ignorance of existing olfactory identification impairment can be another important independent variable in at least one classification model for predicting probability or likelihood of Alzheimer's disease. In addition, demographics information, such as gender, age or age range or date of birth, race, ethnicity, level of education, smoking status, and other relevant demographics data can be included in the classification model or models.

In a further refinement of classification models for diagnosing or predicting the development of diseases which are associated with certain gene alleles, variants, or mutations, such as Alzheimer's disease, the presence or absence of such gene alleles, variants, or mutations can be incorporated as biomarkers into the classification model for predicting the target disease likelihood. Some known gene alleles, variants, and mutations which are either positively correlated with or negatively correlated with development of Alzheimer's disease are disclosed earlier in this patent. Such gene information can further increase the accuracy of classification models for predicting Alzheimer's disease. Test results for any biomarkers which are either positively correlated with or are negatively correlated with the target disease or family of diseases, such as biomarkers disclosed earlier in this patent, can be included as targeted independent variables in the classification model or models for predicting probability of the target disease or family of diseases.

In one example, the demographics information and biomarkers referenced earlier for an Alzheimer's disease classification model (age, gender, education level, smoking status, olfactory identification test score, ApoE genotype, the presence of only one Klotho-VS haplotype, and the presence of particular mutations of the APP gene, PSEN1 gene, and the PSEN2 gene which cause early-onset Alzheimer's) can be selected as the applicable biomarkers and demographics independent variables for analysis of a set of data, including Alzheimer's diagnoses by physicians, with a machine learning tool such as WEKA, and classification using a suitable technique such as logistic regression can be selected to create a suitable classification model using this learning tool. It should be noted that there is an interaction between the presence of ApoE-4 allele(s) and the presence of one copy of the Klotho-VS haplotype, and this variable interaction should be incorporated into this Alzheimer's classification model example, since the presence of exactly one copy of this haplotype can reduce the probability of Alzheimer's by ~35% if and only if there is at least one copy of ApoE-4 allele. One advantage of this classification model example is that none of the independent variables require any invasive biomarker tests, such as blood tests or cerebrospinal fluid tests. As noted earlier, Step 8425C can include creation of more than one classification model that is incorporated into the diagnostic application software. Another classification model can include an olfactory test score independent variable, demographic independent variables, and biomarker independent variables which require blood tests or cerebrospinal fluid tests. By including appropriate blood or cerebrospinal fluid biomarkers, this additional classification model can confirm an earlier diagnostic result of a classification model which only relies on noninvasive tests, or it can be used instead of such a classification model, if desired, since it may have better sensitivity and specificity with respect to the target disease. SPSS Statistics is another popular tool which can perform logistic regression if the data meets certain guidelines. It should be noted that some independent variables such as education level or olfactory identification test score can be ordinal variables, if desired, such as the olfactory test score (category A, category B, category C) example or the olfactory test PASS/FAIL score example in the detailed description of Step 8420D. Some embodiments of the classification models can include an ordinal dependent variable with 3 classes, such as Disease Likely Now, Disease Likely Within 5 Years, and Disease Unlikely. The One-vs-Rest method can be used for 3-class classification in logistic regression, as one example. In order to determine whether the target disease is likely within a specified time period, during machine learning the classification algorithm can include the duration between date of the result, when Step 8432 is completed, and the date of target disease diagnosis, by a physician, of the person associated with that result. This duration is simply calculated by subtracting the date of result from the date of diagnosis, then converting this duration from days into a more suitable unit of time, which can be years for neurodegenerative diseases such as Alzheimer's. In some embodiments of the classification model, if the target disease is diagnosed shortly after date of this result, which can be within a few months for neurodegenerative diseases, the classification model can classify the result as Disease Likely Now during the initial machine learning phase, as one example. A typical minimum sample size required for creating a logistic regression model is $S=(10\times N)/P$, where S is minimum sample size, N is number of independent variables in the regression model, and P is the probability of least frequent outcome among the independent variables, where $1>P>0$. In this Alzheimer's model example, the least frequent outcome is a particular mutation of the PSEN2 gene which causes early-onset Alzheimer's disease. In disease diagnostic classification when the test result is negative significantly more often than when the test result is positive, it may be advantageous to use undersampling of the majority class (negative test result) in one embodiment or oversampling of the minority class (positive test result) in an alternate embodiment during machine learning, in order to increase the likelihood of correctly classifying positive test results. WEKA and some other machine learning software allow such undersampling and oversampling options. In addition, WEKA offers a cost sensitive classifier option which can reweight the training data as appropriate based on imbalance between proportion of negative test results versus proportion of positive test results. WEKA also offers a class balancer filter which can be used to yield a training dataset where the positive test result class and the negative test result class are approximately balanced. SMOTE is an advanced filter available in WEKA and other machine learning software which can significantly enhance the likelihood of correctly classifying positive diagnostic results despite an initial imbalance in a training dataset. Additional information regarding such techniques is available online in WEKA Blog, as well as numerous other online sources known in the machine learning field.

In some Alzheimer's classification models, one independent variable can be the presence of at least one particular mutation of any known gene (APP gene, PSEN1 gene, and PSEN2 gene) which causes early-onset Alzheimer's disease. This would reduce the number of independent variables in the classification model by 2, thereby potentially reducing the minimum sample size required for logistic regression.

Once the classification model or models have been developed or refined, the latest method for determining result is created. The classification model or models can be translated into a lookup table, or a decision flowchart, or any form suitable for diagnostic application software, which can include at least one classification model (such as a logistic regression model) used to determine result. Step 8425C can result in new or updated diagnostic application software which determines result by evaluating individual components of digital indicia data and available relevant target personal data, including applicable test results such as olfactory identification test score. This diagnostic application software can execute, at least in part, at least one of Step 8420A, Step 8420C, Step 8420D, Step 8420E, Step 8421, Step 8424A, Step 8424B, Step 7026, Step 8428, Step 8429, Step 8430, Step 8431, Step 8432, Step 8433, Step 8434, Step 8435, Step 8436, Step 8437, Step 8438, Step 8440, Step 8442, and Step 8444 in some embodiments. In some embodiments, this diagnostic application software can additionally execute, at least in part, at least one of Step 8446, Step 8448, Step 8450, Step 8452, Step 8454, Step 8456, Step 8458, Step 8460, Step 8462, and Step 8464. In other embodiments, other application software instead can execute, at least in part, at least one of these steps within a different computing system.

Step 8425D comprises accessing data from the database referenced in Step 8436. This step can include accessing data from a tested population database within a first mass storage device. At least a portion of this data is subsequently used during Step 8425C. It should be noted that the various mass storage devices referenced in this patent typically store relevant data for hundreds to potentially thousands of people. This can exceed the internal digital memory storage capacity of a typical mobile device, so some or all of the mass storage devices can be external to the mobile device where digital memory can be. This step can be executed at least in part by application software in some embodiments. This data can comprise at least some of the data stored during Step 8436 associated with every result selected, including the result, the date of result, and corresponding relevant target personal data for each person. In some embodiments of Step 8425D, this step can occur substantially concurrent with Step 8423. Subsequently this data and data from Step 8423 can be included in the training dataset, validation dataset, and test dataset used during machine learning in Step 8425C. Before the categorization model has been created that is used to determine the result, in one embodiment this step can comprise accessing a first set of data from the database that that is associated with a first subset of the people who used the smell testing device during Step 8420C, including the test score from Step 8420D and corresponding relevant target personal data of each person in this first subset, accessing a second set of data from the database that that is associated with a second subset of the people who used the smell testing device during Step 8420C, including the test score from Step 8420D and corresponding relevant target personal data of each person in this second subset, and accessing a third set of data from the database that that is associated with a third subset of the people who used the smell testing device during Step 8420C, including the test score from Step 8420D and corresponding relevant target personal data of each person in this third subset. Before this categorization model has been created, in another embodiment this step can comprise accessing a first set of data from the database that that is associated with a first subset of the people who used the testing device referenced in Step 8422, including the quantity of correct responses to scents from Step 8430 and corresponding relevant target personal data of each person in this first subset, accessing a second set of data from the database that is associated with a second subset of the people who used the testing device referenced in Step 8422, including the quantity of correct responses to scents from Step 8430 and corresponding relevant target personal data of each person in this second subset, and accessing a third set of data from the database that is associated with a third subset of the people who used the testing device referenced in Step 8422, including the quantity of correct responses to scents from Step 8430 and corresponding relevant target personal data of each person in this third subset. In some embodiments, an application software program can execute, at least in part, Step 8425A, Step 8425B, Step 8425C, and Step 8425D.

Step 7026 comprises orienting the image. This may not be necessary if the relevant exposed indicia are all circular, if the relevant exposed indicia are all color-coded, or if the relevant exposed indicia presented can be decoded without orienting the image.

Step 8427 comprises transmitting the latest method for determining result to at least one mobile device or desktop computer. This step can be executed at least in part by application software in some embodiments. This step can comprise first submitting diagnostic application software from Step 8425C to an online distributor of application software, such as iOS App Store or Google Play Store, or providing an online link on alternate website with this diagnostic application software that allows subsequent transmission of this diagnostic application software from this website to a mobile device (a technique known as sideloading), followed by initiating transmission of this diagnostic application software from the online distributor or the alternate website to at least one mobile device or desktop computer. Transmission can occur via a Wi-Fi network, via a cellular data network, via other cell phone network technology, via a combination of these technologies, or via any other transmission means known in the industry. A business which manufactures or distributes or markets the testing device or which developed this diagnostic application software can offer this online link on a website as an alternative to a distributor of application software. Transfer of this diagnostic application software can occur when mobile device settings allow for automatic application software updates or when a person manually initiates loading latest diagnostic application software onto mobile device per instructions. Mobile apps are normally accessible through the mobile device or a website so that apps can be queued up for download the next time the user is on the device. Although several methods are described for sending new or updated diagnostic application software to at least one mobile device or desktop computer, alternative methods known in the industry can be used instead for this purpose.

Step 8428 determines the disposition of indicia. In some embodiments, this comprises using circle detection and color filter algorithm(s) to identify color-coded circular indicia on the used testing device from a digital image created during step 8424A. In other embodiments this can be determined by alternative means, such as identifying the shape of each indicium, which can be a polygon or an alphanumeric character or a symbol or any other shape, or the position of each indicium. In some embodiments of the testing device, it may not be possible or convenient to capture all the indicia in a single image, so it may be necessary to repeat steps 8424A, 8424B, 7026, 8428, 8430, and 8431 at least one time, as illustrated by line connecting Step 8431 with Step 8424A in FIG. 84*a* and FIG. 84*b*. As described earlier, some embodiments of the testing device can comprise a set of two or more cover+base assemblies. In some such embodiments, the testing device can comprise a set of two or more of the cover+base assembly shown in FIG. 77. This allows a greater quantity of smell test substance patches with corresponding cover tabs and color-coded circular smell test indicia, and/or a greater quantity of color-coded circular non-olfactory warning-sign indicia with corresponding cover tabs, and/or a greater quantity of color-coded circular demographics indicia with corresponding cover tabs, and/or a greater quantity of color-coded circular gene-variant indicia with corresponding cover tabs, and/or a greater quantity of color-coded circular blood-biomarker indicia or color-coded cerebral spinal fluid biomarker indicia with corresponding cover tabs. In such embodiments, it may be more convenient to capture each cover+base assembly in a separate image. As described earlier, the diagnostic application software can include a diameter filter algorithm in addition to the circle detection and color filter algorithm(s) to recognize in a digital image the unique assembly ID indicium of each rectangular opaque anterior cover 95 plus rectangular posterior base 80 assembly in embodiments with more than one such assembly. In embodiments with multiple rectangular opaque anterior cover 95 plus rectangular posterior base 80 assemblies, each assembly ID indicium 102A, 102B, 102C, 102D, et cetera can be a different color.

Step 8429 comprises enabling the latest method for determining result in mobile device or desktop computer. This can be enabling the latest diagnostic application software in the mobile device or desktop computer, as well as disabling or removing earlier diagnostic application software if necessary.

Step 8430 comprises digitizing indicia data. This step can comprise using a counting algorithm to determine the quantity of each category of indicia. In some embodiments, this can comprise counting the quantity of circular indicia of each color and diameter combination.

Step 8431 is a decision step: Have all the relevant indicia presented on used testing device been digitized? This step determines whether all the relevant indicia presented on the used testing device have been digitized, based on the expected quantity of each category of indicia and based on the expected quantity of different assembly ID indicia associated with the used testing device. If not, then display a statement on mobile device screen that an additional image of the used testing device must be captured, repeating Step 8424A, Step 8424B, Step 7026, Step 8428, Step 8430, and Step 8431. In some embodiments of the testing device, this can comprise capturing one image of all indicia presented per cover+base assembly.

Step 8432 can comprise determining result by evaluating individual components of digital indicia data, if available, and available relevant target personal data. This step analyzes digitized indicia data associated with the used testing device, if available from Step 8430, and relevant target personal data from Step 8421, if available, to determine the result. This data can be analyzed via a lookup table, a decision flowchart, at least one classification model, a combination of these methods, or other methodology known in the medical research field. This step can be executed by diagnostic application software, as noted in detailed description of Step 8425C.

In some embodiments of the diagnostic application software, once applicable new biomarker data, such as target gene test results included in a diagnostic classification model, is available in this app, the diagnostic application software can use push notification to provide a message, such as a text message or a message displayed on mobile device screen, stating that the test results are available and can be viewed when the application software is activated. The final result, once the applicable biomarker tests and smell test(s) have been completed, can comprise a binary diagnosis, such as target disease test is positive or negative. Alternatively, this result can comprise a determination that the target disease or family of diseases is likely or unlikely. In some embodiments, this result can comprise estimated probability that the person has the target disease or family of diseases now. In other embodiments, the result can comprise estimated probability that the person will develop the target disease or family of diseases within a specified time-period, such as within 5 years. Alternatively, the result can comprise a determination that the target disease or family of diseases is likely or unlikely within a specified time-period, such as 5 years. In some embodiments, when the estimated probability of the target disease or family of diseases is less than 50%, the result can categorize this probability as unlikely, and similarly when the estimated probability of the target disease or family of diseases is more than 50%, the result can categorize this probability as likely.

The result can include additional information, such as recommendation that the test is repeated every 5 years and a recommendation that person should contact an appropriate physician with specialized knowledge of the target disease regarding a positive test result or a test result which indicates that target disease or family of diseases is likely within a specified time-period. As an example, if the target disease is Alzheimer's, the recommendation can be that person should contact a board-certified neurologist or psychiatrist who typically treats Alzheimer's patients. In addition, the result can comprise information regarding the limitations of the test, such as the test result is dependent on the information available, and the accuracy of the test result can be increased with additional information such as additional biomarker data. The result can also include a disclaimer statement, composed by an attorney, that the result is not a substitute for final diagnosis confirmation by a physician.

Step 8433 is a decision step: Are there any non-olfactory biomarker test results missing? This decision is based on any non-olfactory biomarker test results which are included in at least one classification model used to predict likelihood of target disease or family of diseases, as mentioned in detailed description of Step 8425C. As an example, if the target disease is Alzheimer's disease, one of the non-olfactory biomarkers can be level of P-tau217, as mentioned earlier. If the person who used the testing device was not tested yet for level of P-tau217 in his blood, then this non-olfactory biomarker test result is missing. If the answer to this decision step question "Are there any non-olfactory biomarker test results missing?" is YES, then proceed to Step 8437. If the answer to this decision step question is NO, then proceed to Step 8435.

Step 8434 comprises displaying result. The result can be displayed on a mobile device screen, computer screen, computer printout, or other commonly used methods for displaying information.

Step 8435 is END. This occurs if the answer to decision Step 8433 question is NO.

Step 8436 comprises adding a set of data and result into a database. This set of data can include the date of Step 8420E when smell test score is entered into memory, together with the date of Step 8424B when the used testing device image was captured and the date when Step 8432 was completed, which all can be associated in the database with other data for the person who used both testing devices. In some embodiments, Step 8436 can store this set of data, including the result, in the diagnostic database, within the digital memory. This enables the diagnostic application software to execute, at least in part, one or more of Step 8436, Step 8446, Step 8448, Step 8450, Step 8452, Step 8454, Step 8456, Step 8458, Step 8460, Step 8462, and Step 8464. Execution by this diagnostic application software of one or more of these subsequent steps can occur on-demand by user any time after Step 8436. In some embodiments, this diagnostic application software can execute one of more of these steps automatically, such as after completion of Step 8432. Some embodiments of this diagnostic application software can execute, at least in part, one or more of these steps periodically, which can be at a time interval selected by person who used the testing device(s), such as monthly, quarterly, or annually. In some embodiments, Step 8436 can store this set of data, including the result, in the tested population database, within the first mass storage device. This tested population database can be at a medical facility, disease tracking organization, a transportation hub, school, a business which manufactures or distributes or markets the testing device, or a business which is screening people for a disease, et cetera. This step can be used to add test result into personal medical record of the person who used the testing device. This step can include some or all of the target personal data from Step 8421 that is associated with the used testing device. In some embodiments, the result can be added into database stored in digital memory within the mobile device or in a desktop computer, which can be instead of or in addition to a remote database elsewhere.

Step 8437 comprises displaying comment regarding any missing non-olfactory biomarker test results. This can be a comment specifying which non-olfactory biomarker test results are missing, such as "P-tau217 test result is missing". In addition, this comment can include statement regarding improving the accuracy of target disease test result, such as "The Alzheimer's test result will be more accurate if you also get tested for P-tau217." This comment can be displayed on screen of the mobile device and/or on the screen of a desktop computer and/or in a printout. If the person subsequently gets tested for any missing biomarker or biomarkers, then Step 8420A, Step 8421, Step 8432, and Step 8434 can be repeated, either automatically once new biomarker test data is available or on-demand, which can provide a more accurate result.

Step 8438 comprises analyzing data, results associated with at least one set of used testing devices to derive at least one target dependent variable for a target population. This step is useful for analyzing data and summarizing results from multiple people, particularly larger populations, which sometimes requires more memory storage capacity than the memory storage available in a mobile device. This is appropriate for determining such statistics as disease positivity rate in a target population, a change in disease positivity rate over time, the correlation between target disease incidence and age of disease onset, the correlation between target disease incidence and years of education completed, the correlation between target disease incidence and gender, the correlation between target disease incidence and ethnicity, the specificity and sensitivity of the present diagnostic test with respect to diagnoses of target disease by a physician, or other statistics of interest to disease tracking organizations, medical centers, universities, businesses, et cetera.

Step 8440 comprises transmitting at least one derived target dependent variable to at least one mobile device or desktop computer. Transmission can occur via a Wi-Fi network, via a cellular data network, via other cell phone network technology, or via any other transmission means known in the industry. Transmission can occur whenever there is new derived target dependent variables data or at set periodical intervals, such as daily, weekly, monthly, or annually, or on demand per user request.

Step 8442 comprises displaying information relevant to at least one derived target dependent variable on at least one mobile device or desktop computer. This step provides access to data derived from the tested population to people via display screens on their mobile devices. Information displayed such as disease positivity rate or recommendations based on disease positivity rate of target population can provide useful information, such as whether further precautions are necessary to reduce the spread of a contagious disease among the target population tested.

Step 8444 comprises transmitting a set of data, which can include results, target dependent variables' data, and corresponding demographics data associated with the people who were tested, to at least one additional remote database server or other mass storage device. Step 8444 can include sending and storing this set of data in a population dependent variables' database within a second mass storage device. This allows organizations to access population data for the targeted disease or family of diseases via database servers at these organizations, which can include disease tracking organizations such as World Health Organization, US Centers For Disease Control.

Step 8446 comprises accessing within database a set of data and result associated with a person and repeating periodically for each set of data and result in database. This step accesses a set of data and result associated with a person who was tested for target disease or family of diseases, such as dementia. Whenever there is new result, this result and the set of data associated with that result can be accessed promptly from database. In addition, periodically each set of data and corresponding result in database can be accessed. In some embodiments, the application software which executes this step, at least in part, can offer multiple options, selected by a user, for automatically accessing this data monthly, quarterly, annually, or whenever a new set of data is available, and this application software can offer on-demand access to data upon request by a user. In some embodiments, Step 8446 can include accessing a set of data and result associated with a person from the diagnostic database within the digital memory, referenced in the detailed description of Step 8420A. In some such embodiments, Step 8446 can be executed by the diagnostic application software referenced earlier. These embodiments are particularly suitable for people who desire prompt feedback regarding open clinical trials when the result indicates that they have the target illness. Shortly after the result has been determined in Step 8432, the diagnostic application software can execute Step 8446 and subsequent steps, including displaying open applicable clinical trials, if any, in Step 7058. In some embodiments, Step 8446 can include accessing data from the tested population database within the first mass storage device, referenced in the detailed description of Step 8436. Such embodiments are particularly suitable for accessing data from a larger population of people who have been tested.

Step 8448 is a decision made by the person who used the testing device: Does person agree to be notified of relevant clinical trials? This binary YES/NO decision can be entered during Step 8420A, as well as other target personal data entered during this step. Alternately this decision can be made at Step 8448, such as responding to a question displayed on mobile device screen by clicking an on-screen button. This question can be "Would you like to be notified regarding relevant clinical trials which may be appropriate for treating your disease?" or another similar question. There can be an on-screen button labelled YES and another on-screen button labelled NO, or other on-screen buttons which serve the same function regarding this decision step. In some embodiments of the application software, the response can be typed by the person on a keypad.

Step 8450 is a decision based on the result determined during Step 8432 regarding person who used the testing device: Does result indicate that the target disease is likely at the time of the test or at a future time? The result can comprise a binary diagnosis (positive or negative test result for target disease or family of diseases), or likelihood that person has the target disease or family of diseases at the time of the test, or likelihood that person will develop the target disease within a specified time-period, such as within five years.

Step 8452 accesses available clinical trials information. This information can be accessed via the internet from a suitable database, such as a database associated with www.clinicaltrials.gov website and/or other relevant websites with database of clinical trials. Each clinical trial description in the database typically includes the name of target disease or family of diseases, the status of the clinical trial (not yet recruiting, recruiting volunteers, recruiting ended, trial ongoing, trial completed, et cetera), locations of trial, interventions (drug treatments, device treatments, gene treatments, et cetera), title of the clinical trial study, and criteria for eligibility to participate in trial, which can include demographics information (age range, gender, ethnicity, education level), patient's stage of the disease, gene information (such as ApoE-4 allele present or absent), symptoms (such as impaired olfactory sense, impaired memory, etc.), biomarkers, et cetera.

Step 8454 and decision Step 8456 compare multiple clinical trials' eligibility criteria in database with the person's test result and other relevant personal data (demographic information, stage of disease, available gene information, symptoms information, relevant biomarkers, et cetera). Step 8454 can comprise keyword search of each clinical trial's eligibility/acceptance criteria based on target personal data, including the person's test result. These steps can comprise at least one suitable algorithm for comparing each clinical trial's eligibility/acceptance criteria with a person's test result and corresponding target personal data. Such algorithms can be developed or refined manually, or via machine learning methodology, or via existing algorithms known in the medical, scientific, or search engine fields can be used during these steps. Existing search engines provide a convenient method for searching websites such as www.clinicaltrials.gov for applicable clinical trials based on relevant personal data, including medical test results, to execute, at least in part, Step 8454.

Based on decision Step 8456, if the person's result and relevant personal data meet the eligibility (acceptance) criteria for at least one clinical trial, then proceed to Step 8458. If not, then proceed to Step 8462.

Step 8458 comprises providing the relevant clinical trials information to the person. Only trials which are currently recruiting volunteers and which have eligibility/acceptance requirements that the person meets will be provided to the person. This information can include name of the clinical trial, location(s) of the trial, trial eligibility criteria, type of treatment(s) in the trial, start and completion dates of the trial, trial contact names, phase of trial, and purpose of trial. The relevant clinical trials information can be provided via display on a mobile device screen, via display on a desktop computer, via printout from a computer, via an email message or text message, or other known means for providing information. This relevant clinical trials' information can be generated by diagnostic application software or other appropriate application software, based on information from at least one clinical trials database. This information can be sent via internet or other known transmission means to mobile device or desktop computer if Step 8458, Step 8456, Step 8454, or Step 8452 occurred remotely.

Step 8460 comprises responding regarding at least one relevant clinical trial if interested. This step can provide a convenient option for the person to respond to at least one relevant clinical trial. This option can be at least one on-screen button on a mobile device or desktop computer display screen, for example. There can be two on-screen buttons, such as INTERESTED button and NOT INTERESTED button, and the person selects the appropriate button for each relevant clinical trial displayed on the screen. Once an on-screen button has been selected, either the diagnostic application software will automatically send response regarding the corresponding clinical trial if relevant personal contact information (such as phone number, email address, mailing address) is already available in digital memory (Step 8436), or the person next will be asked to enter the relevant personal contact information via mobile device display screen, mobile device keypad, or computer keyboard in order to complete the response to the desired clinical trials. The response can be sent via the internet (such as via an email message, or via an onscreen hyperlink), via text message, or any other suitable known transmission method. In one embodiment of the diagnostic application software, when an on-screen button indicating interest in a relevant clinical trial is selected, an email message can be automatically generated and sent to at least one email contact associated with that clinical trial via the internet. This email message can specify interest in participation in the clinical trial and can include the person's name and contact information, which can include email address, mailing address, home address, and telephone number. This email message can also specify that the person meets all the eligibility/acceptance criteria for the clinical trial. In a similar embodiment of the diagnostic application software, when a person selects a clinical trial contact person's name with an on-screen button, a similar email message can be automatically generated and sent to that contact person's email address via the internet.

Step 8462 comprises providing feedback regarding lack of relevant clinical trials which are currently open to participants. This feedback can be provided via display on a mobile device screen, via display of a desktop computer, via printout from a computer, via an email message or text message, or other known means for providing information. This feedback can be a statement such as "According to the www.clinicaltrials.gov website, there are currently no relevant clinical trials open for volunteers which are applicable for you, based on trial eligibility criteria." This information can be sent via internet or other known transmission means to mobile device or desktop computer if Step 8462, Step 8456, Step 8454, or Step 8452 occurred remotely. This step can be executed, at least in part, by application software, such as diagnostic application software, in the mobile device or desktop computer in some embodiments.

Step 8464 comprises storing in the digital memory the clinical trial information for each clinical trial that a person responded positively to during Step 8460, thereby allowing the person to conveniently access this clinical trial information in the future. This information can be added into the diagnostic database within the digital memory. Step 8464 can occur substantially concurrent with Step 8460 in some embodiments, or this step can occur after Step 8460 in other embodiments. Some embodiments of the diagnostic application software can execute Step 8464.

After completing Step 8458 or Step 8462, repeat Step 8446 and subsequent steps for another set of data and result, as shown in FIG. 84a and FIG. 84b flowchart.

Although exemplary embodiments of the invention have been described in detail and in language specific to structural features and/or methodological acts above, it is to be understood that those skilled in the art will readily appreciate that many additional modifications are possible in the exemplary embodiments without materially departing from the novel teachings and advantages of the invention. Moreover, it is to be understood that the subject matter defined in the appended claims is not necessarily limited to the specific features or acts described above. Accordingly, these and all such modifications are intended to be included within the scope of this invention construed in breadth and scope in accordance with the appended claims.

What is claimed is:

1. A method for diagnosing a target illness comprising the steps of:
   obtaining a smell testing device comprising a plurality of smell test substances;
   responding to each smell test substance of said smell testing device as part of a smell test;
   determining a score of the smell test;
   obtaining target personal data of a person who responded to said smell testing device, including said score of said smell test;
   determining a result by evaluating said target personal data, including said score of said smell test; and
   displaying said result.

2. The method of claim 1, which comprises:
   diagnostic application software which executes, at least in part, at least one of said steps; and
   a computing system having a display screen;
   wherein said computing system executes said diagnostic application software and said display screen displays said result.

3. The method of claim 2, comprising the steps of:
   searching internet resources for open applicable clinical trials of potential treatments of said target illness for said person who has been diagnosed with said target illness by said diagnostic application software and who meets eligibility criteria of one or more open applicable clinical trials, including any applicable demographics criteria, biomarkers criteria, genetics criteria and symptoms criteria, for said open applicable clinical trials; and
   providing notification of said open applicable clinical trials to said person.

4. The method of claim 3, wherein said diagnostic application software executes, at least in part, at least one of the steps of searching internet resources and providing notification.

5. The method of claim 3, wherein the step of providing notification comprises displaying information regarding said open applicable clinical trials on said display screen.

6. The method of claim 5, comprising:
   providing a method for responding to said open applicable clinical trials;
   wherein a person who is interested can respond to at least one of said open applicable clinical trials.

7. The method of claim 6, wherein at least one feature selected from the group consisting of onscreen buttons and onscreen hyperlinks provides said method for responding.

8. The method of claim 3, comprising:
   adding data, including said result, said score of said smell test and other said target personal data of said person who responds to said smell testing device, into a database; and
   periodically accessing within said database at least a subset of said target personal data and said result of said person.

9. The method of claim 8, comprising:
   providing feedback to said person regarding lack of said open applicable clinical trials if said internet resources indicate that at least one of acceptance criteria of each open clinical trial of potential treatments of said target illness does not match at least one relevant datum of said target personal data of said person.

10. The method of claim 9, comprising:
providing a method for responding to each said open applicable clinical trial if said internet resources indicate open clinical trials of potential treatments for said target illness and indicate that criteria of at least one of said open clinical trials match said target personal data and said result for said person, wherein said method for responding comprises responding via at least one feature selected from the group consisting of onscreen buttons, onscreen hyperlinks, and onscreen forms which are accepted using a user interface selected from the group consisting of computing device touchscreens, computing device keypads and computing device keyboards;
wherein if said person responds affirmatively to express interest in one of said open applicable clinical trials, information regarding said person is transmitted via an internet to a point of contact on said internet associated with said open applicable clinical trial.

11. The method of claim 10, comprising:
storing information regarding said open applicable clinical trials in at least one database associated with said diagnostic application software;
wherein said information including clinical trials' contacts information, clinical trials' site locations, clinical trials' acceptance criteria, clinical trials' dates, and clinical trials' potential treatments under investigation is available for retrieval.

12. The method of claim 11, wherein said diagnostic application software executes, at least in part, at least one of the method steps of:
adding data, including said result, said score of said smell test and other said target personal data of said person who responds to said smell testing device, into a database;
periodically accessing within said database at least a subset of said target personal data and said result of said person;
providing feedback to said person regarding lack of said open applicable clinical trials if said internet resources indicate that at least one of acceptance criteria of each open clinical trial of potential treatments of said target illness does not match at least one relevant datum of said target personal data of said person;
providing a method for responding to each said open applicable clinical trial if said internet resources indicate open clinical trials of potential treatments for said target illness and indicate that criteria of at least one of said open clinical trials match said target personal data and said result for said person; and
storing said information regarding said open applicable clinical trials in said at least one database associated with said diagnostic application software.

13. The method of claim 12, wherein said target illness is Alzheimer's disease.

14. The method of claim 8, comprising:
providing a method for responding to each said open applicable clinical trial if said internet resources indicate presence of open clinical trials of potential treatments for said target illness and that said clinical trials' acceptance criteria of at least one of said open clinical trials matches said target personal data and said result for said person;
wherein said method for responding comprises responding via at least one feature selected from the group consisting of onscreen buttons, onscreen hyperlinks, and onscreen forms which is accepted using a feature selected from the group consisting of computing system touchscreens, computing system keypads, and computing system keyboards; and
wherein if said person responds affirmatively to express interest in one of said open applicable clinical trials, information regarding said person is transmitted via an internet to a point of contact on said internet associated with said open applicable clinical trial.

15. The method of claim 14, comprising:
storing information regarding said open applicable clinical trials in at least one database associated with said diagnostic application software;
wherein said information including clinical trials' contacts information, clinical trials' site locations, clinical trials' acceptance criteria, clinical trials' dates, and clinical trials' potential treatments under investigation is available for retrieval.

16. The method of claim 15, wherein said diagnostic application software executes, at least in part, at least one of the method steps of:
adding data, including said result, said score of said smell test and other said target personal data of said person who responds to said smell testing device, into a database;
periodically accessing within said database at least a subset of said target personal data and said result of said person;
providing a method for responding to each said open applicable clinical trial if said internet resources indicate presence of open clinical trials of potential treatments for said target illness and that said clinical trials' acceptance criteria of at least one of said open clinical trials matches said target personal data and said result for said person; and
storing said information regarding said open applicable clinical trials in said at least one database associated with said diagnostic application software.

17. The method of claim 16, wherein said target illness is Alzheimer's disease.

18. The method of claim 14, comprising:
periodically storing information regarding said open applicable clinical trials in at least one database associated with said diagnostic application software; and
wherein said information including clinical trials' contacts information, clinical trials' site locations, clinical trials' acceptance criteria, clinical trials' dates, and clinical trials' potential treatments under investigation is available for retrieval.

19. The method of claim 8, comprising:
repeating the step of adding data and the step of periodically accessing within said database at least a subset of said target personal data and said result for each person who responds to said smell test.

20. The method of claim 8, comprising:
periodically providing feedback to said person regarding lack of said open applicable clinical trials if said internet resources indicate that at least one of acceptance criteria of each open clinical trial of potential treatments of said target illness does not match at least one relevant datum of said target personal data of said person.

21. The method of claim 20, comprising:
providing a method for responding to each said open applicable clinical trial if said internet resources indicate open clinical trials of potential treatments for said target illness and indicate that criteria of at least one of said open clinical trials match said target personal data and said result for said person, wherein said method for responding comprises responding via at least one feature selected from the group consisting of onscreen buttons, onscreen hyperlinks, and onscreen forms which are accepted using a user interface selected from the group consisting of computing device touchscreens, computing device keypads and computing device keyboards;
wherein if said person responds affirmatively to express interest in one of said open applicable clinical trials, information regarding said person is transmitted via an internet to a point of contact on said internet associated with said open applicable clinical trial.

22. The method of claim 21, comprising:
storing information regarding said open applicable clinical trials in at least one database associated with said diagnostic application software;
wherein said information including clinical trials' contacts information, clinical trials' site locations, clinical trials' acceptance criteria, clinical trials' dates, and clinical trials' potential treatments under investigation is available for retrieval.

23. The method of claim 8, comprising:
periodically repeating the step of adding data and the step of periodically accessing within said database at least a subset of said target personal data and said result for each person who responds to said smell test.

24. The method of claim 2, wherein said target illness is at least one type of dementia.

25. The method of claim 24, wherein said target illness is Alzheimer's disease.

26. The method of claim 25, wherein said smell testing device is an olfactory identification testing device.

27. The method of claim 26;
wherein said olfactory identification testing device comprises a set of different odorous substances;
wherein each of the different odorous substances is disposed in a separate discrete region of said olfactory identification testing device; and
wherein each said separate discrete region has a unique odor.

28. The method of claim 27:
wherein said olfactory identification testing device comprises a set of anterior indicia;
wherein each anterior indicium in said set of anterior indicia is disposed on said olfactory identification testing device proximal to a different corresponding said separate discrete region; and
wherein each said anterior indicium comprises a unique identifier that differentiates each said anterior indicium.

29. The method of claim 28, wherein each said anterior indicium comprises a unique integer.

30. The method of claim 26, wherein said olfactory identification testing device comprises a set of different odorous substances selected from the group consisting of peppermint-scented substances, banana-scented substances, clove-scented substances, fish-scented substances, leather-scented substances, lemon-scented substances, lilac-scented substances, menthol-scented substances, natural-gas-scented substances, orange-scented substances, paint-thinner-scented substances, peanut-scented substances, pine-apple-scented substances, rose-scented substances, smoke-scented substances, soap-scented substances, and strawberry-scented substances.

31. The method of claim 30:
wherein each of the different odorous substances is disposed in a separate discrete region of said olfactory identification testing device; and
wherein each said separate discrete region has a different unique order.

32. The method of claim 31, comprising:
a set of identification indicia;
wherein each identification indicium in said set of identification indicia is disposed on said olfactory identification testing device proximal to a different corresponding said separate discrete region; and
wherein each said identification indicium comprises a unique identifier that differentiates each said identification indicium.

33. The method of claim 32, wherein each said identification indicium comprises at least one alphanumeric character.

34. The method of claim 32 comprising:
storing said target personal data in a digital memory;
wherein said computing system comprises a user interface adapted and configured to enable entering at least some of said target personal data; and
wherein said at least some of said target personal data is entered via at least one element selected from the group consisting of touch screens, onscreen keyboards, onscreen buttons, offscreen keyboards, and other user interfaces of said computing system.

35. The method of claim 26, wherein said olfactory identification testing device comprises a set of different odorous substances selected from the group consisting of clove-scented substances, leather-scented substances, lemon-scented substances, lilac-scented substances, menthol-scented substances, natural-gas-scented substances, pineapple-scented substances, smoke-scented substances, soap-scented substances, and strawberry-scented substances.

36. The method of claim 26, wherein said olfactory identification testing device comprises a set of different odorous substances selected from the group consisting of fish-scented substances, leather-scented substances, orange-scented substances, peppermint-scented substances, and rose-scented substances.

37. The method of claim 25, comprising:
a method for diagnosing mild cognitive impairment;
wherein said diagnostic application software is adapted and configured to classify whether said person has Alzheimer's disease, or mild cognitive impairment, or neither illness.

38. The method of claim 25, wherein said target personal data includes at least one datum selected from the biomarkers group consisting of levels of phosphorylated tau proteins in bodily fluids, levels of amyloid-beta proteins in bodily fluids, ratios of two proteins in bodily fluids, presence of an ApoE-4 gene allele, presence of an ApoE-2 gene allele, a number of copies of said ApoE-2 gene allele, a number of copies of an ApoE-3 gene allele, a number of copies of said ApoE-4 gene allele, presence of an APP gene mutation associated with early-onset Alzheimer's disease, presence of a PSEN1 gene mutation associated with early-onset Alzheimer's disease, presence of a PSEN2 gene mutation associated with early-onset Alzheimer's disease, presence of an ABCA7 gene variant associated with Alzheimer's disease, presence of a CLU gene variant associated with Alzheimer's disease, presence of a CR1 gene variant associated with Alzheimer's disease, presence of a PICALM gene variant associated with Alzheimer's disease, presence of a PLD3 gene variant associated with Alzheimer's disease, presence of a TREM2 gene variant associated with Alzheimer's disease, presence of a SDRL1 gene variant associated with Alzheimer's disease, levels of microRNA molecules associated with Alzheimer's disease, levels of other proteins positively correlated with Alzheimer's disease, levels of other proteins negatively correlated with Alzheimer's disease and number of copies of a Klotho-VS haplotype.

39. The method of claim 38, wherein said smell testing device is an olfactory identification testing device.

40. The method of claim 39, comprising the steps of:
initiating an internet search for open applicable clinical trials of potential treatments of said target illness via said diagnostic application software;
determining if a person diagnosed with said target illness meets clinical trial eligibility criteria based on said target personal data; and
providing notification of matching applicable clinical trials to said person.

41. The method of claim 40, wherein said diagnostic application software executes, at least in part, at least one of the method steps of:
determining said score of the smell test;
obtaining said target personal data of said person who responded to said smell testing device, including said score of said smell test;
determining a result by evaluating said target personal data, including said score of said smell test;
displaying said result;
initiating said internet search for said open applicable clinical trials of potential treatments of said target illness via said diagnostic application software;
determining if said person diagnosed with said target illness meets clinical trial eligibility criteria based on said target personal data; and
providing said notification of matching applicable clinical trials to said person.

42. The method of claim 39, comprising:
automatically initiating an internet search for treatments of said target illness via said diagnostic application software;
determining if a person diagnosed with said target illness meets treatment eligibility criteria based on said target personal data; and
providing notification of matching applicable treatments to said person.

43. The method of claim 42, wherein said treatments are medications.

44. The method of claim 38, wherein said target personal data comprises at least one datum selected from the biomarkers group consisting of levels of a P-tau 181 protein in bodily fluids, levels of a P-tau 217 protein in bodily fluids, levels of an amyloid-beta 42 protein in bodily fluids, levels of an amyloid-beta 40 protein in bodily fluids, a ratio of amyloid-beta 42::amyloid-beta 40 proteins in bodily fluids, dementia blood test panel levels, including CBC levels, electrolytes levels, a TSH level, a T4 total level, a vitamin B12 level, a CRP level and a sedimentation rate, abnormal serum cholesterol levels, abnormal blood sugar levels, a high resting heart rate and abnormal blood pressure levels.

45. The method of claim 24, comprising:
a method for diagnosing mild cognitive impairment;
wherein said diagnostic application software is adapted and configured to classify whether said person has dementia, or mild cognitive impairment, or neither illness.

46. The method of claim 2, wherein said smell testing device comprises:
a base having an anterior surface;
a cover having an anterior surface and a posterior surface, and comprising:
at least one removable tab;
at least one odorous substance;
an adhesive disposed between said base and said cover; and
at least one indicium disposed on said anterior surface of said cover.

47. The method of claim 46, wherein said smell testing device comprises:
a plurality of said removable tabs, each said removable tab having an anterior surface and a posterior surface; and
a plurality of said at least one indicium;
wherein said at least one odorous substance is disposed in discrete regions contiguous with a surface of said cover, and wherein each of said discrete regions is proximal to a corresponding indicium in said plurality of said at least one indicium.

48. The method of claim 47:
wherein said at least one odorous substance is disposed in said discrete regions as smell test substance patches; and
wherein each of said smell test substance patches is substantially contiguous with the posterior surface of a different corresponding removable tab and is substantially contiguous with the anterior surface of said base.

49. The method of claim 48, wherein each said corresponding indicium is disposed on said anterior surface of said different corresponding removable tab.

50. The method of claim 48, wherein at least one of said smell test substance patches comprise a microencapsulated scent.

51. The method of claim 48, wherein said smell testing device comprises at least one substantially odorless smell test substance patch that is substantially contiguous with said posterior surface of a corresponding removable tab and is substantially contiguous with said anterior surface of said base.

52. The method of claim 51, wherein said smell testing device comprises an olfactory detection testing device that tests olfactory ability to detect scent among each of said smell test substance patches and which tests olfactory ability to correctly discern that each said at least one substantially odorless smell test substance patch has no scent.

53. The method of claim 48, wherein each of said smell test substance patch comprises an odorous substance having a unique scent, wherein each of said smell test substance patches has a different scent.

54. The method of claim 48, wherein at least two of said smell test substance patches comprise an odorous substance having an identical scent.

55. The method of claim 54:
wherein at least two of said smell test substance patches each have a different, unique pungency; and
wherein said smell testing device tests a person's olfactory threshold for at least one odor.

56. The method of claim 2, wherein said target personal data includes at least one datum selected from the group consisting of presence of genetic biomarkers associated with said target illness, presence of blood biomarkers associated with said target illness, presence of cerebrospinal fluid biomarkers associated with said target illness, presence of saliva biomarkers associated with said target illness, presence of urine biomarkers associated with said target illness, presence of symptoms associated with said target illness, diagnoses of illnesses at least sometimes associated with said target illness, ignorance of existing olfactory impairment data, gender data, age data, education level data, race data, ethnicity data, smoking status data, and relatives with said target illness data.

57. The method of claim 56:
wherein said target illness is Alzheimer's disease; and
wherein said target personal data comprises at least one datum selected from the biomarkers group consisting of levels of phosphorylated tau proteins in bodily fluids, levels of amyloid-beta proteins in bodily fluids, ratios of two proteins in bodily fluids, presence of an ApoE-4 gene allele, presence of an ApoE-2 gene allele, a number of copies of said ApoE-2 gene allele, a number of copies of an ApoE-3 gene allele, a number of copies of said ApoE-4 gene allele, presence of an APP gene mutation associated with early-onset Alzheimer's disease, presence of a PSEN1 gene mutation associated with early-onset Alzheimer's disease, presence of a PSEN2 gene mutation associated with early-onset Alzheimer's disease, presence of an ABCA7 gene variant associated with Alzheimer's disease, presence of a CLU gene variant associated with Alzheimer's disease, presence of a CR1 gene variant associated with Alzheimer's disease, presence of a PICALM gene variant associated with Alzheimer's disease, presence of a PLD3 gene variant associated with Alzheimer's disease, presence of a TREM2 gene variant associated with Alzheimer's disease, presence of a SDRL1 gene variant associated with Alzheimer's disease, levels of microRNA molecules associated with Alzheimer's disease, levels of other proteins positively correlated with Alzheimer's disease, levels of other proteins negatively correlated with Alzheimer's disease and number of copies of a Klotho-VS haplotype.

58. The method of claim 57, wherein said diagnostic application software comprises at least one classification model for diagnosing Alzheimer's disease.

59. The method of claim 58:
wherein said diagnostic application software comprises at least one classification model for determining the likelihood of developing Alzheimer's disease within a specified time period after said determining said result; and
wherein said result differentiates between a current Alzheimer's disease diagnosis, an Alzheimer's disease within a specified time period diagnosis, and an Alzheimer's disease will not occur within the specified time period diagnosis.

60. The method of claim 59, comprising:
creating said at least one classification model for determining the likelihood of developing Alzheimer's disease within a specified time-period after said determining a result using an artificial intelligence methodology adapted and configured for developing classification models; and
sending said method for determining said result to said computing system;

wherein said method for determining said result comprises said at least one classification model for determining whether a person will develop Alzheimer's disease within said specified time-period after determining a result.

61. The method of claim 58:
wherein said diagnostic application software comprises a classification model for diagnosing mild cognitive impairment; and
wherein said result differentiates between an Alzheimer's disease diagnosis, a mild cognitive impairment diagnosis, and a cognitively normal diagnosis.

62. The method of claim 58, wherein said presence of symptoms associated with said target illness comprises at least one symptom selected from the group consisting of excessive daytime napping, breaking laws, eating rancid food, eating non-food items, changes in gait, misplacing items more frequently, an inability to recognize sarcasm, more frequent falling, increased forgetfulness, and compulsive behaviors.

63. The method of claim 58, wherein said diagnoses of illnesses at least sometimes associated with said target illness comprises at least one illness diagnosis selected from the group consisting of a periodontal gum disease diagnosis, a depression diagnosis, a stroke diagnosis, a bipolar disorder diagnosis, a schizophrenia diagnosis, a post-traumatic stress disorder diagnosis, a chronic stress diagnosis, an ADD diagnosis, and an ADHD diagnosis.

64. The method of claim 58:
wherein said smell testing device and said diagnostic application software are adapted and configured to evaluate odor identification accuracy and odor threshold sensitivity;
wherein said diagnostic application software determines an olfactory identification score and an odor threshold score; and
wherein said result is based in part on said olfactory identification score and said odor threshold score.

65. The method of claim 64:
wherein said at least one classification model comprises at least one supervised machine learning-derived model selected from the group consisting of logistic regression-derived models, random forest-derived models, naïve bayes-derived models, stochastic gradient descent-derived models, K-nearest neighbors-derived models, decision tree-derived models, support vector machine-derived models, and multinomial regression-derived models; and
wherein said at least one classification model comprises a supervised machine learning-derived model selected from the group consisting of binary classification models and multiclass classification models.

66. The method of claim 64, wherein said at least one classification model comprises at least one independent variable associated with medical data selected from the group consisting of levels of a P-tau 181 protein in bodily fluids, levels of a P-tau 217 protein in bodily fluids, levels of an amyloid-beta 42 protein in bodily fluids, levels of an amyloid-beta 40 protein in bodily fluids, ratio of amyloid-beta 42::amyloid-beta 40 proteins in bodily fluids, dementia blood test panel levels, including CBC levels, electrolytes levels, a TSH level, a T4 total level, a vitamin B12 level, a CRP level, and a sedimentation rate, abnormal serum cholesterol levels, abnormal blood sugar levels, a high resting heart rate, abnormal blood pressure levels, a periodontal gum disease diagnosis, a depression diagnosis, a stroke diagnosis, a bipolar disorder diagnosis, a schizophrenia diagnosis, a post-traumatic stress disorder diagnosis, a chronic stress diagnosis, an ADD diagnosis, and an ADHD diagnosis.

67. The method of claim 66:
wherein said at least one classification model comprises an ordinal logistic regression-derived model; and
wherein said ordinal regression-derived model executes multiclass classification which differentiates between three classes, Alzheimer's disease present, Alzheimer's disease within a specified time period, and no Alzheimer's disease within said specified time period.

68. The method of claim 64:
wherein said at least one classification model comprises an ordinal logistic regression-derived model; and
wherein said ordinal regression-derived model executes multiclass classification which differentiates between three classes, Alzheimer's disease present, Alzheimer's disease within a specified time period, and no Alzheimer's disease within said specified time period.

69. The method of claim 64:
wherein said smell testing device comprises a set of different odorous substances;
wherein said smell testing device and said diagnostic application software are adapted and configured to determine said olfactory identification score based on responses to at least a first subset of said set of different odorous substances, each having a unique scent;
wherein said smell testing device and said diagnostic application software are adapted and configured to determine said odor threshold score based on responses to at least a second subset of said set of different odorous substances;
wherein said second subset of said set of different odorous substances comprises a plurality of one odorous substance having different concentrations, each having a unique pungency;
wherein said olfactory identification score is a first independent variable in at least one of said at least one classification models; and
wherein said odor threshold score is a second independent variable in at least one of said at least one classification models.

70. The method of claim 69:
wherein said computing system comprises at least one element selected from the group consisting of touch screens, onscreen keyboards, onscreen buttons, off-screen keyboards, and other user interfaces; and
wherein said person responds to each odorous substance in said set of different odorous substances via said at least one element.

71. The method of claim 70:
wherein said display screen simultaneously displays at least two said onscreen buttons which correspond to a common smell test substance;
wherein said diagnostic application software is adapted and configured to register an inability to detect an odor associated with a particular odorous substance having a unique pungency in said second subset of said set of different odorous substances when said person selects an undetected-scent onscreen button corresponding with said particular odorous substance having a unique pungency;
wherein said diagnostic application software is adapted and configured to register an ability to detect an odor associated with said particular odorous substance having a unique pungency when said person selects a detected-scent onscreen button corresponding with said particular odorous substance having a unique pungency;
wherein said diagnostic application software is adapted and configured to register a multiple-choice odor-identification response to each odorous substance in said first subset of said set of different odorous substances each time said person selects a scent-name onscreen button among a set of different scent-name onscreen buttons representing multiple scent choices for a corresponding odorous substance in said first subset said set of different odorous substances;
wherein said display screen simultaneously displays said set of different scent-name onscreen buttons representing multiple scent choices for a corresponding odorous substance in said first subset said set of different odorous substances;
wherein each of said different scent-name onscreen buttons has scent-name indicia disposed proximal to the corresponding scent-name onscreen button on said display screen;
wherein the scent-name indicia corresponding with one of the scent-name onscreen buttons in said set of different scent-name onscreen buttons accurately identifies a scent of said corresponding odorous substance;
wherein indicia referencing scent not detected is disposed proximal to each said undetected-scent onscreen button on said display screen;
wherein indicia referencing scent detected is disposed proximal to each said detected-scent onscreen button on said display screen;
wherein each pair of said undetected-scent onscreen button and said detected-scent onscreen button is associated with a corresponding different odorous substance having a unique pungency; and
wherein said diagnostic application software determines said odor threshold score based, at least in part, on a quantity of said detected-scent onscreen buttons selected during said smell test.

72. The method of claim 69, comprising:
searching internet resources for open applicable clinical trials of potential treatments of said target illness for said person who has been diagnosed with said target illness by said diagnostic application software and who meets eligibility criteria of one or more open applicable clinical trials, including any applicable demographics criteria, biomarkers criteria, genetics criteria and symptoms criteria, for said open applicable clinical trials; and
providing notification of said open applicable clinical trials to said person;
wherein said diagnostic application software executes, at least in part, at least one of the steps of searching internet resources and providing notification; and
wherein the step of providing notification comprises displaying information regarding said open applicable clinical trials on said display screen.

73. The method of claim 72, comprising:
providing a method for responding to said open applicable clinical trials;
wherein a person who is interested can respond to at least one of said open applicable clinical trials; and
wherein at least one feature selected from the group consisting of onscreen buttons and onscreen hyperlinks provides said method for responding.

74. The method of claim 69, comprising:
automatically initiating an internet search for treatments of said target illness via said diagnostic application software;
determining if a person diagnosed with said target illness meets treatment eligibility criteria based on said target personal data; and
providing notification of matching applicable treatments to said person.

75. The method of claim 74, wherein said treatments comprise medications.

76. The method of claim 64, comprising:
creating said at least one classification model for diagnosing Alzheimer's disease using an artificial intelligence methodology adapted and configured for developing classification models; and
sending said method for determining said result to said computing system;
wherein said method for determining said result comprises said at least one classification model for diagnosing Alzheimer's disease.

77. The method of claim 58, comprising:
creating said at least one classification model for diagnosing Alzheimer's disease using an artificial intelligence methodology adapted and configured for developing classification models; and
sending said method for determining said result to said computing system;
wherein said method for determining said result comprises said at least one classification model for diagnosing Alzheimer's disease.

78. The method of claim 57, wherein said target personal data comprises at least one datum selected from the biomarkers group consisting of levels of a P-tau 181 protein in bodily fluids, levels of a P-tau 217 protein in bodily fluids, levels of an amyloid-beta 42 protein in bodily fluids, levels of an amyloid-beta 40 protein in bodily fluids, and a ratio of amyloid-beta 42::amyloid-beta 40 proteins in bodily fluids, dementia blood test panel levels, including CBC levels, electrolytes levels, a TSH level, a T4 total level, a vitamin B12 level, a CRP level and a sedimentation rate, abnormal serum cholesterol levels, abnormal blood sugar levels, a high resting heart rate, and abnormal blood pressure levels.

79. The method of claim 2:
wherein said diagnostic application software determines a likelihood that said target illness is present at a time when said smell test was completed; and
wherein said result is based at least in part on said likelihood that said target illness was present at said time.

80. The method of claim 2:
wherein said diagnostic application software determines a likelihood of developing said target illness within a specified time period after completion of said smell test; and
wherein said result is based at least in part on said likelihood of developing said target illness within said specified time period.

81. The method of claim 2:
wherein the step of determining a score of said smell test comprises determining a total quantity of correct responses to said smell test; and
wherein said score is a numeric variable.

82. The method of claim 2:
wherein the step of determining a score of said smell test comprises determining a total quantity of incorrect responses to said smell test; and
wherein said score is a numeric variable.

83. The method of claim 2, wherein the step of determining a score of said smell test comprises:
determining a total quantity of correct responses to said smell test; and
converting said total quantity of correct responses to said smell test into an ordinal score.

84. The method of claim 2, wherein the step of determining a score of said smell test comprises:
determining a total quantity of incorrect responses to said smell test; and
converting said total quantity of incorrect responses to said smell test into an ordinal score.

85. The method of claim 2, wherein said smell testing device comprises:
a component having an anterior surface; and
at least one smell test substance patch disposed on said anterior surface.

86. The method of claim 85, wherein said at least one smell test substance patch comprises a microencapsulated odorous substance.

87. The method of claim 2, wherein said smell testing device comprises:
a component having an anterior surface;
a plurality of smell test substance patches disposed on said anterior surface; and
a set of anterior indicia;
wherein each anterior indicium in said set of anterior indicia is disposed on said anterior surface adjacent to a different corresponding smell test substance patch in said plurality of smell test substance patches.

88. The method of claim 87, wherein each anterior indicium in said set of anterior indicia is unique.

89. The method of claim 2, wherein said smell testing device is an olfactory identification testing device.

90. The method of claim 2, wherein said diagnostic application software comprises at least one classification model for diagnosing said target illness to determine, at least in part, said result.

91. The method of claim 90:
wherein said at least one classification model comprises at least one supervised machine learning-derived model selected from the group consisting of logistic regression-derived models, random forest-derived models, naïve bayes-derived models, stochastic gradient descent-derived models, K-nearest neighbors-derived models, decision tree-derived models, support vector machine-derived models, and multinomial regression-derived models; and
wherein said at least one classification model comprises a supervised machine learning-derived model selected from the group consisting of binary classification models and multiclass classification models.

92. The method of claim 90:
wherein said target illness is Alzheimer's disease; and
wherein said at least one classification model comprises at least one independent variable associated with a biomarker selected from the group consisting of levels of phosphorylated tau proteins in bodily fluids, levels of amyloid-beta proteins in bodily fluids, ratios of two proteins in bodily fluids, presence of an ApoE-4 gene allele, presence of an ApoE-2 gene allele, the number of copies of said ApoE-2 gene allele, the number of copies of an ApoE-3 gene allele, the number of copies of said ApoE-4 gene allele, presence of an APP gene mutation associated with early-onset Alzheimer's disease, presence of a PSEN1 gene mutation associated with early-onset Alzheimer's disease, presence of a PSEN2 gene mutation associated with early-onset Alzheimer's disease, presence of an ABCA7 gene variant associated with Alzheimer's disease, presence of a CLU gene variant associated with Alzheimer's disease, presence of a CR1 gene variant associated with Alzheimer's disease, presence of a PICALM gene variant associated with Alzheimer's disease, presence of a PLD3 gene variant associated with Alzheimer's disease, presence of a TREM2 gene variant associated with Alzheimer's disease, presence of a SDRL1 gene variant associated with Alzheimer's disease, levels of microRNA molecules associated with Alzheimer's disease, levels of other proteins positively correlated with Alzheimer's disease, levels of other proteins negatively correlated with Alzheimer's disease and number of copies of a Klotho-VS haplotype.

93. The method of claim 92, wherein at least one of said at least one independent variable associated with a biomarker represents a level of said biomarker within a bodily fluid.

94. The method of claim 93, wherein said level of said biomarker is represented by an ordinal number.

95. The method of claim 94, wherein said ordinal number is 0 if said level of said biomarker is not above a specified level, and said ordinal number is 1 if said level of said biomarker is above said specified level.

96. The method of claim 94, wherein said ordinal number is 0 if said level of said biomarker is not below a specified level, and said ordinal number is −1 if said level of said biomarker is below said specified level.

97. The method of claim 93, wherein said level of said biomarker is represented by a quantity, wherein said quantity indicates a concentration of said biomarker in said bodily fluid.

98. The method of claim 92:
wherein at least one of said at least one independent variable associated with a biomarker is the binary presence or absence of said biomarker; and
wherein the independent variable has a first prescribed value if said biomarker is present, and said independent variable has a second prescribed value if said biomarker is absent.

99. The method of claim 92, wherein one of said at least one independent variable associated with a biomarker represents an integer quantity of said biomarker.

100. The method of claim 99, wherein said biomarker is a gene variant, wherein said one of said at least one independent variable represents a number of copies of said gene variant.

101. The method of claim 92, wherein said at least one classification model comprises at least one independent variable associated with a biomarker selected from the group consisting of levels of a P-tau 181 protein in bodily fluids, levels of a P-tau 217 protein in bodily fluids, levels of an amyloid-beta 42 protein in bodily fluids, levels of an amyloid-beta 40 protein in bodily fluids, ratio of amyloid-beta 42::amyloid-beta 40 proteins in bodily fluids, dementia blood test panel levels, including CBC levels, electrolytes levels, a TSH level, a T4 total level, a vitamin B12 level, a CRP level and a sedimentation rate, abnormal serum cholesterol levels, abnormal blood sugar levels, a high resting heart rate, and abnormal blood pressure levels.

102. The method of claim 90, comprising:
determining if a biomarker test result is missing; and
displaying a comment regarding the missing biomarker test result,
wherein said comment provides an indicator to complete appropriate testing to obtain said missing biomarker test result; and
wherein at least one of said at least one classification model determines said result based, at least in part, on said missing biomarker test result.

103. The method of claim 102, wherein said target illness is Alzheimer's disease.

104. The method of claim 90, wherein said at least one classification model comprises an ordinal logistic regression-derived model.

105. The method of claim 104:
wherein said target illness is Alzheimer's disease; and
wherein said ordinal regression-derived model executes multiclass classification which differentiates between three classes, Alzheimer's disease present, Alzheimer's disease within a specified time period, and no Alzheimer's disease within said specified time period.

106. The method of claim 2, wherein said diagnostic application software comprises a decision flow chart for determining, at least in part, said result.

107. The method of claim 2, wherein said diagnostic application software comprises a lookup table for determining, at least in part, said result.

108. The method of claim 2, comprising steps of:
accessing at least one clinical trials website;
comparing said target personal data of a person diagnosed with said target illness with eligibility criteria of each open clinical trial, referenced on said at least one clinical trials website, of a potential treatment of said target illness to determine whether each said open clinical trial is applicable for said person; and
providing notification of each open clinical trial which is applicable based on said eligibility criteria to said person diagnosed with said target illness.

109. The method of claim 108, wherein said diagnostic application software executes, at least in part, at least one of said steps of:
determining said score of said smell test;
obtaining said target personal data of said person who responded to said smell testing device, including said score of said smell test;
determining said result by evaluating said target personal data, including said score of said smell test;
displaying said result;
accessing said at least one clinical trials website;
comparing said target personal data of said person diagnosed with said target illness with eligibility criteria of each open clinical trial, referenced on said at least one clinical trials website, of a potential treatment of said target illness to determine whether each said open clinical trial is applicable for said person; and
providing said notification of each open clinical trial which is applicable based on said eligibility criteria to said person diagnosed with said target illness.

110. The method of claim 109, wherein said step of providing notification comprises displaying information regarding at least one open clinical trial which is applicable based on said eligibility criteria on said display screen.

111. The method of claim 110, comprising:
a step of providing a method for responding to said at least one open clinical trial which is applicable based on said eligibility criteria;
wherein said person who is interested can respond to at least one open clinical trial which is applicable based on said eligibility criteria.

112. The method of claim 111, wherein at least one feature selected from the group consisting of onscreen buttons and onscreen hyperlinks provides said method for responding.

113. The method of claim 108, which comprises application software adapted and configured to execute, at least in part, at least one of said steps of:
- determining said score of said smell test;
- obtaining said target personal data of said person who responded to said smell testing device, including said score of said smell test;
- determining said result by evaluating said target personal data, including said score of said smell test;
- displaying said result;
- accessing said at least one clinical trials website;
- comparing said target personal data of said person diagnosed with said target illness with eligibility criteria of each open clinical trial, referenced on said at least one clinical trials website, of a potential treatment of said target illness to determine whether each said open clinical trial is applicable for said person; and
- providing said notification of each open clinical trial which is applicable based on said eligibility criteria to said person diagnosed with said target illness.

114. The method of claim 113, wherein the step of providing notification comprises a method selected from the group consisting of email messaging, text messaging, instant messaging, smart phone messaging application software, and websites on the World Wide Web.

115. The method of claim 2, comprising the steps of:
- creating a method for determining said result based on analysis of said target personal data, including said score of said smell test; and
- sending said method for determining said result to said computing system.

116. The method of claim 115, comprising the steps of:
- determining appropriate biomarkers associated with said target illness;
- selecting at least one classification method for diagnosing said target illness;
- adding data, including said score of said smell test and said target personal data for people who have responded to said smell test, into a database; and
- accessing data, including said score of said smell test and said target personal data associated with multiple people, from said database;
- wherein said method for determining said result includes at least one classification model;
- wherein said result is determined, at least in part, based on analysis of at least one biomarker associated with said target illness; and wherein at least one application software program is adapted and configured to execute, at least in part, at least one of the method steps of:
- determining said appropriate biomarkers associated with said target illness;
- selecting said at least one classification method for diagnosing said target illness;
- adding said data, including said score of said smell test and said target personal data for people who have responded to said smell test, into said database;
- accessing said data, including said score of said smell test and said target personal data associated with multiple people, from said database;
- creating said method for determining said result based on analysis of said target personal data, including said score of said smell test; and
- sending said method for determining said result to said computing system.

117. The method of claim 116, comprising:
- accessing medical records of people who respond to said smell test;
- wherein said target personal data includes at least one datum within the medical records of said person who responds to said smell test; and
- wherein at least one of said at least one classification model determines said result based at least in part on said at least one datum within the medical records of said person.

118. The method of claim 116:
- wherein said at least one classification method comprises at least one supervised machine learning method selected from the group consisting of logistic regression, random forest, naïve bayes, stochastic gradient descent, K-nearest neighbors, decision tree, support vector machine, and multinomial regression; and
- wherein said at least one classification method comprises a supervised machine learning method selected from the group consisting of binary classification methods and multiclass classification methods.

119. The method of claim 118:
- wherein said classification method comprises using a SMOTE filter sampling algorithm;
- wherein said SMOTE filter sampling algorithm addresses class imbalance machine learning issues; and
- wherein said SMOTE filter sampling algorithm increases accuracy of positive disease diagnoses.

120. The method of claim 119, wherein said target illness is Alzheimer's disease.

121. The method of claim 116, wherein said at least one classification method comprises an ordinal logistic regression method.

122. The method of claim 115:
- wherein the step of creating a method for determining said result comprises utilizing machine learning to develop at least one classification model for diagnosing said target illness; and
- wherein at least one application software program is adapted and configured to execute, at least in part, said machine learning.

123. The method of claim 122, wherein said machine learning is at least one form of supervised machine learning.

124. The method of claim 123,
- wherein said at least one form of supervised machine learning is selected from the group consisting of logistic regression, random forest, naïve bayes, stochastic gradient descent, K-nearest neighbors, decision tree, support vector machine, and multinomial regression; and
- wherein said at least one classification model comprises a supervised machine learning-derived model selected from the group consisting of binary classification models and multiclass classification models.

125. The method of claim 124:
- wherein said at least one form of supervised machine learning comprises using a SMOTE filter sampling algorithm;
- wherein said SMOTE filter sampling algorithm addresses class imbalance machine learning issues;
- wherein said SMOTE filter sampling algorithm increases accuracy of positive disease diagnoses; and
- wherein said target illness is Alzheimer's disease.

126. The method of claim 123, wherein said at least one form of supervised machine learning comprises an ordinal logistic regression method.

127. The method of claim 2, comprising:
adding data, including said result, said score of said smell test and other said target personal data for said person who responded to said smell testing device, into a database; and
analyzing the data associated with multiple people who responded to said smell test in said database to determine at least one derived target dependent variable for a target population.

128. The method of claim 127, comprising:
sending a set of data to at least one additional database;
wherein said at least one derived target dependent variable, and at least one datum from said target personal data for multiple people is instantiated in said at least one additional database.

129. The method of claim 127, comprising:
sending at least one of said at least one derived target dependent variable to at least one computing device.

130. The method of claim 129, comprising:
displaying at least one of said at least one derived target dependent variable on at least one of said at least one computing device.

131. A method for diagnosing a target illness, comprising the steps of:
obtaining a used testing device having indicia, including exposed indicia, said exposed indicia based, at least in part, on odorous smell identification test results;
capturing an image of said exposed indicia on said used testing device with a mobile device;
transforming said image into digital image data;
determining a disposition of said exposed indicia from said digital image data; and
displaying a result, based at least in part on said disposition of said exposed indicia.

132. The method of claim 131, comprising the steps of:
entering target personal data of a person who used said used testing device into a digital memory;
accessing said digital memory to retrieve relevant target personal data of said person; and
determining said result, based in part on said relevant target personal data.

133. The method of claim 132, which comprises the steps of:
accessing at least one clinical trials website;
comparing said target personal data of said person diagnosed with said target illness, based on said result, with eligibility criteria of each open clinical trial, referenced on said at least one clinical trials website, of a potential treatment of said target illness to determine which of said open clinical trial is applicable for said person; and
providing notification of each of the open clinical trials applicable for said person to said person diagnosed with said target illness.

134. The method of claim 131:
wherein at least some of said exposed indicia correspond with at least some target personal data of a person who used said used testing device; and
which comprises the steps of:
accessing at least one clinical trials website to locate open clinical trials;
comparing said target personal data of said person diagnosed with said target illness, based on said result, with the eligibility criteria of each open clinical trial, referenced on said at least one clinical trials website, of a potential treatment of said target illness to determine whether each said open clinical trial is applicable for said person; and
providing notification of each of the applicable open clinical trials to said person diagnosed with said target illness;
wherein said person can reveal said target personal data by exposing some of said indicia which are applicable while using said used testing device.

135. The method of claim 131:
wherein at least some of said indicia correspond to personal demographics' data;
wherein a person can reveal said personal demographics' data which are applicable while using said used testing device by exposing applicable indicia; and
wherein said result is based in part on the disposition of said applicable indicia.

136. The method of claim 135, wherein said indicia include at least some indicia corresponding to demographics data selected from the group consisting of age data, gender data, race data, ethnicity data, smoking status data, education level data, and relatives who have been diagnosed with said target illness data.

137. The method of claim 131:
wherein at least some of said indicia correspond to personal biomarkers' data;
wherein a person can reveal said personal biomarkers' data which are applicable while using said used testing device by exposing applicable indicia; and
wherein said result is based in part on the disposition of said applicable indicia.

138. The method of claim 137;
wherein said indicia include at least one indicium corresponding to at least one biomarker selected from the biomarkers group consisting of genetic biomarkers, saliva biomarkers, urine biomarkers, blood biomarkers, and cerebrospinal fluid biomarkers; and
wherein a person can reveal a specific biomarker, selected from said biomarkers group, which is applicable.

139. The method of claim 131:
wherein said indicia include at least one indicium corresponding to awareness of an existing olfactory identification impairment;
wherein a person can reveal an awareness of said existing olfactory identification impairment while using said used testing device by exposing the applicable indicium; and
wherein said result is based in part on the disposition of said applicable indicium.

140. The method of claim 131;
wherein said indicia include at least one indicium corresponding to at least one non-olfactory symptom;
wherein a person can reveal at least one non-olfactory symptom while using said used testing device by exposing applicable indicia; and
wherein said result is based in part on the disposition of said applicable indicia.

141. The method of claim 131:
wherein said indicia include at least one indicium corresponding to at least one illness which is sometimes associated with said target illness;
wherein a person can reveal at least one illness which is sometimes associated with said target illness while using said used testing device by exposing applicable indicia; and
wherein said result is based in part on the disposition of said applicable indicia.

142. The method of claim 131, wherein said target illness is at least one type of dementia.

143. The method of claim 142, wherein said target illness is Alzheimer's disease.

144. The method of claim 131, comprising diagnostic application software that executes, at least in part, at least one of said steps of:
capturing said image of said exposed indicia on said used testing device with said mobile device;
transforming said image into said digital image data;
determining said disposition of said exposed indicia from said digital image data; and
displaying said result, based at least in part on said disposition of said exposed indicia.

145. The method of claim 144, wherein said diagnostic application software comprises a decision flowchart for executing, at least in part, at least one of said steps of:
capturing said image of said exposed indicia on said used testing device with said mobile device;
transforming said image into said digital image data;
determining said disposition of said exposed indicia from said digital image data; and
displaying said result, based at least in part on said disposition of said exposed indicia.

146. The method of claim 144, wherein said diagnostic application software comprises at least one classification model for determining, at least in part, said result.

147. The method of claim 144, wherein said diagnostic application software comprises at least one lookup table for determining, at least in part, said result.

148. The method of claim 144,
wherein at least some of said indicia are circular color-coded indicia which can be exposed by a person using said used testing device;
wherein said diagnostic application software comprises at least one algorithm for circle detection, color filtering, and counting to determine the quantity of circular color-coded indicia of each color; and
wherein said diagnostic application software determines, at least in part, said result based on said quantity of circular color-coded indicia of each color in said digital image data.

149. The method of claim 131, wherein at least some of said indicia are color-coded indicia.

150. The method of claim 149, wherein said color-coded indicia are circular color-coded indicia.

151. A method for diagnosing a target illness, comprising the steps of:
obtaining a used testing device having indicia, including exposed indicia, said exposed indicia based, at least in part, on results of a test selected from the group consisting of odorous smell detection test and odorous smell threshold tests;
capturing an image of said exposed indicia on said used testing device with a mobile device;
transforming said image into digital image data;
determining a disposition of said exposed indicia from said digital image data; and
displaying a result, based at least in part on said disposition of said exposed indicia.

152. The method of claim 151, comprising the steps of:
entering target personal data of a person who used said used testing device into a digital memory;
accessing said digital memory to retrieve the relevant target personal data of said person; and
determining said result, based in part on said relevant target personal data.

153. The method of claim 152, comprising the steps of:
accessing at least one clinical trials website to determine open clinical trials;
comparing said target personal data of said person diagnosed with said target illness, based on said result, with the eligibility criteria of each open clinical trial, referenced on said at least one clinical trials website, of a potential treatment of said target illness to determine whether each said open clinical trial is applicable for said person; and
providing notification of at least one open clinical trial which is applicable based on said eligibility criteria to said person diagnosed with said target illness.

154. The method of claim 151, wherein at least some of said exposed indicia correspond with at least some target personal data of a person who used said used testing device, and which comprises the steps of:
accessing at least one clinical trials website;
comparing said target personal data of a person diagnosed with said target illness, based on said result, with eligibility criteria of each open clinical trial, referenced on said at least one clinical trials website, of a potential treatment of said target illness to determine whether each said open clinical trial is applicable for said person; and
providing notification of at least one of said open clinical trials which is applicable based on said eligibility criteria to said person diagnosed with said target illness;
wherein said a person can reveal said target personal data by exposing some of said indicia which are applicable while using said used testing device.

155. The method of claim 151:
wherein at least some of said indicia correspond to personal demographics' data;
wherein a person can reveal said personal demographics' data which are applicable while using said used testing device by exposing applicable indicia; and
wherein said result is based in part on the disposition of said applicable indicia.

156. The method of claim 155, wherein said indicia include at least some indicia corresponding to demographics' data selected from the group consisting of age data, gender data, race data, ethnicity data, education level data, smoking status data, and relatives who have been diagnosed with said target illness data.

157. The method of claim 151:
wherein at least one of said indicia corresponds to personal biomarkers' data;
wherein a person can reveal said personal biomarkers' data which are applicable while using said used testing device by exposing applicable indicia; and
wherein said result is based in part on the disposition of said applicable indicia.

158. The method of claim 157:
wherein said indicia include at least one indicium corresponding to at least one biomarker selected from the group consisting of genetic biomarkers, saliva biomarkers, urine biomarkers, blood biomarkers, and cerebrospinal fluid biomarkers; and
wherein a person can reveal a specific biomarker, selected from said group as, which is applicable.

159. The method of claim 151:
wherein said indicia comprise at least one indicium corresponding to at least one non-olfactory symptom;

wherein a person can reveal at least one non-olfactory symptom while using said used testing device by exposing an applicable at least one indicium; and wherein said result is based in part on the disposition of said applicable at least one indicium.

160. The method of claim 151:
wherein said indicia include at least one indicium corresponding to at least one illness which is sometimes associated with said target illness;
wherein a person can reveal at least one illness which is sometimes associated with said target illness while using said used testing device by exposing an applicable at least one indicium; and
wherein said result is based in part on the disposition of said applicable at least one indicium.

161. The method of claim 151, wherein said target illness is at least one type of coronavirus disease.

162. The method of claim 161, wherein said target illness is COVID-19 disease.

163. The method of claim 151, which comprises diagnostic application software that executes, at least in part, at least one of said steps of:
capturing said image of said exposed indicia on said used testing device with said mobile device;
transforming said image into said digital image data;
determining said disposition of said exposed indicia from said digital image data; and
displaying said result, based at least in part on said disposition of said exposed indicia.

164. The method of claim 163, wherein said diagnostic application software comprises a decision flowchart for executing, at least in part, at least one of said steps of:
capturing said image of said exposed indicia on said used testing device with said mobile device;
transforming said image into said digital image data;
determining said disposition of said exposed indicia from said digital image data; and
displaying said result, based at least in part on said disposition of said exposed indicia.

165. The method of claim 163, wherein said diagnostic application software comprises at least one classification model for determining, at least in part, said result.

166. The method of claim 163, wherein said diagnostic application software comprises at least one lookup table for determining, at least in part, said result.

167. The method of claim 163:
wherein at least some of said indicia are circular color-coded indicia adapted and configured to be exposed by a person using said used testing device;
wherein said diagnostic application software comprises at least one algorithm for circle detection, color filtering, and counting to determine the quantity of the circular color-coded indicia of each color; and
wherein said diagnostic application software determines, at least in part, said result based on said quantity of said circular color-coded indicia of each color in said digital image data.

168. The method of claim 151, wherein at least some of said indicia are color-coded indicia.

169. The method of claim 168, wherein said color-coded indicia are circular color-coded indicia.

170. The method of claim 151, wherein said target illness is at least one type of dementia.

171. The method of claim 170, wherein said target illness is Alzheimer's disease.

172. A method for diagnosing a target disease comprising the steps of:
obtaining a smell testing device comprising a plurality of smell test substances;
responding to each smell test substance of the smell testing device;
recording temporal data regarding capturing an image of this response;
scoring a number of smell test substances correctly identified to determine a test score number;
entering into digital memory the test score number with other target personal data of a person who used smell testing device;
entering target personal data of said person into digital memory;
obtaining a used testing device for analysis;
capturing an image of indicia presented on said used testing device with a mobile device;
orienting said image;
determining disposition of said indicia;
accessing said digital memory to retrieve relevant target personal data associated with said used testing device;
digitizing indicia data;
determining if all relevant indicia present on used testing device have been digitized;
periodically comparing relevant personal medical record data with a result of each corresponding used testing device using machine learning methodology to refine at least one classification model for predicting likelihood of target disease or family of diseases within a specified time period, based on result of smell test and other relevant target personal data, and create latest method for determining result based on the classification model(s);
transmitting a latest method for determining result to at least one mobile device;
enabling the latest method for determining result in mobile device;
determining said result by evaluating individual components of digital indicia data and available relevant target personal data;
displaying said result;
determining if any nonolfactory biomarker test results are missing;
displaying comment regarding any missing non-olfactory biomarker test results;
adding a set of data and result into a database;
accessing within said database a set of data and result associated with said person, and repeat periodically for each set of data and result in said database;
determining if said person agrees to be notified of relevant clinical trials;
determining if said result indicates that the target disease is present at time of determination of said test score number or at a future time;
analyzing data and results associated with at least one set of used testing devices to derive at least one target parameter for a target population;
transmitting a set of data, including results and target parameters data, to at least one additional remote database server;
transmitting at least one of said target parameters to at least one mobile device;
displaying information relevant to at least one of said target parameters on at least one mobile device;
accessing available clinical trials information;
providing feedback regarding lack of relevant currently open clinical trials which are currently open;

determining if said person's test result and relevant personal data meet acceptance criteria for relevant trials;
comparing available clinical trials' acceptance criteria with the person's test result and other relevant personal data;
providing relevant clinical trials information to the person; and
responding regarding at least one relevant clinical trial, if interested.

* * * * *